US006472505B1

(12) United States Patent
Condon et al.

(10) Patent No.: US 6,472,505 B1
(45) Date of Patent: Oct. 29, 2002

(54) PEPTIDE PARATHYROID HORMONE ANALOGS

(75) Inventors: Stephen M. Condon, Chester Springs, PA (US); Isabelle Morize, Sevran (FR)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 0 days.

(21) Appl. No.: 09/228,990

(22) Filed: Jan. 12, 1999

Related U.S. Application Data

(63) Continuation of application No. PCT/US98/09843, filed on May 13, 1998.
(60) Provisional application No. 60/046,742, filed on May 14, 1997.

(51) Int. Cl.[7] .......................... A61K 38/00; C07K 5/00; C07K 7/00
(52) U.S. Cl. ............................. 530/317; 514/9; 514/11
(58) Field of Search ............................. 530/317; 514/9, 514/11

(56) References Cited

U.S. PATENT DOCUMENTS

| | | |
|---|---|---|
| 4,086,196 A | 4/1978 | Tregear |
| 4,423,037 A | 12/1983 | Rosenblatt et al. |
| 4,427,827 A | 1/1984 | Stevenson |
| 4,656,250 A | 4/1987 | Morita et al. |
| 4,771,124 A | 9/1988 | Rosenblatt et al. |
| 5,229,489 A | 7/1993 | Kanmera et al. |
| 5,434,246 A | 7/1995 | Fukuda et al. |
| 5,446,130 A | 8/1995 | Kanmera et al. |
| 5,494,679 A | 2/1996 | Sage et al. |
| 5,556,940 A | 9/1996 | Willick et al. |
| 5,589,452 A | 12/1996 | Krstenansky et al. |
| 5,599,792 A | 2/1997 | Kronis et al. |
| 5,607,915 A | 3/1997 | Patton |
| 5,693,616 A | 12/1997 | Krstenansky et al. |
| 5,695,955 A | 12/1997 | Krstenansky et al. |
| 5,717,062 A | 2/1998 | Chorev et al. |
| 5,723,577 A | 3/1998 | Dong |

FOREIGN PATENT DOCUMENTS

| | | |
|---|---|---|
| DE | 195 08 672 A1 | 9/1996 |
| EP | 93104500.9 | 9/1993 |
| EP | 747817 A2 | 12/1996 |
| WO | WO94/02510 | 2/1994 |
| WO | WO95/11988 | 5/1995 |
| WO | WO 96/03437 | 2/1996 |
| WO | WO96/40193 | 12/1996 |
| WO | WO97/02834 | 1/1997 |

OTHER PUBLICATIONS

Chorev et al., Cyclic Parathyroid Hormone RelatedProtein Antagonists: Lysine 13 to Aspartic Acid 17 [i to (i+4)] side chain to side chaine lactamization, Biochemistry 1991 30, 5968–5974.

Morley et al., Parathyroid hormone analogues for treatment of osteoporosis and hypercalcaemia, Exp. Opin. Ther. Patents (1998) 8(1).

Bisello et al., Mono–and bicyclc analogs of parathyroid hormone–related protein. 1. synthesis and Biological studies, Biochemistry 1997, 36, 3293–3299.

Rixon et al., Parathyroid hormone fragments may stimulate bone growthin ovariectomized rats by activating adenylyl cyclase, Journal of bone and Mineral Research 1994, 9, 1179–1189.

Whitfield et al., Stimulation of the Growth of Femoral Trabecular Bone in ovariectomized rats by the novel parathyroid hormone fragment, hPTH–(1–31)NH2 (Ostabolin), Calcif. Tissue Int. (1996) 58:81–87.

Maretto et al., Mono–and bycyclic analogs of parathyroid hormone–related protein. 2. Conformational Analysis of antagonists by CD, NMR, and distance geometry calculations, Biochemistry 1997, 3300–3307.

Barbier et al., Bioactivities and Secondary Structures of Constrained analogues of human parathyroid hormone: cyclic lactams of the receptor binding region, J. Med. Chem. 1997, 40, 1373–1380.

Mierke et al., Conformational Studies of Mono–and Bicyclic parathyroid hormone–related protein–derived agonists, Biochemistry 1997, 36, 10372–10383.

Waelchli et al., Dipeptide mimetics can substitute for the receptor activation domain resulting in highly potent analogues of hPTH(1–36) fragment, Bioorganic and Medicinal Chemistry Letters, 1996, 6:1151–1156.

Boericke et al., Iontophoretic Delivery of Human Parathyroid Hormone (1–34) in Swine, Proceed. Intern. Symp. Control. rel. Bioact. Mater. 1996, 23:318.

Leaffer et al., Modulation of Osteogenic Cell Ultrastructure by RS–23581, an analog of human parathyroid hormone (PTH)–related peptide–(1–34), and bovine PTH–(1–34)., Endocrinology 1995, 136(8):3624–3631.

Vickery et al., RS–66271, a C–terminally substituted analog of huan parathyroid hormone–related protein (1–34), Increases trabecular and cortical bone in ovariectomized osteopenic rats, J. Bone and Min. Res., 1996, 11(12):1943.

Pellegrini et al., Conformational Studies of RS–66271, an analog of parathyroid hormone–related protein with pronounced bone anabolic activity, J. Med. Chem. 1997, 40, 3025–3031.

Neugebauer et al., Structure of protein kinase C stimulating activities of lactam analogues of human parathyroid hormone fragment, Int. J. Peptide Protein Res., 1994, 43:555–562.

(List continued on next page.)

Primary Examiner—Avis M. Davenport
(74) Attorney, Agent, or Firm—Irving Newman

(57) ABSTRACT

This invention is directed to cyclic and acyclic analogs of hPTH(1–34) and hPTHrP(1–34), to pharmaceutical compositions comprising these peptide compounds, and to a method of treating diseases associated with calcium regulation in the body.

8 Claims, No Drawings

OTHER PUBLICATIONS

Chorev et al., Structure–Function analysis of parathyroid hormone and parathyroid hormone–related protein, The Parathyroids Raven Press, Ltd. New York (1994) 139–156.

Chorev et al., Approaches to Studying the biomolecular interaction between the parathyroid hormone/parathyroid hormone–related receptor and its ligands., Miner. Electrolyte Metab. 1995, 21, 133–139.

Cohen et al., Analogues of parathyroid hormone modified at positions 3 and 6., J. Biol. Chem. 1991, 266, 1997–2004.

Gardella et al., Parathyroid Hormone (PTH)–PTH–related hybrid peptides reval funtional interactions between the 1–14 and 15–34 domains of the ligand, J. Biol. Chem. 1995, 270, 6584–6588.

Gardella et al., scanning mutagenesis ofthe 23–35 region of parathyroid hormone reveals important determinants of receptor binding., Calcium Regulating Hormones and Bone Metabolism. Elsevier Science Publishers. 1992, pp. 218–222.

Gombert et al., Parathyroid hormone domain for protein kinase C stimulation located within amphiphilic helix, Pept. Chem., Struct. Biol. Proc. Proc. Am. Pept. Symp. 13th, 1993, 37–39.

Jouishomme et al., Further definition of the protein kinase C activation domain of parathyroid hormone, J. Bone Miner. Res. 1994, 9, 943–949.

Klaus et al., Investigation of the solution structure of the human parathyroid hormone fragment (1–34) by 1H NMR spectroscopy, Distance Geometry, andMolecular Dynamics Calculations, Biochemistry 1991, 30, 6936–6942.

Lane et al., Bone–selective analogs of human PTH(1–34) increase bone formation in an ovariectomized rat model, J. Bone Min. Res. 1996, 11, 614–625.

Marx et al., Structure of human parathyroid horone 1–37 in solution., J. Biol. Chem. 1995, 270, 15194–15202.

Neugebauer et al., Solution structure and adenylate cyclase stimulating activities of the C–terminal truncated human parathyroid hormone analogues, Biochemistry 1995, 34, 8835–8842.

Neugebauer et al., Structural elements of human parathyroid hormone and their possible relation to biological activities., Biochemistry 1992, 31, 2056–2063.

Neugebauer et al., Lactam analogues of a human parathyroid (hPTH) domain for protein kinase c (PKC) stimulation., Peptides, 1992 Schneider et al. (eds.) ESCOM Publishers B.V. 1993.

Nussbaum et al., Design of analogues of parathyroid hormone: a conformational approach., J. Prot. Chem. 1985, 4, 391–406.

Rosenblatt et al., Chemical and Biological properties of synthetic, sulfur–free analogues of parathyroid hormone., J. Biol. Chem. 1976, 251, 159–164.

Surewicz et al., Structure–function relationships in human parathyroid hormone: the essential role of amphiphilic alpha–helix., Pept. Chem., Struct. Biol. Proc. Am. Pept. Symp. 13th, 1993.

Wray et al., The structure of human parathyroid hormone from a study of fragments in solution using 1H NMR spectroscopy and its biological implications, Biochemistry 1994, 33, 1684–1693.

Zull et al., Effect of Methionine oxidation and deletion of amino–terminal residues on the conformation of parathyroid hormone, J. Biol. Chem. 1990, 265, 5571–5676.

Strickland et al., Structure of human parathyroid hormone(1–34) in the presence of solvents and micelles., Biochemistry 32:6050–6057 (1993).

Iida–Klein et al., Truncation of the carboxyl–terminal region of the rat parathyroid hormone (PTH)/PTH–related peptide receptor enhances PTH stimulation of adenylyl cyclase but not phospholipase C, J. Biol. Chem. 270(15):8458–8465 (1995).

Peacock et al., Inheritance of calcium absorption, calcium-regulating hormones and bone turnover., Cohn et al. (eds) Calcium regulating hormones and bone metabolism (1992).

SEQUENCE LISTING (1) GENERAL INFORMATION:

(iii) NUMBER OF SEQUENCES: 88

(2) INFORMATION FOR SEQ ID NO:1:

(i) SEQUENCE CHARACTERISTICS:
      (A) LENGTH: 34 amino acids
      (B) TYPE: amino acid
      (C) STRANDEDNESS:
      (D) TOPOLOGY: Not Relevant (ii) MOLECULE TYPE: peptide (v) FRAGMENT TYPE: N-terminal (xi) SEQUENCE DESCRIPTION: SEQ ID NO:1:

Ser Val Ser Glu Ile Gln Leu Met His Asn Leu Gly Lys His Leu Asn
1            5                10              15

Ser Met Glu Arg Val Glu Trp Leu Arg Lys Lys Leu Gln Asp Val His
          20                25              30

Asn Phe (2) INFORMATION FOR SEQ ID NO:2:

(i) SEQUENCE CHARACTERISTICS:
        (A) LENGTH: 34 amino acids
        (B) TYPE: amino acid
        (C) STRANDEDNESS:
        (D) TOPOLOGY: Not Relevant (ii) MOLECULE TYPE: peptide (v) FRAGMENT TYPE: N-terminal (xi) SEQUENCE DESCRIPTION: SEQ ID NO:2:

```
Ala Val Ser Glu His Gln Leu Leu His Asp Lys Gly Lys Ser Ile Gln
1               5                   10                  15

Asp Leu Arg Arg Arg Phe Phe Leu His His Leu Ile Ala Glu Ile His
                20                  25                  30

Thr Ala
```

(2) INFORMATION FOR SEQ ID NO:3:

(i) SEQUENCE CHARACTERISTICS:
        (A) LENGTH: 31 amino acids
        (B) TYPE: amino acid
        (C) STRANDEDNESS:
        (D) TOPOLOGY: Not Relevant (ii) MOLECULE TYPE: peptide (v) FRAGMENT TYPE: N-terminal (ix) FEATURE:
        (A) NAME/KEY: Peptide
        (B) LOCATION: 8
        (D) OTHER INFORMATION: /product= "Nle"

(ix) FEATURE:
        (A) NAME/KEY: Peptide
        (B) LOCATION: 18..22
        (D) OTHER INFORMATION: /product= "OTHER"
            /note= "The side chains of Lys at position 18 and Asp at
            position 22 are linked by an amide bond. "

(ix) FEATURE:
        (A) NAME/KEY: Peptide
        (B) LOCATION: 31
        (D) OTHER INFORMATION: /product= "OTHER"
            /note= "This C-terminal amino acid is an amide, i.e.,
            CONH2."

(xi) SEQUENCE DESCRIPTION: SEQ ID NO:3:

```
Ala Val Ser Glu Ile Gln Leu Xaa His Asn Leu Gly Lys His Leu Asn
1               5                   10                  15

Ser Lys Glu Arg Val Asp Trp Leu Arg Lys Leu Leu Gln Asp Val
                20                  25                  30
```

(2) INFORMATION FOR SEQ ID NO:4:

(i) SEQUENCE CHARACTERISTICS:
        (A) LENGTH: 31 amino acids
        (B) TYPE: amino acid
        (C) STRANDEDNESS:
        (D) TOPOLOGY: Not Relevant (ii) MOLECULE TYPE: peptide (v) FRAGMENT TYPE: N-terminal (ix) FEATURE:
        (A) NAME/KEY: Peptide (B) LOCATION: 8
        (D) OTHER INFORMATION: /product= "Nle"

(ix) FEATURE:
        (A) NAME/KEY: Peptide
        (B) LOCATION: 31
        (D) OTHER INFORMATION: /product= "OTHER"
            /note= "This sequence has an amide C-terminus (i.e.,
            CONH2), rather than a carboxy C-terminus (i.e., COOH)."

(xi) SEQUENCE DESCRIPTION: SEQ ID NO:4:

Ala Val Ser Glu Ile Gln Leu Xaa His Asn Leu Gly Lys His Leu Asn
1               5                   10                  15

Ser Lys Glu Arg Val Asp Trp Leu Arg Lys Leu Leu Gln Asp Val
            20                  25                  30

(2) INFORMATION FOR SEQ ID NO:5:

(i) SEQUENCE CHARACTERISTICS:
        (A) LENGTH: 31 amino acids
        (B) TYPE: amino acid
        (C) STRANDEDNESS:
        (D) TOPOLOGY: Not Relevant (ii) MOLECULE TYPE: peptide (v) FRAGMENT TYPE: N-terminal (ix) FEATURE:
        (A) NAME/KEY: Peptide
        (B) LOCATION: 8
        (D) OTHER INFORMATION: /product= "Nle"

(ix) FEATURE:
        (A) NAME/KEY: Peptide
        (B) LOCATION: 18..22
        (D) OTHER INFORMATION: /product= "OTHER"
            /note= "The side chains of Lys at position 18 and Asp at
            position 22 are linked by an amide bond."

(ix) FEATURE:
        (A) NAME/KEY: Peptide
        (B) LOCATION: 31
        (D) OTHER INFORMATION: /product= "OTHER"
            /note= "This C-terminal amino acid is an amide, i.e.,
            CONH2."

(xi) SEQUENCE DESCRIPTION: SEQ ID NO:5:

Ala Ala Ser Glu Ile Gln Leu Xaa His Asn Leu Gly Lys His Leu Asn
1               5                   10                  15

Ser Lys Glu Arg Val Asp Trp Leu Arg Lys Leu Leu Gln Asp Val
            20                  25                  30

(2) INFORMATION FOR SEQ ID NO:6:

(i) SEQUENCE CHARACTERISTICS:
        (A) LENGTH: 31 amino acids
        (B) TYPE: amino acid
        (C) STRANDEDNESS:
        (D) TOPOLOGY: Not Relevant (ii) MOLECULE TYPE: peptide (v) FRAGMENT TYPE: N-terminal (ix) FEATURE:
        (A) NAME/KEY: Peptide
        (B) LOCATION: 8
        (D) OTHER INFORMATION: /product= "Nle"

(ix) FEATURE:
        (A) NAME/KEY: Peptide
        (B) LOCATION: 18..22

```
        (D) OTHER INFORMATION: /product= "OTHER"
            /note= "The side chains of Lys at position 18 and Asp at
            position 22 are linked by an amide bond. "

(ix) FEATURE:
        (A) NAME/KEY: Peptide
        (B) LOCATION: 31
        (D) OTHER INFORMATION: /product= "OTHER"
            /note= "This C-terminal amino acid is an amide, i.e.,
            CONH2."

(xi) SEQUENCE DESCRIPTION: SEQ ID NO:6:

Ala Val Ala Glu Ile Gln Leu Xaa His Asn Leu Gly Lys His Leu Asn
1               5                   10                  15

Ser Lys Glu Arg Val Asp Trp Leu Arg Lys Leu Leu Gln Asp Val
            20                  25                  30

(2) INFORMATION FOR SEQ ID NO:7:

(i) SEQUENCE CHARACTERISTICS:
        (A) LENGTH: 31 amino acids
        (B) TYPE: amino acid
        (C) STRANDEDNESS:
        (D) TOPOLOGY: Not Relevant (ii) MOLECULE TYPE: peptide (v) FRAGMENT TYPE: N-terminal (ix) FEATURE:
        (A) NAME/KEY: Peptide
        (B) LOCATION: 8
        (D) OTHER INFORMATION: /product= "Nle"

(ix) FEATURE:
        (A) NAME/KEY: Peptide
        (B) LOCATION: 18..22
        (D) OTHER INFORMATION: /product= "OTHER"
            /note= "The side chains of Lys at position 18 and Asp at
            position 22 are linked by an amide bond. "

(ix) FEATURE:
        (A) NAME/KEY: Peptide
        (B) LOCATION: 31
        (D) OTHER INFORMATION: /product= "OTHER"
            /note= "This C-terminal amino acid is an amide, i.e.,
            CONH2."

(xi) SEQUENCE DESCRIPTION: SEQ ID NO:7:

Ala Val Ser Ala Ile Gln Leu Xaa His Asn Leu Gly Lys His Leu Asn
1               5                   10                  15

Ser Lys Glu Arg Val Asp Trp Leu Arg Lys Leu Leu Gln Asp Val
            20                  25                  30

(2) INFORMATION FOR SEQ ID NO:8:

(i) SEQUENCE CHARACTERISTICS:
        (A) LENGTH: 31 amino acids
        (B) TYPE: amino acid
        (C) STRANDEDNESS:
        (D) TOPOLOGY: Not Relevant (ii) MOLECULE TYPE: peptide (v) FRAGMENT TYPE: N-terminal (ix) FEATURE:
        (A) NAME/KEY: Peptide
        (B) LOCATION: 8
        (D) OTHER INFORMATION: /product= "Nle"

(ix) FEATURE:
        (A) NAME/KEY: Peptide
```

```
            (B) LOCATION: 18..22
            (D) OTHER INFORMATION: /product= "OTHER"
                /note= "The side chains of Lys at position 18 and Asp at
                position 22 are linked by an amide bond."

(ix) FEATURE:
            (A) NAME/KEY: Peptide
            (B) LOCATION: 31
            (D) OTHER INFORMATION: /product= "OTHER"
                /note= "This C-terminal amino acid is an amide, i.e.,
                CONH2."

(xi) SEQUENCE DESCRIPTION: SEQ ID NO:8:

Ala Val Ser Glu Ala Gln Leu Xaa His Asn Leu Gly Lys His Leu Asn
1               5                  10                  15

Ser Lys Glu Arg Val Asp Trp Leu Arg Lys Leu Leu Gln Asp Val
            20                  25                  30

(2) INFORMATION FOR SEQ ID NO:9:

(i) SEQUENCE CHARACTERISTICS:
            (A) LENGTH: 31 amino acids
            (B) TYPE: amino acid
            (C) STRANDEDNESS:
            (D) TOPOLOGY: Not Relevant (ii) MOLECULE TYPE: peptide (v) FRAGMENT TYPE: N-terminal (ix) FEATURE:
            (A) NAME/KEY: Peptide
            (B) LOCATION: 8
            (D) OTHER INFORMATION: /product= "Nle"

(ix) FEATURE:
            (A) NAME/KEY: Peptide
            (B) LOCATION: 18..22
            (D) OTHER INFORMATION: /product= "OTHER"
                /note= "The side chains of Lys at position 18 and Asp at
                position 22 are linked by an amide bond."

(ix) FEATURE:
            (A) NAME/KEY: Peptide
            (B) LOCATION: 31
            (D) OTHER INFORMATION: /product= "OTHER"
                /note= "This C-terminal amino acid is an amide, i.e.,
                CONH2."

(xi) SEQUENCE DESCRIPTION: SEQ ID NO:9:

Ala Val Ser Glu Ile Ala Leu Xaa His Asn Leu Gly Lys His Leu Asn
1               5                  10                  15

Ser Lys Glu Arg Val Asp Trp Leu Arg Lys Leu Leu Gln Asp Val
            20                  25                  30

(2) INFORMATION FOR SEQ ID NO:10:

(i) SEQUENCE CHARACTERISTICS:
            (A) LENGTH: 31 amino acids
            (B) TYPE: amino acid
            (C) STRANDEDNESS:
            (D) TOPOLOGY: Not Relevant (ii) MOLECULE TYPE: peptide (v) FRAGMENT TYPE: N-terminal (ix) FEATURE:
            (A) NAME/KEY: Peptide
            (B) LOCATION: 8
            (D) OTHER INFORMATION: /product= "Nle"

(ix) FEATURE:
```

```
        (A) NAME/KEY: Peptide
        (B) LOCATION: 18..22
        (D) OTHER INFORMATION: /product= "OTHER"
            /note= "The side chains of Lys at position 18 and Asp at
            position 22 are linked by an amide bond. "

(ix) FEATURE:
        (A) NAME/KEY: Peptide
        (B) LOCATION: 31
        (D) OTHER INFORMATION: /product= "OTHER"
            /note= "This C-terminal amino acid is an amide, i.e.,
            CONH2."

(xi) SEQUENCE DESCRIPTION: SEQ ID NO:10:

Ala Val Ser Glu Ile Gln Ala Xaa His Asn Leu Gly Lys His Leu Asn
1               5                  10                  15

Ser Lys Glu Arg Val Asp Trp Leu Arg Lys Leu Leu Gln Asp Val
            20                  25                  30

(2) INFORMATION FOR SEQ ID NO:11:

(i) SEQUENCE CHARACTERISTICS:
        (A) LENGTH: 31 amino acids
        (B) TYPE: amino acid
        (C) STRANDEDNESS:
        (D) TOPOLOGY: Not Relevant (ii) MOLECULE TYPE: peptide (v) FRAGMENT TYPE: N-terminal (ix) FEATURE:
        (A) NAME/KEY: Peptide
        (B) LOCATION: 8
        (D) OTHER INFORMATION: /product= "Nle"

(ix) FEATURE:
        (A) NAME/KEY: Peptide
        (B) LOCATION: 18..22
        (D) OTHER INFORMATION: /product= "OTHER"
            /note= "The side chains of Lys at position 18 and Asp at
            position 22 are linked by an amide bond. "

(ix) FEATURE:
        (A) NAME/KEY: Peptide
        (B) LOCATION: 31
        (D) OTHER INFORMATION: /product= "OTHER"
            /note= "This C-terminal amino acid is an amide, i.e.,
            CONH2."

(xi) SEQUENCE DESCRIPTION: SEQ ID NO:11:

Ala Val Ser Glu Ile Gln Leu Xaa Ala Asn Leu Gly Lys His Leu Asn
1               5                  10                  15

Ser Lys Glu Arg Val Asp Trp Leu Arg Lys Leu Leu Gln Asp Val
            20                  25                  30

(2) INFORMATION FOR SEQ ID NO:12:

(i) SEQUENCE CHARACTERISTICS:
        (A) LENGTH: 31 amino acids
        (B) TYPE: amino acid
        (C) STRANDEDNESS:
        (D) TOPOLOGY: Not Relevant (ii) MOLECULE TYPE: peptide (v) FRAGMENT TYPE: N-terminal (ix) FEATURE:
        (A) NAME/KEY: Peptide
        (B) LOCATION: 8
        (D) OTHER INFORMATION: /product= "Nle"
```

```
    (ix) FEATURE:
         (A) NAME/KEY: Peptide
         (B) LOCATION: 18..22
         (D) OTHER INFORMATION: /product= "OTHER"
             /note= "The side chains of Lys at position 18 and Asp at
             position 22 are linked by an amide bond."

(ix) FEATURE:
         (A) NAME/KEY: Peptide
         (B) LOCATION: 31
         (D) OTHER INFORMATION: /product= "OTHER"
             /note= "This C-terminal amino acid is an amide, i.e.,
             CONH2."

(xi) SEQUENCE DESCRIPTION: SEQ ID NO:12:

Ala Val Ser Glu Ile Gln Leu Xaa His Ala Leu Gly Lys His Leu Asn
1               5                  10                  15

Ser Lys Glu Arg Val Asp Trp Leu Arg Lys Leu Leu Gln Asp Val
            20                  25                  30

(2) INFORMATION FOR SEQ ID NO:13:

(i) SEQUENCE CHARACTERISTICS:
        (A) LENGTH: 31 amino acids
        (B) TYPE: amino acid
        (C) STRANDEDNESS:
        (D) TOPOLOGY: Not Relevant (ii) MOLECULE TYPE: peptide (v) FRAGMENT TYPE: N-terminal (ix) FEATURE:
         (A) NAME/KEY: Peptide
         (B) LOCATION: 8
         (D) OTHER INFORMATION: /product= "Nle"

(ix) FEATURE:
         (A) NAME/KEY: Peptide
         (B) LOCATION: 18..22
         (D) OTHER INFORMATION: /product= "OTHER"
             /note= "The side chains of Lys at position 18 and Asp at
             position 22 are linked by an amide bond."

(ix) FEATURE:
         (A) NAME/KEY: Peptide
         (B) LOCATION: 31
         (D) OTHER INFORMATION: /product= "OTHER"
             /note= "This C-terminal amino acid is an amide,i.e.,
             CONH2."

(xi) SEQUENCE DESCRIPTION: SEQ ID NO:13:

Ala Val Ser Glu Ile Gln Leu Xaa His Asn Ala Gly Lys His Leu Asn
1               5                  10                  15

Ser Lys Glu Arg Val Asp Trp Leu Arg Lys Leu Leu Gln Asp Val
            20                  25                  30

(2) INFORMATION FOR SEQ ID NO:14:

(i) SEQUENCE CHARACTERISTICS:
        (A) LENGTH: 31 amino acids
        (B) TYPE: amino acid
        (C) STRANDEDNESS:
        (D) TOPOLOGY: Not Relevant (ii) MOLECULE TYPE: peptide (v) FRAGMENT TYPE: N-terminal (ix) FEATURE:
         (A) NAME/KEY: Peptide
         (B) LOCATION: 8
         (D) OTHER INFORMATION: /product= "Nle"
```

```
    (ix) FEATURE:
         (A) NAME/KEY: Peptide
         (B) LOCATION: 18..22
         (D) OTHER INFORMATION: /product= "OTHER"
             /note= "The side chains of Lys at position 18 and Asp at
             position 22 are linked by an amide bond. "

(ix) FEATURE:
         (A) NAME/KEY: Peptide
         (B) LOCATION: 31
         (D) OTHER INFORMATION: /product= "OTHER"
             /note= "This C-terminal amino acid is an amide, i.e.,
             CONH2."

(xi) SEQUENCE DESCRIPTION: SEQ ID NO:14:

Ala Val Ser Glu Ile Gln Leu Xaa His Asn Leu Ala Lys His Leu Asn
1               5                  10                  15

Ser Lys Glu Arg Val Asp Trp Leu Arg Lys Leu Leu Gln Asp Val
            20                  25                  30

(2) INFORMATION FOR SEQ ID NO:15:

(i) SEQUENCE CHARACTERISTICS:
         (A) LENGTH: 31 amino acids
         (B) TYPE: amino acid
         (C) STRANDEDNESS:
         (D) TOPOLOGY: Not Relevant (ii) MOLECULE TYPE: peptide (v) FRAGMENT TYPE: N-terminal (ix) FEATURE:
         (A) NAME/KEY: Peptide
         (B) LOCATION: 8
         (D) OTHER INFORMATION: /product= "Nle"

(ix) FEATURE:
         (A) NAME/KEY: Peptide
         (B) LOCATION: 18..22
         (D) OTHER INFORMATION: /product= "OTHER"
             /note= "The side chains of Lys at position 18 and Asp at
             position 22 are linked by an amide bond. "

(ix) FEATURE:
         (A) NAME/KEY: Peptide
         (B) LOCATION: 31
         (D) OTHER INFORMATION: /product= "OTHER"
             /note= "This C-terminal amino acid is an amide, i.e.,
             CONH2."

(xi) SEQUENCE DESCRIPTION: SEQ ID NO:15:

Ala Val Ser Glu Ile Gln Leu Xaa His Asn Leu Gly Ala His Leu Asn
1               5                  10                  15

Ser Lys Glu Arg Val Asp Trp Leu Arg Lys Leu Leu Gln Asp Val
            20                  25                  30

(2) INFORMATION FOR SEQ ID NO:16:

(i) SEQUENCE CHARACTERISTICS:
         (A) LENGTH: 31 amino acids
         (B) TYPE: amino acid
         (C) STRANDEDNESS:
         (D) TOPOLOGY: Not Relevant (ii) MOLECULE TYPE: peptide (v) FRAGMENT TYPE: N-terminal (ix) FEATURE:
         (A) NAME/KEY: Peptide
         (B) LOCATION: 8
```

(D) OTHER INFORMATION: /product= "Nle"

(ix) FEATURE:
        (A) NAME/KEY: Peptide
        (B) LOCATION: 18..22
        (D) OTHER INFORMATION: /product= "OTHER"
            /note= "The side chains of Lys at position 18 and Asp at
            position 22 are linked by an amide bond. "

(ix) FEATURE:
        (A) NAME/KEY: Peptide
        (B) LOCATION: 31
        (D) OTHER INFORMATION: /product= "OTHER"
            /note= "This C-terminal amino acid is an amide,i.e.,
            CONH2."

(xi) SEQUENCE DESCRIPTION: SEQ ID NO:16:

Ala Val Ser Glu Ile Gln Leu Xaa His Asn Leu Gly Lys Ala Leu Asn
1               5                   10                  15

Ser Lys Glu Arg Val Asp Trp Leu Arg Lys Leu Leu Gln Asp Val
            20                  25                  30

(2) INFORMATION FOR SEQ ID NO:17:

(i) SEQUENCE CHARACTERISTICS:
        (A) LENGTH: 31 amino acids
        (B) TYPE: amino acid
        (C) STRANDEDNESS:
        (D) TOPOLOGY: Not Relevant (ix) FEATURE:
        (A) NAME/KEY: Peptide
        (B) LOCATION: 18..22
        (D) OTHER INFORMATION: /product= "OTHER"
            /note= "The side chains of Lys at position 18 and Asp at
            position 22 are linked by an amide bond."

(ix) FEATURE:
        (A) NAME/KEY: Peptide
        (B) LOCATION: 31
        (D) OTHER INFORMATION: /product= "OTHER"
            /note= "This C-terminal amino acid is an amide, i.e.,
            CONH2."

(ix) FEATURE:
        (A) NAME/KEY: Peptide
        (B) LOCATION: 8
        (D) OTHER INFORMATION: /product= "Nle"

(xi) SEQUENCE DESCRIPTION: SEQ ID NO:17:

Ala Val Ser Glu Ile Gln Leu Xaa His Asn Leu Gly Lys His Ala Asn
1               5                   10                  15

Ser Lys Glu Arg Val Asp Trp Leu Arg Lys Leu Leu Gln Asp Val
            20                  25                  30

(2) INFORMATION FOR SEQ ID NO:18:

(i) SEQUENCE CHARACTERISTICS:
        (A) LENGTH: 31 amino acids
        (B) TYPE: amino acid
        (C) STRANDEDNESS:
        (D) TOPOLOGY: Not Relevant (ix) FEATURE:
        (A) NAME/KEY: Peptide
        (B) LOCATION: 18..22
        (D) OTHER INFORMATION: /product= "OTHER"
            /note= "The side chains of Lys at position 18 and Asp at
            position 22 are linked by an amide bond. "

(ix) FEATURE:
        (A) NAME/KEY: Peptide
        (B) LOCATION: 8

(D) OTHER INFORMATION: /product= "Nle"

(ix) FEATURE:
            (A) NAME/KEY: Peptide
            (B) LOCATION: 31
            (D) OTHER INFORMATION: /product= "OTHER"
                /note= "This C-terminal amino acid is an amide, i.e.,
                CONH2."

(xi) SEQUENCE DESCRIPTION: SEQ ID NO:18:

Ala Val Ser Glu Ile Gln Leu Xaa His Asn Leu Gly Lys His Leu Ala
1               5                   10                  15

Ser Lys Glu Arg Val Asp Trp Leu Arg Lys Leu Leu Gln Asp Val
            20                  25                  30

(2) INFORMATION FOR SEQ ID NO:19:

(i) SEQUENCE CHARACTERISTICS:
        (A) LENGTH: 31 amino acids
        (B) TYPE: amino acid
        (C) STRANDEDNESS:
        (D) TOPOLOGY: Not Relevant (ii) MOLECULE TYPE: peptide (v) FRAGMENT TYPE: N-terminal (ix) FEATURE:
        (A) NAME/KEY: Peptide
        (B) LOCATION: 8
        (D) OTHER INFORMATION: /product= "Nle"

(ix) FEATURE:
        (A) NAME/KEY: Peptide
        (B) LOCATION: 18..22
        (D) OTHER INFORMATION: /product= "OTHER"
            /note= "The side chains of Lys at position 18 and Asp at
            position 22 are linked by an amide bond."

(ix) FEATURE:
        (A) NAME/KEY: Peptide
        (B) LOCATION: 31
        (D) OTHER INFORMATION: /product= "OTHER"
            /note= "This C-terminal amino acid is an amide, i.e.,
            CONH2."

(xi) SEQUENCE DESCRIPTION: SEQ ID NO:19:

Ala Val Ser Glu Ile Gln Leu Xaa His Asn Leu Gly Lys His Leu Asn
1               5                   10                  15

Ala Lys Glu Arg Val Asp Trp Leu Arg Lys Leu Leu Gln Asp Val
            20                  25                  30

(2) INFORMATION FOR SEQ ID NO:20:

(i) SEQUENCE CHARACTERISTICS:
        (A) LENGTH: 31 amino acids
        (B) TYPE: amino acid
        (C) STRANDEDNESS:
        (D) TOPOLOGY: Not Relevant (ii) MOLECULE TYPE: peptide (v) FRAGMENT TYPE: N-terminal (ix) FEATURE:
        (A) NAME/KEY: Peptide
        (B) LOCATION: 8
        (D) OTHER INFORMATION: /product= "Nle"

(ix) FEATURE:
        (A) NAME/KEY: Peptide
        (B) LOCATION: 18..22
        (D) OTHER INFORMATION: /product= "OTHER"

/note= "The side chains of Lys at position 18 and Asp at
            position 22 are linked by an amide bond. "

(ix) FEATURE:
        (A) NAME/KEY: Peptide
        (B) LOCATION: 31
        (D) OTHER INFORMATION: /product= "OTHER"
            /note= "This C-terminal amino acid is an amide, i.e.,
            CONH2."

(xi) SEQUENCE DESCRIPTION: SEQ ID NO:20:

Gly Val Ser Glu Ile Gln Leu Xaa His Asn Leu Gly Lys His Leu Asn
1               5                   10                  15

Ser Lys Glu Arg Val Asp Trp Leu Arg Lys Leu Leu Gln Asp Val
            20                  25                  30

(2) INFORMATION FOR SEQ ID NO:21:

(i) SEQUENCE CHARACTERISTICS:
        (A) LENGTH: 31 amino acids
        (B) TYPE: amino acid
        (C) STRANDEDNESS:
        (D) TOPOLOGY: Not Relevant (ii) MOLECULE TYPE: peptide (v) FRAGMENT TYPE: N-terminal (ix) FEATURE:
        (A) NAME/KEY: Peptide
        (B) LOCATION: 8
        (D) OTHER INFORMATION: /product= "Nle"

(ix) FEATURE:
        (A) NAME/KEY: Peptide
        (B) LOCATION: 18..22
        (D) OTHER INFORMATION: /product= "OTHER"
            /note= "The side chains of Lys at position 18 and Asp at
            position 22 are linked by an amide bond. "

(ix) FEATURE:
        (A) NAME/KEY: Peptide
        (B) LOCATION: 31
        (D) OTHER INFORMATION: /product= "OTHER"
            /note= "This C-terminal amino acid is an amide, i.e.,
            CONH2."

(xi) SEQUENCE DESCRIPTION: SEQ ID NO:21:

Ala Gly Ser Glu Ile Gln Leu Xaa His Asn Leu Gly Lys His Leu Asn
1               5                   10                  15

Ser Lys Glu Arg Val Asp Trp Leu Arg Lys Leu Leu Gln Asp Val
            20                  25                  30

(2) INFORMATION FOR SEQ ID NO:22:

(i) SEQUENCE CHARACTERISTICS:
        (A) LENGTH: 31 amino acids
        (B) TYPE: amino acid
        (C) STRANDEDNESS:
        (D) TOPOLOGY: Not Relevant (ii) MOLECULE TYPE: peptide (v) FRAGMENT TYPE: N-terminal (ix) FEATURE:
        (A) NAME/KEY: Peptide
        (B) LOCATION: 8
        (D) OTHER INFORMATION: /product= "Nle"

(ix) FEATURE:
        (A) NAME/KEY: Peptide
        (B) LOCATION: 18..22

(D) OTHER INFORMATION: /product= "OTHER"
            /note= "The side chains of Lys at position 18 and Asp at
            position 22 are linked by an amide bond. "

(ix) FEATURE:
        (A) NAME/KEY: Peptide
        (B) LOCATION: 31
        (D) OTHER INFORMATION: /product= "OTHER"
            /note= "This C-terminal amino acid is an amide, i.e.,
            CONH2."

(xi) SEQUENCE DESCRIPTION: SEQ ID NO:22:

Ala Val Gly Glu Ile Gln Leu Xaa His Asn Leu Gly Lys His Leu Asn
1               5                   10                  15

Ser Lys Glu Arg Val Asp Trp Leu Arg Lys Leu Leu Gln Asp Val
            20                  25                  30

(2) INFORMATION FOR SEQ ID NO:23:

(i) SEQUENCE CHARACTERISTICS:
        (A) LENGTH: 31 amino acids
        (B) TYPE: amino acid
        (C) STRANDEDNESS:
        (D) TOPOLOGY: Not Relevant (ii) MOLECULE TYPE: peptide (v) FRAGMENT TYPE: N-terminal (ix) FEATURE:
        (A) NAME/KEY: Peptide
        (B) LOCATION: 8
        (D) OTHER INFORMATION: /product= "Nle"

(ix) FEATURE:
        (A) NAME/KEY: Peptide
        (B) LOCATION: 18..22
        (D) OTHER INFORMATION: /product= "OTHER"
            /note= "The side chains of Lys at position 18 and Asp at
            position 22 are linked by an amide bond. "

(ix) FEATURE:
        (A) NAME/KEY: Peptide
        (B) LOCATION: 31
        (D) OTHER INFORMATION: /product= "OTHER"
            /note= "This C-terminal amino acid is an amide, i.e.,
            CONH2."

(xi) SEQUENCE DESCRIPTION: SEQ ID NO:23:

Ala Val Ser Gly Ile Gln Leu Xaa His Asn Leu Gly Lys His Leu Asn
1               5                   10                  15

Ser Lys Glu Arg Val Asp Trp Leu Arg Lys Leu Leu Gln Asp Val
            20                  25                  30

(2) INFORMATION FOR SEQ ID NO:24:

(i) SEQUENCE CHARACTERISTICS:
        (A) LENGTH: 31 amino acids
        (B) TYPE: amino acid
        (C) STRANDEDNESS:
        (D) TOPOLOGY: Not Relevant (ii) MOLECULE TYPE: peptide (v) FRAGMENT TYPE: N-terminal (ix) FEATURE:
        (A) NAME/KEY: Peptide
        (B) LOCATION: 8
        (D) OTHER INFORMATION: /product= "Nle"

(ix) FEATURE:
        (A) NAME/KEY: Peptide

```
            (B) LOCATION: 18..22
            (D) OTHER INFORMATION: /product= "OTHER"
                /note= "The side chains of Lys at position 18 and Asp at
                position 22 are linked by an amide bond."

(ix) FEATURE:
            (A) NAME/KEY: Peptide
            (B) LOCATION: 31
            (D) OTHER INFORMATION: /product= "OTHER"
                /note= "This C-terminal amino acid is an amide,i.e.,
                CONH2."

(xi) SEQUENCE DESCRIPTION: SEQ ID NO:24:

Ala Val Ser Glu Gly Gln Leu Xaa His Asn Leu Gly Lys His Leu Asn
1               5                  10                  15

Ser Lys Glu Arg Val Asp Trp Leu Arg Lys Leu Leu Gln Asp Val
            20                  25                  30

(2) INFORMATION FOR SEQ ID NO:25:

(i) SEQUENCE CHARACTERISTICS:
        (A) LENGTH: 31 amino acids
        (B) TYPE: amino acid
        (C) STRANDEDNESS:
        (D) TOPOLOGY: Not Relevant (ii) MOLECULE TYPE: peptide (v) FRAGMENT TYPE: N-terminal (ix) FEATURE:
        (A) NAME/KEY: Peptide
        (B) LOCATION: 8
        (D) OTHER INFORMATION: /product= "Nle"

(ix) FEATURE:
        (A) NAME/KEY: Peptide
        (B) LOCATION: 18..22
        (D) OTHER INFORMATION: /product= "OTHER"
            /note= "The side chains of Lys at position 18 and Asp at
            position 22 are linked by an amide bond."

(ix) FEATURE:
        (A) NAME/KEY: Peptide
        (B) LOCATION: 31
        (D) OTHER INFORMATION: /product= "OTHER"
            /note= "This C-terminal amino acid is an amide, i.e.,
            CONH2."

(xi) SEQUENCE DESCRIPTION: SEQ ID NO:25:

Ala Val Ser Glu Ile Gly Leu Xaa His Asn Leu Gly Lys His Leu Asn
1               5                  10                  15

Ser Lys Glu Arg Val Asp Trp Leu Arg Lys Leu Leu Gln Asp Val
            20                  25                  30

(2) INFORMATION FOR SEQ ID NO:26:

(i) SEQUENCE CHARACTERISTICS:
        (A) LENGTH: 31 amino acids
        (B) TYPE: amino acid
        (C) STRANDEDNESS:
        (D) TOPOLOGY: Not Relevant (ii) MOLECULE TYPE: peptide (v) FRAGMENT TYPE: N-terminal (ix) FEATURE:
        (A) NAME/KEY: Peptide
        (B) LOCATION: 8
        (D) OTHER INFORMATION: /product= "Nle"

(ix) FEATURE:
```

```
            (A) NAME/KEY: Peptide
            (B) LOCATION: 18..22
            (D) OTHER INFORMATION: /product= "OTHER"
                /note= "The side chains of Lys at position 18 and Asp at
                position 22 are linked by an amide bond. "

(ix) FEATURE:
            (A) NAME/KEY: Peptide
            (B) LOCATION: 31
            (D) OTHER INFORMATION: /product= "OTHER"
                /note= "This C-terminal amino acid is an amide, i.e.,
                CONH2."

(xi) SEQUENCE DESCRIPTION: SEQ ID NO:26:

Ala Val Ser Glu Ile Gln Gly Xaa His Asn Leu Gly Lys His Leu Asn
1               5                  10                 15

Ser Lys Glu Arg Val Asp Trp Leu Arg Lys Leu Leu Gln Asp Val
            20                  25                 30

(2) INFORMATION FOR SEQ ID NO:27:

(i) SEQUENCE CHARACTERISTICS:
            (A) LENGTH: 31 amino acids
            (B) TYPE: amino acid
            (C) STRANDEDNESS:
            (D) TOPOLOGY: Not Relevant (ii) MOLECULE TYPE: peptide (v) FRAGMENT TYPE: N-terminal (ix) FEATURE:
            (A) NAME/KEY: Peptide
            (B) LOCATION: 18..22
            (D) OTHER INFORMATION: /product= "OTHER"
                /note= "The side chains of Lys at position 18 and Asp at
                position 22 are linked by an amide bond. "

(ix) FEATURE:
            (A) NAME/KEY: Peptide
            (B) LOCATION: 31
            (D) OTHER INFORMATION: /product= "OTHER"
                /note= "This C-terminal amino acid is an amide, i.e.,
                CONH2."

(xi) SEQUENCE DESCRIPTION: SEQ ID NO:27:

Ala Val Ser Glu Ile Gln Leu Gly His Asn Leu Gly Lys His Leu Asn
1               5                  10                 15

Ser Lys Glu Arg Val Asp Trp Leu Arg Lys Leu Leu Gln Asp Val
            20                  25                 30

(2) INFORMATION FOR SEQ ID NO:28:

(i) SEQUENCE CHARACTERISTICS:
            (A) LENGTH: 31 amino acids
            (B) TYPE: amino acid
            (C) STRANDEDNESS:
            (D) TOPOLOGY: Not Relevant (ii) MOLECULE TYPE: peptide (v) FRAGMENT TYPE: N-terminal (ix) FEATURE:
            (A) NAME/KEY: Peptide
            (B) LOCATION: 8
            (D) OTHER INFORMATION: /product= "Nle"

(ix) FEATURE:
            (A) NAME/KEY: Peptide
            (B) LOCATION: 18..22
            (D) OTHER INFORMATION: /product= "OTHER"
                /note= "The side chains of Lys at position 18 and Asp at
``` position 22 are linked by an amide bond. "

(ix) FEATURE:
        (A) NAME/KEY: Peptide
        (B) LOCATION: 31
        (D) OTHER INFORMATION: /product= "OTHER"
            /note= "This C-terminal amino acid is an amide, i.e.,
            CONH2."

(xi) SEQUENCE DESCRIPTION: SEQ ID NO:28:

Ala Val Ser Glu Ile Gln Leu Xaa Gly Asn Leu Gly Lys His Leu Asn
1               5                   10                  15

Ser Lys Glu Arg Val Asp Trp Leu Arg Lys Leu Leu Gln Asp Val
            20                  25                  30

(2) INFORMATION FOR SEQ ID NO:29:

(i) SEQUENCE CHARACTERISTICS:
        (A) LENGTH: 31 amino acids
        (B) TYPE: amino acid
        (C) STRANDEDNESS:
        (D) TOPOLOGY: Not Relevant (ii) MOLECULE TYPE: peptide (v) FRAGMENT TYPE: N-terminal (ix) FEATURE:
        (A) NAME/KEY: Peptide
        (B) LOCATION: 8
        (D) OTHER INFORMATION: /product= "Nle"

(ix) FEATURE:
        (A) NAME/KEY: Peptide
        (B) LOCATION: 18..22
        (D) OTHER INFORMATION: /product= "OTHER"
            /note= "The side chains of Lys at position 18 and Asp at
            position 22 are linked by an amide bond. "

(ix) FEATURE:
        (A) NAME/KEY: Peptide
        (B) LOCATION: 31
        (D) OTHER INFORMATION: /product= "OTHER"
            /note= "This C-terminal amino acid is an amide, i.e.,
            CONH2."

(xi) SEQUENCE DESCRIPTION: SEQ ID NO:29:

Ala Val Ser Glu Ile Gln Leu Xaa His Gly Leu Gly Lys His Leu Asn
1               5                   10                  15

Ser Lys Glu Arg Val Asp Trp Leu Arg Lys Leu Leu Gln Asp Val
            20                  25                  30

(2) INFORMATION FOR SEQ ID NO:30:

(i) SEQUENCE CHARACTERISTICS:
        (A) LENGTH: 31 amino acids
        (B) TYPE: amino acid
        (C) STRANDEDNESS:
        (D) TOPOLOGY: Not Relevant (ii) MOLECULE TYPE: peptide (v) FRAGMENT TYPE: N-terminal (ix) FEATURE:
        (A) NAME/KEY: Peptide
        (B) LOCATION: 8
        (D) OTHER INFORMATION: /product= "Nle"

(ix) FEATURE:
        (A) NAME/KEY: Peptide
        (B) LOCATION: 18..22
        (D) OTHER INFORMATION: /product= "OTHER"

```
            /note= "The side chains of Lys at position 18 and Asp at
            position 22 are linked by an amide bond."

(ix) FEATURE:
        (A) NAME/KEY: Peptide
        (B) LOCATION: 31
        (D) OTHER INFORMATION: /product= "OTHER"
            /note= "This C-terminal amino acid is an amide, i.e.,
            CONH2."

(xi) SEQUENCE DESCRIPTION: SEQ ID NO:30:

Ala Val Ser Glu Ile Gln Leu Xaa His Asn Gly Gly Lys His Leu Asn
1               5                   10                  15

Ser Lys Glu Arg Val Asp Trp Leu Arg Lys Leu Leu Gln Asp Val
            20                  25                  30

(2) INFORMATION FOR SEQ ID NO:31:

(i) SEQUENCE CHARACTERISTICS:
        (A) LENGTH: 31 amino acids
        (B) TYPE: amino acid
        (C) STRANDEDNESS:
        (D) TOPOLOGY: Not Relevant (ii) MOLECULE TYPE: peptide (v) FRAGMENT TYPE: N-terminal (ix) FEATURE:
        (A) NAME/KEY: Peptide
        (B) LOCATION: 8
        (D) OTHER INFORMATION: /product= "Nle"

(ix) FEATURE:
        (A) NAME/KEY: Peptide
        (B) LOCATION: 18..22
        (D) OTHER INFORMATION: /product= "OTHER"
            /note= "The side chains of Lys at position 18 and Asp at
            position 22 are linked by an amide bond."

(ix) FEATURE:
        (A) NAME/KEY: Peptide
        (B) LOCATION: 31
        (D) OTHER INFORMATION: /product= "OTHER"
            /note= "This C-terminal amino acid is an amide, i.e.,
            CONH2."

(xi) SEQUENCE DESCRIPTION: SEQ ID NO:31:

Ala Val Ser Glu Ile Gln Leu Xaa His Asn Leu Gly Gly His Leu Asn
1               5                   10                  15

Ser Lys Glu Arg Val Asp Trp Leu Arg Lys Leu Leu Gln Asp Val
            20                  25                  30

(2) INFORMATION FOR SEQ ID NO:32:

(i) SEQUENCE CHARACTERISTICS:
        (A) LENGTH: 31 amino acids
        (B) TYPE: amino acid
        (C) STRANDEDNESS:
        (D) TOPOLOGY: Not Relevant (ii) MOLECULE TYPE: peptide (v) FRAGMENT TYPE: N-terminal (ix) FEATURE:
        (A) NAME/KEY: Peptide
        (B) LOCATION: 8
        (D) OTHER INFORMATION: /product= "Nle"

(ix) FEATURE:
        (A) NAME/KEY: Peptide
        (B) LOCATION: 18..22
```

```
            (D) OTHER INFORMATION: /product= "OTHER"
                /note= "The side chains of Lys at position 18 and Asp at
                position 22 are linked by an amide bond."

(ix) FEATURE:
            (A) NAME/KEY: Peptide
            (B) LOCATION: 31
            (D) OTHER INFORMATION: /product= "OTHER"
                /note= "This C-terminal amino acid is an amide, i.e.,
                CONH2."

(xi) SEQUENCE DESCRIPTION: SEQ ID NO:32:

Ala Val Ser Glu Ile Gln Leu Xaa His Asn Leu Gly Lys Gly Leu Asn
1               5                   10                  15

Ser Lys Glu Arg Val Asp Trp Leu Arg Lys Leu Leu Gln Asp Val
            20                  25                  30

(2) INFORMATION FOR SEQ ID NO:33:

(i) SEQUENCE CHARACTERISTICS:
        (A) LENGTH: 31 amino acids
        (B) TYPE: amino acid
        (C) STRANDEDNESS:
        (D) TOPOLOGY: Not Relevant (ii) MOLECULE TYPE: peptide (v) FRAGMENT TYPE: N-terminal (ix) FEATURE:
        (A) NAME/KEY: Peptide
        (B) LOCATION: 8
        (D) OTHER INFORMATION: /product= "Nle"

(ix) FEATURE:
        (A) NAME/KEY: Peptide
        (B) LOCATION: 18..22
        (D) OTHER INFORMATION: /product= "OTHER"
            /note= "The side chains of Lys at position 18 and Asp at
            position 22 are linked by an amide bond."

(ix) FEATURE:
        (A) NAME/KEY: Peptide
        (B) LOCATION: 31
        (D) OTHER INFORMATION: /product= "OTHER"
            /note= "This C-terminal amino acid is an amide, i.e.,
            CONH2."

(xi) SEQUENCE DESCRIPTION: SEQ ID NO:33:

Ala Val Ser Glu Ile Gln Leu Xaa His Asn Leu Gly Lys His Gly Asn
1               5                   10                  15

Ser Lys Glu Arg Val Asp Trp Leu Arg Lys Leu Leu Gln Asp Val
            20                  25                  30

(2) INFORMATION FOR SEQ ID NO:34:

(i) SEQUENCE CHARACTERISTICS:
        (A) LENGTH: 31 amino acids
        (B) TYPE: amino acid
        (C) STRANDEDNESS:
        (D) TOPOLOGY: Not Relevant (ii) MOLECULE TYPE: peptide (v) FRAGMENT TYPE: N-terminal (ix) FEATURE:
        (A) NAME/KEY: Peptide
        (B) LOCATION: 8
        (D) OTHER INFORMATION: /product= "Nle"

(ix) FEATURE:
        (A) NAME/KEY: Peptide
```

```
        (B) LOCATION: 18..22
        (D) OTHER INFORMATION: /product= "OTHER"
            /note= "The side chains of Lys at position 18 and Asp at
            position 22 are linked by an amide bond."

(ix) FEATURE:
        (A) NAME/KEY: Peptide
        (B) LOCATION: 31
        (D) OTHER INFORMATION: /product= "OTHER"
            /note= "This C-terminal amino acid is an amide, i.e.,
            CONH2."

(xi) SEQUENCE DESCRIPTION: SEQ ID NO:34:

Ala Val Ser Glu Ile Gln Leu Xaa His Asn Leu Gly Lys His Leu Gly
1               5                  10                  15

Ser Lys Glu Arg Val Asp Trp Leu Arg Lys Leu Leu Gln Asp Val
            20                  25                  30

(2) INFORMATION FOR SEQ ID NO:35:

(i) SEQUENCE CHARACTERISTICS:
        (A) LENGTH: 31 amino acids
        (B) TYPE: amino acid
        (C) STRANDEDNESS:
        (D) TOPOLOGY: Not Relevant (ii) MOLECULE TYPE: peptide (v) FRAGMENT TYPE: N-terminal (ix) FEATURE:
        (A) NAME/KEY: Peptide
        (B) LOCATION: 8
        (D) OTHER INFORMATION: /product= "Nle"

(ix) FEATURE:
        (A) NAME/KEY: Peptide
        (B) LOCATION: 18..22
        (D) OTHER INFORMATION: /product= "OTHER"
            /note= "The side chains of Lys at position 18 and Asp at
            position 22 are linked by an amide bond."

(ix) FEATURE:
        (A) NAME/KEY: Peptide
        (B) LOCATION: 31
        (D) OTHER INFORMATION: /product= "OTHER"
            /note= "This C-terminal amino acid is an amide, i.e.,
            CONH2."

(xi) SEQUENCE DESCRIPTION: SEQ ID NO:35:

Ala Val Ser Glu Ile Gln Leu Xaa His Asn Leu Gly Lys His Leu Asn
1               5                  10                  15

Gly Lys Glu Arg Val Asp Trp Leu Arg Lys Leu Leu Gln Asp Val
            20                  25                  30

(2) INFORMATION FOR SEQ ID NO:36:

(i) SEQUENCE CHARACTERISTICS:
        (A) LENGTH: 31 amino acids
        (B) TYPE: amino acid
        (C) STRANDEDNESS:
        (D) TOPOLOGY: Not Relevant (ii) MOLECULE TYPE: peptide (v) FRAGMENT TYPE: N-terminal (ix) FEATURE:
        (A) NAME/KEY: Peptide
        (B) LOCATION: 1
        (D) OTHER INFORMATION: /product= "OTHER"
            /note= "Xaa in position 1 is D-Proline."
```

```
(ix) FEATURE:
    (A) NAME/KEY: Peptide
    (B) LOCATION: 8
    (D) OTHER INFORMATION: /product= "Nle"

(ix) FEATURE:
    (A) NAME/KEY: Peptide
    (B) LOCATION: 18..22
    (D) OTHER INFORMATION: /product= "OTHER"
        /note= "The side chains of Lys at position 18 and Asp at
        position 22 are linked by an amide bond."

(ix) FEATURE:
    (A) NAME/KEY: Peptide
    (B) LOCATION: 31
    (D) OTHER INFORMATION: /product= "OTHER"
        /note= "This C-terminal amino acid is an amide, i.e.,
        CONH2."

(xi) SEQUENCE DESCRIPTION: SEQ ID NO:36:

Xaa Val Ser Glu Ile Gln Leu Xaa His Asn Leu Gly Lys His Leu Asn
1               5                   10                  15

Ser Lys Glu Arg Val Asp Trp Leu Arg Lys Leu Leu Gln Asp Val
            20                  25                  30

(2) INFORMATION FOR SEQ ID NO:37:

(i) SEQUENCE CHARACTERISTICS:
        (A) LENGTH: 31 amino acids
        (B) TYPE: amino acid
        (C) STRANDEDNESS:
        (D) TOPOLOGY: Not Relevant (ii) MOLECULE TYPE: peptide (v) FRAGMENT TYPE: N-terminal (ix) FEATURE:
        (A) NAME/KEY: Peptide
        (B) LOCATION: 3
        (D) OTHER INFORMATION: /product= "OTHER"
            /note= "The Xaa in position 3 is D-Proline."

(ix) FEATURE:
        (A) NAME/KEY: Peptide
        (B) LOCATION: 8
        (D) OTHER INFORMATION: /product= "Nle"

(ix) FEATURE:
        (A) NAME/KEY: Peptide
        (B) LOCATION: 18..22
        (D) OTHER INFORMATION: /product= "OTHER"
            /note= "The side chains of Lys at position 18 and Asp at
            position 22 are linked by an amide bond."

(ix) FEATURE:
        (A) NAME/KEY: Peptide
        (B) LOCATION: 31
        (D) OTHER INFORMATION: /product= "OTHER"
            /note= "This C-terminal amino acid is an amide, i.e.,
            CONH2."

(xi) SEQUENCE DESCRIPTION: SEQ ID NO:37:

Ala Val Xaa Glu Ile Gln Leu Xaa His Asn Leu Gly Lys His Leu Asn
1               5                   10                  15

Ser Lys Glu Arg Val Asp Trp Leu Arg Lys Leu Leu Gln Asp Val
            20                  25                  30

(2) INFORMATION FOR SEQ ID NO:38:

(i) SEQUENCE CHARACTERISTICS:
        (A) LENGTH: 31 amino acids
        (B) TYPE: amino acid
```

(C) STRANDEDNESS:
        (D) TOPOLOGY: Not Relevant (ii) MOLECULE TYPE: peptide (v) FRAGMENT TYPE: N-terminal (ix) FEATURE:
        (A) NAME/KEY: Peptide
        (B) LOCATION: 6
        (D) OTHER INFORMATION: /product= "OTHER"
            /note= "The Xaa in position 6 is D-Proline."

(ix) FEATURE:
        (A) NAME/KEY: Peptide
        (B) LOCATION: 8
        (D) OTHER INFORMATION: /product= "Nle"

(ix) FEATURE:
        (A) NAME/KEY: Peptide
        (B) LOCATION: 18..22
        (D) OTHER INFORMATION: /product= "OTHER"
            /note= "The side chains of Lys at position 18 and Asp at
            position 22 are linked by an amide bond. "

(ix) FEATURE:
        (A) NAME/KEY: Peptide
        (B) LOCATION: 31
        (D) OTHER INFORMATION: /product= "OTHER"
            /note= "This C-terminal amino acid is an amide,i.e.,
            CONH2."

(xi) SEQUENCE DESCRIPTION: SEQ ID NO:38:

Ala Val Ser Glu Ile Xaa Leu Xaa His Asn Leu Gly Lys His Leu Asn
1               5                  10                  15

Ser Lys Glu Arg Val Asp Trp Leu Arg Lys Leu Leu Gln Asp Val
            20                  25                  30

(2) INFORMATION FOR SEQ ID NO:39:

(i) SEQUENCE CHARACTERISTICS:
        (A) LENGTH: 31 amino acids
        (B) TYPE: amino acid
        (C) STRANDEDNESS:
        (D) TOPOLOGY: Not Relevant (ii) MOLECULE TYPE: peptide (v) FRAGMENT TYPE: N-terminal (ix) FEATURE:
        (A) NAME/KEY: Peptide
        (B) LOCATION: 7
        (D) OTHER INFORMATION: /product= "OTHER"
            /note= "The Xaa in position 7 is D-Proline."

(ix) FEATURE:
        (A) NAME/KEY: Peptide
        (B) LOCATION: 8
        (D) OTHER INFORMATION: /product= "Nle"

(ix) FEATURE:
        (A) NAME/KEY: Peptide
        (B) LOCATION: 18..22
        (D) OTHER INFORMATION: /product= "OTHER"
            /note= "The side chains of Lys at position 18 and Asp at
            position 22 are linked by an amide bond. "

(ix) FEATURE:
        (A) NAME/KEY: Peptide
        (B) LOCATION: 31
        (D) OTHER INFORMATION: /product= "OTHER"
            /note= "This C-terminal amino acid is an amide, i.e.,
            CONH2."

(xi) SEQUENCE DESCRIPTION: SEQ ID NO:39:

Ala Val Ser Glu Ile Gln Xaa Xaa His Asn Leu Gly Lys His Leu Asn
1               5                   10                  15

Ser Lys Glu Arg Val Asp Trp Leu Arg Lys Leu Leu Gln Asp Val
            20                  25                  30

(2) INFORMATION FOR SEQ ID NO:40:

(i) SEQUENCE CHARACTERISTICS:
        (A) LENGTH: 31 amino acids
        (B) TYPE: amino acid
        (C) STRANDEDNESS:
        (D) TOPOLOGY: Not Relevant (ii) MOLECULE TYPE: peptide (v) FRAGMENT TYPE: N-terminal (ix) FEATURE:
        (A) NAME/KEY: Peptide
        (B) LOCATION: 8
        (D) OTHER INFORMATION: /product= "Nle"

(ix) FEATURE:
        (A) NAME/KEY: Peptide
        (B) LOCATION: 9
        (D) OTHER INFORMATION: /product= "OTHER"
            /note= "The Xaa in position 9 is D-Proline."

(ix) FEATURE:
        (A) NAME/KEY: Peptide
        (B) LOCATION: 18..22
        (D) OTHER INFORMATION: /product= "OTHER"
            /note= "The side chains of Lys at position 18 and Asp at
            position 22 are linked by an amide bond. "

(ix) FEATURE:
        (A) NAME/KEY: Peptide
        (B) LOCATION: 31
        (D) OTHER INFORMATION: /product= "OTHER"
            /note= "This C-terminal amino acid is an amide, i.e.,
            CONH2."

(xi) SEQUENCE DESCRIPTION: SEQ ID NO:40:

Ala Val Ser Glu Ile Gln Leu Xaa Xaa Asn Leu Gly Lys His Leu Asn
1               5                   10                  15

Ser Lys Glu Arg Val Asp Trp Leu Arg Lys Leu Leu Gln Asp Val
            20                  25                  30

(2) INFORMATION FOR SEQ ID NO:41:

(i) SEQUENCE CHARACTERISTICS:
        (A) LENGTH: 31 amino acids
        (B) TYPE: amino acid
        (C) STRANDEDNESS:
        (D) TOPOLOGY: Not Relevant (ii) MOLECULE TYPE: peptide (v) FRAGMENT TYPE: N-terminal (ix) FEATURE:
        (A) NAME/KEY: Peptide
        (B) LOCATION: 8
        (D) OTHER INFORMATION: /product= "Nle"

(ix) FEATURE:
        (A) NAME/KEY: Peptide
        (B) LOCATION: 10
        (D) OTHER INFORMATION: /product= "OTHER"
            /note= "The Xaa in position 10 is D-Proline."

(ix) FEATURE:
        (A) NAME/KEY: Peptide (B) LOCATION: 18..22
            (D) OTHER INFORMATION: /product= "OTHER"
                /note= "The side chains of Lys at position 18 and Asp at
                position 22 are linked by an amide bond. "

(ix) FEATURE:
            (A) NAME/KEY: Peptide
            (B) LOCATION: 31
            (D) OTHER INFORMATION: /product= "OTHER"
                /note= "This C-terminal amino acid is an amide, i.e.,
                CONH2."

(xi) SEQUENCE DESCRIPTION: SEQ ID NO:41:

Ala Val Ser Glu Ile Gln Leu Xaa His Xaa Leu Gly Lys His Leu Asn
1               5                  10                  15

Ser Lys Glu Arg Val Asp Trp Leu Arg Lys Leu Leu Gln Asp Val
            20                  25                  30

(2) INFORMATION FOR SEQ ID NO:42:

(i) SEQUENCE CHARACTERISTICS:
            (A) LENGTH: 31 amino acids
            (B) TYPE: amino acid
            (C) STRANDEDNESS:
            (D) TOPOLOGY: Not Relevant (ii) MOLECULE TYPE: peptide (v) FRAGMENT TYPE: N-terminal (ix) FEATURE:
            (A) NAME/KEY: Peptide
            (B) LOCATION: -10
            (D) OTHER INFORMATION: /product= "Nle"

(ix) FEATURE:
            (A) NAME/KEY: Peptide
            (B) LOCATION: -4
            (D) OTHER INFORMATION: /product= "OTHER"
                /note= "The Xaa in position 14 is D-Proline."

(ix) FEATURE:
            (A) NAME/KEY: Protein
            (B) LOCATION: 1..5
            (D) OTHER INFORMATION: /product= "OTHER"
                /note= "The side chains of Lys at position 18 and Asp at
                position 22 are linked by an amide bond, and this
                sequence has an amide C-terminus (i.e., CONH2), rather
                than a carboxy C-Terminus (i.e., COOH)."

(xi) SEQUENCE DESCRIPTION: SEQ ID NO:42:

Ala Val Ser Glu Ile Gln Leu Xaa His Asn Leu Gly Lys Xaa Leu Asn
        -15                 -10                 -5

Ser Lys Glu Arg Val Asp Trp Leu Arg Lys Leu Leu Gln Asp Val
1               5                   10

(2) INFORMATION FOR SEQ ID NO:43:

(i) SEQUENCE CHARACTERISTICS:
            (A) LENGTH: 31 amino acids
            (B) TYPE: amino acid
            (C) STRANDEDNESS:
            (D) TOPOLOGY: Not Relevant (ii) MOLECULE TYPE: peptide (v) FRAGMENT TYPE: N-terminal (ix) FEATURE:
            (A) NAME/KEY: Peptide
            (B) LOCATION: 8
            (D) OTHER INFORMATION: /product= "Nle"

```
        (ix) FEATURE:
             (A) NAME/KEY: Peptide
             (B) LOCATION: 15
             (D) OTHER INFORMATION: /product= "OTHER"
                   /note= "The Xaa in position 15 is D-Proline."

(ix) FEATURE:
             (A) NAME/KEY: Peptide
             (B) LOCATION: 18..22
             (D) OTHER INFORMATION: /product= "OTHER"
                   /note= "The side chains of Lys at position 18 and Asp at
                   position 22 are linked by an amide bond. "

(ix) FEATURE:
             (A) NAME/KEY: Peptide
             (B) LOCATION: 31
             (D) OTHER INFORMATION: /product= "OTHER"
                   /note= "This C-terminal amino acid is an amide, i.e.,
                   CONH2."

(xi) SEQUENCE DESCRIPTION: SEQ ID NO:43:

Ala Val Ser Glu Ile Gln Leu Xaa His Asn Leu Gly Lys His Xaa Asn
1               5                   10                  15

Ser Lys Glu Arg Val Asp Trp Leu Arg Lys Leu Leu Gln Asp Val
            20                  25                  30

(2) INFORMATION FOR SEQ ID NO:44:

(i) SEQUENCE CHARACTERISTICS:
        (A) LENGTH: 31 amino acids
        (B) TYPE: amino acid
        (C) STRANDEDNESS:
        (D) TOPOLOGY: Not Relevant (ii) MOLECULE TYPE: peptide (v) FRAGMENT TYPE: N-terminal (ix) FEATURE:
         (A) NAME/KEY: Peptide
         (B) LOCATION: 8
         (D) OTHER INFORMATION: /product= "Nle"

(ix) FEATURE:
         (A) NAME/KEY: Peptide
         (B) LOCATION: 16
         (D) OTHER INFORMATION: /product= "OTHER"
               /note= "The Xaa in position 16 is D-Proline."

(ix) FEATURE:
         (A) NAME/KEY: Peptide
         (B) LOCATION: 18..22
         (D) OTHER INFORMATION: /product= "OTHER"
               /note= "The side chains of Lys at position 18 and Asp at
               position 22 are linked by an amide bond. "

(ix) FEATURE:
         (A) NAME/KEY: Peptide
         (B) LOCATION: 31
         (D) OTHER INFORMATION: /product= "OTHER"
               /note= "This C-terminal amino acid is an amide, i.e.,
               CONH2."

(xi) SEQUENCE DESCRIPTION: SEQ ID NO:44:

Ala Val Ser Glu Ile Gln Leu Xaa His Asn Leu Gly Lys His Leu Xaa
1               5                   10                  15

Ser Lys Glu Arg Val Asp Trp Leu Arg Lys Leu Leu Gln Asp Val
            20                  25                  30

(2) INFORMATION FOR SEQ ID NO:45:

(i) SEQUENCE CHARACTERISTICS:
        (A) LENGTH: 31 amino acids
```

```
            (B) TYPE: amino acid
            (C) STRANDEDNESS:
            (D) TOPOLOGY: Not Relevant (ii) MOLECULE TYPE: peptide (v) FRAGMENT TYPE: N-terminal (ix) FEATURE:
            (A) NAME/KEY: Peptide
            (B) LOCATION: 8
            (D) OTHER INFORMATION: /product= "Nle"

(ix) FEATURE:
            (A) NAME/KEY: Peptide
            (B) LOCATION: 17
            (D) OTHER INFORMATION: /product= "OTHER"
                /note= "The Xaa in position 17 is D-Proline."

(ix) FEATURE:
            (A) NAME/KEY: Peptide
            (B) LOCATION: 18..22
            (D) OTHER INFORMATION: /product= "OTHER"
                /note= "The side chains of Lys at position 18 and Asp at
                position 22 are linked by an amide bond. "

(ix) FEATURE:
            (A) NAME/KEY: Peptide
            (B) LOCATION: 31
            (D) OTHER INFORMATION: /product= "OTHER"
                /note= "This C-terminal amino acid is an amide, i.e.,
                CONH2."

(xi) SEQUENCE DESCRIPTION: SEQ ID NO:45:

Ala Val Ser Glu Ile Gln Leu Xaa His Asn Leu Gly Lys His Leu Asn
1               5                  10                  15

Xaa Lys Glu Arg Val Asp Trp Leu Arg Lys Leu Leu Gln Asp Val
            20                  25                  30

(2) INFORMATION FOR SEQ ID NO:46:

(i) SEQUENCE CHARACTERISTICS:
            (A) LENGTH: 34 amino acids
            (B) TYPE: amino acid
            (C) STRANDEDNESS:
            (D) TOPOLOGY: Not Relevant (ii) MOLECULE TYPE: peptide (v) FRAGMENT TYPE: N-terminal (ix) FEATURE:
            (A) NAME/KEY: Peptide
            (B) LOCATION: 8
            (D) OTHER INFORMATION: /product= "Nle"

(ix) FEATURE:
            (A) NAME/KEY: Peptide
            (B) LOCATION: 18..22
            (D) OTHER INFORMATION: /product= "OTHER"
                /note= "The side chains of Lys at position 18 and Asp at
                position 22 are linked by an amide bond. "

(ix) FEATURE:
            (A) NAME/KEY: Peptide
            (B) LOCATION: 34
            (D) OTHER INFORMATION: /product= "OTHER"
                /note= "This C-terminal amino acid is an amide, i.e.,
                CONH2."

(xi) SEQUENCE DESCRIPTION: SEQ ID NO:46:

Ala Val Ser Glu Ile Gln Leu Xaa His Asn Leu Gly Lys His Leu Asn
1               5                  10                  15

Ser Lys Glu Arg Val Asp Trp Leu Arg Lys Leu Leu Gln Asp Val His
```

20                  25                  30
Asn Phe (2) INFORMATION FOR SEQ ID NO:47:

(i) SEQUENCE CHARACTERISTICS:
        (A) LENGTH: 31 amino acids
        (B) TYPE: amino acid
        (C) STRANDEDNESS:
        (D) TOPOLOGY: Not Relevant (ii) MOLECULE TYPE: peptide (v) FRAGMENT TYPE: N-terminal (ix) FEATURE:
        (A) NAME/KEY: Peptide
        (B) LOCATION: 8
        (D) OTHER INFORMATION: /product= "Nle"

(ix) FEATURE:
        (A) NAME/KEY: Peptide
        (B) LOCATION: 18..22
        (D) OTHER INFORMATION: /product= "OTHER"
            /note= "The side chains of Lys at position 18 and Asp at
            position 22 are linked by an amide bond. "

(ix) FEATURE:
        (A) NAME/KEY: Peptide
        (B) LOCATION: 31
        (D) OTHER INFORMATION: /product= "OTHER"
            /note= "This C-terminal amino acid is an amide, i.e.,
            CONH2."

(xi) SEQUENCE DESCRIPTION: SEQ ID NO:47:

Ala Val Ser Glu Ile Gln Leu Xaa His Asn Leu Gly Lys His Leu Asn
1               5                  10                  15

Ser Asp Glu Arg Val Lys Trp Leu Arg Lys Leu Leu Gln Asp Val
                20                  25                  30

(2) INFORMATION FOR SEQ ID NO:48:

(i) SEQUENCE CHARACTERISTICS:
        (A) LENGTH: 31 amino acids
        (B) TYPE: amino acid
        (C) STRANDEDNESS:
        (D) TOPOLOGY: Not Relevant (ii) MOLECULE TYPE: peptide (v) FRAGMENT TYPE: N-terminal (ix) FEATURE:
        (A) NAME/KEY: Peptide
        (B) LOCATION: 8
        (D) OTHER INFORMATION: /product= "Nle"

(ix) FEATURE:
        (A) NAME/KEY: Peptide
        (B) LOCATION: 18
        (D) OTHER INFORMATION: /product= "Orn"

(ix) FEATURE:
        (A) NAME/KEY: Peptide
        (B) LOCATION: 18..22
        (D) OTHER INFORMATION: /product= "OTHER"
            /note= "The side chains of Orn at position 18 and Asp at
            position 22 are linked by an amide bond. "

(ix) FEATURE:
        (A) NAME/KEY: Peptide
        (B) LOCATION: 31
        (D) OTHER INFORMATION: /product= "OTHER"
            /note= "This C-terminal amino acid is an amide, i.e.,

```
                CONH2."

(xi) SEQUENCE DESCRIPTION: SEQ ID NO:48:

Ala Val Ser Glu Ile Gln Leu Xaa His Asn Leu Gly Lys His Leu Asn
1               5                   10                  15

Ser Xaa Glu Arg Val Asp Trp Leu Arg Lys Leu Leu Gln Asp Val
            20                  25                  30

(2) INFORMATION FOR SEQ ID NO:49:

(i) SEQUENCE CHARACTERISTICS:
        (A) LENGTH: 31 amino acids
        (B) TYPE: amino acid
        (C) STRANDEDNESS:
        (D) TOPOLOGY: Not Relevant (ii) MOLECULE TYPE: peptide (v) FRAGMENT TYPE: N-terminal (ix) FEATURE:
        (A) NAME/KEY: Peptide
        (B) LOCATION: 8
        (D) OTHER INFORMATION: /product= "Nle"

(ix) FEATURE:
        (A) NAME/KEY: Peptide
        (B) LOCATION: 22
        (D) OTHER INFORMATION: /product= "Orn"

(ix) FEATURE:
        (A) NAME/KEY: Peptide
        (B) LOCATION: 18..22
        (D) OTHER INFORMATION: /product= "OTHER"
            /note= "The side chain of Asp at position 18 and Orn at
            position 22 are linked by an amide bond."

(ix) FEATURE:
        (A) NAME/KEY: Peptide
        (B) LOCATION: 31
        (D) OTHER INFORMATION: /product= "OTHER"
            /note= "This C-terminal amino acid is an amide, i.e.,
            CONH2."

(xi) SEQUENCE DESCRIPTION: SEQ ID NO:49:

Ala Val Ser Glu Ile Gln Leu Xaa His Asn Leu Gly Lys His Leu Asn
1               5                   10                  15

Ser Asp Glu Arg Val Xaa Trp Leu Arg Lys Leu Leu Gln Asp Val
            20                  25                  30

(2) INFORMATION FOR SEQ ID NO:50:

(i) SEQUENCE CHARACTERISTICS:
        (A) LENGTH: 31 amino acids
        (B) TYPE: amino acid
        (C) STRANDEDNESS:
        (D) TOPOLOGY: Not Relevant (ii) MOLECULE TYPE: peptide (v) FRAGMENT TYPE: N-terminal (ix) FEATURE:
        (A) NAME/KEY: Peptide
        (B) LOCATION: 8
        (D) OTHER INFORMATION: /product= "Nle"

(ix) FEATURE:
        (A) NAME/KEY: Peptide
        (B) LOCATION: 18..22
        (D) OTHER INFORMATION: /product= "OTHER"
            /note= "The side chains of Lys at position 18 and Glu at
            position 22 are linked by an amide bond."
```

(ix) FEATURE:
              (A) NAME/KEY: Peptide
              (B) LOCATION: 31
              (D) OTHER INFORMATION: /product= "OTHER"
                    /note= "This C-terminal amino acid is an amide, i.e.,
                    CONH2."

(xi) SEQUENCE DESCRIPTION: SEQ ID NO:50:

Ala Val Ser Glu Ile Gln Leu Xaa His Asn Leu Gly Lys His Leu Asn
1               5                   10                  15

Ser Lys Glu Arg Val Glu Trp Leu Arg Lys Leu Leu Gln Asp Val
            20                  25                  30

(2) INFORMATION FOR SEQ ID NO:51:

(i) SEQUENCE CHARACTERISTICS:
              (A) LENGTH: 31 amino acids
              (B) TYPE: amino acid
              (C) STRANDEDNESS:
              (D) TOPOLOGY: Not Relevant (ii) MOLECULE TYPE: peptide (v) FRAGMENT TYPE: N-terminal (ix) FEATURE:
              (A) NAME/KEY: Protein
              (B) LOCATION: 1
              (D) OTHER INFORMATION: /product= "Nle"

(ix) FEATURE:
              (A) NAME/KEY: Peptide
              (B) LOCATION: 11
              (D) OTHER INFORMATION: /product= "Orn"

(ix) FEATURE:
              (A) NAME/KEY: Peptide
              (B) LOCATION: 11..15
              (D) OTHER INFORMATION: /product= "OTHER"
                    /note= "The side chains of Orn at position 18 and Glu at
                    position 22 are linked by an amide bond. "

(ix) FEATURE:
              (A) NAME/KEY: Peptide
              (B) LOCATION: 24
              (D) OTHER INFORMATION: /product= "OTHER"
                    /note= "This C-terminal amino acid is an amide, i.e.,
                    CONH2."

(xi) SEQUENCE DESCRIPTION: SEQ ID NO:51:

Ala Val Ser Glu Ile Gln Leu Xaa His Asn Leu Gly Lys His Leu Asn
        -5                  1                   5

Ser Xaa Glu Arg Val Glu Trp Leu Arg Lys Leu Leu Gln Asp Val
10                  15                  20

(2) INFORMATION FOR SEQ ID NO:52:

(i) SEQUENCE CHARACTERISTICS:
              (A) LENGTH: 30 amino acids
              (B) TYPE: amino acid
              (C) STRANDEDNESS:
              (D) TOPOLOGY: Not Relevant (ii) MOLECULE TYPE: peptide (v) FRAGMENT TYPE: N-terminal (ix) FEATURE:
              (A) NAME/KEY: Peptide
              (B) LOCATION: 8
              (D) OTHER INFORMATION: /product= "Nle"

```
    (ix) FEATURE:
         (A) NAME/KEY: Peptide
         (B) LOCATION: 18..22
         (D) OTHER INFORMATION: /product= "OTHER"
             /note= "The side chains of Lys at position 18 and Asp at
             position 22 are linked by an amide bond. "

(ix) FEATURE:
         (A) NAME/KEY: Peptide
         (B) LOCATION: 30
         (D) OTHER INFORMATION: /product= "OTHER"
             /note= "This C-terminal amino acid is an amide, i.e.,
             CONH2."

(xi) SEQUENCE DESCRIPTION: SEQ ID NO:52:

Ala Val Ser Glu Ile Gln Leu Xaa His Asn Leu Gly Lys His Leu Asn
1               5                  10                  15

Ser Lys Glu Arg Val Asp Trp Leu Arg Lys Leu Leu Gln Asp
            20                  25                  30

(2) INFORMATION FOR SEQ ID NO:53:

(i) SEQUENCE CHARACTERISTICS:
        (A) LENGTH: 29 amino acids
        (B) TYPE: amino acid
        (C) STRANDEDNESS:
        (D) TOPOLOGY: Not Relevant (ii) MOLECULE TYPE: peptide (v) FRAGMENT TYPE: N-terminal (ix) FEATURE:
         (A) NAME/KEY: Peptide
         (B) LOCATION: 8
         (D) OTHER INFORMATION: /product= "Nle"

(ix) FEATURE:
         (A) NAME/KEY: Peptide
         (B) LOCATION: 18..22
         (D) OTHER INFORMATION: /product= "OTHER"
             /note= "The side chains of Lys at position 18 and Asp at
             position 22 are linked by an amide bond. "

(ix) FEATURE:
         (A) NAME/KEY: Peptide
         (B) LOCATION: 29
         (D) OTHER INFORMATION: /product= "OTHER"
             /note= "This C-terminal amino acid is an amide, i.e.,
             CONH2."

(xi) SEQUENCE DESCRIPTION: SEQ ID NO:53:

Ala Val Ser Glu Ile Gln Leu Xaa His Asn Leu Gly Lys His Leu Asn
1               5                  10                  15

Ser Lys Glu Arg Val Asp Trp Leu Arg Lys Leu Leu Gln
            20                  25

(2) INFORMATION FOR SEQ ID NO:54:

(i) SEQUENCE CHARACTERISTICS:
        (A) LENGTH: 28 amino acids
        (B) TYPE: amino acid
        (C) STRANDEDNESS:
        (D) TOPOLOGY: Not Relevant (ii) MOLECULE TYPE: peptide (v) FRAGMENT TYPE: N-terminal (ix) FEATURE:
         (A) NAME/KEY: Peptide
         (B) LOCATION: 8
         (D) OTHER INFORMATION: /product= "Nle"
```

```
        (ix) FEATURE:
              (A) NAME/KEY: Peptide
              (B) LOCATION: 18..22
              (D) OTHER INFORMATION: /product= "OTHER"
                    /note= "The side chains of Lys at position 18 and Asp at
                    position 22 are linked by an amide bond. "

(ix) FEATURE:
              (A) NAME/KEY: Peptide
              (B) LOCATION: 28
              (D) OTHER INFORMATION: /product= "OTHER"
                    /note= "This C-terminal amino acid is an amide, i.e.,
                    CONH2."

(xi) SEQUENCE DESCRIPTION: SEQ ID NO:54:

Ala Val Ser Glu Ile Gln Leu Xaa His Asn Leu Gly Lys His Leu Asn
1               5                  10                  15

Ser Lys Glu Arg Val Asp Trp Leu Arg Lys Leu Leu
            20                  25

(2) INFORMATION FOR SEQ ID NO:55:

(i) SEQUENCE CHARACTERISTICS:
            (A) LENGTH: 27 amino acids
            (B) TYPE: amino acid
            (C) STRANDEDNESS:
            (D) TOPOLOGY: Not Relevant (ii) MOLECULE TYPE: peptide (v) FRAGMENT TYPE: N-terminal (ix) FEATURE:
            (A) NAME/KEY: Peptide
            (B) LOCATION: 8
            (D) OTHER INFORMATION: /product= "Nle"

(ix) FEATURE:
            (A) NAME/KEY: Peptide
            (B) LOCATION: 18..22
            (D) OTHER INFORMATION: /product= "OTHER"
                    /note= "The side chains of Lys at position 18 and Asp at
                    position 22 are linked by an amide bond. "

(ix) FEATURE:
            (A) NAME/KEY: Peptide
            (B) LOCATION: 27
            (D) OTHER INFORMATION: /product= "OTHER"
                    /note= "This C-terminal amino acid is an amide, i.e.,
                    CONH2."

(xi) SEQUENCE DESCRIPTION: SEQ ID NO:55:

Ala Val Ser Glu Ile Gln Leu Xaa His Asn Leu Gly Lys His Leu Asn
1               5                  10                  15

Ser Lys Glu Arg Val Asp Trp Leu Arg Lys Leu
            20                  25

(2) INFORMATION FOR SEQ ID NO:56:

(i) SEQUENCE CHARACTERISTICS:
            (A) LENGTH: 22 amino acids
            (B) TYPE: amino acid
            (C) STRANDEDNESS:
            (D) TOPOLOGY: Not Relevant (ii) MOLECULE TYPE: peptide (v) FRAGMENT TYPE: N-terminal (ix) FEATURE:
            (A) NAME/KEY: Peptide
            (B) LOCATION: 9..13
```

```
            (D) OTHER INFORMATION: /product= "OTHER"
                /note= "The side chains of Lys at position 9 and Asp at
                position 13 are linked by an amide bond. "

(ix) FEATURE:
            (A) NAME/KEY: Peptide
            (B) LOCATION: 22
            (D) OTHER INFORMATION: /product= "OTHER"
                /note= "This C-terminal amino acid is an amide, i.e.,
                CONH2."

(xi) SEQUENCE DESCRIPTION: SEQ ID NO:56:

Asn Leu Gly Lys His Leu Asn Ser Lys Glu Arg Val Asp Trp Leu Arg
1               5                   10                  15

Lys Leu Leu Gln Asp Val
            20

(2) INFORMATION FOR SEQ ID NO:57:

(i) SEQUENCE CHARACTERISTICS:
            (A) LENGTH: 23 amino acids
            (B) TYPE: amino acid
            (C) STRANDEDNESS:
            (D) TOPOLOGY: Not Relevant (ii) MOLECULE TYPE: peptide (v) FRAGMENT TYPE: N-terminal (ix) FEATURE:
            (A) NAME/KEY: Peptide
            (B) LOCATION: 10..14
            (D) OTHER INFORMATION: /product= "OTHER"
                /note= "The side chains of Lys at position 10 and Asp at
                position 14 are linked by an amide bond. "

(ix) FEATURE:
            (A) NAME/KEY: Peptide
            (B) LOCATION: 23
            (D) OTHER INFORMATION: /product= "OTHER"
                /note= "This C-terminal amino acid is an amide, i.e.,
                CONH2."

(xi) SEQUENCE DESCRIPTION: SEQ ID NO:57:

His Asn Leu Gly Lys His Leu Asn Ser Lys Glu Arg Val Asp Trp Leu
1               5                   10                  15

Arg Lys Leu Leu Gln Asp Val
            20

(2) INFORMATION FOR SEQ ID NO:58:

(i) SEQUENCE CHARACTERISTICS:
            (A) LENGTH: 24 amino acids
            (B) TYPE: amino acid
            (C) STRANDEDNESS:
            (D) TOPOLOGY: Not Relevant (ii) MOLECULE TYPE: peptide (v) FRAGMENT TYPE: N-terminal (ix) FEATURE:
            (A) NAME/KEY: Peptide
            (B) LOCATION: 1
            (D) OTHER INFORMATION: /product= "Nle"

(ix) FEATURE:
            (A) NAME/KEY: Peptide
            (B) LOCATION: 11..15
            (D) OTHER INFORMATION: /product= "OTHER"
                /note= "The side chains of Lys at position 11 and Asp at
                position 15 are linked by an amide bond. "
```

```
        (ix) FEATURE:
             (A) NAME/KEY: Peptide
             (B) LOCATION: 24
             (D) OTHER INFORMATION: /product= "OTHER"
                 /note= "This C-terminal amino acid is an amide, i.e.,
                 CONH2."

(xi) SEQUENCE DESCRIPTION: SEQ ID NO:58:

Xaa His Asn Leu Gly Lys His Leu Asn Ser Lys Glu Arg Val Asp Trp
1               5                   10                  15

Leu Arg Lys Leu Leu Gln Asp Val
            20

(2) INFORMATION FOR SEQ ID NO:59:

(i) SEQUENCE CHARACTERISTICS:
         (A) LENGTH: 25 amino acids
         (B) TYPE: amino acid
         (C) STRANDEDNESS:
         (D) TOPOLOGY: Not Relevant (ii) MOLECULE TYPE: peptide (v) FRAGMENT TYPE: N-terminal (ix) FEATURE:
         (A) NAME/KEY: Peptide
         (B) LOCATION: 2
         (D) OTHER INFORMATION: /product= "Nle"

(ix) FEATURE:
         (A) NAME/KEY: Peptide
         (B) LOCATION: 12..16
         (D) OTHER INFORMATION: /product= "OTHER"
             /note= "The side chains of Lys at position 12 and Asp at
             position 16 are linked by an amide bond. "

(ix) FEATURE:
         (A) NAME/KEY: Peptide
         (B) LOCATION: 25
         (D) OTHER INFORMATION: /product= "OTHER"
             /note= "This C-terminal amino acid is an amide, i.e.,
             CONH2."

(xi) SEQUENCE DESCRIPTION: SEQ ID NO:59:

Leu Xaa His Asn Leu Gly Lys His Leu Asn Ser Lys Glu Arg Val Asp
1               5                   10                  15

Trp Leu Arg Lys Leu Leu Gln Asp Val
            20                  25

(2) INFORMATION FOR SEQ ID NO:60:

(i) SEQUENCE CHARACTERISTICS:
         (A) LENGTH: 26 amino acids
         (B) TYPE: amino acid
         (C) STRANDEDNESS:
         (D) TOPOLOGY: Not Relevant (ii) MOLECULE TYPE: peptide (v) FRAGMENT TYPE: N-terminal (ix) FEATURE:
         (A) NAME/KEY: Peptide
         (B) LOCATION: 3
         (D) OTHER INFORMATION: /product= "Nle"

(ix) FEATURE:
         (A) NAME/KEY: Peptide
         (B) LOCATION: 13..17
         (D) OTHER INFORMATION: /product= "OTHER"
             /note= "The side chains of Lys at position 13 and Asp at
             position 17 are linked by an amide bond. "
```

```
    (ix) FEATURE:
         (A) NAME/KEY: Peptide
         (B) LOCATION: 26
         (D) OTHER INFORMATION: /product= "OTHER"
             /note= "This C-terminal amino acid is an amide, i.e.,
             CONH2."

(xi) SEQUENCE DESCRIPTION: SEQ ID NO:60:

Gln Leu Xaa His Asn Leu Gly Lys His Leu Asn Ser Lys Glu Arg Val
1               5                  10                  15

Asp Trp Leu Arg Lys Leu Leu Gln Asp Val
            20                  25

(2) INFORMATION FOR SEQ ID NO:61:

(i) SEQUENCE CHARACTERISTICS:
        (A) LENGTH: 27 amino acids
        (B) TYPE: amino acid
        (C) STRANDEDNESS:
        (D) TOPOLOGY: Not Relevant (ii) MOLECULE TYPE: peptide (v) FRAGMENT TYPE: N-terminal (ix) FEATURE:
         (A) NAME/KEY: Peptide
         (B) LOCATION: 4
         (D) OTHER INFORMATION: /product= "Nle"

(ix) FEATURE:
         (A) NAME/KEY: Peptide
         (B) LOCATION: 14..18
         (D) OTHER INFORMATION: /product= "OTHER"
             /note= "The side chains of Lys at position 14 and Asp at
             position 18 are linked by an amide bond. "

(ix) FEATURE:
         (A) NAME/KEY: Peptide
         (B) LOCATION: 27
         (D) OTHER INFORMATION: /product= "OTHER"
             /note= "This C-terminal amino acid is an amide, i.e.,
             CONH2."

(xi) SEQUENCE DESCRIPTION: SEQ ID NO:61:

Ile Gln Leu Xaa His Asn Leu Gly Lys His Leu Asn Ser Lys Glu Arg
1               5                  10                  15

Val Asp Trp Leu Arg Lys Leu Leu Gln Asp Val
            20                  25

(2) INFORMATION FOR SEQ ID NO:62:

(i) SEQUENCE CHARACTERISTICS:
        (A) LENGTH: 28 amino acids
        (B) TYPE: amino acid
        (C) STRANDEDNESS:
        (D) TOPOLOGY: Not Relevant (ii) MOLECULE TYPE: peptide (v) FRAGMENT TYPE: N-terminal (ix) FEATURE:
         (A) NAME/KEY: Peptide
         (B) LOCATION: 5
         (D) OTHER INFORMATION: /product= "Nle"

(ix) FEATURE:
         (A) NAME/KEY: Peptide
         (B) LOCATION: 15..19
         (D) OTHER INFORMATION: /product= "OTHER"
             /note= "The side chains of Lys at position 15 and Asp at
``` position 19 are linked by an amide bond. "

(ix) FEATURE:
        (A) NAME/KEY: Peptide
        (B) LOCATION: 28
        (D) OTHER INFORMATION: /product= "OTHER"
            /note= "This C-terminal amino acid is an amide, i.e.,
            CONH2."

(xi) SEQUENCE DESCRIPTION: SEQ ID NO:62:

Glu Ile Gln Leu Xaa His Asn Leu Gly Lys His Leu Asn Ser Lys Glu
1               5                   10                  15

Arg Val Asp Trp Leu Arg Lys Leu Leu Gln Asp Val
            20                  25

(2) INFORMATION FOR SEQ ID NO:63:

(i) SEQUENCE CHARACTERISTICS:
        (A) LENGTH: 29 amino acids
        (B) TYPE: amino acid
        (C) STRANDEDNESS:
        (D) TOPOLOGY: Not Relevant (ii) MOLECULE TYPE: peptide (v) FRAGMENT TYPE: N-terminal (ix) FEATURE:
        (A) NAME/KEY: Peptide
        (B) LOCATION: 6
        (D) OTHER INFORMATION: /product= "Nle"

(ix) FEATURE:
        (A) NAME/KEY: Peptide
        (B) LOCATION: 16..20
        (D) OTHER INFORMATION: /product= "OTHER"
            /note= "The side chains of Lys at position 16 and Asp at
            position 20 are linked by an amide bond. "

(ix) FEATURE:
        (A) NAME/KEY: Peptide
        (B) LOCATION: 29
        (D) OTHER INFORMATION: /product= "OTHER"
            /note= "This C-terminal amino acid is an amide, i.e.,
            CONH2."

(xi) SEQUENCE DESCRIPTION: SEQ ID NO:63:

Ser Glu Ile Gln Leu Xaa His Asn Leu Gly Lys His Leu Asn Ser Lys
1               5                   10                  15

Glu Arg Val Asp Trp Leu Arg Lys Leu Leu Gln Asp Val
            20                  25

(2) INFORMATION FOR SEQ ID NO:64:

(i) SEQUENCE CHARACTERISTICS:
        (A) LENGTH: 30 amino acids
        (B) TYPE: amino acid
        (C) STRANDEDNESS:
        (D) TOPOLOGY: Not Relevant (ii) MOLECULE TYPE: peptide (v) FRAGMENT TYPE: N-terminal (ix) FEATURE:
        (A) NAME/KEY: Peptide
        (B) LOCATION: 7
        (D) OTHER INFORMATION: /product= "Nle"

(ix) FEATURE:
        (A) NAME/KEY: Peptide
        (B) LOCATION: 17..21
        (D) OTHER INFORMATION: /product= "OTHER"

/note= "The side chains of Lys at position 17 and Asp at
         position 21 are linked by an amide bond. "

(ix) FEATURE:
         (A) NAME/KEY: Peptide
         (B) LOCATION: 30
         (D) OTHER INFORMATION: /product= "OTHER"
             /note= "This C-terminal amino acid is an amide, i.e.,
             CONH2."

(xi) SEQUENCE DESCRIPTION: SEQ ID NO:64:

Val Ser Glu Ile Gln Leu Xaa His Asn Leu Gly Lys His Leu Asn Ser
1               5                  10                  15

Lys Glu Arg Val Asp Trp Leu Arg Lys Leu Leu Gln Asp Val
            20                  25                  30

(2) INFORMATION FOR SEQ ID NO:65:

(i) SEQUENCE CHARACTERISTICS:
         (A) LENGTH: 28 amino acids
         (B) TYPE: amino acid
         (C) STRANDEDNESS:
         (D) TOPOLOGY: Not Relevant (ii) MOLECULE TYPE: peptide (v) FRAGMENT TYPE: N-terminal (ix) FEATURE:
         (A) NAME/KEY: Peptide
         (B) LOCATION: 2
         (D) OTHER INFORMATION: /product= "Nle"

(ix) FEATURE:
         (A) NAME/KEY: Peptide
         (B) LOCATION: 12..16
         (D) OTHER INFORMATION: /product= "OTHER"
             /note= "The side chains of Lys at position 12 and Asp at
             position 16 are linked by an amide bond. "

(ix) FEATURE:
         (A) NAME/KEY: Peptide
         (B) LOCATION: 28
         (D) OTHER INFORMATION: /product= "OTHER"
             /note= "This C-terminal amino acid is an amide, i.e.,
             CONH2."

(xi) SEQUENCE DESCRIPTION: SEQ ID NO:65:

Leu Xaa His Asn Leu Gly Lys His Leu Asn Ser Lys Glu Arg Val Asp
1               5                  10                  15

Trp Leu Arg Lys Leu Leu Gln Asp Val His Asn Phe
            20                  25

(2) INFORMATION FOR SEQ ID NO:66:

(i) SEQUENCE CHARACTERISTICS:
         (A) LENGTH: 31 amino acids
         (B) TYPE: amino acid
         (C) STRANDEDNESS:
         (D) TOPOLOGY: Not Relevant (ii) MOLECULE TYPE: peptide (v) FRAGMENT TYPE: N-terminal (ix) FEATURE:
         (A) NAME/KEY: Peptide
         (B) LOCATION: 8
         (D) OTHER INFORMATION: /product= "Nle"

(ix) FEATURE:
         (A) NAME/KEY: Peptide
         (B) LOCATION: 18

(D) OTHER INFORMATION: /product= "Nle"

(ix) FEATURE:
                    (A) NAME/KEY: Peptide
                    (B) LOCATION: 10..14
                    (D) OTHER INFORMATION: /product= "OTHER"
                        /note= "The side chains of Lys at position 10 and Asp at
                        position 14 are linked by an amide bond."

(ix) FEATURE:
                    (A) NAME/KEY: Peptide
                    (B) LOCATION: 31
                    (D) OTHER INFORMATION: /product= "OTHER"
                        /note= "This C-terminal amino acid is an amide, i.e.,
                        CONH2."

(xi) SEQUENCE DESCRIPTION: SEQ ID NO:66:

Ala Val Ser Glu Ile Gln Leu Xaa His Lys Leu Gly Lys Asp Leu Asn
1               5                  10                  15

Ser Xaa Glu Arg Val Glu Trp Leu Arg Lys Leu Leu Gln Asp Val
            20                  25                  30

(2) INFORMATION FOR SEQ ID NO:67:

(i) SEQUENCE CHARACTERISTICS:
                (A) LENGTH: 31 amino acids
                (B) TYPE: amino acid
                (C) STRANDEDNESS:
                (D) TOPOLOGY: Not Relevant (ii) MOLECULE TYPE: peptide (v) FRAGMENT TYPE: N-terminal (ix) FEATURE:
                (A) NAME/KEY: Peptide
                (B) LOCATION: 8
                (D) OTHER INFORMATION: /product= "Nle"

(ix) FEATURE:
                (A) NAME/KEY: Peptide
                (B) LOCATION: 14..18
                (D) OTHER INFORMATION: /product= "OTHER"
                    /note= "The side chains of Lys at position 14 and Asp at
                    position 18 are linked by an amide bond."

(ix) FEATURE:
                (A) NAME/KEY: Peptide
                (B) LOCATION: 31
                (D) OTHER INFORMATION: /product= "OTHER"
                    /note= "This C-terminal amino acid is an amide, i.e.,
                    CONH2."

(xi) SEQUENCE DESCRIPTION: SEQ ID NO:67:

Ala Val Ser Glu Ile Gln Leu Xaa His Asn Leu Gly Lys Lys Leu Asn
1               5                  10                  15

Ser Asp Glu Arg Val Glu Trp Leu Arg Lys Leu Leu Gln Asp Val
            20                  25                  30

(2) INFORMATION FOR SEQ ID NO:68:

(i) SEQUENCE CHARACTERISTICS:
                (A) LENGTH: 31 amino acids
                (B) TYPE: amino acid
                (C) STRANDEDNESS:
                (D) TOPOLOGY: Not Relevant (ii) MOLECULE TYPE: peptide (v) FRAGMENT TYPE: N-terminal (ix) FEATURE:
                (A) NAME/KEY: Peptide

```
          (B) LOCATION: 8
          (D) OTHER INFORMATION: /product= "Nle"

(ix) FEATURE:
          (A) NAME/KEY: Peptide
          (B) LOCATION: 18
          (D) OTHER INFORMATION: /product= "Nle"

(ix) FEATURE:
          (A) NAME/KEY: Peptide
          (B) LOCATION: 17..21
          (D) OTHER INFORMATION: /product= "OTHER"
              /note= "The side chain of Lys at position 17 and Asp
              at position 21 are linked by an amide bond. "

(ix) FEATURE:
          (A) NAME/KEY: Peptide
          (B) LOCATION: 31
          (D) OTHER INFORMATION: /product= "OTHER"
              /note= "This C-terminal amino acid is an amide, i.e.,
              CONH2."

(xi) SEQUENCE DESCRIPTION: SEQ ID NO:68:

Ala Val Ser Glu Ile Gln Leu Xaa His Asn Leu Gly Lys His Leu Asn
1               5                  10                  15

Lys Xaa Glu Arg Asp Glu Trp Leu Arg Lys Leu Leu Gln Asp Val
            20                  25                  30

(2) INFORMATION FOR SEQ ID NO:69:

(i) SEQUENCE CHARACTERISTICS:
          (A) LENGTH: 31 amino acids
          (B) TYPE: amino acid
          (C) STRANDEDNESS:
          (D) TOPOLOGY: Not Relevant (ii) MOLECULE TYPE: peptide (v) FRAGMENT TYPE: N-terminal (ix) FEATURE:
          (A) NAME/KEY: Peptide
          (B) LOCATION: 8
          (D) OTHER INFORMATION: /product= "Nle"

(ix) FEATURE:
          (A) NAME/KEY: Peptide
          (B) LOCATION: 18
          (D) OTHER INFORMATION: /product= "Nle"

(ix) FEATURE:
          (A) NAME/KEY: Peptide
          (B) LOCATION: 21..25
          (D) OTHER INFORMATION: /product= "OTHER"
              /note= "The side chains of Lys at position 21 and Asp at
              position 25 are linked by an amide bond. "

(ix) FEATURE:
          (A) NAME/KEY: Peptide
          (B) LOCATION: 31
          (D) OTHER INFORMATION: /product= "OTHER"
              /note= "This C-terminal amino acid is an amide, i.e.,
              CONH2."

(xi) SEQUENCE DESCRIPTION: SEQ ID NO:69:

Ala Val Ser Glu Ile Gln Leu Xaa His Asn Leu Gly Lys His Leu Asn
1               5                  10                  15

Ser Xaa Glu Arg Lys Glu Trp Leu Asp Lys Leu Leu Gln Asp Val
            20                  25                  30

(2) INFORMATION FOR SEQ ID NO:70:

(i) SEQUENCE CHARACTERISTICS:
```

```
            (A) LENGTH: 31 amino acids
            (B) TYPE: amino acid
            (C) STRANDEDNESS:
            (D) TOPOLOGY: Not Relevant (ii) MOLECULE TYPE: peptide (v) FRAGMENT TYPE: N-terminal (ix) FEATURE:
            (A) NAME/KEY: Peptide
            (B) LOCATION: 8
            (D) OTHER INFORMATION: /product= "Nle"

(ix) FEATURE:
            (A) NAME/KEY: Peptide
            (B) LOCATION: 18
            (D) OTHER INFORMATION: /product= "Nle"

(ix) FEATURE:
            (A) NAME/KEY: Peptide
            (B) LOCATION: 25..29
            (D) OTHER INFORMATION: /product= "OTHER"
                /note= "The side chains of Lys at position 25 and Asp at
                position 29 are linked by an amide bond."

(ix) FEATURE:
            (A) NAME/KEY: Peptide
            (B) LOCATION: 31
            (D) OTHER INFORMATION: /product= "OTHER"
                /note= "This C-terminal amino acid is an amide, i.e.,
                CONH2."

(xi) SEQUENCE DESCRIPTION: SEQ ID NO:70:

Ala Val Ser Glu Ile Gln Leu Xaa His Asn Leu Gly Lys His Leu Asn
1               5                   10                  15

Ser Xaa Glu Arg Val Glu Trp Leu Lys Lys Leu Leu Asp Asp Val
            20                  25                  30

(2) INFORMATION FOR SEQ ID NO:71:

(i) SEQUENCE CHARACTERISTICS:
            (A) LENGTH: 34 amino acids
            (B) TYPE: amino acid
            (C) STRANDEDNESS:
            (D) TOPOLOGY: Not Relevant (ii) MOLECULE TYPE: peptide (v) FRAGMENT TYPE: N-terminal (ix) FEATURE:
            (A) NAME/KEY: Peptide
            (B) LOCATION: 18..22
            (D) OTHER INFORMATION: /product= "OTHER"
                /note= "The side chains of Lys at position 18 and Asp at
                position 22 are linked by an amide bond. "

(ix) FEATURE:
            (A) NAME/KEY: Peptide
            (B) LOCATION: 34
            (D) OTHER INFORMATION: /product= "OTHER"
                /note= "This C-terminal amino acid is an amide, i.e.,
                CONH2."

(xi) SEQUENCE DESCRIPTION: SEQ ID NO:71:

Ala Val Ser Glu His Gln Leu Leu His Asp Lys Gly Lys Ser Ile Gln
1               5                   10                  15

Asp Lys Arg Arg Arg Asp Phe Leu His His Leu Ile Ala Glu Ile His
            20                  25                  30

Thr Ala
```

(2) INFORMATION FOR SEQ ID NO:72:

(i) SEQUENCE CHARACTERISTICS:
        (A) LENGTH: 34 amino acids
        (B) TYPE: amino acid
        (C) STRANDEDNESS:
        (D) TOPOLOGY: Not Relevant (ii) MOLECULE TYPE: peptide (v) FRAGMENT TYPE: N-terminal (ix) FEATURE:
        (A) NAME/KEY: Peptide
        (B) LOCATION: 18..22
        (D) OTHER INFORMATION: /product= "OTHER"
            /note= "The side chains of Lys at position 18 and Asp at
            position 22 are linked by an amide bond. "

(ix) FEATURE:
        (A) NAME/KEY: Peptide
        (B) LOCATION: 34
        (D) OTHER INFORMATION: /product= "OTHER"
            /note= "This C-terminal amino acid is an amide, i.e.,
            CONH2."

(xi) SEQUENCE DESCRIPTION: SEQ ID NO:72:

```
Ala Val Ser Glu His Gln Leu Leu His Asp Lys Gly Lys Ser Ile Gln
1               5                   10                  15

Asp Lys Arg Arg Arg Asp Leu Leu Glu Lys Leu Leu Glu Lys Leu His
            20                  25                  30

Thr Ala
```

(2) INFORMATION FOR SEQ ID NO:73:

(i) SEQUENCE CHARACTERISTICS:
        (A) LENGTH: 31 amino acids
        (B) TYPE: amino acid
        (C) STRANDEDNESS:
        (D) TOPOLOGY: Not Relevant (ii) MOLECULE TYPE: peptide (v) FRAGMENT TYPE: N-terminal (ix) FEATURE:
        (A) NAME/KEY: Peptide
        (B) LOCATION: 8
        (D) OTHER INFORMATION: /product= "Nle"

(ix) FEATURE:
        (A) NAME/KEY: Peptide
        (B) LOCATION: 13..17
        (D) OTHER INFORMATION: /product= "OTHER"
            /note= "The side chains of Lys at position 13 and Asp at
            position 17 are linked by an amide bond. "

(ix) FEATURE:
        (A) NAME/KEY: Peptide
        (B) LOCATION: 18..22
        (D) OTHER INFORMATION: /product= "OTHER"
            /note= "The side chains of Lys at position 18 and Asp at
            position 22 are linked by an amide bond."

(ix) FEATURE:
        (A) NAME/KEY: Peptide
        (B) LOCATION: 31
        (D) OTHER INFORMATION: /product= "OTHER"
            /note= "This C-terminal amino acid is an amide,i.e.,
            CONH2."

(xi) SEQUENCE DESCRIPTION: SEQ ID NO:73:

```
Ala Val Ser Glu Ile Gln Leu Xaa His Asn Leu Gly Lys His Leu Asn
1               5                   10                  15
```

Asp Lys Glu Arg Val Asp Trp Leu Arg Lys Leu Leu Gln Asp Val
            20                  25                  30

(2) INFORMATION FOR SEQ ID NO:74:

(i) SEQUENCE CHARACTERISTICS:
        (A) LENGTH: 31 amino acids
        (B) TYPE: amino acid
        (C) STRANDEDNESS:
        (D) TOPOLOGY: Not Relevant (ii) MOLECULE TYPE: peptide (v) FRAGMENT TYPE: N-terminal (ix) FEATURE:
        (A) NAME/KEY: Peptide
        (B) LOCATION: 8
        (D) OTHER INFORMATION: /product= "Nle"

(ix) FEATURE:
        (A) NAME/KEY: Peptide
        (B) LOCATION: 18..22
        (D) OTHER INFORMATION: /product= "OTHER"
            /note= "The side chain of Lys at position 18 and Asp at
            position 22 are linked by an amide bond."

(ix) FEATURE:
        (A) NAME/KEY: Peptide
        (B) LOCATION: 26..30
        (D) OTHER INFORMATION: /product= "OTHER"
            /note= "The side chain of Lys at position 26 and Asp at
            position 30 are linked by an amide bond."

(ix) FEATURE:
        (A) NAME/KEY: Peptide
        (B) LOCATION: 31
        (D) OTHER INFORMATION: /product= "OTHER"
            /note= "This C-terminal amino acid is an amide,i.e.,
            CONH2."

(xi) SEQUENCE DESCRIPTION: SEQ ID NO:74:

Ala Val Ser Glu Ile Gln Leu Xaa His Asn Leu Gly Lys His Leu Asn
1               5                   10                  15

Ser Lys Glu Arg Val Asp Trp Leu Arg Lys Leu Leu Gln Asp Val
            20                  25                  30

(2) INFORMATION FOR SEQ ID NO:75:

(i) SEQUENCE CHARACTERISTICS:
        (A) LENGTH: 34 amino acids
        (B) TYPE: amino acid
        (C) STRANDEDNESS:
        (D) TOPOLOGY: Not Relevant (ii) MOLECULE TYPE: peptide (v) FRAGMENT TYPE: N-terminal (ix) FEATURE:
        (A) NAME/KEY: Peptide
        (B) LOCATION: 8
        (D) OTHER INFORMATION: /product= "Nle"

(ix) FEATURE:
        (A) NAME/KEY: Peptide
        (B) LOCATION: 13..17
        (D) OTHER INFORMATION: /product= "OTHER"
            /note= "The side chain of Lys at position 13 and Asp at
            position 17 are linked by an amide bond."

(ix) FEATURE:
        (A) NAME/KEY: Peptide
        (B) LOCATION: 18..22

(D) OTHER INFORMATION: /product= "OTHER"
            /note= "The side chain of Lys at position 18 and Asp at
            position 22 are linked by an amide bond."

(ix) FEATURE:
        (A) NAME/KEY: Peptide
        (B) LOCATION: 34
        (D) OTHER INFORMATION: /product= "OTHER"
            /note= "This C-terminal amino acid is an amide, i.e.,
            CONH2."

(xi) SEQUENCE DESCRIPTION: SEQ ID NO:75:

Ala Val Ser Glu Ile Gln Leu Xaa His Asn Leu Gly Lys His Leu Asn
1               5                   10                  15

Asp Lys Glu Arg Val Asp Trp Leu Arg Lys Leu Leu Gln Asp Val His
            20                  25                  30

Asn Phe (2) INFORMATION FOR SEQ ID NO:76:

(i) SEQUENCE CHARACTERISTICS:
        (A) LENGTH: 31 amino acids
        (B) TYPE: amino acid
        (C) STRANDEDNESS:
        (D) TOPOLOGY: Not Relevant (ii) MOLECULE TYPE: peptide (v) FRAGMENT TYPE: N-terminal (ix) FEATURE:
        (A) NAME/KEY: Peptide
        (B) LOCATION: 8
        (D) OTHER INFORMATION: /product= "Nle"

(ix) FEATURE:
        (A) NAME/KEY: Peptide
        (B) LOCATION: 18
        (D) OTHER INFORMATION: /product= "Nle"

(ix) FEATURE:
        (A) NAME/KEY: Peptide
        (B) LOCATION: 13..17
        (D) OTHER INFORMATION: /product= "OTHER"
            /note= "The side chain of Lys at position 13 and Asp at
            position 17 are linked by an amide bond."

(ix) FEATURE:
        (A) NAME/KEY: Peptide
        (B) LOCATION: 26..30
        (D) OTHER INFORMATION: /product= "OTHER"
            /note= "The side chains of Lys at position 26 and Asp at
            position 30 are linked by an amide bond. "

(ix) FEATURE:
        (A) NAME/KEY: Peptide
        (B) LOCATION: 31
        (D) OTHER INFORMATION: /product= "OTHER"
            /note= "The C-terminal amino acid is an amide,i.e.,
            CONH2."

(xi) SEQUENCE DESCRIPTION: SEQ ID NO:76:

Ala Val Ser Glu Ile Gln Leu Xaa His Asn Leu Gly Lys His Leu Asn
1               5                   10                  15

Asp Xaa Glu Arg Val Glu Trp Leu Arg Lys Leu Leu Gln Asp Val
            20                  25                  30

(2) INFORMATION FOR SEQ ID NO:77:

(i) SEQUENCE CHARACTERISTICS:
        (A) LENGTH: 28 amino acids
        (B) TYPE: amino acid

```
            (C) STRANDEDNESS:
            (D) TOPOLOGY: Not Relevant (ii) MOLECULE TYPE: peptide (v) FRAGMENT TYPE: N-terminal (ix) FEATURE:
            (A) NAME/KEY: Peptide
            (B) LOCATION: 12..16
            (D) OTHER INFORMATION: /product= "OTHER"
                /note= "The side chains of Lys at position 12 and Asp at
                position 16 are linked by an amide bond."

(ix) FEATURE:
            (A) NAME/KEY: Peptide
            (B) LOCATION: 28
            (D) OTHER INFORMATION: /product= "OTHER"
                /note= "This C-terminal amino acid is an amide, i.e.,
                CONH2."

(xi) SEQUENCE DESCRIPTION: SEQ ID NO:77:

Leu Leu His Asp Lys Gly Lys Ser Ile Gln Asp Lys Arg Arg Arg Asp
1               5                   10                  15

Phe Leu His His Leu Ile Ala Glu Ile His Thr Ala
            20                  25

(2) INFORMATION FOR SEQ ID NO:78:

(i) SEQUENCE CHARACTERISTICS:
            (A) LENGTH: 28 amino acids
            (B) TYPE: amino acid
            (C) STRANDEDNESS:
            (D) TOPOLOGY: Not Relevant (ii) MOLECULE TYPE: peptide (v) FRAGMENT TYPE: N-terminal (ix) FEATURE:
            (A) NAME/KEY: Peptide
            (B) LOCATION: 2
            (D) OTHER INFORMATION: /product= "Nle"

(ix) FEATURE:
            (A) NAME/KEY: Peptide
            (B) LOCATION: 7..11
            (D) OTHER INFORMATION: /product= "OTHER"
                /note= "The side chains of Lys at position 7 and Asp at
                position 11 are lined by an amide bond."

(ix) FEATURE:
            (A) NAME/KEY: Peptide
            (B) LOCATION: 12..16
            (D) OTHER INFORMATION: /product= "OTHER"
                /note= "The side chains of Lys at position 12 and Asp at
                position 16 are linked by amide bonds."

(ix) FEATURE:
            (A) NAME/KEY: Peptide
            (B) LOCATION: 28
            (D) OTHER INFORMATION: /product= "OTHER"
                /note= "This C-terminal amino acid is an amide,i.e.,
                CONH2."

(xi) SEQUENCE DESCRIPTION: SEQ ID NO:78:

Leu Xaa His Asn Leu Gly Lys His Leu Asn Asp Lys Glu Arg Val Asp
1               5                   10                  15

Trp Leu Arg Lys Leu Leu Gln Asp Val His Asn Phe
            20                  25

(2) INFORMATION FOR SEQ ID NO:79:
```

(i) SEQUENCE CHARACTERISTICS:
        (A) LENGTH: 28 amino acids
        (B) TYPE: amino acid
        (C) STRANDEDNESS:
        (D) TOPOLOGY: Not Relevant (ii) MOLECULE TYPE: peptide (v) FRAGMENT TYPE: N-terminal (ix) FEATURE:
        (A) NAME/KEY: Peptide
        (B) LOCATION: 2
        (D) OTHER INFORMATION: /product= "Nle"

(ix) FEATURE:
        (A) NAME/KEY: Peptide
        (B) LOCATION: 12..16
        (D) OTHER INFORMATION: /product= "OTHER"
            /note= "The side chains of Lys at position 12 and Asp at
            position 16 are linked by an amide bond."

(ix) FEATURE:
        (A) NAME/KEY: Peptide
        (B) LOCATION: 20..24
        (D) OTHER INFORMATION: /product= "OTHER"
            /note= "The side chains of Lys at position 20 and Asp at
            position 24 are linked by an amide bond."

(ix) FEATURE:
        (A) NAME/KEY: Peptide
        (B) LOCATION: 28
        (D) OTHER INFORMATION: /product= "OTHER"
            /note= "This C-terminal amino acid is an amide, i.e.,
            CONH2."

(xi) SEQUENCE DESCRIPTION: SEQ ID NO:79:

Leu Xaa His Asn Leu Gly Lys His Leu Asn Ser Lys Glu Arg Val Asp
1               5                   10                  15

Trp Leu Arg Lys Leu Leu Gln Asp Val His Asn Phe
                20                  25

(2) INFORMATION FOR SEQ ID NO:80:

(i) SEQUENCE CHARACTERISTICS:
        (A) LENGTH: 31 amino acids
        (B) TYPE: amino acid
        (C) STRANDEDNESS:
        (D) TOPOLOGY: Not Relevant (ii) MOLECULE TYPE: peptide (v) FRAGMENT TYPE: N-terminal (ix) FEATURE:
        (A) NAME/KEY: Peptide
        (B) LOCATION: 8
        (D) OTHER INFORMATION: /product= "Nle"

(ix) FEATURE:
        (A) NAME/KEY: Peptide
        (B) LOCATION: 13..17
        (D) OTHER INFORMATION: /product= "OTHER"
            /note= "The side chains of Lys at position 13 and Asp at
            position 17 are linked by an amide bond."

(ix) FEATURE:
        (A) NAME/KEY: Peptide
        (B) LOCATION: 18..22
        (D) OTHER INFORMATION: /product= "OTHER"
            /note= "The side chains of Lys at position 18 and Asp at
            position 22 are linked by an amide bond."

(ix) FEATURE:
        (A) NAME/KEY: Peptide
        (B) LOCATION: 26..30

```
            (D) OTHER INFORMATION: /product= "OTHER"
                /note= "The side chains of Lys at position 26 and Asp at
                position 30 are linked by an amide bond."

(ix) FEATURE:
            (A) NAME/KEY: Peptide
            (B) LOCATION: 31
            (D) OTHER INFORMATION: /product= "OTHER"
                /note= "This C-terminal amino acid is an amide, i.e.,
                CONH2."

(xi) SEQUENCE DESCRIPTION: SEQ ID NO:80:

Ala Val Ser Glu Ile Gln Leu Xaa His Asn Leu Gly Lys His Leu Asn
 1               5                  10                  15

Asp Lys Glu Arg Val Asp Trp Leu Arg Lys Leu Leu Gln Asp Val
            20                  25                  30

(2) INFORMATION FOR SEQ ID NO:81:

(i) SEQUENCE CHARACTERISTICS:
            (A) LENGTH: 31 amino acids
            (B) TYPE: amino acid
            (C) STRANDEDNESS:
            (D) TOPOLOGY: Not Relevant (ii) MOLECULE TYPE: peptide (v) FRAGMENT TYPE: N-terminal (ix) FEATURE:
            (A) NAME/KEY: Peptide
            (B) LOCATION: 18..22
            (D) OTHER INFORMATION: /product= "OTHER"
                /note= "The side chains of Lys at position 18 and Asp at
                position 22 are linked by an amide bond."

(ix) FEATURE:
            (A) NAME/KEY: Peptide
            (B) LOCATION: 31
            (D) OTHER INFORMATION: /product= "OTHER"
                /note= "This C-terminal amino acid is an amide, i.e.,
                CONH2."

(xi) SEQUENCE DESCRIPTION: SEQ ID NO:81:

Ala Val Ser Glu Ile Gln Leu Ala His Asn Leu Gly Lys His Leu Asn
 1               5                  10                  15

Ser Lys Glu Arg Val Asp Trp Leu Arg Lys Leu Leu Gln Asp Val
            20                  25                  30

(2) INFORMATION FOR SEQ ID NO:82:

(i) SEQUENCE CHARACTERISTICS:
            (A) LENGTH: 31 amino acids
            (B) TYPE: amino acid
            (C) STRANDEDNESS:
            (D) TOPOLOGY: Not Relevant (ii) MOLECULE TYPE: peptide (v) FRAGMENT TYPE: N-terminal (ix) FEATURE:
            (A) NAME/KEY: Peptide
            (B) LOCATION: 2
            (D) OTHER INFORMATION: /product= "OTHER"
                /note= "The Xaa in position 2 is D-Proline."

(ix) FEATURE:
            (A) NAME/KEY: Peptide
            (B) LOCATION: 8
            (D) OTHER INFORMATION: /product= "Nle"

(ix) FEATURE:
```

(A) NAME/KEY: Peptide
                    (B) LOCATION: 18..22
                    (D) OTHER INFORMATION: /product= "OTHER"
                        /note= "The side chains of Lys at position 18 and Asp at
                        position 22 are linked by an amide bond."

(ix) FEATURE:
                    (A) NAME/KEY: Peptide
                    (B) LOCATION: 31
                    (D) OTHER INFORMATION: /product= "OTHER"
                        /note= "This C-terminal amino acid is an amide, i.e.,
                        CONH2."

(xi) SEQUENCE DESCRIPTION: SEQ ID NO:82:

Ala Xaa Ser Glu Ile Gln Leu Xaa His Asn Leu Gly Lys His Leu Asn
1               5                   10                  15

Ser Lys Glu Arg Val Asp Trp Leu Arg Lys Leu Leu Gln Asp Val
            20                  25                  30

(2) INFORMATION FOR SEQ ID NO:83:

(i) SEQUENCE CHARACTERISTICS:
                (A) LENGTH: 31 amino acids
                (B) TYPE: amino acid
                (C) STRANDEDNESS:
                (D) TOPOLOGY: Not Relevant (ii) MOLECULE TYPE: peptide (v) FRAGMENT TYPE: N-terminal (ix) FEATURE:
                (A) NAME/KEY: Peptide
                (B) LOCATION: 4
                (D) OTHER INFORMATION: /product= "OTHER"
                    /note= "The Xaa in position 4 is D-Proline."

(ix) FEATURE:
                (A) NAME/KEY: Peptide
                (B) LOCATION: 8
                (D) OTHER INFORMATION: /product= "Nle"

(ix) FEATURE:
                (A) NAME/KEY: Peptide
                (B) LOCATION: 18..22
                (D) OTHER INFORMATION: /product= "OTHER"
                    /note= "The side chains of Lys at position 18 and Asp at
                    position 22 are linked by an amide bond."

(ix) FEATURE:
                (A) NAME/KEY: Peptide
                (B) LOCATION: 31
                (D) OTHER INFORMATION: /product= "OTHER"
                    /note= "This C-terminal amino acid is an amide, i.e.,
                    CONH2."

(xi) SEQUENCE DESCRIPTION: SEQ ID NO:83:

Ala Val Ser Xaa Ile Gln Leu Xaa His Asn Leu Gly Lys His Leu Asn
1               5                   10                  15

Ser Lys Glu Arg Val Asp Trp Leu Arg Lys Leu Leu Gln Asp Val
            20                  25                  30

(2) INFORMATION FOR SEQ ID NO:84:

(i) SEQUENCE CHARACTERISTICS:
                (A) LENGTH: 31 amino acids
                (B) TYPE: amino acid
                (C) STRANDEDNESS:
                (D) TOPOLOGY: Not Relevant (ii) MOLECULE TYPE: peptide (v) FRAGMENT TYPE: N-terminal (ix) FEATURE:
              (A) NAME/KEY: Peptide
              (B) LOCATION: 5
              (D) OTHER INFORMATION: /product= "OTHER"
                    /note= "The Xaa in position 5 is D-Proline."

(ix) FEATURE:
              (A) NAME/KEY: Peptide
              (B) LOCATION: 8
              (D) OTHER INFORMATION: /product= "Nle"

(ix) FEATURE:
              (A) NAME/KEY: Peptide
              (B) LOCATION: 18..22
              (D) OTHER INFORMATION: /product= "OTHER"
                    /note= "The side chains of Lys at position 18 and Asp at
                    position 22 are linked by an amide bond."

(ix) FEATURE:
              (A) NAME/KEY: Peptide
              (B) LOCATION: 31
              (D) OTHER INFORMATION: /product= "OTHER"
                    /note= "This C-terminal amino acid is an amide, i.e.,
                    CONH2."

(xi) SEQUENCE DESCRIPTION: SEQ ID NO:84:

Ala Val Ser Glu Xaa Gln Leu Xaa His Asn Leu Gly Lys His Leu Asn
1               5                   10                  15

Ser Lys Glu Arg Val Asp Trp Leu Arg Lys Leu Leu Gln Asp Val
            20                  25                  30

(2) INFORMATION FOR SEQ ID NO:85:

(i) SEQUENCE CHARACTERISTICS:
              (A) LENGTH: 31 amino acids
              (B) TYPE: amino acid
              (C) STRANDEDNESS:
              (D) TOPOLOGY: Not Relevant (ii) MOLECULE TYPE: peptide (v) FRAGMENT TYPE: N-terminal (ix) FEATURE:
              (A) NAME/KEY: Peptide
              (B) LOCATION: 8
              (D) OTHER INFORMATION: /product= "OTHER"
                    /note= "The Xaa in position 8 is D-Proline."

(ix) FEATURE:
              (A) NAME/KEY: Peptide
              (B) LOCATION: 18..22
              (D) OTHER INFORMATION: /product= "OTHER"
                    /note= "The side chains of Lys at position 18 and Asp at
                    position 22 are linked by an amide bond."

(ix) FEATURE:
              (A) NAME/KEY: Peptide
              (B) LOCATION: 31
              (D) OTHER INFORMATION: /product= "OTHER"
                    /note= "This C-terminal amino acid is an amide, i.e.,
                    CONH2."

(xi) SEQUENCE DESCRIPTION: SEQ ID NO:85:

Ala Val Ser Glu Ile Gln Leu Xaa His Asn Leu Gly Lys His Leu Asn
1               5                   10                  15

Ser Lys Glu Arg Val Asp Trp Leu Arg Lys Leu Leu Gln Asp Val
            20                  25                  30

(2) INFORMATION FOR SEQ ID NO:86:

(i) SEQUENCE CHARACTERISTICS:

(A) LENGTH: 31 amino acids
        (B) TYPE: amino acid
        (C) STRANDEDNESS:
        (D) TOPOLOGY: Not Relevant (ii) MOLECULE TYPE: peptide (v) FRAGMENT TYPE: N-terminal (ix) FEATURE:
        (A) NAME/KEY: Peptide
        (B) LOCATION: 8
        (D) OTHER INFORMATION: /product= "Nle"

(ix) FEATURE:
        (A) NAME/KEY: Peptide
        (B) LOCATION: 11
        (D) OTHER INFORMATION: /product= "OTHER"
            /note= "The Xaa in position 11 is D-Proline."

(ix) FEATURE:
        (A) NAME/KEY: Peptide
        (B) LOCATION: 18..22
        (D) OTHER INFORMATION: /product= "OTHER"
            /note= "The side chains of Lys at position 18 and Asp at
            position 22 are linked by an amide bond."

(ix) FEATURE:
        (A) NAME/KEY: Peptide
        (B) LOCATION: 31
        (D) OTHER INFORMATION: /product= "OTHER"
            /note= "This C-terminal amino acid is an amide, i.e.,
            CONH2."

(xi) SEQUENCE DESCRIPTION: SEQ ID NO:86:

Ala Val Ser Glu Ile Gln Leu Xaa His Asn Xaa Gly Lys His Leu Asn
1               5                   10                  15

Ser Lys Glu Arg Val Asp Trp Leu Arg Lys Leu Leu Gln Asp Val
            20                  25                  30

(2) INFORMATION FOR SEQ ID NO:87:

(i) SEQUENCE CHARACTERISTICS:
        (A) LENGTH: 31 amino acids
        (B) TYPE: amino acid
        (C) STRANDEDNESS:
        (D) TOPOLOGY: Not Relevant (ii) MOLECULE TYPE: peptide (v) FRAGMENT TYPE: N-terminal (ix) FEATURE:
        (A) NAME/KEY: Peptide
        (B) LOCATION: 8
        (D) OTHER INFORMATION: /product= "Nle"

(ix) FEATURE:
        (A) NAME/KEY: Peptide
        (B) LOCATION: 12
        (D) OTHER INFORMATION: /product= "OTHER"
            /note= "The Xaa in position 12 is D-Proline."

(ix) FEATURE:
        (A) NAME/KEY: Peptide
        (B) LOCATION: 18..22
        (D) OTHER INFORMATION: /product= "OTHER"
            /note= "The side chains of Lys at position 18 and Asp at
            position 22 are linked by an amide bond."

(ix) FEATURE:
        (A) NAME/KEY: Peptide
        (B) LOCATION: 31
        (D) OTHER INFORMATION: /product= "OTHER"
            /note= "This C-terminal amino acid is an amide, i.e.,
            CONH2."

(xi) SEQUENCE DESCRIPTION: SEQ ID NO:87:

```
Ala Val Ser Glu Ile Gln Leu Xaa His Asn Leu Xaa Lys His Leu Asn
1               5                  10                  15

Ser Lys Glu Arg Val Asp Trp Leu Arg Lys Leu Leu Gln Asp Val
            20                  25                  30
```

(2) INFORMATION FOR SEQ ID NO:88:

(i) SEQUENCE CHARACTERISTICS:
        (A) LENGTH: 31 amino acids
        (B) TYPE: amino acid
        (C) STRANDEDNESS:
        (D) TOPOLOGY: Not Relevant (ii) MOLECULE TYPE: peptide (v) FRAGMENT TYPE: N-terminal (ix) FEATURE:
        (A) NAME/KEY: Peptide
        (B) LOCATION: 8
        (D) OTHER INFORMATION: /product= "Nle"

(ix) FEATURE:
        (A) NAME/KEY: Peptide
        (B) LOCATION: 13
        (D) OTHER INFORMATION: /product= "OTHER"
            /note= "The Xaa in position 13 is D-Proline."

(ix) FEATURE:
        (A) NAME/KEY: Peptide
        (B) LOCATION: 18..22
        (D) OTHER INFORMATION: /product= "OTHER"
            /note= "The side chains of Lys at position 18 and Asp at
            position 22 are linked by an amide bond."

(ix) FEATURE:
        (A) NAME/KEY: Peptide
        (B) LOCATION: 31
        (D) OTHER INFORMATION: /product= "OTHER"
            /note= "This C-terminal amino acid is an amide, i.e.,
            CONH2."

(xi) SEQUENCE DESCRIPTION: SEQ ID NO:88:

```
Ala Val Ser Glu Ile Gln Leu Xaa His Asn Leu Gly Xaa His Leu Asn
1               5                  10                  15

Ser Lys Glu Arg Val Asp Trp Leu Arg Lys Leu Leu Gln Asp Val
            20                  25                  30
```

PEPTIDE PARATHYROID HORMONE ANALOGS

CROSS REFERENCE TO RELATED APPLICATIONS

This is a continuation of International Patent Application No. PCT/US98/09843, filed May 13, 1998, which claims benefit of U.S. Ser. No. 60/046,742 filed May 14, 1997, now abandoned.

TECHNICAL FIELD

This invention is directed to compounds and their preparation, to pharmaceutical compositions containing the compounds and to their use in the treatment of physiological conditions capable of being modulated by agonist or antagonist activity on parathyroid hormone receptors. More particularly, this invention is directed to peptide parathyroid hormone analogs and peptide parathyroid hormone related protein analogs.

BACKGROUND OF THE INVENTION

Human parathyroid hormone (hPTH) is an 84 amino acid protein which is a major regulator of calcium homeostasis. Parathyroid hormone-related protein (hPTHrP) is a 139 to 171 amino acid protein with N-terminal homology to hPTH. The N-terminal fragments of hPTH and hPTHrP, particularly those consisting of amino acids 1–34, retain the full biological activity of the parent hormone.

hPTH(1–34) has the following amino acid sequence:
Ser-Val-Ser-Glu-Ile-Gln-Leu-Met-His-Asn-Leu-Gly-Lys-His-Leu-Asn-Ser-Met-
Glu-Arg-Val-Glu-Trp-Leu-Arg-Lys-Lys-Leu-Gln-Asp-Val-His-Asn-Phe. (SEQ ID NO: 1)

hPTHrP has the following amino acid sequence:
Ala-Val-Ser-Glu-His-Gln-Leu-Leu-His-Aso-Lys-Gly-Lys-Ser-Ile-(Gln-Aso-Leu-
Arg-Arg-Arg-Phe-Phe-Leu-His-His-Leu-Ile-Ala-Glu-Ile-His-Thr-Ala. (SEQ ID NO: 2)

The biological activity of hPTH is reflected in the activation of two secondary messenger systems: G-protein coupled adenylyl cyclase (AC) and G-protein coupled and uncoupled protein kinase C (PKC) activity. The N-terminal fragments hPTH(1–34)OH and hPTH(1–31)NH2 have been demonstrated to be anabolic with respect to bone formation in humans and ovariectomized rats, respectively. This increase in bone growth has been demonstrated to be coupled with stimulation of adenylyl cyclase activity. Analogs of these N-terminal fragments have significant therapeutic potential for the treatment of physiological conditions associated with bone cell calcium regulation including hypocalcemia; osteoporosis; osteopenia; and disorders associated with osteoporosis and osteopenia such as hyperparathyroidism, hypoparathyroidism, and Cushings syndrome; glucocorticoid- and immunosuppressant-induced osteopaenia; and bone fracture and bone refracture repair.

It has also been established that deletion of up to six amino acid residues from the N-terminus of hPTH(1–34) markedly decreases the resulting analog's ability to stimulate adenylyl cyclase while having little effect on receptor binding. Thus, analogs of hPTH(1–34) truncated by up to six amino acid residues at the N-teminus inhibit the action of PTH and are useful in the treatment of disorders characterized by an excess of PTH such as hyperparathyrodism and hyperparathyrodism-related hypercalcemia crisis, hypercalcemia of malignancy, renal failure and hypertension.

Acyclic analogs of hPTH(1–27) to (1–34) are disclosed in U.S. Pat. No. 4,086,196. Acyclic analogs of hPTH(1–34) and hPTHrP (1–34) are disclosed in U.S. Pat. No. 5,589,452. [Nle$^8$, Nle$^{18}$, Tyr$^{34}$, or Phe$^{34}$]hPTH(1–34) are disclosed in U.S. Pat. No. 4,656,250. [Nle$^8$, Nle$^{18}$, Tyr$^{34}$]hPTH(1–34) and N-truncated derivatives thereof are disclosed in U.S. Pat. Nos. 4,771,124 and 4,423,037. Other acyclic analogs of PTH(1–34) are disclosed in U.S. Pat. Nos. 5,723,577 and 5,434,246, WO 97/02834, EPA 561 412-A1, EPA 748,817-A2, WO-94/02510, WO9603437, and WO951 1988-A 1. Analogs of hPTH(1–28)NH$_2$ to hPTH(1–31)NH$_2$ and [Leu$^{27}$]hPTH(1–28)NH$_2$ to [Leu$^{27}$]hPTH(1–33)NH$_2$ are decribed in U.S. Pat. No. 5,556,940. Acyclic antagonists of the PTH receptor including N-terminally-truncated analogs of PTH are disclosed in U.S. Pat. Nos. 5,446,130, 5,229,489, 4,771,124 and 4,423,037.

Cyclic and bicyclic analogs of hPTH and hPTHrP have been disclosed. Cyclo(Lys$^{26}$-Asp$^{30}$)[Leu$^{27}$]hPTH(1–34)NH$_2$ and cyclo(Lys$^{27}$-Asp$^{30}$)hPTH(1–34)NH$_2$ are disclosed in U.S. Pat. No. 5,556,940. Cyclo(Lys$^{26}$-Asp$^{30}$)[Leu$^{27}$]hPTH(1–31)NH$_2$, cyclo(Glu$^{22}$-Lys$^{26}$)[Leu$^{27}$]hPTH(1–31)NH$_2$, and cyclo(Lys$^{27}$-Asp$^{30}$)hPTH(1–31)NH$_2$ are decribed by Barbier, et al., *J. Med. Chem.* 1997, 40, 1373. Monocyclic and bicyclic derivatives of hPTH(1–34) or hPTHrP(1–34) are disclosed in patent documents WO 96/40193. DE19508672-A1, and by A. Bisello. et al., in *Biochemistry* 1997, 36, 3293. Cyclo(Lys$^{13}$-Asp$^{17}$)hPTHrP(7–34)NH$_2$, a potent antagonist of the PTH rceptor, is disclosed by M. Chorev, et al., *Biochemistry* 1991, 30, 5698. Also, Kanmera, et al., has described a series of amide-containing analogs of hPTHrP, *Peptide Chemistry* 1993: Okada, Y., ed.; Protein Research Foundation, Osaka, 1994, 321–324."

SUMMARY OF THE INVENTION

This invention is directed to a cyclic peptide compound of formula I

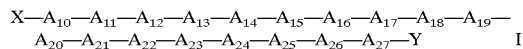

or a pharmaceutically acceptable salt or prodrug thereof wherein

X is selected from the group consisting of
(a) $R_{1a}$—$A_0$—$A_1$—$A_2$—$A_3$—$A_4$—$A_5$—$A_6$—$A_7$—$A_8$—$A_9$—,
(b) $R_{1a}$—$A_2$—$A_3$—$A_4$—$A_5$—$A_6$—$A_7$—$A_8$—$A_9$—,
(c) $R_{1b}$—$A_3$—$A_4$—$A_5$—$A_6$—$A_7$—$A_8$—$A_9$—,
(d) $R_{1a}$—$A_4$—$A_5$—$A_6$—$A_7$—$A_8$—$A_9$—,
(e) $R_{1a}$—$A_5$—$A_6$—$A_7$—$A_8$—$A_9$—,
(f) $R_{1a}$—$A_6$—$A_7$—$A_8$—$A_9$—,
(g) $R_{1a}$—$A_7$—$A_8$—$A_9$—,
(h) $R_{1a}$—$A_8$—$A_9$—,
(i) $R_{1a}$—$A_9$—, and
(j) $R_{1a}$—;

Y is selected from the group consisting of
(a) —$R_3$,
(b) —$A_{28}$—$R_3$,
(c) —$A_{28}$—$A_{29}$—$R_3$,
(d) —$A_{28}$—$A_{29}$—$A_{30}$—$R_3$,
(e) —$A_{28}$—$A_{29}$—$A_{30}$—$A_{31}$—$R_3$,
(f) —$A_{28}$—$A_{29}$—$A_{30}$—$A_{31}$—$A_{32}$—$R_3$,
(g) —$A_{28}$—$A_{29}$—$A_{30}$—$A_{31}$—$A_{32}$—$A_{33}$—$R_3$, and
(h) —$A_{28}$—$A_{29}$—$A_{30}$—$A_{31}$—$A_{32}$—$A_{33}$—$A_{34}$—$R_3$;

$R_{1a}$ is H, alkyl, aralkyl or —$COR_2$;

$R_{1b}$ is $R_{1a}$ or a group of formula

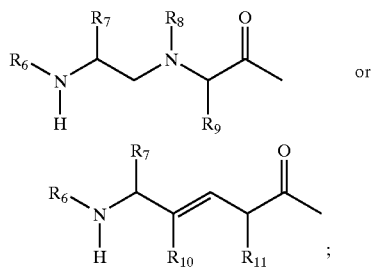

$R_2$ is alkyl, alkenyl, alkynyl, aryl or aralkyl;
$R_3$ is a group of formula $A_{35}$—$OR_4$ or $A_{35}$—$NR_4R_5$;
$R_4$ and $R_5$ are independently H or lower alkyl;
$R_6$ and $R_9$ are independently H or alkyl;
$R_7$ is alkyl;
$R_8$ is H, alkyl or $COR_2$;
$R_{10}$ is H or halogen;
$R_{11}$ is alkyl or aralkyl;
m is 1, 2 or 3;
n is 3 or 4;
$A_0$ is absent or a peptide of from one to six amino acid residues;
$A_1$ is Ser, Ala, Gly or D-Pro, or an equivalent amino acid thereof;
$A_2$ is Ala, Val or Gly, or an equivalent amino acid thereof;
$A_3$ is Ala, Ser, Gly or D-Pro, or an equivalent amino acid thereof;
$A_4$ is Glu, Ala or Gly, or an equivalent amino acid thereof;
$A_5$ is Ile, His, Ala or Gly, or an equivalent amino acid thereof;
$A_6$ is Ala, Gln, Gly or D-Pro, or an equivalent amino acid thereof;
$A_7$ is Ala, Leu, Gly, or an equivalent amino acid thereof;
$A_8$ is Leu, Nle, Gly or D-Pro, or an equivalent amino acid thereof;
$A_9$ is His, Ala, D-Pro or Gly, or an equivalent amino acid thereof;
$A_{10}$ is Ala, Asn, Asp, Cys, homo-Cys, Glu, Gly, Lys, Orn, Ser, Thr, D-Pro, —NHCH($CH_2$)$_m$$NH_2$)CO— or —NHCH[($CH_2$)$_n$$CO_2$H]CO—;
$A_{11}$ is Ala, Gly, Leu or Lys, or an equivalent amino acid thereof;
$A_{12}$ is Ala or Gly, or an equivalent amino acid thereof;
$A_{13}$ is Ala, Asn, Asp, Cys, homo-Cys, Glu, Gly, Lys, Orn, Ser, Thr, —NHCH($CH_2$)$_m$$NH_2$)CO— or —NHCH[($CH_2$)$_n$$CO_2$H]CO—;
$A_{14}$ is Ala, Asn, Asp, Cys, homo-Cys, Glu, Gly, His, Lys, Orn, Ser, Thr, D-Pro, —NHCH($CH_2$)$_m$$NH_2$)CO— or —NHCH[($CH_2$)$_n$$CO_2$H]CO—;
$A_{15}$ is Ala, Gly, Ile, D-Pro or Leu, or an equivalent amino acid thereof;
$A_{16}$ is Asn, Ala, Gly, D-Pro or Gln, or an equivalent amino acid thereof;
$A_{17}$ is Ala, Asn, Asp, Cys, homo-Cys, Glu, Gly, Lys, Orn, Ser, Thr, D-Pro, —NHCH($CH_2$)$_m$$NH_2$)CO— or —NHCH[($CH_2$)$_n$$CO_2$H]CO—;
$A_{18}$ is Asp, Cys, homo-Cys, Glu, His, Leu, Lys, Or, Nle, Ser, Thr, —NHCH($CH_2$)$_m$$NH_2$)CO— or —NHCH[($CH_2$)$_n$$CO_2$H]CO—;
$A_{19}$ is Arg or Glu, or an equivalent amino acid thereof;
$A_{20}$ is Arg or an equivalent amino acid thereof;
$A_{21}$ is Arg, Asp, Cys, homo-Cys, Glu, Lys, Orn, Ser, Thr, Val, —NHCH($CH_2$)$_m$$NH_2$)CO— or —NHCH[($CH_2$)$_n$$CO_2$H]CO—;
$A_{22}$ is Asp, Cys, homo-Cys, Glu, His, Lys, Orn, Phe, Ser, Thr, —NHCH($CH_2$)$_m$$NH_2$)CO— or —NHCH[($CH_2$)$_n$$CO_2$H]CO—;
$A_{23}$ is Leu, Phe or Trp, or an equivalent amino acid thereof;
$A_{24}$ is Leu or an equivalent amino acid thereof;
$A_{25}$ is Arg, Asp, Cys, homo-Cys, Glu, His, Lys, Orn, D-Pro, Ser, Thr, —NHCH($CH_2$)$_m$$NH_2$)CO— or —NHCH[($CH_2$)$_n$$CO_2$H]CO—;
$A_{26}$ is Asp, Cys, homo-Cys, Glu, His, Lys, Orn, Ser, Thr, —NHCH($CH_2$)$_m$$NH_2$)CO— or —NHCH[($CH_2$)$_n$$CO_2$H]CO—;
$A_{27}$ is Leu or Lys, or an equivalent amino acid thereof;
$A_{28}$ is Ile or Leu, or an equivalent amino acid thereof;
$A_{29}$ is Ala, Asp, Cys, homo-Cys, Glu, Gln, Lys, Orn, Ser, Thr, —NHCH($CH_2$)$_m$$NH_2$)CO— or —NHCH[($CH_2$)$_n$$CO_2$H]CO—;
$A_{30}$ is Asp, Cys, homo-Cys, Glu, Gly, Lys, Orn, Ser, Thr, —NHCH($CH_2$)$_m$$NH_2$)CO— or —NHCH[($CH_2$)$_n$$CO_2$H]CO—;
$A_{31}$ is Ile, Leu or Val, or an equivalent amino acid thereof;
$A_{32}$ is His, or an equivalent amino acid thereof;
$A_{33}$ is Asn or Thr, or an equivalent amino acid thereof;
$A_{34}$ is Ala or Phe, or an equivalent amino acid thereof;
$A_{35}$ is absent or a peptide of from 1 to 4 amino acids; and
the side chains of at least one of the following pairs of amino acid residues, $A_{10}$ and $A_{14}$, $A_{13}$ and $A_{17}$, $A_{14}$ and $A_{18}$, $A_{17}$ and $A_{21}$, $A_{18}$ and $A_{22}$, $A_{21}$ and $A_{25}$, $A_{25}$ and $A_{29}$ and $A_{26}$ and $A_{30}$ are linked through an amide, ester, disulfide or lanthionine bond to form a bridge, and the side chain of each of the following amino acid residues, $A_{10}$, $A_{13}$, $A_{14}$, $A_{17}$, $A_{18}$, $A_{21}$, $A_{22}$, $A_{25}$, $A_{26}$, $A_{29}$, and $A_{30}$ contributes, at most, to the formation of a single bridge; provided that when the side chains of the following pairs of amino acid acid residues, $A_{13}$ and $A_{17}$ or $A_{26}$ and $A_{30}$ are linked through an amide, disulfide or lanthionine bond to form a bridge, then the side chains of at least one of the following pairs of amino acid residues, $A_{10}$ and $A_{14}$, $A_{14}$ and $A_{18}$, $A_{17}$ and $A_{21}$, $A_{18}$ and $A_{22}$, $A_{21}$ and $A_{25}$ and $A_{25}$ and $A_{29}$ are also linked through an amide, ester, disulfide or lanthionine bond.

In another aspect, this invention is directed to a peptide compound of formula II

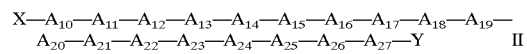

or a pharmaceutically acceptable salt or prodrug thereof wherein
X is selected from the group consisting of
(a) $R_{1a}$—$A_0$—$A_1$—$A_2$—$A_3$—$A_4$—$A_5$—$A_6$—$A_7$—$A_8$—$A_9$—,
(b) $R_{1a}$—$A_2$—$A_3$—$A_4$—$A_5$—$A_6$—$A_7$—$A_8$—$A_9$—,
(c) $R_{1b}$—$A_3$—$A_4$—$A_5$—$A_6$—$A_7$—$A_8$—$A_9$—,
(d) $R_{1a}$—$A_4$—$A_5$—$A_6$—$A_7$—$A_8$—$A_9$—,
(e) $R_{1a}$—$A_5$—$A_6$—$A_7$—$A_8$—$A_9$—,
(f) $R_{1a}$—$A_6$—$A_7$—$A_8$—$A_9$—,
(g) $R_{1a}$—$A_7$—$A_8$—$A_9$—, (h) $R_{1a}$—$A_8$—$A_9$—,
(i) $R_{1a}$—$A_9$—, and
(j) $R_{1a}$—;

Y is selected from the group consisting of
(a) —$R_3$,
(b) —$A_{28}$—$R_3$,
(c) —$A_{28}$—$A_{29}$—$R_3$,
(d) —$A_{28}$—$A_{29}$—$A_{30}$—$R_3$,
(e) —$A_{28}$—$A_{29}$—$A_{30}$—$A_{31}$—$R_3$,
(f) —$A_{28}$—$A_{29}$—$A_{30}$—$A_{31}$—$A_{32}$—$R_3$,
(g) —$A_{28}$—$A_{29}$—$A_{30}$—$A_{31}$—$A_{32}$—$A_{33}$—$R_3$, and
(h) —$A_{28}$—$A_{29}$—$A_{30}$—$A_{31}$—$A_{32}$—$A_{33}$—$A_{34}$—$R_3$;

$R_{1a}$ is H, alkyl, aralkyl or —$COR_2$;
$R_{1b}$ is $R_{1a}$ or a group of formula

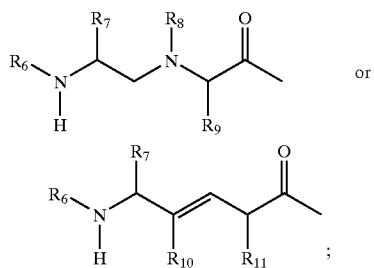

or ;

$R_2$ is alkyl, alkenyl, alkynyl, aryl or aralkyl;
$R_3$ is a group of formula $A_{35}$—$OR_4$ or $A_{35}$—$NR_4R_5$;
$R_4$ and $R_5$ are independently H or lower alkyl;
$R_6$ and $R_9$ are independently H or alkyl;
$R_7$ is alkyl;
$R_8$ is H, alkyl or $COR_2$;
$R_{10}$ is H or halogen;
$R_{11}$ is alkyl or aralkyl;
$A_0$ is absent or a peptide of from one to six amino acid residues;
$A_1$ is Ser, Ala, Gly or D-Pro, or an equivalent amino acid thereof;
$A_2$ is Ala, Val or Gly, or an equivalent amino acid thereof;
$A_3$ is Ala, Ser, Gly or D-Pro, or an equivalent amino acid thereof;
$A_4$ is Glu, Ala or Gly, or an equivalent amino acid thereof;
$A_5$ is Ile, His, Ala or Gly, or an equivalent amino acid thereof;
$A_6$ is Ala, Gln, Gly or D-Pro, or an equivalent amino acid thereof;
$A_7$ is Ala, Leu or Gly, or an equivalent amino acid thereof;
$A_8$ is Leu, Nle, Gly or D-Pro, or an equivalent amino acid thereof;
$A_9$ is His, Ala, Gly or D-Pro, or an equivalent amino acid thereof;
$A_{10}$ is Ala, Asn, Gly Lys, Asp or D-Pro, or an equivalent amino acid thereof;
$A_{11}$ is Ala, Gly, Leu or Lys, or an equivalent amino acid thereof;
$A_{12}$ is Ala or Gly, or an equivalent amino acid thereof;
$A_{13}$ is Ala, Gly or Lys, or an equivalent amino acid thereof;
$A_{14}$ is Ala, Gly, His, Ser, Asp, Lys or D-Pro, or an equivalent amino acid thereof;
$A_{15}$ is Ala, Gly, Ile, D-Pro or Leu, or an equivalent amino acid thereof;
$A_{16}$ is Asn, Ala, Gly, D-Pro or Gln, or an equivalent amino acid thereof;
$A_{17}$ is Ala, Asp, Gly, Ser, Lys or D-Pro, or an equivalent amino acid thereof;
$A_{18}$ is Lys, or an equivalent amino acid thereof;
$A_{19}$ is Arg or Glu, or an equivalent amino acid thereof;
$A_{20}$ is Arg, or an equivalent amino acid thereof;
$A_{21}$ is Arg, Lys, Asp or Val, or an equivalent amino acid thereof;
$A_{22}$ is Asp, Lys, Orn or Glu, or an equivalent amino acid thereof;
$A_{23}$ is Leu, Phe or Trp, or an equivalent amino acid thereof;
$A_{24}$ is Leu, or an equivalent amino acid thereof;
$A_{25}$ is Arg, His, Asp, Lys or Glu, or an equivalent amino acid thereof;
$A_{26}$ is Lys or His, or an equivalent amino acid thereof;
$A_{27}$ is Leu or Lys, or an equivalent amino acid thereof;
$A_{28}$ is Ile or Leu, or an equivalent amino acid thereof;
$A_{29}$ is Ala, Asp, Glu or Gln, or an equivalent amino acid thereof;
$A_{30}$ is Asp, Lys or Glu, or an equivalent amino acid thereof;
$A_{31}$ is Ile, Leu or Val, or an equivalent amino acid thereof;
$A_{32}$ is His, or an equivalent amino acid thereof;
$A_{33}$ is Asn, or an equivalent amino acid thereof; and
$A_{34}$ is Ala or Phe, or an equivalent amino acid thereof; and
$A_{35}$ is absent or a peptide of from 1 to 4 amino acids.

The peptide compounds of the present invention possess useful properties, more particularly pharmaceutical properties. They are especially useful for treating disease states capable of being modulated by compounds which bind to parathyroid hormone receptors either with or without commitant stimulation of adenylyl cyclase activity. The present invention is therefore also directed to the pharmaceutical use of the peptide compounds and pharmaceutical compositions containing the peptide compounds.

DETAILED DESCRIPTION OF THE INVENTION

As used above and throughout the specification, the following terms, unless otherwise indicated, shall be understood to have the following meanings.

Definitions of Terms

"Patient" includes both human and other mammals.

"Alkyl" means an aliphatic hydrocarbon group which may be straight or branched having about 1 to about 20 carbon atoms in the chain. Branched means that one or more lower alkyl groups are attached to a linear alkyl chain. "Lower alkyl" means about 1 to 4 carbon atoms in the chain which may be straight or branched. Alkyl groups are exemplified by methyl, ethyl, n- and iso-propyl, n-, sec-, iso- and tert-butyl, and the like.

"Alkenyl" means aliphatic hydrocarbon group containing a carbon-carbon double bond and which may be straight or branched having about 2 to about 20 carbon atoms in the chain. "Lower alkenyl" means about 2 to 4 carbon atoms in the chain which may be straight or branched. Exemplary alkenyl groups include ethenyl, propenyl, n-butenyl, i-butenyl, 3-methylbut-2-enyl, n-pentenyl, heptenyl, octenyl, cyclohexylbutenyl and decenyl.

"Alkynyl" means aliphatic hydrocarbon group containing a carbon-carbon triple bond and which may be straight or branched having about 2 to about 20 carbon atoms in the chain. "Lower alkynyl" means about 2 to 4 carbon atoms in the chain which may be straight or branched. Exemplary alkynyl groups include ethynyl, propynyl, n-butynyl, 3-methylbut-2-ynyl, n-pentynyl, heptynyl, octynyl and decynyl.

"Alkylene" denotes a divalent group derived from a straight or branched chain saturated hydrocarbon by the removal of two hydrogen atoms, for example methylene, 1,2-ethylene, 1,1-ethylene, 1,3-propylene, 2,2-dimethylpropylene, and the like.

"Aralkyl" means an aryl group attached to the parent molecular moiety through an alkylene. Preferred aralkyls contain a lower alkyl moiety. Representative aralkyl groups include benzyl, 2-phenethyl, naphthlenemethyl. and the like. A preferred aralkyl group is benzyl.

"Aryl" means an aromatic monocyclic or multicyclic ring system of 6 to about 14 carbon atoms. preferably of about 6 to about 10 carbon atoms. The aryl is optionally substituted with one or more substituents selected from alkyl, hydroxy, halogen and haloalkyl. Representative aryl groups include phenyl and naphtlyl.

"Amino acid" means an amino acid selected from the group consisting of natural and unnaturai amino acids as defined herein. The amino acids may be neutral, positive or negative depending on the substituents in the side chain. "Neutral amino acid" means an amino acid containing uncharged side chain substituents. Exemplary neutral amino acids include alanine, valine, leucine, isoleucine, proline, phenylalanine, tryptophan, methionine, glycine, serine, threonine and cysteine. "Positive amino acid" means an amino acid in which the side chain substituents are positively charged at physiological pH. Exemplary positive amino acids include lysine, arginine and histidine. "Negative amino acid" means an amino acid in which the side chain substituents bear a net negative charge at physiological pH. Exemplary negative amino acids include aspartic acid and glutamic acid. Preferred amino acids are α-amino acids. The most preferred amino acids are α-amino acids having L stereochemistry at the α-carbon.

"Natural amino acid" means an α-amino acid selected from the group consisting of alanine, valine, leucine, isoleucine, proline, phenylalanine, tryptophan, methionine, glycine, serine, threonine, cysteine, tyrosine, asparagine, glutamine, lysine, arginine, histidine, aspartic acid and glutamic acid.

"Unnatural amino acid" means an amino acid for which is no nucleic acid codon. Examples of unnatural amino acids include, for example, the D-isomers of the natural α-amino acids such as D-proline (D-P, D-Pro) as indicated above; Aib (aminobutyric acid), bAib (3-aminoisobutyric acid), Nva (norvaline), β-Ala, Aad (2-aminoadipic acid), bAad (3-aminoadipic acid), Abu (2-aminobutyric acid), Gaba (γ-aminobutyric acid), Acp (6-aminocaproic acid), Dbu (2,4-diaminobutryic acid), α-aminopimelic acid, TMSA (trimethylsilyl-Ala), aIle (allo-isoleucine), Nle (norleucine), tert-Leu, Cit (citrulline), Orn (ornithine, O), Dpm (2,2'-diaminopimelic acid), Dpr (2,3-diaminopropionic acid), α- or β-Nal, Cha (cyclohexyl-Ala), hydroxyproline, Sar (sarcosine), and the like; cyclic amino acids; $N^\alpha$-alkylated amino acids such as MeGly ($N^\alpha$-methylglycine), EtGly ($N^\alpha$-ethylglycine) and EtAsn ($N^\alpha$-ethylasparagine); and amino acids in which the α-carbon bears two side-chain substituents.

"Peptide" and "polypeptide" mean a polymer in which the monomers are amino acid residues joined together through amide bonds. Preferred peptide compounds of the present invention are those comprising α-amino acids. "Peptide compound" means a compound comprising a peptide as defined herein.

"Amino acid residue" means the individual amino acid units incorporated into the peptide compounds of the invention.

The names of natural and unnatural amino acids and residues thereof used herein follow the naming conventions suggested by the IUPAC Commission on the Nomenclature of Organic Chemistry and the IUPAC-IUB Commission on Biochemical Nomenclature as set out in "Nomenclature of α-Amino Acids (Recommendations, 1974)" Biochemistry, 14(2), (1975). To the extent that the names and abbreviations of amino acids and residues thereof employed in this specification and appended claims differ from those noted, differing names and abbreviations will be made clear.

"Equivalent amino acid" means an amino acid which may be substituted for another amino acid in the peptide compounds according to the invention without any appreciable loss of function. In making such changes, substitutions of like amino acids is made on the basis of relative similarity of side chain substituents, for example regarding size, charge, hydrophilicity, hydropathicity and hydrophobicity as described herein. The phrase "or an equivalent amino acid thereof" when used following a list of individual amino acids means an equivalent of each of the individual amino acids included in the list.

As detailed in U.S. Pat. No. 4,554,101, incorporated herein by reference, the following hydrophilicity values have been assigned to amino acid residues: Arg (+3.0); Lys (+3.0); Asp (+3.0); Glu (+3.0); Ser (+0.3); Asn (+0.2); Gln (+0.2); Gly (0); Pro (−0.5); Thr (−0.4); Ala (−0.5); Cys (−1.0); Met (−1.3); Val (−1.5); Leu (−1.8); Ile (−1.8); Tyr (−2.3); Phe (−2.5); and Trp (−3.4). It is understood that an amino acid residue can be substituted for another having a similar hydrophilicity value (e.g., within a value of plus or minus 2.0) and still obtain a biologically equivalent polypeptide.

In a similar manner, substitutions can be made on the basis of similarity in hydropathic index. Each amino acid residue has been assigned a hydropathic index on the basis of its hydrophobicity and charge characteristics. Those hydropathic index values are: Ile (+4.5); Val (+4.2); Leu (+3.8); Phe (+2.8); Cys (+2.5); Met (+1.9); Ala (+1.8); Gly (−0.4); Thr (−0.7); Ser (−0.8); Trp (−0.9); Tyr (−1.3); Pro (−1.6); His (−3.2); Glu (−3.5); Gln (−3.5); Asp (−3.5); Asn (−3.5); Lys (−3.9); and Arg (−4.5). In making a substitution based on the hydropathic index, a value of within plus or minus 2.0 is preferred.

In the peptide compounds of this invention, the ester, amide, disulfide or lanthionine bond which links two amino acid residues is formed between the side-chain functionalities. Thus, an amide is bond is formed between the side-chain carboxyl group of an acidic amino acid residue and the side-chain amino group of a basic amino acid residue. Preferred acidic amino acid residues include Asp, Glu, —NHCH[(CH$_2$)$_3$CO$_2$H]CO— and —NHCH[(CH$_2$)$_4$CO$_2$H]CO—, Asp being most preferred. Preferred basic amino acid residues include His, Lys, Orn, —NHCH(CH$_2$NH$_2$)CO— and —NHCH[(CH$_2$)$_2$NH$_2$]CO—, Lys being most preferred.

Ester bonds are formed between the side-chain carboxyl group of an acidic amino acid residue as described above and the side chain hydroxy group of an amino acid residue such as Ser, Thr, Tyr and the like, Ser and Thr being especially preferred.

Disulfides are formed from amino acid residues containing side chain sulfhydryl groups. Cys is especiaiiy preferred for the tormation or disulfide bonds. Lanthionine bridges are formed by desulfurization of the corresponding disulfide.

The number of atoms in the bridge resulting from the amide, ester, disulfide or lanthionine bond formed as described above will vary depending on the length of the side chain and the type of bond (i.e., amide, ester, disulfide or lanthionine). The bridge preferably comprises from 4 to 12 atoms, more preferably from 6 to 10 atoms. A further preferred number of atoms contained in the bridge is 7, this bridge preferably comprising an amide bond between the side-chain functionalities of a Lys and an Asp residue.

A representative peptide compound of the present invention is denoted, for example, as cyclo($K^{18}$—$D^{22}$)[$A^1$, $Nle^8$, $K^{18}$, $D^{22}$, $L^{27}$]hPTH(1–31)$NH_2$ with the linked amino acid residues in the parenthesis following "cyclo" and substituted amino acids from the natural sequence are placed in brackets. hPTH stands for human parathyroid hormone and hPTHrP for human parathyroid hormone-related protein. The numbers in the second parenthesis refer to the number of amino acid residues in the peptide compound, beginning at the N-terminus (i.e., the first 31 amino acids of hPTH).

Where the peptide compound of the present invention is substituted with a basic moiety, acid addition salts are formed and are simply a more convenient form for use; and in practice, use of the salt form inherently amounts to use of the free base form. The acids which can be used to prepare the acid addition salts include preferably those which produce, when combined with the free base, pharmaceutically acceptable salts, that is, salts whose anions are non-toxic to the patient in pharmaceutical doses of the salts, so that the beneficial effects inherent in the free base are not vitiated by side effects ascribable to the anions. Although pharmaceutically acceptable salts of said basic compounds are preferred, all acid addition salts are useful as sources of the free base form even if the particular salt, per se, is desired only as an intermediate product as, for example, when the salt is formed only for purposes of purification, and identification, or when it is used as intermediate in preparing a pharmaceutically acceptable salt by ion exchange procedures. Pharmaceutically acceptable salts within the scope of the invention are those derived from the following acids: mineral acids such as hydrochloric acid, sulfuric acid, phosphoric acid and sulfamic acid; and organic acids such as acetic acid, citric acid, lactic acid, tartaric acid, malonic acid, methanesufoniic acid, ethanesulfonic acid, benzenesulfonic acid, p-toluenesulfonic acid, cyclohexylsulfamic acid, quinic acid, and the like. The corresponding acid addition salts comprise the following: hydrohalides, e.g. hydrochloride and hydrobromide, sulfate, phosphate, nitrate, sulfamate, acetate, citrate, lactate, tartarate, malonate, oxalate, salicylate, propionate, succinate, fumarate, maleate, methylene-bis-β-hydroxynaphthoates, gentisates, mesylates, isethionates and di-p-toluoyltartratesmethanesulfonate, ethanesulfonate, benzenesulfonate, p-toluenesulfonate, cyclolhexylsulfamate and quinate, respectively.

According to a further feature of the invention, acid addition saits of the peptide compounds of this invention are prepared by reaction of the free base with the appropriate acid, by the application or adaptation of known methods. For example, the acid addition salts of the peptide compounds of this invention are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

Preferred acid addition salts are the trifluoroacetate, acetate and hydrochloride. The acetate and tetrahydrochloride salts are especially preferred.

The peptide compounds of this invention can be regenerated from the salts by the application or adaptation of known methods. For example, parent peptide compounds of the invention can be regenerated from their acid addition salts by treatment with an alkali, e.g. aqueous sodium bicarbonate solution or aqueous ammonia solution.

Where the peptide compound of the invention is substituted with an acidic moiety, base addition salts may be formed and are simply a more convenient form for use; and in practice, use of the salt form inherently amounts to use of the free acid form. The bases which can be used to prepare the base addition salts include preferably those which produce, when combined with the free acid, pharmaceutically acceptable salts, that is, salts whose cations are non-toxic to the animal organism in pharmaceutical doses of the salts, so that the beneficial effects inherent in the free acid are not vitiated by side effects ascribable to the cations. Pharmaceutically acceptable salts, including for example alkali and alkaline earth metal salts, within the scope of the invention are those derived from the following bases: sodium hydride, sodium hydroxide, potassium hydroxide, calcium hydroxide, aluminum hydroxide, lithium hydroxide, magnesium hydroxide, zinc hydroxide, ammonia, trimethylammonia, triethylammonia, ethylenediamine, n-methyl-glucamine, lysine, arginine, ornithine, choline, N,N'-dibenzylethylenediamine, chloroprocaine, diethanolamine, procaine, n-benzylphenethylamine, diethylamine, piperazine, tris (hydroxymethyl)aminomethane, tetramethylammmonium hydroxide, and the like.

Metal salts of peptide compounds of the present invention may be obtained by contacting a hydride, hydroxide, carbonate or similar reactive compound of the chosen metal in an aqueous or organic solvent with the free acid form of the peptide compound. The aqueous solvent employed may be water or it may be a mixture of water with an organic solvent, preferably an alcohol such as methanol or ethanol, a ketone such as acetone, an aliphatic ether such as tetrahydrofuran, or an ester such as ethyl acetate. Such reactions are normally conducted at ambient temperature but they may, if desired, be conducted with heating.

Amine salts of peptide compounds of the present invention may be obtained by contacting an amine in an aqueous or organic solvent with the free acid form of the peptide compound. Suitable aqueous solvents include water and mixtures of water with alcohols such as methanol or ethanol, ethers such as tetrahydrofuran, nitriles such as acetonitrile, or ketones such as acetone. Amino acid salts may be similarly prepared.

The base addition salts of the peptide compounds of this invention can be regenerated from the salts by the application or adaptation of known methods. For example, parent peptide compounds of the invention can be regenerated from their base addition salts by treatment with an acid, e.g. hydrochloric acid.

As well as being useful in themselves as active compounds, salts of peptide compounds of the invention are useful for the purposes of purification of the peptide compounds, for example by exploitation of the solubility differences between the salts and the parent peptide compounds. side products and/or starting materials by techniques well known to those skilled in the art.

"Pharmaceutically acceptable ester" means esters which hydrolyze in vivo and include those that break down readily in the human body to leave the parent peptide compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters includes formates, acetates, propionates, butyrates, acrylates and ethylsuccinates.

"Prodrug" means a compound which is rapidly transformed in vivo to yield the parent peptide compound, for example by hydrolysis in blood. "Pharmaceutically acceptable prodrug" means a compound which is, within the scope of sound medical judgement, suitable for pharmaceutical use in a patient without undue toxicity, irritation, allergic response, and the like, and effective for the intended use, including a pharmaceutically acceptable ester as well as a zwitterionic form, where possible, of the peptide compounds of the invention. Pharmaceutically acceptable prodrugs according to the invention are described in T. Higuchi and V. Stella, *Pro-drugs as Novel Delivery Systems*, Vol. 14 of the A.C.S. Symposium Series, and in Edward B. Roche, ed., *Bioreversible Carriers in Drug Design*, American Pharmaceutical Association and Pergamon Press, 1987, both of which are incorporated herein by reference.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolable solvates. Representative solvates include ethanoiates, methanolates, and the like. "Hydrate" is a solvate wherein the solvent molecule (s) is/are $H_2O$.

The peptide compounds of the present invention may contain asymmetric centers in addition to the chiral centers in the backbone of the peptide compound. These asymmetric centers may independently be in either the R or S configuration. It will also be apparent to those skilled in the art that certain peptide compounds of formula I may exhibit geometrical isomerism. Geometrical isomers include the cis and trans forms of peptide compounds of the invention having alkenyl moieties. The present invention comprises the individual geometrical isomers and stereoisomers and mixtures thereof.

Such isomers can be separated from their mixtures. by the application or adaptation of known methods, for example chromatographic techniques and recrystallization techniques, or they are separately prepared from the appropriate isomers of their intermediates, for example by the application or adaptation of methods described herein.

Preferred Embodiments

Peptide compounds contemplated as falling within the scope of the present invention include, but are not limited to
cyclo($K^{18}$—$D^{22}$)[$A^1$,$Nle^8$,$K^{18}$,$D^{22}$,$L^{27}$]hPTH(1–31)$NH_2$ (SEQ ID NO: 3)
[$A^1$,$Nle^8$,$K^{18}$,$D^{22}$,$L^{27}$]hPTH(1–31)$NH_2$ (SEQ ID NO: 4)

cyclo($K^{18}$—$D^{22}$)[$A^{1,2}Nle^8$,$K^{18}$,$D^{22}$,$L^{27}$]hPTH(1–31)$NH_2$ (SEQ ID NO: 5)
cyclo($K^{18}$—$D^{22}$)[$A^{1,3}Nle^8$,$K^{18}$,$D^{22}$,$L^{27}$]hPTH(1–31)$NH_2$ (SEQ ID NO: 6)
cyclo($K^{18}$—$D^{22}$)[$A^{1,4}Nle^8$,$K^{18}$,$D^{22}$,$L^{27}$]hPTH(1–31)$NH_2$ (SEQ ID NO: 7)
cyclo($K^{18}$—$D^{22}$)[$A^{1,5}Nle^8$,$K^{18}$,$D^{22}$,$L^{27}$]hPTH(1–31)$NH_2$ (SEQ ID NO: 8)
cyclo($K^{18}$—$D^{22}$)[$A^{1,6}Nle^8$,$K^{18}$,$D^{22}$,$L^{27}$]hPTH(1–31)$NH_2$ (SEQ ID NO: 9)
cyclo($K^{18}$—$D^{22}$)[$A^{1,7}Nle^8$,$K^{18}$,$D^{22}$,$L^{27}$]hPTH(1–31)$NH_2$ (SEQ ID NO: 10)
cyclo($K^{18}$—$D^{22}$)[$A^{1,9}Nle^8$,$K^{18}$,$D^{22}$,$L^{27}$]hPTH(1–31)$NH_2$ (SEQ ID NO: 11)
cyclo($K^{18}$—$D^{22}$)[$A^{1,10}Nle^8$,$K^{18}$,$D^{22}$,$L^{27}$]hPTH(1–31)$NH_2$ (SEQ ID NO: 12)
cyclo($K^{18}$—$D^{22}$)[$A^{1,11}Nle^8$,$K^{18}$,$D^{22}$,$L^{27}$]hPTH(1–31)$NH_2$ (SEQ ID NO: 13)
cyclo($K^{18}$—$D^{22}$)[$A^{1,12}Nle^8$,$K^{18}$,$D^{22}$,$L^{27}$]hPTH(1–31)$NH_2$ (SEQ ID NO: 14)
cyclo($K^{18}$—$D^{22}$)[$A^{1,13}Nle^8$,$K^{18}$,$D^{22}$,$L^{27}$]hPTH(1–31)$NH_2$ (SEQ ID NO: 15)
cyclo($K^{18}$—$D^{22}$)[$A^{1,14}Nle^8$,$K^{18}$,$D^{22}$,$L^{27}$]hPTH(1–31)$NH_2$ (SEQ ID NO: 16)
cyclo($K^{18}$—$D^{22}$)[$A^{1,15}Nle^8$,$K^{18}$,$D^{22}$,$L^{27}$]hPTH(1–31)$NH_2$ (SEQ ID NO: 17)
cyclo($K^{18}$—$D^{22}$)[$A^{1,16}Nle^8$,$K^{18}$,$D^{22}$,$L^{27}$]hPTH(1–31)$NH_2$ (SEQ ID NO: 18)
cyclo($K^{18}$—$D^{22}$)[$A^{1,17}Nle^8$,$K^{18}$,$D^{22}$,$L^{27}$]hPTH(1–31)$NH_2$ (SEQ ID NO: 19)
cyclo($K^{18}$—$D^{22}$)[$G^1$,$Nle^8$,$K^{18}$,$D^{22}$,$L^{27}$]hPTH(1–31)$NH_2$ (SEQ ID NO: 20)
cyclo($K^{18}$—$D^{22}$)[$A^1$,$G^2Nle^8$,$K^{18}$,$D^{22}$,$L^{27}$]hPTH(1–31)$NH_2$ (SEQ ID NO: 21)
cyclo($K^{18}$—$D^{22}$)[$A^1$,$G^3Nle^8$,$K^{18}$,$D^{22}$,$L^{27}$]hPTH(1–31)$NH_2$ (SEQ ID NO: 22)
cyclo($K^{18}$—$D^{22}$)[$A^1$,$G^4Nle^8$,$K^{18}$,$D^{22}$,$L^{27}$]hPTH(1–31)$NH_2$ (SEQ ID NO: 23)
cyclo($K^{18}$—$D^{22}$)[$A^1$,$G^5Nle^8$,$K^{18}$,$D^{22}$,$L^{27}$]hPTH(1–31)$NH_2$ (SEQ ID NO: 24)
cyclo($K^{18}$—$D^{22}$)[$A^1$,$G^6Nle^8$,$K^{18}$,$D^{22}$,$L^{27}$]hPTH(1–31)$NH_2$ (SEQ ID NO: 25)
cyclo($K^{18}$—$D^{22}$)[$A^1$,$G^7Nle^8$,$K^{18}$,$D^{22}$,$L^{27}$]hPTH(1–31)$NH_2$ (SEQ ID NO: 26)
cyclo($K^{18}$—$D^{22}$)[$A^1$,$G^8$,$K^{18}$,$D^{22}$,$L^{27}$]hPTH(1–31)$NH_2$ (SEQ ID NO: 27)
cyclo($K^{18}$—$D^{22}$)[$A^1$,$G^9Nle^8$,$K^{18}$,$D^{22}$,$L^{27}$]hPTH(1–31)$NH_2$ (SEQ ID NO: 28)
cyclo($K^{18}$—$D^{22}$)[$A^1$,$G^{10}Nle^8$,$K^{18}$,$D^{22}$,$L^{27}$]hPTH(1–31)$NH_2$ (SEQ ID NO: 29)
cyclo($K^{18}$—$D^{22}$)[$A^1$,$G^{11}Nle^8$,$K^{18}$,$D^{22}$,$L^{27}$]hPTH(1–31)$NH_2$ (SEQ ID NO: 30)
cyclo($K^{18}$—$D^{22}$)[$A^1$,$G^{13}Nle^8$,$K^{18}$,$D^{22}$,$L^{27}$]hPTH(1–31)$NH_2$ (SEQ ID NO: 31)
cyclo($K^{18}$—$D^{22}$)[$A^1$,$G^{14}Nle^8$,$K^{18}$,$D^{22}$,$L^{27}$]hPTH(1–31)$NH_2$ (SEQ ID NO: 32)
cyclo($K^{18}$—$D^{22}$)[$A^1$,$G^{15}Nle^8$,$K^{18}$,$D^{22}$,$L^{27}$]hPTH(1–31)$NH_2$ (SEQ ID NO: 33)
cyclo($K^{18}$—$D^{22}$)[$A^1$,$G^{16}Nle^8$,$K^{18}$,$D^{22}$,$L^{27}$]hPTH(1–31)$NH_2$ (SEQ ID NO: 34)
cyclo($K^{18}$—$D^{22}$)[$A^1$,$G^{17}Nle^8$,$K^{18}$,$D^{22}$,$L^{27}$]hPTH(1–31)$NH_2$ (SEQ ID NO: 35)

cyclo($K^{18}$—$D^{22}$)[D—$P^1$,Nle$^8$,$K^{18}$,$D^{22}$,$L^{27}$]hPTH(1–31)NH$_2$ (SEQ ID NO: 36)

cyclo($K^{18}$—$D^{22}$)[$A^1$,D—$P^3$,Nle$^8$,$K^{18}$,$D^{22}$,$L^{27}$]hPTH(1–31)NH$_2$ (SEQ ID NO: 37)

cyclo($K^{18}$—$D^{22}$)[$A^1$,D—$P^6$,Nle$^8$,$K^{18}$,$D^{22}$,$L^{27}$]hPTH(1–31)NH$_2$ (SEQ ID NO: 38)

cyclo($K^{18}$—$D^{22}$)[$A^1$,D—$P^7$,Nle$^8$,$K^{18}$,$D^{22}$,$L^{27}$]hPTH(1–31)NH$_2$ (SEQ ID NO: 39)

cyclo($K^{18}$—$D^{22}$)[$A^1$,D—$P^9$,Nle$^8$,$K^{18}$,$D^{22}$,$L^{27}$]hPTH(1–31)NH$_2$ (SEQ ID NO: 40)

cyclo($K^{18}$—$D^{22}$)[$A^1$,D—$P^{10}$,Nle$^8$,$K^{18}$,$D^{22}$,$L^{27}$]hPTH(1–31)NH$_2$ (SEQ ID NO: 41)

cyclo($K^{18}$—$D^{22}$)[$A^1$,D—$P^{14}$,Nle$^8$,$K^{18}$,$D^{22}$,$L^{27}$]hPTH(1–31)NH$_2$ (SEQ ID NO: 42)

cyclo($K^{18}$—$D^{22}$)[$A^1$,D—$P^{15}$,Nle$^8$,$K^{18}$,$D^{22}$,$L^{27}$]hPTH(1–31)NH$_2$ (SEQ ID NO: 43)

cyclo($K^{18}$—$D^{22}$)[$A^1$,D—$P^{16}$,Nle$^8$,$K^{18}$,$D^{22}$,$L^{27}$]hPTH(1–31)NH$_2$ (SEQ ID NO: 44)

cyclo($K^{18}$—$D^{22}$)[$A^1$,D—$P^{17}$,Nle$^8$,$K^{18}$,$D^{22}$,$L^{27}$]hPTH(1–31)NH$_2$ (SEQ ID NO: 45)

cyclo($K^{18}$—$D^{22}$)[$A^1$,Nle$^8$,$K^{18}$,$D^{22}$,$L^{27}$]hPTH(1–34)NH$_2$ (SEQ ID NO: 46)

cyclo($D^{18}$—$K^{22}$)[$A^1$,Nle$^8$,$D^{18}$,$K^{22}$,$L^{27}$]hPTH(1–31)NH$_2$ (SEQ ID NO: 47)

cyclo($O^{18}$—$D^{22}$)[$A^1$,Nle$^8$,$O^{18}$,$D^{22}$,$L^{27}$]hPTH(1–31)NH$_2$ (SEQ ID NO: 48)

cyclo($D^{18}$—$O^{22}$)[$A^1$,Nle$^8$,$D^{18}$,$O^{22}$,$L^{27}$]hPTH(1–31)NH$_2$ (SEQ ID NO: 49)

cyclo($K^{18}$—$E^{22}$)[$A^1$,Nle$^8$,$K^{18}$,$E^{22}$,$L^{27}$]hPTH(1–31)NH$_2$ (SEQ ID NO: 50)

cyclo($O^{18}$—$E^{22}$)[$A^1$,Nle$^8$,$O^{18}$,$E^{22}$,$L^{27}$]hPTH(1–31)NH$_2$ (SEQ ID NO: 51)

cyclo($K^{18}$—$D^{22}$)[$A^1$,Nle$^8$,$K^{18}$,$D^{22}$,$L^{27}$]hPTH(1–30)NH$_2$ (SEQ ID NO: 52)

cyclo($K^{18}$—$D^{22}$)[$A^1$,Nle$^8$,$K^{18}$,$D^{22}$,$L^{27}$]hPTH(1–29)NH$_2$ (SEQ ID NO: 53)

cyclo($K^{18}$—$D^{22}$)[$A^1$,Nle$^8$,$K^{18}$,$D^{22}$,$L^{27}$]hPTH(1–28)NH$_2$ (SEQ ID NO: 54)

cyclo($K^{18}$—$D^{22}$)[$A^1$,Nle$^8$,$K^{18}$,$D^{22}$,$L^{27}$]hPTH(1–27)NH$_2$ (SEQ ID NO: 55)

cyclo($K^{18}$—$D^{22}$)[$K^{18}$,$D^{22}$,$L^{27}$]hPTH(10–31)NH$_2$ (SEQ ID NO: 56)

cyclo($K^{18}$—$D^{22}$)[$K^{18}$,$D^{22}$,$L^{27}$]hPTH(9–31)NH$_2$ (SEQ ID NO: 57)

cyclo($K^{18}$—$D^{22}$)[Nle$^8$,$K^{18}$,$D^{22}$,$L^{27}$]hPTH(8–31)NH$_2$ (SEQ ID NO: 58)

cyclo($K^{18}$—$D^{22}$)[Nle$^8$,$K^{18}$,$D^{22}$,$L^{27}$]hPTH(7–31)NH$_2$ (SEQ ID NO: 59)

cyclo($K^{18}$—$D^{22}$)[Nle$^8$,$K^{18}$,$D^{22}$,$L^{27}$]hPTH(6–31)NH$_2$ (SEQ ID NO: 60)

cyclo($K^{18}$—$D^{22}$)[Nle$^8$,$K^{18}$,$D^{22}$,$L^{27}$]hPTH(5–31)NH$_2$ (SEQ ID NO: 61)

cyclo($K^{18}$—$D^{22}$)[Nle$^8$,$K^{18}$,$D^{22}$,$L^{27}$]hPTH(4–31)NH$_2$ (SEQ ID NO: 62)

cyclo($K^{18}$—$D^{22}$)[Nle$^8$,$K^{18}$,$D^{22}$,$L^{27}$]hPTH(3–31)NH$_2$ (SEQ ID NO: 63)

cyclo($K^{18}$—$D^{22}$)[Nle$^8$,$K^{18}$,$D^{22}$,$L^{27}$]hPTH(2–31)NH$_2$ (SEQ ID NO: 64)

cyclo($K^{18}$—$D^{22}$)[Nle$^8$,$K^{18}$,$D^{22}$,$L^{27}$]hPTH(7–34)NH$_2$ (SEQ ID NO: 65)

cyclo($K^{10}$—$D^{14}$)[$A^1$,Nle$^{8,18}$,$K^{10}$,$D^{14}$,$L^{27}$]hPTH(1–31)NH$_2$ (SEQ ID NO: 66)

cyclo($K^{14}$—$D^{18}$)[$A^1$,Nle$^8$,$K^{14}$,$D^{18}$,$L^{27}$]hPTH(1–31)NH$_2$ (SEQ ID NO: 67)

cyclo($K^{17}$—$D^{21}$)[$A^1$,Nle$^{8,18}$,$K^{17}$,$D^{21}$,$L^{27}$]hPTH(1–31)NH$_2$ (SEQ ID NO: 68)

cyclo($K^{21}$—$D^{25}$)[$A^1$,Nle$^{8,18}$,$K^{21}$,$D^{25}$,$L^{27}$]hPTH(1–31)NH$_2$ (SEQ ID NO: 69)

cyclo($K^{25}$—$D^{29}$)[$A^1$,Nle$^{8,18}$,$K^{25}$,$D^{29}$,$L^{27}$]hPTH(1–31)NH$_2$ (SEQ ID NO: 70)

cyclo($K^{18}$—$D^{22}$)[$K^{18}$,$D^{22}$,$L^{27}$]hPTH(1–34)NH$_2$ (SEQ ID NO: 71)

cyclo($K^{18}$—$D^{22}$)[$K^{18,26,30}$,$D^{22}$,$L^{23,28,31}$,$E^{25,29}$]hPTH(1–34)NH$_2$ (SEQ ID NO: 72)

bicyclo($K^{13}$—$D^{17}$,$K^{18}$—$D^{22}$)[$A^1$,Nle$^8$,$D^{17,22}$,$L^{27}$]hPTH(1–31)NH$_2$ (SEQ ID NO: 73)

bicyclo($K^{18}$—$D^{22}$,$K^{26}$—$D^{30}$)[$A^1$,Nle$^8$,$K^{18}$$D^{22}$,$L^{27}$]hPTH(1–31)NH$_2$ (SEQ ID NO: 74)

bicyclo($K^{13}$—$D^{17}$,$K^{18}$—$D^{22}$)[$A^1$,Nle$^8$,$D^{17,22}$,$K^{18}$,$L^{27}$]hPTH(1–34)NH$_2$ (SEQ ID NO: 75)

cyclo($K^{18}$—$D^{22}$)[$K^{18}$,$D^{22}$]hPTH(7–34)NH$_2$ (SEQ ID NO: 77)

bicyclo($K^{13}$—$D^{17}$,$K^{18}$—$D^{22}$)[Nle$^8$,K,$D^{17,22}$,$L^{27}$]hPTH(7–34)NH$_2$ (SEQ ID NO: 78)

bicyclo($K^{18}$—$D^{22}$,$K^{26}$—$D^{30}$)[Nle$^8$,$K^{18}$,$D^{22}$,$L^{27}$]hPTH(7–34)NH$_2$ (SEQ ID NO: 79)

tricyclo($K^{13}$—$D^{17}$,$K^{18}$—$D^{22}$,$K^{26}$—$D^{30}$)[$A^1$,Nle$^8$,$K^{18}$,$D^{17,22}$,$L^{27}$]hPTH(1–31)NH$_2$ (SEQ ID NO: 80)

or a pharmaceutically acceptable salt or prodrug thereof.

A preferred cyclic peptide compound of formula 2 has formula I above wherein the bridge formed from the side chains of one pair of amino acid residues is non-overlapping with a bridge formed between the side chains of another pair of amino acid residues.

A more preferred cyclic peptide compound of formula 3 has formula 2 above wherein $A_{10}$ is Ala, Asn, Asp, Gly or Lys; $A_{13}$ is Ala, Gly or Lys; $A_{14}$ is Ala, Asp, Gly, His, Lys or Ser; $A_{17}$ is Ala, Asp, Gly, Lys or Ser; $A_{18}$ is Asp, Leu, Lys, Orn or Nle; $A_2$, is Arg, Asp, Lys or Val; $A_{22}$ is Asp, Glu, Lys, Orn or Phe; $A_{25}$ is Arg, Asp, Glu, His or Lys; $A_{26}$ is His or Lys; $A_{29}$ is Ala, Asp, Glu or Gln; $A_{30}$ is Asp, Glu or Lys, and the side chains of at least one of the following pairs of amino acid residues, $A_{10}$ and $A_{14}$, $A_{13}$ and $A_{17}$, $A_{14}$ and $A_{18}$, $A_{17}$ and $A_{21}$, $A_{18}$ and $A_{22}$, $A_{21}$ and $A_{25}$, $A_{25}$ and $A_{29}$ and $A_{26}$ and $A_{30}$ are linked through an amide bond to form a bridge, and the side chain of each of the following amino acid residues, $A_{10}$, $A_{13}$, $A_{14}$, $A_{17}$, $A_{18}$, $A_{21}$, $A_{22}$, $A_{25}$, $A_{26}$, $A_{29}$, and $A_{30}$, contributes, at most, to the formation of a single and non-overlapping bridge; provided (a) that when the side chains of the pair of amino acid residues $A_{13}$ and $A_{17}$ are linked through an amide bond to form a bridge, then the side chains of at least one of the following pairs of amino acid residues, $A_{18}$ and $A_{22}$, $A_{21}$ and $A_{25}$, and $A_{25}$ and $A_{29}$ are also linked through an amide bond to form a bridge;

(b) that when the side chains of the following pair of amino acid residues $A_{26}$ and $A_{30}$ are linked through an amide bond to form a bridge, then the side chains of at least one of the following pairs of amino acid residues $A_{10}$ and $A_{14}$, $A_{14}$ and $A_{18}$, $A_{17}$ and $A_{21}$, $A_{18}$ and $A_{22}$ and $A_{21}$ and $A_{25}$ are also linked through an amide bond to form a bridge; and (c) that when the side chains of the following pairs of amino acid residues $A_{13}$ and $A_{17}$ and $A_{26}$ and $A_{30}$ are linked through an amide bond to form a bridge, then the side chains of one of the following pairs of amino acid residues $A_{18}$ and $A_{22}$ and $A_{21}$ and $A_{25}$ are also linked through an amide bond to form a bridge.

Another more preferred cyclic peptide compound of formula 4 has formula 3 above wherein $R_{1a}$ is H and Y is $NH_2$.

Certain cyclic peptide compounds of this invention possess agonist activity on the parathyroid hormone receptor and accordingly are useful in the treatment of physiological conditions associated with bone cell calcium regulation including hypocalcemia; osteoporosis; osteopenia; and disorders associated with osteoporosis and osteopenia such as hyperparathyroidism, hypoparathyroidism, and Cushings syndrome; glucocorticoid- and immunosuppressant-induced osteopaenia: and bone fracture and bone refracture repair.

A preferred cyclic peptide agonist compound of formula 5 has formula 4 above wherein X is (a) $R_{1a}$—$A_1$—$A_2$—$A_3$—$A_4$—$A_5$—$A_6$—$A_7$—$A_8$—$A_9$—, (b) $R_{1a}$—$A_2$—$A_3$—$A_4$—$A_5$—$A_6$—$A_7$—$A_8$—$A_9$— or (c) $R_{1a}$—$A_3$—$A_4$—$A_5$—$A_6$—$A_7$—$A_8$—$A_9$—.

A more preferred cyclic peptide agonist compound of formula 6 has formula 5 above wherein $A_1$ is Ala, Gly or D-Pro; $A_1$ is Nle and $A_{27}$ is Leu.

Another more preferred cyclic peptide agonist compound of formula 7 has formula 6 above wherein (i) the side chains of $A_{10}$ and $A_{14}$ are linked through an amide bond to form a bridge;

(ii) the side chains of $A_{14}$ and $A_{18}$ are linked through an amide bond to form a bridge;

(iii) the side chains of $A_{17}$ and $A_{21}$ are linked through an amide bond to form a bridge;

(iv) the side chains of $A_{18}$ and $A_{22}$ are linked through an amid bond to form a bridge;

(v) the side chains of $A_{21}$ and $A_{25}$ are linked through an amide bond to form a bridge; or (vi) the side chains of $A_{25}$ and $A_{29}$ are linked through an amide bond to form a bridge.

Another more preferred cyclic peptide agonist compound has formula (i) above wherein $A_{10}$ is Asp or Lys; $A_{13}$ is Lys; $A_{14}$ is Asp or Lys; $A_{17}$ is Asp or Ser; $A_{18}$ is Nle; $A_{21}$ is Arg or Val; $A_{22}$ is Glu or Phe; $A_{25}$ is Arg or His; $A_{26}$ is Lys or His, $A_{29}$ is Ala or Gln; and $A_{30}$ is Asp or Glu; and the side-chains of $A_{10}$ and $A_{14}$ are linked through an amide bond to form a bridge.

Another more preferred cyclic peptide agonist compound has formula (ii) above wherein $A_{10}$ is Asn or Asp; $A_{13}$ is Lys; $A_{14}$ is Asp or Lys; $A_{17}$ is Asp or Ser; $A_{18}$ is Nle; $A_{21}$ is Arg or Val; $A_{22}$ is Glu or Phe; $A_{25}$ is Arg or His; $A_{26}$ is His or Lys; $A_{29}$ is Ala or Gln; and $A_{30}$ is Asp or Glu; and the side chains of $A_{14}$ and $A_{18}$ are linked through an amide bond to form a bridge.

Another more preferred cyclic peptide agonist compound has formula (iii) above wherein $A_{10}$ is Asn or Asp; $A_{13}$ is Lys; $A_{14}$ is His or Ser; $A_{17}$ is Asp or Lys; $A_{18}$ is Nle; $A_{21}$ is Asp or Lys; $A_{21}$ is Glu or Phe; $A_{25}$ is Arg or His; $A_{26}$ is His or Lys; $A_{29}$ is Ala or Gln; and $A_{30}$ is Asp or Glu; and the side chains of $A_{17}$ and $A_{21}$ are linked through an amide bond to form a bridge.

Another more preferred cyclic peptide agonist compound has formula (iv) above wherein $A_{10}$ is Asn or Asp; $A_{13}$ is Lys; $A_{14}$ is His or Ser; $A_{17}$ is Asp or Ser; $A_{18}$ is Asp, Lys or Orn; $A_{21}$ is Arg or Val; $A_{22}$ is Asp, Glu, Lys or Orn; $A_{25}$ is Arg or His; $A_{26}$ is His or Lys; $A_{29}$ is Ala or Gln; and $A_{30}$ is Asp or Glu; and the side chains of $A_{18}$ and $A_{22}$ are linked through an amide bond to form a bridge.

Another more preferred cyclic peptide agonist compound has formula (v) above wherein $A_{10}$ is Asn or Asp; $A_{13}$ is Lys; $A_{14}$ is His or Ser; $A_{17}$ is Asp or Ser; $A_{18}$ is Nle; $A_{21}$ is Asp or Lys; $A_{22}$ is Glu or Phe; $A_{25}$ is Asp or Lys; $A_{26}$ is His or Lys; $A_{29}$ is Ala or Gln; and $A_{30}$ is Asp or Glu; and the side chains of $A_{21}$ and $A_{25}$ are linked through an amide bond to form a bridge.

Another more preferred cyclic peptide agonist compound has formula (vi) above wherein $A_{10}$ is Asn or Asp; $A_{13}$ is Lys; $A_{14}$ is His or Ser; $A_{17}$ is Asp or Ser; $A_{18}$ is Nle; $A_{21}$ is Arg or Val; $A_{22}$ is Glu or Phe; $A_{25}$ is Asp or Lys; $A_{26}$ is His or Lys; $A_{29}$ is Asp or Lys; and $A_{30}$ is Asp or Glu; and the side chains of $A_{25}$ and $A_{29}$ are linked through an amide bond to form a bridge.

Another more preferred cyclic peptide agonist compound of formula 8 has formula 6 above wherein (vii) the side-chains of $A_{13}$ and $A_{17}$ are linked through an amide bond and the side-chains of $A_{18}$ and $A_{22}$ are linked through an amide bond to form a bridge; or (viii) the side-chains of $A_{18}$ and $A_{22}$ are linked through an amide bond and the side-chains of $A_{26}$ and $A_{30}$ are linked through an amide bond to form a bridge.

Another more preferred cyclic peptide agonist compound has formula (vii) above wherein $A_{10}$ is Asn or Asp; $A_{13}$ is Lys or Asp; $A_{14}$ is His or Ser; $A_{17}$ is Lys or Asp; $A_{18}$ is Lys or Asp; $A_{21}$ is Val or Arg; $A_{22}$ is Glu, Lys or Asp; $A_{25}$ is Arg or His; $A_{26}$ is His or Lys; $A_{29}$ is Ala or Gln; and $A_{30}$ is Asp or Glu; and the side-chains of $A_{13}$ and $A_{17}$ are linked through an amide bond and the side-chains of $A_{18}$ and $A_{22}$ are linked through an amide bond to form a bridge.

Another more preferred cyclic peptide agonist compound has formula (viii) above wherein $A_{10}$ is Asn or Asp; $A_{13}$ is Lys; $A_{14}$ is His or Ser; $A_{18}$ is Ser or Asp; $A_{18}$ is Lys or Asp; $A_{21}$ is Val or Arg; $A_{22}$ is Glu, Lys or Asp; $A_{25}$ is Arg or His; $A_{26}$ is Lys or Asp; $A_{29}$ is Ala or Gln; and $A_{30}$ is Lys or Asp; and the side-chains of $A_{26}$ and $A_{30}$ are linked through an amide bond and the side-chains of $A_{18}$ and $A_{22}$ are linked through an amide bond to form a bridge.

Another more preferred cyclic peptide agonist compound of formula 9 has formula 6 above wherein the side-chains of $A_{13}$ and $A_{17}$ are linked through an amide bond and the side-chains of $A_{18}$ and $A_{22}$ are linked through an amide bond and the side chains of $A_{26}$ and $A_{30}$ are linked through an amide bond to form a bridge.

Another more preferred cyclic peptide agonist compound of formula 10 has formula 9 above wherein $A_{10}$ is Asn or Asp; $A_{13}$ is Lys or Asp; $A_{14}$ is His or Ser; $A_{17}$ is Lys or Asp; $A_{18}$ is Lys or Asp; $A_{21}$ Val or Arg; $A_{22}$ is Glu, Lys, or Asp, $A_{25}$ is Arg or His; $A_{26}$ is Lys or Asp; $A_{29}$ is Ala or Gln; and $A_{30}$ is Lys or Asp.

More preferred cyclic peptide agonist compounds of this invention include:

Cyclo($K^{18}$—$D^{22}$)[$A^1$,$Nle^8$,$K^{18}$,$D^{22}$,$L^{27}$]hPTH(1–31)$NH_2$ (SEQ ID NO: 3);

Cyclo($K^{18}$—$D^{22}$)[$A^{1,2}$,$Nle^8$,$K^{18}$,$D^{22}$,$L^{27}$]hPTH(1–31)$NH_2$ (SEQ ID NO: 5);

Cyclo($K^{18}$—$D^{22}$)[$A^{1,3}$,$Nle^8$,$K^{18}$,$D^{22}$,$L^{27}$]hPTH(1–31)$NH_2$ (SEQ ID NO: 6);

Cyclo($K^{18}$—$D^{22}$)[$A^{1,4}$,$Nle^8$,$K^{18}$,$D^{22}$,$L^{27}$]hPTH(1–31)$NH_2$ (SEQ ID NO: 7);

Cyclo($K^{18}$—$D^{22}$)[$A^{1,5}$,$Nle^8$,$K^{18}$,$D^{22}$,$L^{27}$]hPTH(1–31)$NH_2$ (SEQ ID NO: 8);

Cyclo($K^{18}$—$D^{22}$)[$A^{1,6}$,$Nle^8$,$K^{18}$,$D^{22}$,$L^{27}$]hPTH(1–31)$NH_2$ (SEQ ID NO: 9);

Cyclo($K^{18}$—$D^{22}$)[$A^{1,7}$,$Nle^8$,$K^{18}$,$D^{22}$,$L^{27}$]hPTH(1–31)$NH_2$ (SEQ ID NO: 10);

Cyclo($K^{18}$—$D^{22}$)[$A^{1,9}$,$Nle^8$,$K^{18}$,$D^{22}$,$L^{27}$]hPTH(1–31)$NH_2$ (SEQ ID NO: 11);

Cyclo(K$^{18}$—D$^{22}$)[A$^{1,10}$,Nle$^8$,K$^{18}$,D$^{22}$,L$^{27}$]hPTH(1–31)NH$_2$ (SEQ ID NO: 12);
Cyclo(K$^{18}$—D$^{22}$)[A$^{1,11}$,Nle$^8$,K$^{18}$,D$^{22}$,L$^{27}$]hPTH(1–31)NH$_2$ (SEQ ID NO: 13);
Cyclo(K$^{18}$—D$^{22}$)[A$^{1,12}$,Nle$^8$,K$^{18}$,D$^{22}$,L$^{27}$]hPTH(1–31)NH$_2$ (SEQ ID NO: 14);
Cyclo(K$^{18}$—D$^{22}$)[A$^{1,13}$,Nle$^8$,K$^{18}$,D$^{22}$,L$^{27}$]hPTH(1–31)NH$_2$ (SEQ ID NO: 15);
Cyclo(K$^{18}$—D$^{22}$)[A$^{1,14}$,Nle$^8$,K$^{18}$,D$^{22}$,L$^{27}$]hPTH(1–31)NH$_2$ (SEQ ID NO: 16);
Cyclo(K$^{18}$—D$^{22}$)[A$^{1,15}$,Nle$^8$,K$^{18}$,D$^{22}$,L$^{27}$]hPTH(1–31)NH$_2$ (SEQ ID NO: 17);
Cyclo(K$^{18}$—D$^{22}$)[A$^{1,16}$,Nle$^8$,K$^{18}$,D$^{22}$,L$^{27}$]hPTH(1–31)NH$_2$ (SEQ ID NO: 18);
Cyclo(K$^{18}$—D$^{22}$)[A$^{1,17}$,Nle$^8$,K$^{18}$,D$^{22}$,L$^{27}$]hPTH(1–31)NH$_2$ (SEQ ID NO: 19);
Cyclo(K$^{18}$—D$^{22}$)[G$^1$,Nle$^8$,K$^{18}$,D$^{22}$,L$^{27}$]hPTH(1–31)NH$_2$ (SEQ ID NO: 20);
Cyclo(K$^{18}$—D$^{22}$)[A$^1$,G$^2$,Nle$^8$,K$^{18}$,D$^{22}$,L$^{27}$]hPTH(1–31)NH$_2$ (SEQ ID NO: 21);
Cyclo(K$^{18}$—D$^{22}$)[A$^1$,G$^3$,Nle$^8$,K$^{18}$,D$^{22}$,L$^{27}$]hPTH(1–31)NH$_2$ (SEQ ID NO: 22);
Cyclo(K$^{18}$—D$^{22}$)[A$^1$,G$^4$,Nle$^8$,K$^{18}$,D$^{22}$,L$^{27}$]hPTH(1–31)NH$_2$ (SEQ ID NO: 23);
Cyclo(K$^{18}$—D$^{22}$)[A$^1$,G$^5$,Nle$^8$,K$^{18}$,D$^{22}$,L$^{27}$]hPTH(1–31)NH$_2$ (SEQ ID NO: 24);
Cyclo(K$^{18}$—D$^{22}$)[A$^1$,G$^6$,Nle$^8$,K$^{18}$,D$^{22}$,L$^{27}$]hPTH(1–31)NH$_2$ (SEQ ID NO: 25);
Cyclo(K$^{18}$—D$^{22}$)[A$^1$,G$^7$,Nle$^8$,K$^{18}$,D$^{22}$,L$^{27}$]hPTH(1–31)NH$_2$ (SEQ ID NO: 26);
Cyclo(K$^{18}$—D$^{22}$)[A$^1$,G$^8$,K$^{18}$,D$^{22}$,L$^{27}$]hPTH(1–31)NH$_2$ (SEQ ID NO: 27);
Cyclo(K$^{18}$—D$^{22}$)[A$^1$,G$^9$,Nle$^8$,K$^{18}$,D$^{22}$,L$^{27}$]hPTH(1–31)NH$_2$ (SEQ ID NO: 28);
Cyclo(K$^{18}$—D$^{22}$)[A$^1$,G$^{10}$,Nle$^8$,K$^{18}$,D$^{22}$,L$^{27}$]hPTH(1–31)NH$_2$ (SEQ ID NO: 29);
Cyclo(K$^{18}$—D$^{22}$)[A$^1$,G$^{11}$,Nle$^8$,K$^{18}$,D$^{22}$,L$^{27}$]hPTH(1–31)NH$_2$ (SEQ ID NO: 30);
Cyclo(K$^{18}$—D$^{22}$)[A$^1$,G$^{13}$,Nle$^8$,K$^{18}$,D$^{22}$,L$^{27}$]hPTH(1–31)NH$_2$ (SEQ ID NO: 31);
Cyclo(K$^{18}$—D$^{22}$)[A$^1$,G$^{14}$,Nle$^8$,K$^{18}$,D$^{22}$,L$^{27}$]hPTH(1–31)NH$_2$ (SEQ ID NO: 32);
Cyclo(K$^{18}$—D$^{22}$)[A$^1$,G$^{15}$,Nle$^8$,K$^{18}$,D$^{22}$,L$^{27}$]hPTH(1–31)NH$_2$ (SEQ ID NO: 33);
Cyclo(K$^{18}$—D$^{22}$)[A$^1$,G$^{16}$,Nle$^8$,K$^{18}$,D$^{22}$,L$^{27}$]hPTH(1–31)NH$_2$ (SEQ ID NO: 34);
Cyclo(K$^{18}$—D$^{22}$)[A$^1$,G$^{17}$,Nle$^8$,K$^{18}$,D$^{22}$,L$^{27}$]hPTH(1–31)NH$_2$ (SEQ ID NO: 35);
Cyclo(K$^{18}$—D$^{22}$)[D—P$^1$,Nle$^8$,K$^{18}$,D$^{22}$,L$^{27}$]hPTH(1–31)NH$_2$ (SEQ ID NO: 36);
Cyclo(K$^{18}$—D$^{22}$)[A$^1$,D—P$^3$,Nle$^8$,K$^{18}$,D$^{22}$,L$^{27}$]hPTH(1–31)NH$_2$ (SEQ ID NO: 37);
Cyclo(K$^{18}$—D$^{22}$)[A$^1$,D—P$^6$,Nle$^8$,K$^{18}$,D$^{22}$,L$^{27}$]hPTH(1–31)NH$_2$ (SEQ ID NO: 38);
Cyclo(K$^{18}$—D$^{22}$)[A$^1$,D—P$^7$,Nle$^8$,K$^{18}$,D$^{22}$,L$^{27}$]hPTH(1–31)NH$_2$ (SEQ ID NO: 39);
Cyclo(K$^{18}$—D$^{22}$)[A$^1$,D—P$^9$,Nle$^8$,K$^{18}$,D$^{22}$,L$^{27}$]hPTH(1–31)NH$_2$ (SEQ ID NO: 40);
Cyclo(K$^{18}$—D$^{22}$)[A$^1$,D—P$^{10}$,Nle$^8$,K$^{18}$,D$^{22}$,L$^{27}$]hPTH(1–31)NH$_2$ (SEQ ID NO: 41);
Cyclo(K$^{18}$—D$^{22}$)[A$^1$,D—P$^{14}$,Nle$^8$,K$^{18}$,D$^{22}$,L$^{27}$]hPTH(1–31)NH$_2$ (SEQ ID NO: 42);
Cyclo(K$^{18}$—D$^{22}$)[A$^1$,D—P$^{15}$,Nle$^8$,K$^{18}$,D$^{22}$,L$^{27}$]hPTH(1–31)NH$_2$ (SEQ ID NO: 43);
Cyclo(K$^{18}$—D$^{22}$)[A$^1$,D—P$^{16}$,Nle$^8$,K$^{18}$,D$^{22}$,L$^{27}$]hPTH(1–31)NH$_2$ (SEQ ID NO: 44);
Cyclo(K$^{18}$—D$^{22}$)[A$^1$,D—P$^{17}$,Nle$^8$,K$^{18}$,D$^{22}$,L$^{27}$]hPTH(1–31)NH$_2$ (SEQ ID NO: 45);
Cyclo(K$^{18}$—D$^{22}$)[A$^1$,Nle$^8$,K$^{18}$,D$^{22}$,L$^{27}$]hPTH(1–34)NH$_2$ (SEQ ID NO: 46);
Cyclo(K$^{18}$—D$^{22}$)[A$^1$,Nle$^8$,D$^{18}$,K$^{22}$,L$^{27}$]hPTH(1–31)NH$_2$ (SEQ ID NO: 47);
Cyclo(O$^{18}$—D$^{22}$)[A$^1$,Nle$^8$,O$^{18}$,O$^{22}$,L$^{27}$]hPTH(1–31)NH$_2$ (SEQ ID NO: 48);
Cyclo(D$^{18}$—O$^{22}$)[A$^1$,Nle$^8$,D$^{18}$,O$^{22}$,L$^{27}$]hPTH(1–31)NH$_2$ (SEQ ID NO: 49);
Cyclo(K$^{18}$—E$^{22}$)[A$^1$,Nle$^8$,K$^{18}$,E$^{22}$,L$^{27}$]hPTH(1–31)NH$_2$ (SEQ ID NO: 50);
Cyclo(O$^{18}$—E$^{22}$)[A$^1$,Nle$^8$,O$^{18}$,E$^{22}$,L$^{27}$]hPTH(1–31)NH$_2$ (SEQ ID NO: 51);
Cyclo(K$^{18}$—D$^{22}$)[A$^1$,Nle$^8$,K$^{18}$,D$^{22}$,L$^{27}$]hPTH(1–30)NH$_2$ (SEQ ID NO: 52);
Cyclo(K$^{18}$—D$^{22}$)[A$^1$,Nle$^8$,K$^{18}$,D$^{22}$,L$^{27}$]hPTH(1–29)NH$_2$ (SEQ ID NO: 53);
Cyclo(K$^{18}$—D$^{22}$)[A$^1$,Nle$^8$,K$^{18}$,D$^{22}$,L$^{27}$]hPTH(1–28)NH$_2$ (SEQ ID NO: 54);
Cyclo(K$^{18}$—D$^{22}$)[A$^1$,Nle$^8$,K$^{18}$,D$^{22}$,L$^{27}$]hPTH(1–27)NH$_2$ (SEQ ID NO: 55);
Cyclo(K$^{18}$—D$^{22}$)[Nle$^8$,K$^{18}$,D$^{22}$,L$^{27}$]hPTH(3–31)NH$_2$ (SEQ ID NO: 63);
Cyclo(K$^{18}$—D$^{22}$)[Nle$^8$,K$^{18}$,D$^{22}$,L$^{27}$]hPTH(2–31)NH$_2$ (SEQ ID NO: 64);
Cyclo(K$^{10}$—D$^{14}$)[A$^1$,Nle$^{8,18}$,K$^{10}$,D$^{14}$,L$^{27}$]hPTH(1–31)NH$_2$ (SEQ ID NO: 66);
Cyclo(K$^{14}$—D$^{18}$)[A$^1$,Nle$^8$,K$^{14}$,D$^{18}$,L$^{27}$]hPTH(1–31)NH$_2$ (SEQ ID NO: 67);
Cyclo(K$^{17}$—D$^{21}$)[A$^1$,Nle$^{8,18}$,K$^{17}$,D$^{21}$,L$^{27}$]hPTH(1–31)NH$_2$ (SEQ ID NO: 68);
Cyclo(K$^{21}$—D$^{25}$)[A$^1$,Nle$^{8,18}$,K$^{21}$,D$^{25}$,L$^{27}$]hPTH(1–31)NH$_2$ (SEQ ID NO: 69);
Cyclo(K$^{25}$—D$^{29}$)[A$^1$,Nle$^{8,18}$,K$^{25}$,D$^{29}$,L$^{27}$]hPTH(1–31)NH$_2$ (SEQ ID NO: 70);
Cyclo(K$^{18}$—D$^{22}$)[K$^{18}$,D$^{22}$]hPTH(1–34)NH$_2$ (SEQ ID NO: 71);
Cyclo(K$^{18}$—D$^{22}$)[K$^{18,26,30}$,D$^{22}$,L$^{23,28,31}$,E$^{25,29}$]hPTH(1–34)NH$_2$ (SEQ ID NO: 72);
Bicyclo(K$^{13}$—D$^{17}$,K$^{18}$—D$^{22}$)[A$^1$,Nle$^8$,D$^{17,22}$,K$^{18}$,L$^{27}$]hPTH(1–31)NH$_2$ (SEQ ID NO: 73);
Bicyclo(K$^{18}$—D$^{22}$,K$^{26}$—D$^{30}$)[A$^1$,Nle$^8$,K$^{18}$,D$^{22}$,L$^{27}$]hPTH(1–31)NH$_2$ (SEQ ID NO: 74);
Tricyclo(K$^{13}$—D$^{17}$,K$^{18}$—D$^{22}$,K$^{26}$—D$^{30}$)[A$^1$,Nle$^8$,K$^{18}$,D$^{17,22}$,L$^{27}$]hPTH(1–31)NH$_2$ (SEQ ID NO: 80);

or a pharmaceutically acceptable salt or prodrug thereof.

Still more preferred cyclic peptide agonist compounds of this invention include:

Cyclo(K$^{18}$—D$^{22}$)[A$^1$,Nle$^8$,K$^{18}$,D$^{22}$,L$^{27}$]hPTH(1–31)NH$_2$ (SEQ ID NO: 3);
Cyclo(K$^{18}$—D$^{22}$)[A$^1$,Nle$^8$,K$^{18}$,D$^{22}$,L$^{27}$]hPTH(1–34)NH$_2$ (SEQ ID NO: 46);
Cyclo(K$^{18}$—D$^{22}$)[A$^{1,3}$,Nle$^8$,K$^{18}$,D$^{22}$,L$^{27}$]hPTH(1–31)NH$_2$ (SEQ ID NO: 6);
Cyclo(K$^{18}$—D$^{22}$)[A$^{1,6}$,Nle$^8$,K$^{18}$,D$^{22}$,L$^{27}$]hPTH(1–31)NH$_2$ (SEQ ID NO: 9);
Cyclo(K$^{18}$—D$^{22}$)[A$^{1,10}$,Nle$^8$,K$^{18}$,D$^{22}$,L$^{27}$]hPTH(1–31)NH$_2$ (SEQ ID NO: 12);

Cyclo(K$^{18}$—D$^{22}$)[A$^{1,11}$,Nle$^8$,K$^{18}$,D$^{22}$,L$^{27}$]hPTH(1–31)NH$_2$ (SEQ ID NO: 13);
Cyclo(K$^{18}$—D$^{22}$)[A$^{1,12}$,Nle$^8$,K$^{18}$,D$^{22}$,L$^{27}$]hPTH(1–31)NH$_2$ (SEQ ID NO: 14);
Cyclo(K$^{18}$—D$^{22}$)[A$^{1,13}$,Nle$^8$,K$^{18}$,D$^{22}$,L$^{27}$]hPTH(1–31)NH$_2$ (SEQ ID NO: 15);
Cyclo(K$^{18}$—D$^{22}$)[A$^{1,14}$,Nle$^8$,K$^{18}$,D$^{22}$,L$^{27}$]hPTH(1–31)NH$_2$ (SEQ ID NO: 16);
Cyclo(K$^{18}$—D$^{22}$)[A$^{1,15}$,Nle$^8$,K$^{18}$,D$^{22}$,L$^{27}$]hPTH(1–31)NH$_2$ (SEQ ID NO: 17);
Cyclo(K$^{18}$—D$^{22}$)[A$^{1,16}$,Nle$^8$,K$^{18}$,D$^{22}$,L$^{27}$]hPTH(1–31)NH$_2$ (SEQ ID NO: 18);
Cyclo(K$^{18}$—D$^{22}$)[A$^{1,17}$,Nle$^8$,K$^{18}$,D$^{22}$,L$^{27}$]hPTH(1–31)NH$_2$ (SEQ ID NO: 19);
Cyclo(K$^{18}$—D$^{22}$)[G$^1$,Nle$^8$,K$^{18}$,D$^{22}$,L$^{27}$]hPTH(1–31)NH$_2$ (SEQ ID NO: 20);
Cyclo(K$^{18}$—D$^{22}$)[A$^1$,G$^2$,Nle$^8$,K$^{18}$,D$^{22}$,L$^{27}$]hPTH(1–31)NH$_2$ (SEQ ID NO: 21);
Cyclo(K$^{18}$—D$^{22}$)[A$^1$,G$^3$,Nle$^8$,K$^{18}$,D$^{22}$,L$^{27}$]hPTH(1–31)NH$_2$ (SEQ ID NO: 22);
Cyclo(K$^{18}$—D$^{22}$)[A$^1$,G$^{10}$,Nle$^8$,K$^{18}$,D$^{22}$,L$^{27}$]hPTH(1–31)NH$_2$ (SEQ ID NO: 29);
Cyclo(K$^{18}$—D$^{22}$)[A$^1$,G$^{13}$,Nle$^8$,K$^{18}$,D$^{22}$,L$^{27}$]hPTH(1–31)NH$_2$ (SEQ ID NO: 31);
Cyclo(K$^{18}$—D$^{22}$)[A$^1$,G$^{16}$,Nle$^8$,K$^{18}$,D$^{22}$,L$^{27}$]hPTH(1–31)NH$_2$ (SEQ ID NO: 34);
Cyclo(K$^{18}$—D$^{22}$)[A$^1$,G$^{17}$,Nle$^8$,K$^{18}$,D$^{22}$,L$^{27}$]hPTH(1–31)NH$_2$ (SEQ ID NO: 35);
Cyclo(K$^{18}$—D$^{22}$)[D—P$^1$,Nle$^8$,K$^{18}$,D$^{22}$,L$^{27}$]hPTH(1–31)NH$_2$ (SEQ ID NO: 36);
Cyclo(D$^{18}$—K$^{22}$)[A$^1$,Nle$^8$,D$^{18}$,K$^{22}$,L$^{27}$]hPTH(1–31)NH$_2$ (SEQ ID NO: 47);
Cyclo(O$^{18}$—D$^{22}$)[A$^1$,Nle$^8$,O$^{18}$,D$^{22}$,L$^{27}$]hPTH(1–31)NH$_2$ (SEQ ID NO: 48);
Cyclo(K$^{18}$—D$^{22}$)[A$^1$,Nle$^8$,K$^{18}$,D$^{22}$,L$^{27}$]hPTH(1–31)NH$_2$ (SEQ ID NO: 49);
Cyclo(D$^{18}$—O$^{22}$)[A$^1$,Nle$^8$,D$^{18}$,O$^{22}$,L$^{27}$]hPTH(1–31)NH$_2$ (SEQ ID NO: 50);
Cyclo(K$^{18}$—E$^{22}$)[A$^1$,Nle$^8$,K$^{18}$,E$^{22}$,L$^{27}$]hPTH(1–31)NH$_2$ (SEQ ID NO: 51);
Cyclo(O$^{18}$—E$^{22}$)[A$^1$,Nle$^8$,O$^{18}$,E$^{22}$,L$^{27}$]hPTH(1–30)NH$_2$ (SEQ ID NO: 52);
Cyclo(K$^{18}$—D$^{22}$)[A$^1$,Nle$^8$,K$^{18}$,D$^{22}$,L$^{27}$]hPTH(1–29)NH$_2$ (SEQ ID NO: 53);
Cyclo(K$^{18}$—D$^{22}$)[A$^1$,Nle$^8$,K$^{18}$,D$^{22}$,L$^{27}$]hPTH(1–28)NH$_2$ (SEQ ID NO: 54);
Cyclo(K$^{10}$—D$^{14}$)[A$^1$,Nle$^{8,18}$,K$^{10}$,D$^{14}$,L$^{27}$]hPTH(1–31)NH$_2$ (SEQ ID NO: 66);
Cyclo(K$^{14}$—D$^{18}$)[A$^1$,Nle$^8$,K$^{14}$,D$^{18}$,L$^{27}$]hPTH(1–31)NH$_2$ (SEQ ID NO: 67);
Cyclo(K$^{17}$—D$^{21}$)[A$^1$,Nle$^{8,18}$,K$^{17}$,D$^{21}$,L$^{27}$]hPTH(1–31)NH$_2$ (SEQ ID NO: 68);
Cyclo(K$^{21}$—D$^{25}$)[A$^1$,Nle$^{8,18}$,K$^{21}$,D$^{25}$,L$^{27}$]hPTH(1–31)NH$_2$ (SEQ ID NO: 69);
Cyclo(K$^{25}$—D$^{29}$)[A$^1$,Nle$^{8,18}$,K$^{25}$,D$^{29}$,L$^{27}$]hPTH(1–31)NH$_2$ (SEQ ID NO: 70);
Cyclo(K$^{18}$—D$^{22}$)[K$^{18}$,D$^{22}$]hPTHrP(1–34)NH$_2$ (SEQ ID NO: 71);
Cyclo(K$^{18}$—D$^{22}$)[K$^{18,26,30}$,D$^{22}$,L$^{23,28,31}$,E$^{25,29}$]hPTHrP(1–34)NH$_2$ (SEQ ID NO: 72);
Bicyclo(K$^{13}$—D$^{17}$,K$^{18}$—D$^{22}$)[A$^1$,Nle$^8$,D$^{17,22}$,K$^{18}$,L$^{27}$]hPTH(1–31)NH$_2$ (SEQ ID NO: 73);
Bicyclo(K$^{18}$—D$^{22}$,K$^{26}$—D$^{30}$)[A$^1$,Nle$^8$,K$^{18}$,D$^{22}$,L$^{27}$]hPTH(1–31)NH$_2$ (SEQ ID NO: 74);
Tricyclo(K$^{13}$—D$^{17}$,K$^{18}$—D$^{22}$,K$^{26}$—D$^{30}$)[A$^1$,Nle$^8$,K$^{18}$,D$^{17,22}$,L$^{27}$]hPTH(1–31)NH$_2$ (SEQ ID NO: 80);
or a pharmaceutically acceptable salt or prodrug thereof.

Still yet more preferred cyclic peptide agonist compounds include:

Cyclo(K$^{18}$—D$^{22}$)[A$^1$,Nle$^8$,K$^{18}$,D$^{22}$,L$^{27}$]hPTH(1–31)NH$_2$ (SEQ ID NO: 3);
Cyclo(K$^{18}$—D$^{22}$)[A$^1$,Nle$^8$,K$^{18}$,D$^{22}$,L$^{27}$]hPTH(1–34)NH$_2$ (SEQ ID NO: 46);
Cyclo(K$^{18}$—D$^{22}$)[A$^{1,10}$,Nle$^8$,K$^{18}$,D$^{22}$,L$^{27}$]hPTH(1–31)NH$_2$ (SEQ ID NO: 12);
Cyclo(K$^{18}$—D$^{22}$)[A$^{1,12}$,Nle$^8$,K$^{18}$,D$^{22}$,L$^{27}$]hPTH(1–31)NH$_2$ (SEQ ID NO: 14);
Cyclo(K$^{18}$—D$^{22}$)[A$^{1,13}$,Nle$^8$,K$^{18}$,D$^{22}$,L$^{27}$]hPTH(1–31)NH$_2$ (SEQ ID NO: 15);
Cyclo(K$^{18}$—D$^{22}$)[A$^{1,14}$,Nle$^8$,K$^{18}$,D$^{22}$,L$^{27}$]hPTH(1–31)NH$_2$ (SEQ ID NO: 16);
Cyclo(K$^{18}$—D$^{22}$)[A$^{1,16}$,Nle$^8$,K$^{18}$,D$^{22}$,L$^{27}$]hPTH(1–31)NH$_2$ (SEQ ID NO: 18);
Cyclo(K$^{18}$—D$^{22}$)[A$^{1,17}$,Nle$^8$,K$^{18}$,D$^{22}$,L$^{27}$]hPTH(1–31)NH$_2$ (SEQ ID NO: 19);
Cyclo(K$^{18}$—D$^{22}$)[A$^1$,G$^3$,Nle$^8$,K$^{18}$,D$^{22}$,L$^{27}$]hPTH(1–31)NH$_2$ (SEQ ID NO: 22);
Cyclo(K$^{18}$—D$^{22}$)[A$^1$,G$^{13}$,Nle$^8$,K$^{18}$,D$^{22}$,L$^{27}$]hPTH(1–31)NH$_2$ (SEQ ID NO: 31);
Cyclo(K$^{18}$—D$^{22}$)[A$^1$,G$^{16}$,Nle$^8$,K$^{18}$,D$^{22}$,L$^{27}$]hPTH(1–31)NH$_2$ (SEQ ID NO: 34);
Cyclo(K$^{18}$—D$^{22}$)[A$^1$,G$^{17}$,Nle$^8$,K$^{18}$,D$^{22}$,L$^{27}$]hPTH(1–31)NH$_2$ (SEQ ID NO: 35);
Cyclo(K$^{18}$—D$^{22}$)[D—P$^1$,Nle$^8$,K$^{18}$,D$^{22}$,L$^{27}$]hPTH(1–31)NH$_2$ (SEQ ID NO: 36);
Cyclo(D$^{18}$—K$^{22}$)[A$^1$,Nle$^8$,D$^{18}$,K$^{22}$,L$^{27}$]hPTH(1–31)NH$_2$ (SEQ ID NO: 47);
Cyclo(K$^{18}$—E$^{22}$)[A$^1$,Nle$^8$,K$^{18}$,E$^{22}$,L$^{27}$]hPTH(1–31)NH$_2$ (SEQ ID NO: 50);
Cyclo(O$^{18}$—E$^{22}$)[A$^1$,Nle$^8$,O$^{18}$,E$^{22}$,L$^{27}$]hPTH(1–31)NH$_2$ (SEQ ID NO: 51);
Cyclo(K$^{18}$—D$^{22}$)[A$^1$,Nle$^8$,K$^{18}$,D$^{22}$,L$^{27}$]hPTH(1–30)NH$_2$ (SEQ ID NO: 52);
Cyclo(K$^{14}$—D$^{18}$)[A$^1$,Nle$^8$,K$^{14}$,D$^{18}$,L$^{27}$]hPTH(1–31)NH$_2$ (SEQ ID NO: 67);
Cyclo(K$^{18}$—D$^{22}$)[K$^{18}$,D$^{22}$]hPTH(1–28)NH$_2$ (SEQ ID NO: 71);
Bicyclo(K$^{13}$—D$^{17}$,K$^{18}$—D$^{22}$)[A$^1$,Nle$^8$,D$^{17,22}$,K$^{18}$,L$^{27}$]hPTH(1–31)NH$_2$ (SEQ ID NO: 73);
Bicyclo(K$^{18}$—D$^{22}$,K$^{26}$—D$^{30}$)[A$^1$,Nle$^8$,K$^{18}$,D$^{22}$,L$^{27}$]hPTH(1–31)NH$_2$ (SEQ ID NO: 74);
Tricyclo(K$^{13}$—D$^{17}$,K$^{18}$—D$^{22}$,K$^{26}$—D$^{30}$)[A$^1$,Nle$^8$,K$^{18}$,D$^{17,22}$,L$^{27}$]hPTH(1–31)NH$_2$ (SEQ ID NO: 80);
or a pharmaceutically acceptable salt or prodrug thereof.

Another still yet more preferred cyclic peptide agonist compound is

Bicyclo(K$^{13}$—D$^{17}$,K$^{26}$—D$^{30}$)[A$^1$,Nle$^{8,18}$,D$^{17}$,L$^{27}$]hPTH(1–31)NH$_2$ (SEQ ID NO: 79)

or a pharmaceutically acceptable salt or prodrug thereof.

Certain cyclic peptide compounds of this invention inhibit the action of PTH. Such cyclic peptide antagonist compounds are useful in the treatment of disorders characterized by an excess of PTH such as hyperparathyrodism and hyperparathyrodism-related hypercalcemia crisis, hypercalcemia of malignancy, renal failure and hypertension.

A preferred cyclic peptide antagonist compound of formula 10 has formula 6 above wherein X is (a) $R_{1a}$—$A_4$—$A_5$—$A_6$—$A_7$—$A_8$—$A_9$—, (b) $R_{1a}$—$A_5$—$A_6$—$A_7$—$A_8$—$A_9$—, (c) $R_{1a}$—$A_6$—$A_7$—$A_8$—$A_9$—, (d) $R_{1a}$—$A_7$—$A_8$—$A_9$—, (e) $R_{1a}$—$A_8$—$A_9$—, (f) $R_{1b}$—$A_9$—, and (g) $R_{1b}$—;

A more preferred cyclic peptide antagonist compound of formula 11 has formula 10 above wherein $A_8$ is Nle and $A_{27}$ is Leu.

Another more preferred cyclic peptide antagonist compound of formula 12 has formula 11 above wherein wherein the side chains of $A_{18}$ and $A_{22}$ are linked through an amide bond to form a bridge.

Another more preferred cyclic peptide antagonist compound of formula 13 has formula 12 above wherein $A_{10}$ is Asn or Asp; $A_{13}$ is Lys; $A_{14}$ is His or Ser; $A_{17}$ is Asp or Ser; $A_{18}$ is Asp, Lys or Orn; $A_{21}$ is Arg or Val; $A_{22}$ is Asp, Glu, Lys or Orn; $A_{25}$ is Arg or His; $A_{26}$ is His or Lys; $A_{29}$ is Ala or Gln; and $A_{30}$ is Asp or Glu.

More preferred cyclic peptide antagonist compounds include:

cyclo($K^{18}$—$D^{22}$)[$K^{18}$,$D^{22}$,$L^{27}$]hPTH(10–31)$NH_2$ (SEQ ID NO: 56);

cyclo($K^{18}$—$D^{22}$)[$K^{18}$,$D^{22}$,$L^{27}$]hPTH(9–31)$NH_2$ (SEQ ID NO: 57);

cyclo($K^{18}$—$D^{22}$)[$Nle^8$,$K^{18}$,$D^{22}$,$L^{27}$]hPTH(8–31)$NH_2$ (SEQ ID NO: 58);

cyclo($K^{18}$—$D^{22}$)[$Nle^8$,$K^{18}$,$D^{22}$,$L^{27}$]hPTH(7–31)$NH_2$ (SEQ ID NO: 59);

cyclo($K^{18}$—$D^{22}$)[$Nle^8$,$K^{18}$,$D^{22}$,$L^{27}$]hPTH(6–31)$NH_2$ (SEQ ID NO: 60);

cyclo($K^{18}$—$D^{22}$)[$Nle^8$,$K^{18}$,$D^{22}$,$L^{27}$]hPTH(5–31)$NH_2$ (SEQ ID NO: 61);

cyclo($K^{18}$—$D^{22}$)[$Nle^8$,$K^{18}$,$D^{22}$,$L^{27}$]hPTH(4–31)$NH_2$ (SEQ ID NO: 62);

cyclo($K^{18}$—$D^{22}$)[$Nle^8$,$K^{18}$,$D^{22}$,$L^{27}$]hPTH(7–34)$NH_2$ (SEQ ID NO: 65); and cyclo($K^{18}$—$D^{22}$)[$K^{18}$,$D^{22}$,]hPTH(7–34)$NH_2$ (SEQ ID NO: 77);

or a pharmaceutically acceptable salt or prodrug thereof.

Certain acyclic peptide compounds of this invention also possess agonist activity on the parathyroid hormone receptor and accordingly are useful in the treatment of physiological conditions associated with bone cell calcium regulation including hypocalcemia; osteoporosis; osteopenia; and disorders associated with osteoporosis and osteopenia such as hyperparathyroidism, hypoparathyroidism, and Cushings syndrome; glucocorticoid- and immunosuppressant-induced osteopaenia; and bone fracture and bone refracture repair.

A preferred acyclic peptide agonist compound of formula 14 is the peptide compound of formula II wherein $R_{1a}$ is H and Y is $NH_2$.

A more preferred acyclic peptide agonist compound of formula 15 has formula 14 above wherein X is (a) $R_{1a}$—$A_1$—$A_2$—$A_3$—$A_4$—$A_5$—$A_6$—$A_7$—$A_8$—$A_9$—, (b) $R_{1a}$—$A_2$—$A_3$—$A_4$—$A_5$—$A_6$—$A_7$—$A_8$—$A_9$— or (c) $R_{1a}$—$A_3$—$A_4$—$A_5$—$A_6$—$A_7$—$A_8$—$A_9$—, Another more preferred acyclic peptide agonist compound of formula 16 has formula 15 above wherein $A_1$ is Ser, Ala, Gly or D-Pro; $A_2$ is Ala, Val or Gly; $A_3$ is Ala, Ser, Gly or D-Pro; $A_4$ is Glu, Ala or Gly; $A_5$ is Ile, His, Ala or Gly; $A_6$ is Ala, Gln, Gly or D-Pro; $A_7$ is Ala, Leu, Gly; $A_8$ is Leu, Nle, Gly or D-Pro; $A_9$ is His, Ala, Gly or D-Pro; $A_{10}$ is Ala, Asn, Gly, Asp or D-Pro; $A_{11}$ is Ala, Gly, Leu or Lys; $A_{12}$ is Ala or Gly; $A_{13}$ is Ala, Gly or Lys; $A_{14}$ is Ala, Gly, His, Ser or D-Pro; $A_{15}$ is Ala, Gly, Ile or D-Pro; $A_{16}$ is Asn, Ala, Gly, D-Pro or Gln; $A_{17}$ is Ala, Asp, Gly, Ser or D-Pro; $A_{18}$ is Lys; $A_{19}$ is Arg or Glu; $A_{20}$ is Arg; $A_{21}$ is Arg or Val; $A_{22}$ is Asp, Lys, Orn or Glu; $A_{23}$ is Leu, Phe or Trp; $A_{24}$ is Leu; $A_{25}$ is Arg or His; $A_{26}$ is Lys or His; $A_{27}$ is Leu or Lys; $A_{28}$ is Ile or Leu or an equivalent amino acid thereof; $A_{29}$ is Ala or Gln; $A_{30}$ is Asp or Glu; $A_3$, is Ile, Leu or Val; $A_{32}$ is His; $A_{33}$ is Asn or Thr; and $A_{34}$ is Ala or Phe.

Another more preferred acyclic peptide agonist compound of formula 17 has formula 16 above wherein $A_1$ is Ala, Gly or D-Pro; $A_8$ is Nle, $A_{22}$ is Asp and $A_{27}$ is Leu.

Another more preferred acyclic peptide agonist compound of formula 18 has formula 17 above wherein X is $R_{1a}$—$A_1$—$A_2$—$A_3$—$A_4$—$A_5$—$A_6$—$A_7$—$A_8$—$A_9$—, A still more preferred acyclic peptide agonist compound is [$A^1$,$Nle^8$,$K^{18}$,$D^{22}$,$L^{27}$]hPTH(1–31)$NH_2$ (SEQ ID NO: 4) or a pharmaceutically acceptable salt or prodrug thereof.

It is to be understood that th;s invention covers all appropriate combinations of the preferred aspects of the invention referred to herein.

Synthesis of the Peptide Compounds

The peptide compounds of the present invention may be synthesized by any techniques that are known to those skilled in the art of peptide synthesis. For solid phase peptide synthesis, a summary of the many techniques may be found in J. M. Stewart and J. D. Young, *Solid Phase Peptide Synthesis*, W. H. Freeman Co. (San Francisco), 1963 and J. Meienhofer, *Hormonal Proteins and Peptides*, vol. 2, p. 46, Academic Press (New York), 1973. For classical solution synthesis see G. Schroder and K. Lupke, *The Peptides*, vol. 1, Academic Press (New York), 1965.

In general, these methods comprise the sequential addition of one or more amino acids or suitably protected amino acids to a growing peptide chain. Normally, either the amino or carboxyl group of the first amino acid is protected by a suitable protecting group. The protected or derivatized amino acid can then either be attached to an inert solid support or utilized in solution by adding the next amino acid in the sequence having the complimentary (amino or carboxyl) group suitably protected, under conditions suitable for forming the amide linkage. The protecting group is then removed from this newly added amino acid residue and the next amino acid (suitably protected) is then added, and so forth. After all the desired amino acids have been linked in the proper sequence, any remaining protecting groups (and any solid support) are removed sequentially or concurrently, to afford the final peptide compound. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide and so forth.

A preferred method of preparing the peptide compounds of the present invention involves solid phase peptide synthesis.

In this particularly preferred method the alpha-amino function is protected by an acid or base sensitive group. Such protecting groups should have the properties of being stable to the conditions of peptide linkage formation, while being readily removable without destruction of the growing peptide chain or racemization of any of the chiral centers contained therein. Suitable protecting groups are 9-fluorenylmethyloxycarbonyl (Fmoc), t-butyloxycarbonyl (Boc), benzyloxycarbonyl (Cbz), biphenylisopropyloxycarbonyl, t-amyloxycarbonyl, isobornyloxycarbonyl, (α,α)dimethyl-3,5-dimethoxybenzyloxycarbonyl, o-nitrophenylsulfenyl, 2-cyano-t-butyloxycarbonyl, and the like. The 9-fluorenylmethyloxycarbonyl (Fmoc) protecting group is preferred.

Particutlarly preferred side chain protecting groups are, for side chain amino groups as in lysine and arginine: 2,2,5,7,8-pentamethylchroman-6-sultonyl (pmc), nitro, p-toluenesulfonyl, 4-methoxybenzenesulfonyl, Cbz, Boc, Alloc (allyloxycarbonyl) and adamantyloxycarbonyl; for tyrosine: benzyl, o-bromobenzyloxycarbonyl, 2,6-dichlorobenzyl, isopropyl, t-butyl (t-Bu), cyclohexyl, cyclopenyl and acetyl (Ac); for serine: t-butyl, benzyl and tetrahydropyranyl; for histidine: trityl, benzyl, Cbz, p-toluenesulfonyl and 2,4-dinitrophenyl; for tryptophan: formyl and Boc; for asparagine and glutamine: Trt (trityl); for aspartic acid and glutamic acid: O-t-Bu and OAllyl.

The cyclic peptide compounds of this invention are preferably prepared using a fragment-based approach in which a fragment of the desired complete peptide compound containing the amide, ester, disulfide or lanthionine bridge (the cyclic peptide fragment) is separately prepared and purified prior to coupling to a resin-bound amino acid or peptide portion of the complete peptide compound. The cyclic peptide fragment is prepared using classical solution phase synthetic techniques or solid phase peptide synthesis methodology as described herein. The synthesis of the complete peptide compound is then accomplished by sequential addition of the remaining amino acid residues to the resin-bound cyclic peptide; by addition of additional cyclic or acyclic peptide fragments to the resin bound cyclic peptide; or by any combination of the above. The preparation of cyclic peptide hPTH analogs using a fragment-based approach is described in U.S. Ser. No. 60/081897, filed Apr. 15, 1998, incorporated herein by reference.

Peptides of this invention wherein $R_{1c}$ is

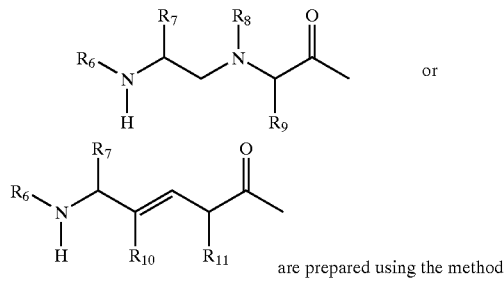

are prepared using the method are prepared using the method described by R. Waelchli et al., *Tetrahedron Lett.*, 6(10), 1151–1156 (1996), incorporated herein by reference.

The following non-limiting examples will serve to further illustrate the preparation of the novel peptides of this invention.

General Methods

The peptide compounds are prepared using Protein Technologies Inc. PAS Automated Solid Phase Peptide Synthesizer using standard Fmoc solid-phase peptide synthesis (SPPS) methodology. The Fmoc-protected amino acids are purchased from either Advanced ChemTech (Louisville, Ky., USA), Bachem (Torrance, Calif., USA), or Senn Chemicals AG (Dielsdorf, Switzerland) and are listed below: Fmoc-Ala-OH, Fmoc-Arg(Pmc)-OH, Fmoc-Asn (Trt)-OH, Fmoc-Asp(OtBu)-OH, Fmoc-Asp(OAllyl), Fmoc-Cys(Acm)-OH, Fmoc-Cys(Trt)-OH, Fmoc-Glu (OtBu)-OH, Fmoc-Glu(OAllyl)-OH, Fmoc-Gln(Trt)-OH, Fmoc-Gly-OH, Fmoc-His(Trt)-OH, Fmoc-Ile-OH, Fmoc-Leu-OH, Fmoc-Lys(Alloc)-OH, Fmoc-Lys(Boc)-OH, Fmoc-Orn(Alloc)-OH, Fmoc-Phe-OH, Fmoc-Ser(tBu)-OH, Fmoc-Thr(tBu)-OH, Fmoc-Trp(Boc)-OH, and Fmoc-Val-OH.

Amino acid analysis is performed by BACHEM Bioscience, King of Prussia, Pa. and is reported as: amino acid residue: value found (value expected).

Sequence analysis is performed at the Microchemical Facility at Emory University School of Medicine, Atlanta, Ga.

Preparation of the Amide-Bridge

Amide-bridged cyclic peptide compounds are prepared by formation of an amide bond between the side-chain carboxyl group of an acidic amino acid residue and the side-chain amino group of a basic amino acid residue in the presence of an activating agent as described above. Preferred acidic amino acid residues include Asp, Glu, —NHCH[(CH$_2$)$_3$CO$_2$H]CO— and —NHCH[(CH$_2$)$_4$CO$_2$H] CO—, Asp being most preferred. Preferred basic amino acid residues include His, Lys, Orn, —NHCH(CH$_2$NH$_2$)CO— and —NHCH[(CH$_2$)$_2$NH$_2$]CO—, Lys being most preferred.

In instances wherein the peptide precursor to the cyclic peptide compound contains more than one acidic or basic amino acid residue, protecting groups for the additional acidic or basic amino acids are selected so that the amino acids to be cyclized may be selectively deprotected. Preferably, the desired acidic and basic amino acid residues are deprotected simultaneously. Furthermore, in addition to being stable to the reagents used to deprotect the selected basic and acidic amino acid residues, the protecting groups on the remaining amino acid residues are selected to be stable to the cyclization conditions employed.

The term "orthogonality" when used in reference to side chain protecting groups refers to a situation as described herein in which there are two or more classes of protecting groups on a molecule, each class most optimally removed under specific conditions, while remaining stable to conditions used to remove protecting groups in other classes. Thus one can remove all protecting groups of one class, while leaving all others intact.

Preferred protecting groups having the desired orthogonality are: for the acidic amino acid residue to be cyclized: allyl; for the basic amino acid residue to by cyclized: allyloxycarbonyl (alloc); for any additional acidic amino acid residues: tert-butyl (tBu); and for any additional basic amino acid residues: tert-butyloxycarbonyl (Boc).

The allyl and allyloxycarbonyl protecting groups are removed simultaneously by treatment with palladium, preferably tetrakis(triphenylphosphine) palladium(O). Formation of the amide bridge is then accomplished as described herein for amide bond formation.

Preparation of the Ester Bridle

Ester-bridged cyclic peptide compounds are prepared by formation of an ester bond between the side-chain carboxyl group of an acidic amino acid residue and the side chain hydroxyl group of a hydroxyl-containing amino acid residue. Preferred acidic amino acid residues include Asp, Glu, —NHCH[$(CH_2)_3C_2H$]CO— and —NHCH[$(CH_2)_4CO_2H$]CO—, Asp being most preferred. Preferred amino a residues containing a side-chain hydroxyl group include Ser, Thr, Tyr and the like, Ser and Thr being especially preferred. Formation of the ester bond is accomplished using the methods and reagents described above for formation of a amide bridge.

Preparation of the Disulfide Bridge

Disulfide-bridged cyclic peptide compounds are prepared by formation of a disulfide bond between amino acid residues containing side chain sulfhydryl groups, of which Cys is especially preferred. Preferred protecting groups for the side-chain sulfhydryl residues are trityl (Trt) and acetamidomethyl (Acm). Treatment of the fully protected peptide precursor to the disulfide-bridged cyclic peptide compound with an oxidizing agent, for example, thallium trifluoroacetate [$Tl(CF_3CO_2)_3$] in dimethylformamide (DMF) effects the selective removal of the Trt or Acm protecting group and concomitant disulfide bond formation.

Preparation of the Lanthionine Bridge

Lanthionine-based variants of the above-described disulfide-bridged analogs are prepared from the disulfide using the desulfurization method described by Harp and Gleason (*J. Org. Chem.* 1971, 36, 73–80). Following oxidative removal of the Cys(Trt) or Cys(Acm) [or, the Homocys derivatives] and disulfide bridge formation. the peptide is treated with tris(diethylamino)phosphine in an appropriate solvent. After the recommended washings, the remaining side chain protective groups are removed as described above. The crude peptide compound is then purified using reverse phase liquid chromatography

EXAMPLE 1

Cyclo($K^{18}$—$D^{22}$)[$A^1$,$Nle^8$,$K^{18}$,$D^{22}$,$L^{27}$]hPTH(1–31)NH$_2$ (SEQ ID NO: 3)

Ala-Val-Ser-Glu-Ile-Gln-Leu-Nle-His-Asn-Leu-Gly-Lys-His-Leu-Asn-Ser-(Lys-Glu-Arg-Val-Asp)-Trp-Leu-Arg-Lys-Leu-Leu-Gln-Asp-Val amide Method A:

Rink Amide MBHA Resin (Nova Biochem, La Jolla, Calif., USA) (0.75 g, 0.41 mmol) is loaded into a reaction vessel and swelled for 10 minutes using DMF (10 mL). The N-terminal Fmoc protective group is then removed over 5 minutes using a solution of 20% piperidine in DMF (15 mL). The resin is washed six times with DMF (15 mL) and then treated over 20 minutes with a solution containing Fmoc-Val-OH (0.34 g, 1.0 mmol) and HBTU (0.38 g, 1.0 mmol) in 0.4 M N-methylmorpholine (NMM)/DMF (5 mL). Following the first amino acid coupling, the resin is washed three times with DMF (15 mL). The deprotection/coupling procedure is repeated using the following amino acid residues: Fmoc-Asp(OtBu)-OH, Fmoc-Gln(Trt)-OH, Fmoc-Leu-OH, Fmoc-Leu-OH, Fmoc-Lys(Boc)-OH, Fmoc-Arg(Pmc)-OH, Fmoc-Leu-OH, Fmoc-Trp(Boc)-OH, Fmoc-Asp(OAllyl)-OH, Fmoc-Val-OH, Fmoc-Arg(Pmc)-OH, Fmoc-Glu(OtBu)-OH, and Fmoc-Lys(Alloc)-OH. The resin-bound peptide is then removed from the instrument and washed five times with DMF (50 mL), five times with THF (50 mL), and five times with diethyl ether (50 mL). After air drying, the resin is suspended under a nitrogen atmosphere in 37:2:1 chloroform/acetic acid/NMM (40 mL). Tetrakis(triphenylphosphine)palladium(0) (2.8 g, 2.4 mmol) is added and the heterogeneous mixture is gently agitated for 2 hours at ambient temperature. The resulting homogeneous solution is filtered and the resin is washed successively with 0.5% diisopropylethylamine/DMF (100 mL), 0.5% sodium diethyldithiocarbonate/DMF (100 mL), and DMF (200 mL). Cyclization between the side chains of Lys$^{18}$ and Asp$^{22}$ is effected over 2 hours using HBTU (0.26 g, 0.62 mmol), HOBT (0.08 g, 0.62 mmol), and NMM (0.14 mL, 1.23 mmol) in anhydrous DMF (20 mL); the cyclization step is then performed a second time. The solvent is removed and the resin is washed successively with DMF (100 mL), THF (100 mL) and diethyl ether (100 mL), and air-dried.

A portion of this resin-bound peptide (0.46 g, approx. 0.1 mmol) is returned to the automated synthesizer and the remaining seventeen amino acid residues are added as described previously in the order: Fmoc-Ser(tBu)-OH, Fmoc-Asn(Trt)-OH, Fmoc-Leu-OH, Fmoc-His(Trt)-OH, Fmoc-Lys(Boc)-OH, Fmoc-Gly-OH, Fmoc-Leu-OH, Fmoc-Asn(Trt)-OH, Fmoc-His(Trt)-OH, Fmoc-Nle-OH, Fmoc-Leu-OH, Fmoc-Gln(Trt)-OH, Fmoc-Ile-OH, Fmoc-Glu(OtBu)-OH, Fmoc-Ser(tBu)-OH, Fmoc-Val-OH, and Fmoc-Ala-OH. The N-terminal Fmoc protective group is removed over 5 minutes using a 20% piperidine/DMF solution (15 mL). The resin-bound peptide is removed from the instrument and washed successively with DMF (100 mL), THF (100 mL), and diethyl ether (100 mL). The air-dried resin is suspended in 10 mL of TFA containing water (0.5 mL), thioanisole (0.5 mL), phenol (0.75 g), and ethanedithiol (0.25 mL). After 2 hours, the TFA solution is filtered into tert-butylmethyl ether (60 mL) at 0° C. which effected the precipitation of the crude peptide. The resin is washed with TFA (2 mL) which is added to the peptide mixture. The peptide mixture is centrifuged at 2500 rpm for 5 minutes and decanted. The crude, white solid is resuspended in diethyl ether (30 mL), centrifuged, and decanted. This washing procedure is repeated four times and the resulting peptide is dried in vacuo, dissolved in water containing 0.1% TFA (50 mL), and lyophilized to dryness.

The crude peptide is purified by reverse-phase high performance liquid chromatography using a Rainin HPLC system equipped with a DYNAMAX-60A semi-preparative 1" C18 column. The mobile phase initiated with water (0.1% TFA) and ramped over 30 minutes to 60% ACN (0.08% TFA)/water (0.1% TFA). The pure fractions eluting at approximately 23 minutes are combined and lyophilized to give 40 mg of the purified peptide.IS-MS: 3634 (M+). Amino Acid Analysis: Asp/Asn: 3.86 (4); Ser: 1.85 (2); Glu/Gln: 4.00 (4); Gly: 0.98 (1); Ala: 0.97 (1); Val: 2.86 (3); Ile: 0.95 (1); Leu: 6.49 (6); Nle: 0.91 (1); Lys: 2.75 (3); His: 2.06 (2); Arg: 2.09 (2); Trp: not determined (1). The position of the amide bridge is confirmed by Edman degradation and tryptic digest mapping.

Method B:

Rink Amide MBHA Resin (Nova Biochem La Jolla. Calif. USA) (0.75 g 0.41 mmol) is loaded into a reaction vessel and swelled for 10 minutes using DMF (10 mL). The N-terminal Fmoc protective group is then removed over 5 minutes using a solution of 20% piperidine in DMF (17 mL). The resin is washed six times with DMF (17 mL) and then treated over 20 minutes with a solution containing Fmoc-Val-OH (0.34 g, 1.0 mmol) and HBTU (0.38 g, 1.0 mmol) in 0.4 M N-methylmorpholine (NMM)/DMF (8 mL). Following the first amino acid coupling, the resin is washed three times with DMF (17 mL). The deprotection/coupling procedure is repeated using the following amino acid residues: Fmoc-Asp(OtBu)-OH, Fmoc-Gln(Trt)-OH, Fmoc-Leu-OH, Fmoc-Leu-OH, Fmoc-Lys(Boc)-OH, Fmoc-Arg(Pmc)-OH, Fmoc-Leu-OH, Fmoc-Trp(Boc)-OH, Fmoc-Asp(OAllyl)-OH, Fmoc-Val-OH, Fmoc-Arg(Pmc)-OH, Fmoc-Glu(OtBu)-OH, Fmoc-Lys(Alloc)-OH, Fmoc-Ser(tBu)-OH, Fmoc-Asn(Trt)-OH, and Fmoc-Leu-OH. The resin-bound peptide is then removed from the instrument and washed five times with DMF (50 mL), five times with THF (50 mL), and five times with diethyl ether (50 mL). After air drying, the resin is suspended under a nitrogen atmosphere in 37:2:1 chloroform/acetic acid/NMM (40 mL). Tetrakis(triphenylphosphine)palladium(0) (1.0 g, 0.86 mmol) is added and the heterogeneous mixture is gently agitated for 2 hours at ambient temperature. The resulting homogeneous solution is filtered and the resin is washed successively with 0.5% diisopropylethylamine/DMF (100 mL), 0.5% sodium diethyldithiocarbonate/DMF (100 mL), and DMF (200 mL). Cyclization between the side chains of $Lys^{18}$ and $Asp^{22}$ is effected over 2 hours using HBTU (0.23 g, 0.62 mmol), HOBT (0.08 g, 0.62 mmol), and NMM (0.13 mL, 1.23 mmol) in anhydrous DMF (20 mL); the cyclization step is then performed a second time. The solvent is removed and the resin is washed successively with DMF (100 mL), THF (100 mL), diethyl ether (100 mL), and air-dried.

The resin-bound peptide (approx. 2.2 g) is returned to the automated synthesizer and the remaining fourteen amino acid residues are added as described previously in the order: Fmoc-His(Trt)-OH, Fmoc-Lys(Boc)-OH, Fmoc-Gly-OH, Fmoc-Leu-OH, Fmoc-Asn(Trt)-OH, Fmoc-His(Trt)-OH, Fmoc-Nle-OH, Fmoc-Leu-OH, Fmoc-Gln(Trt)-OH, Fmoc-Ile-OH, Fmoc-Glu(OtBu)-OH, Fmoc-Ser(tBu)-OH, Fmoc-Val-OH, and Fmoc-Ala-OH. The N-terminal Fmoc protective group is removed over 5 minutes using a 20% piperidine/DMF solution (17 mL). The resin-bound peptide is removed from the instrument and washed successively with DMF (100 mL), THF (100 mL), and diethyl ether (100 mL). The air-dried resin is suspended in 40 mL of TFA containing water (2.0 mL), thioanisole (2.0 mL), phenol (3.0 g), and ethanedithiol (1.0 mL). After 2 hours, the TFA solution is filtered into tert-butylmethyl ether (160 mL) at 0° C. which effects precipitation of the crude peptide. The resin is washed with TFA (2 mL) which is added to the peptide mixture. The peptide mixture is centrifuged at 2500 rpm for 5 minutes and decanted. The crude. white solid is resuspended in diethyl ether (120 mL), centrifuged and decanted. This washing procedure is repeated four times and the resulting peptide is dried in vacuo, dissolved in water containing 0.1% TFA (100 mL), and lyophilized to dryness.

The crude peptide is purified by reverse phase liquid chromatography as described previously to provide 261 mg of material which is shown to be identical by mass spectral and HPLC analysis to an authentic sample prepared by Method A. In addition, the material provided by Method B is identical to that prepared by Method A by in vitro analysis in the ROS 17.2/8 cell cAMP assay (vide supra).
Method C:

Rink Amide MBHA Resin (Nova Biochem, La Jolla, Calif., USA) (0.75 g, 0.41 mmol) is loaded into a reaction vessel and swelled for 10 minutes using DMF (10 mL). The N-terminal Fmoc protective group is then removed over 5 minutes using a solution of 20% piperidine in DMF (17 mL). The resin is washed six times with DMF (17 mL) and then treated over 20 minutes with a solution containing Fmoc-Val-OH (0.34 g, 1.0 mmol) and HBTU (0.38 g, 1.0 mmol) in 0.4 M N-methylmorpholine (NMM)/DMF (8 mL). Following the first amino acid coupling, the resin is washed three times with DMF (17 mL). The deprotection/coupling procedure is repeated using the following amino acid residues: Fmoc-Asp(OtBu)-OH, Fmoc-Gln(Trt)-OH, Fmoc-Leu-OH, Fmoc-Leu-OH, Fmoc-Lys(Boc)-OH, Fmoc-Arg(Pmc)-OH, Fmoc-Leu-OH, Fmoc-Trp(Boc)-OH, Fmoc-Asp(OAllyl)-OH, Fmoc-Val-OH, Fmoc-Arg(Pmc)-OH, Fmoc-Glu(OtBu)-OH, Fmoc-Lys(Alloc)-OH, Fmoc-Ser(tBu)-OH, Fmoc-Asn(Trt)-OH, Fmoc-Leu-OH, Fmoc-His(Trt)-OH, Fmoc-Lys(Boc)-OH, Fmoc-Gly-OH, Fmoc-Leu-OH, Fmoc-Asn(Trt)-OH, Fmoc-His(Trt)-OH, Fmoc-Nle-OH, Fmoc-Leu-OH, Fmoc-Gln(Trt)-OH, Fmoc-Ile-OH, Fmoc-Glu(OtBu)-OH, Fmoc-Ser(tBu)-OH, Fmoc-Val-OH, and Fmoc-Ala-OH. The resin-bound peptide is then removed from the instrument and washed five times with DMF (50 mL), five times with THF (50 mL), and five times with diethyl ether (50 mL). After air drying, the resin is suspended under a nitrogen atmosphere in a 37:2:1 chloroform/acetic acid/NMM solution (40 mL). Tetrakis(triphenylphosphine)palladium(0) (1.0 g, 0.86 mmol) is added and the heterogeneous mixture is gently agitated for 2 hours at ambient temperature. The resulting homogeneous solution is filtered and the resin is washed successively with 0.5% diisopropylethylamine/DMF (100 mL), 0.5% sodium diethyldithiocarbonate/DMF (100 mL), and DMF (200 mL). Cyclization between the side chains of $Lys^{18}$ and $Asp^{22}$ is effected over 2 hours using HBTU (0.23 g, 0.62 mmol), HOBT (0.08 g, 0.62 mmol), and NMM (0.13 mL, 1.23 mmol) in anhydrous DMF (20 mL); the cyclization step is then performed a second time. The solvent is removed and the resin is washed successively with DMF (100 mL), THF (100 mL), diethyl other (100 mL), and air-dried.

The N-terminal Fmoc protective group is removed over 5 minutes using a 20% piperidine/DMF solution (17 mL). The resin-bound peptide is washed successively with DMF (100 mL), THF (100 mL), and diethyl ether (100 mL). The air-dried resin is suspended in 40 mL of TFA containing water (2.0 mL), thioanisole (2.0 mL), phenol (3.0 g), and ethanedithiol (1.0 mL). After 2 hours, the TFA solution is filtered into tert-butylmethyl ether (160 mL) at 0° C. which effects precipitation of the crude peptide. The resin is washed with TFA (2 mL) which is added to the peptide mixture. The peptide mixture is centrifuged at 2500 rpm for 5 minutes and decanted. The crude, white solid is resuspended in diethyl ether (120 mL), centrifuged, and decanted. This washing procedure is repeated four times and the resulting peptide is dried in vacuo, dissolved in water containing 0.1% TFA (100 mL), and lyophilized to dryness.

The crude peptide is purified by reverse phase liquid chromatography as described previously to provide purified peptide which is shown to be identical by mass spectral and HPLC analysis to authentic samples prepared by Methods A and B. In addition, the material provided by Method C is identical to that prepared by Methods A and B by in vitro analysis in the ROS 17.2/8 cell cAMP assay (vide supra).
Method D The fragment-based synthesis of the title compound is described in U.S. Ser. No. 60/081897, filed Apr. 15, 1998, incorporated herein by reference.

EXAMPLE 2

$[A^1,Nle^8,K^{18},D^{22},L^{27}]hPTH(1–31)NH_2$ (SEQ ID NO: 4)

Ala-Val-Ser-Glu-Ile-Gln-Leu-Nle-His-Asn-Leu-Gly-Lys-His-Leu-Asn-Ser-Lys-Glu-Arg-Val-Asp-Trp-Leu-Arg-Lys-Leu-Leu-Gln-Asp-Val amide Rink Amide MBHA Resin (Nova Biochem, La Jolla, Calif., USA) (0.75 g, 0.41 mmol) is loaded into a reaction vessel and swelled for 10 minutes using DMF (10 mL). The N-terminal Fmoc protective group is then removed over 5 minutes using a solution of 20% piperidine in DMF (17 mL). The resin is washed six times with DMF (17 mL) and then is treated over 20 minutes with a solution containing Fmoc-Val-OH (0.34 g, 1.0 mmol) and HBTU (0.38 g, 1.0 mmol) in 0.4 M N-methylmorpholine (NMM)/DMF (8 mL). Following the first amino acid coupling, the resin is washed three times with DMF (17 mL). The deprotection/coupling procedure is repeated using the following amino acid residues: Fmoc-Asp(OtBu)-OH, Fmoc-Gln(Trt)-OH, Fmoc-Leu-OH, Fmoc-Leu-OH, Fmoc-Lys(Boc)-OH, Fmoc-Arg(Pmc)-OH, Fmoc-Leu-OH, Fmoc-Trp(Boc)-OH, Fmoc-Asp(OAllyl)-OH, Fmoc-Val-OH, Fmoc-Arg(Pmc)-OH, Fmoc-Glu(OtBu)-OH, Fmoc-Lys(Alloc)-OH, Fmoc-Ser(tBu)-OH, Fmoc-Asn(Trt)-OH, Fmoc-Leu-OH, Fmoc-His(Trt)-OH, Fmoc-Lys(Boc)-O, Fmoc-Gly-OH, Fmoc-Leu-OH, Fmoc-Asn(Trt)-OH, Fmoc-His(Trt)-OH, Fmoc-Nle-OH, Fmoc-Leu-OH, Fmoc-Gln(Trt)-OH, Fmoc-Ile-OH, Fmoc-Glu(OtBu)-OH, Fmoc-Ser(tBu)-OH, Fmoc-Val-OH, and Fmoc-Ala-OH. The resin-bound peptide is then removed from the instrument and washed five times with DMF (50 mL), five times with THF (50 mL), and five times with diethyl ether (50 mL). After air drying, a portion of the resin (1.5 g, ~0.25 mmol) is suspended under a nitrogen atmosphere in a 37:2:1 chloroform/acetic acid/NMM solution (20 mL). Tetrakis(triphenylphosphine)palladium(0) (0.5 g, 0.43 mmol) is added and the heterogeneous mixture is gently agitated for 2 hours at ambient temperature. The resulting homogeneous solution is filtered and the resin is washed successively with 0.5% diisopropylethylamine/DMF (100 mL), 0.5% sodium diethyldithiocarbonate/DMF (200 mL), DMF (200 mL), THF (100 mL), diethyl ether (100 mL), and air-dried.

The N-terminal Fmoc protective group is removed over 5 minutes using a 20% piperidine/DMF solution (20 mL). The resin-bound peptide is washed successively with DMF (100 mL), THF (100 mL), and diethyl ether (100 mL). The air-dried resin is suspended in 20 mL of TFA containing water (1.0 mL), thioanisole (1.0 mL), phenol (1.5 g), and ethanedithiol (0.5 mL). After 2 hours, the TFA solution is filtered into tert-butylmethyl ether (160 mL) at 0° C. which effects precipitation of the crude peptide. The resin is washed with TFA (2 mL) which is added to the peptide mixture. The peptide mixture is centrifuged at 2500 rpm for 5 minutes and decanted. The crude, white solid is resuspended in diethyl ether (120 mL), centrifuged, and decanted. This washing procedure is repeated four times and the resulting peptide is dried in vacuo, dissolved in water containing 0.1% TFA (100 mL), and lyophilized to dryness.

The crude peptide is purified by reverse phase liquid chromatography as described previously to provide 75 mg of final, purified peptide. IS-MS: 3652 (M+). Amino Acid Analysis: Asp/Asn: 4.00 (4); Ser: 1.78 (2); Glu/Gln: 3.92 (4); Gly: 0.95 (1); Ala: 0.95 (1); Val: 3.03 (3); Ile: 0.90 (1); Lys: 3.06 (3); His: 2.01 (2); Arg: 2.04 (2); Trp: not determined (1). The primary sequence of the peptide is confirmed by Edman degradation. EXAMPLES 3–18

A portion of the resin-bound peptide previously prepared using Method A and terminating with the $K^{18}$—$D^{22}$: amide bridge (0.46 g; ~0.1 mmol) is evenly distributed amongst 17 three mL-wells of a 96-well block of an Advanced Chem Tech 496 MBS instrument. In each well, the N-terminal Fmoc protective group is removed using a 20% piperidine/DMF solution (0.5 mL). A synthesis program which allows for the independent preparation of all seventeen PTH analogs where L-alanine is systematically substituted in each of the seventeen N-terminal positions using standard Fmoc-coupling conditions (0.5 mmol Fmoc-amino acid per coupling step; triple couplings per residue) is employed. Following completion of the programmed synthesis, the PTH analogs are deprotected and removed from the resin using Reagent K (1.0 mL/well) over a two-hour period. The cleavage solutions are then individually added to diethyl ether (8 mL) at ambient temperature. The resulting heterogeneous mixtures of precipitated peptide in diethyl ether are then centrifuged and the supernatant is decanted away from the crude peptides. The solid peptides are washed successively with five portions of diethyl ether (8 mL) followed by drying in vacuo. The white solids are dissolved in water (2 mL) containing 0.1% TFA, froze, and lyophilized.

The peptides are weighed, analyzed by ion-spray mass spectrometry, and assayed for their ability to stimulate the formation of cAMP in ROS 17.2/8 cells using the method described (vide infra).

EXAMPLE 3

Cyclo($K^{18}$—$D^{22}$)[$A^{1,2}$,Nle$^8$,$K^{18}$,$D^{22}$,$L^{27}$]hPTH (1–31)NH$_2$ (SEQ ID NO: 5)

Ala-Ala-Ser-Glu-Ile-Gln-Leu-Nle-His-Asn-Leu-Gly-Lys-His-Leu-Asn-Ser-(Lys-Glu-Arg-Val-Asp)-Trp-Leu-Arg-Lys-Leu-Leu-Gln-Asp-Val amide
IS–MS=3605 (M+).

EXAMPLE 4

Cyclo($K^{18}$—$D^{22}$)[$A^{1,3}$,Nle$^8$,$K^{18}$,$D^{22}$,$L^{27}$]hPTH (1–31)NH$_2$ (SEQ ID NO: 6)

Ala-Val-Ala-Glu-Ile-Gln-Leu-Nle-His-Asn-Leu-Gly-Lys-His-Leu-Asn-Ser-(Lys-Glu-Arg-Val-Asp)-Trp-Leu-Arg-Lys-Leu-Leu-Gln-Asp-Val amide
IS–MS=3617 (M+).

EXAMPLE 5

Cyclo($K^{18}$—$D^{22}$)[$A^{1,4}$,Nle$^8$,$K^{18}$,$D^{22}$,$L^{27}$]hPTH (1–31)NH$_2$ (SEQ ID. NO: 7)

Ala-Val-Ser-Ala-Ile-Gln-Leu-Nle-His-Asn-Leu-Gly-Lys-His-Leu-Asn-Ser-(Lys-Glu-Arg-Val-Asp)-Trp- Leu-Arg-Lys-Leu-Leu-Gln-Asp-Val amide
IS–MS=3575 (M+).

EXAMPLE 6

Cyclo($K^{18}$—$D^{22}$)[$A^{1,5}$,Nle8,$K^{18}$,$D^{22}$,$L^{27}$]hPTH (1–31)NH$_2$ (SEQ ID NO: 8)

Ala-Val-Ser-Glu-Ala-Gln-Leu-Nle-His-Asn-Leu-Gly-Lys-His-Leu-Asn-Ser-(Lys-Glu-Arg-Val-Asp)-Trp-Leu-Arg-Lys-Leu-Leu-Gln-Asp-Val amide
IS–MS=3591 (M+).

EXAMPLE 7

Cyclo($K^{18}$—$D^{22}$)[$A^{1,6}$,Nle$^8$,$K^{18}$,$D^{22}$,$L^{27}$]hPTH (1–31)NH$_2$ (SEQ ID NO: 9)

Ala-Val-Ser-Glu-Ile-Ala-Leu-Nle-His-Asn-Leu-Gly-Lys-His-Leu-Asn-Ser-(Lys-Glu-Arg-Val-Asp)-Trp-Leu-Arg-Lys-Leu-Leu-Gln-Asp-Val amide
IS–MS=3576 (M+).

EXAMPLE 8

Cyclo(K$^{18}$—D$^{22}$)[A$^{1,7}$ Nle$^8$,K$^{18}$,D$^{22}$,L$^{27}$]hPTH
(1–31)NH$_2$ (SEQ ID NO: 10)

Ala-Val-Ser-Glu-Ile-Gln-Ala-Nle-His-Asn-Leu-Gly-Lys-
His-Leu-Asn-Ser-(Lys-Glu-Arg-Val-Asp)-Trp-Leu-
Arg-Lys-Letu-Leu-Gln-Asp-Val amide
IS–MS=3591 (M+).

EXAMPLE 9

Cyclo(K$^{18}$—D $^{22}$)[A$^{1,8}$,K$^{18}$,D$^{22}$,L$^{27}$]hPTH(1–31)
NH$_2$ (SEQ ID NO: 81)

Ala-Val-Ser-Glu-Ile-Gln-Leu-Ala-His-Asn-Leu-Gy-Lys-
His-Leu-Asn-Ser-(Lys-Glu-Arg-Val-Asp)-Trp-Leu-
Arg-Lys-Leu-Leu-Gln-Asp-Val amide
IS–MS=3591 (M+).

EXAMPLE 10

Cyclo(K$^{18}$—D$^{22}$)[A$^{1,9}$,Nle$^8$,K$^{18}$,D$^{22}$,L$^{27}$]hPTH
(1–31)NH$_2$ (SEQ ID NO: 11)

Ala-Val-Ser-Glu-Ile-Gln-Leu-Nle-Ala-Asn-Leu-Gly-
Lys-His-Leu-Asn-Ser-(Lys-Glu-Arg-Val-Asp)-Trp-
Leu-Arg-Lys-Leu-Leu-Gln-Asp-Val amide
IS–MS=3567 (M+).

EXAMPLE 11

Cyclo(K$^{18}$—D$^{22}$)[A$^{1,10}$,Nle$^8$,K$^{18}$,D$^{22}$,L$^{27}$]hPTH
(1–31)NH$_2$ (SEQ ID NO: 12)

Ala-Val-Ser-Glu-Ile-Gln-Leu-Nle-His-Ala-Leu-Gly-Lys-
His-Leu-Asn-Ser-(Lys-Glu-Arg-Val-Asp)-Trp-Leu-
Arg-Lys-Leu-Leu-Gln-Asp-Val amide
IS–MS=3590 (M+).

EXAMPLE 12

Cyclo(K$^{18}$—D$^{22}$)[A$^{1,11}$,Nle$^8$,K$^{18}$,D$^{22}$,L$^2$]hPTH
(1–31)NH$_2$ (SEQ ID NO: 13)

Ala-Val-Ser-Glu-Ile-Gln-Leu-Nle-His-Asn-Ala-Gly-Lys-
His-Leu-Asn-Ser-(Lys-Glu-Arg-Val-Asp)-Trp-Leu-
Arg-Lys-Leu-Leu-Gln-Asp-Val amide
IS–MS=3591 (M+).

EXAMPLE 13

Cyclo(K$^{18}$—D$^{22}$)[A$^{1,12}$ Nle$^8$,K$^{18}$,D$^{22}$,L$^{27}$]hPTH
(1–31)NH$_2$ (SEQ ID NO: 14)

Ala-Val-Ser-Glu-Ile-Gln-Leu-Nle-His-Asn-Leu-Ala-Lys-
His-Leu-Asn-Ser-(Lys-Glu-Arg-Val-Asp)-Trp-Leu-
Arg-Lys-Leu-Leu-Gln-Asp-Val amide
IS–MS=3647 (M+).

EXAMPLE 14

Cyclo(K$^{18}$—D$^{22}$)[A$^{1,13}$,Nle$^8$,K$^{18}$,D$^{22}$,L$^{27}$]hPTH
(1–31)NH$_2$ (SEQ ID NO: 15)

Ala-Val-Ser-Glu-Ile-Gln-Leu-Nle-His-Asn-Leu-Gly-Ala-
His-Leu-Asn-Ser-(Lys-Glu-Arg-Val-Asp)-Trp-Leu-
Arg-Lys-Leu-Leu-Gln-Asp-Val amide
IS–MS=3576 (M+).

EXAMPLE 15

Cyclo(K$^{18}$—D$^{22}$)[A$^{1,14}$,Nle$^8$,K$^{18}$,D$^{22}$,L$^{27}$]hPTH
(1–31)NH$_2$ (SEQ ID NO: 16)

Ala-Val-Ser-Glu-Ile-Gln-Leu-Nle-His-Asn-Leu-Gly-Lys-
Ala-Leu-Asn-Ser-(Lys-Glu-Arg-Val-Asp)-Trp-Leu-
Arg-Lys-Leu-Leu-Gln-Asp-Val amide
IS–MS=3567 (M+).

EXAMPLE 16

Cyclo(K$^{18}$—D$^{22}$)[A$^{1,15}$,Nle$^8$,K$^{18}$,D$^{22}$,L$^{27}$]hPTH
(1–31)NH$_2$ (SEQ ID NO: 17)

Ala-Val-Ser-Glu-Ile-Gln-Leu-Nle-His-Asn-Leu-Gly-Lys-
His-Ala-Asn-Ser-(Lys-Glu-Arg-Val-Asp)-Trp-Leu-
Arg-Lys-Leu-Leu-Gln-Asp-Val amide
IS–MS=3591 (M+).

EXAMPLE 17

Cyclo(K$^{18}$—D$^{22}$)[A$^{1,6}$ Nle$^8$,K$^{18}$,D$^{22}$,L$^{27}$]hPTH
(1–31)NH$_2$ (SEQ ID NO: 18)

Ala-Val-Ser-Glu-Ile-Gln-Leu-Nle-His-Asn-Leu-Gly-Lys-
His-Le-Ala-Ser-(Lys-Glu-Arg-Val-Asp)-Trp-Leu-Arg-
Lys-Leu-Leu-Gln-Asp-Val amide
IS–MS=3590 (M+).

EXAMPLE 18

Cyclo(K$^{18}$—D$^{22}$)[A$^{1,7}$,Nle$^8$,K$^{18}$,D$^{22}$,L$^2$]hPTH(I1–3
1)NH$_2$ (SEQ ID NO: 19)

Ala-Val-Ser-Glu-Ile-Gln-Leu-Nle-His-Asn-Leu-Gly-Lys-
His-Leu-Asn-Ala-(Lys-Glu-Arg-Val-Asp)-Trp-Leu-
Arg-Lys-Leu-Leu-Gln-Asp-Val amide
IS–MS=3617 (M+).

EXAMPLES 19–34

A portion of the resin-bound peptide previously prepared using Method A and terminating with the K$^{18}$—D$^{22}$ amide bridge (0.46 g, ~0.1 mmol) is evenly distributed amongst 17 three mL-wells of a 96-well block of an Advanced ChemTech 496 MBS instrument. In each well, the N-terminal Fmoc protective group is removed using a 20% piperidine/DMF solution (0.5 mL). A synthesis program which allows for the independent preparation of all seventeen PTH analogs where glycine is systematically substituted in each of the seventeen N-terminal positions using standard Fmoc-coupling conditions (0.5 mmol Fmoc-amino acid per coupling step, triple couplings per residue) is employed. Following completion of the programmed synthesis, the PTH analogs are deprotected and removed from the resin using Reagent K (1.0 mL/well) over a two-hour period. The cleavage solutions are then individually added to diethyl ether (8 mL) at ambient temperature. The resulting heterogeneous mixtures of precipitated peptide in diethyl ether are then centrifuged and the supernatant is decanted away from the crude peptides The solid peptides are washed successively with five portions of diethyl ether (8 mL) followed by drying in vacuo. The white solids are dissolved in water (2 mL) containing 0.1% TFA, froze, and lyophilized.

The peptides are weighed, analyzed by ion-spray mass spectrometry, and assayed for their ability to stimulate the formation of cAMP in ROS 17.2/8 cells using the method described (vide infra).

EXAMPLE 19

Cyclo($K^{18}$—$D^{22}$)[$G^1$,$Nle^8$,$K^{18}$,$D^{22}$,$L^{27}$]hPTH(1–31) $NH_2$ (SEQ ID NO: 20)

Gly-Val-Ser-Glu-Ile-Gln-Leu-Nle-His-Asn-Leu-Gly-Lys-His-Leu-Asn-Ser-(Lys-Glu-Arg-Val-Asp)-Trp-Leu-Arg-Lys-Leu-Leu-Gln-Asp-Val amide
IS–MS=3619 (M+).

EXAMPLE 20

Cyclo($K^{18}$—$D^{22}$)[$A^1$,$G^2$,$Nle^8$,$K^{18}$,$D^{22}$,$L^{27}$]hPTH (1–31)$NH_2$ (SEQ ID NO: 21)

Ala-Gly-Ser-Glu-Ile-Gln-Leu-Nle-His-Asn-Leu-Gly-Lys-His-Leu-Asn-Ser-(Lys-Glu-Arg-Val-Asp)-Trp-Leu-Arg-Lys-Leu-Leu-Gln-Asp-Val amide
IS–MS=3591 (M+).

EXAMPLE 21

Cyclo($K^{18}$—$D^{22}$)[$A^1$,$G^3$,$Nle^8$,$K^{18}$,$D^2$,$L^{27}$]hPTH (1–31)$NH_2$(SEQ ID NO: 22)

Ala-Val-Gly-Glu-Ile-Gln-Leu-Nle-His-Asn-Leu-Gly-Lys-His-Leu-Asn-Ser-(Lys-Glu-Arg-Val-Asp)-Trp-Leu-Arg-Lys-Leu-Leu-Gln-Asp-Val amide
IS–MS=3603 (M+).

EXAMPLE 22

Cyclo($K^{18}$—$D^{22}$)[$A^1$,$G^4$,$Nle^8$, $K^{18}$ $D^{22}$,$L^{27}$]hPTH (1–31)$NH_2$ (SEQ ID NO: 23)

Ala-Val-Ser-Gly-Ile-Gln-Leu-Nle-His-Asn-Leu-Gly-Lys-His-Leu-Asn-Ser-(Lys-Glu-Arg-Val-Asp)-Trp- Leu-Arg-Lys-Leu-Leu-Gln-Asp-Val amide
IS–MS=3561 (M+).

EXAMPLE 23

Cyclo($K^{18}$—$D^{22}$)[$A^1$,$G^5$,$Nle^8$,$K^{18}$,$D^{22}$,$L^{27}$]hPTH (1–31)$NH_2$ (SEQ ID NO: 24)

Ala-Val-Ser-Glu-Gly-Gln-Leu-Nle-His-Asn-Leu-Gly-Lys-His-Leu-Asn-Ser-(Lys-Glu-Arg-Val-Asp)-Trp-Leu-Arg-Lys-Leu-Leu-Gln-Asp-Val amide
IS–MS=3577 (M+).

EXAMPLE 24

Cyclo($K^{18}$—$D^{22}$)[$A^1$,$G^6$,$Nle^8$,$K^{18}$,$D^{22}$,$L^{27}$]hPTH (1–31)$NH_2$ (SEQ ID NO: 25)

Ala-Val-Ser-Glu-Ile-Gly-Leu-Nle-His-Asn-Leu-Gly-Lys-His-Leu-Asn-Ser-(Lys-Glu-Arg-Val-Asp)-Trp- Leu-Arg-Lys-Leu-Leu-Gln-Asp-Val amide
IS–MS=3562 (M+).

EXAMPLE 25

Cyclo($K^{18}$—$D^{22}$)[$A^1$,$G^7$,$Nle^8$,$K^{18}$,$D^{22}$,$L^{27}$]hPTH (1–31)$NH_2$ (SEQ ID NO: 26)

Ala-Val-Ser-Glu-Ile-Gln-Gly-Nle-His-Asn-Leu-Gly-Lys-His-Leu-Asn-Ser-(Lys-Glu-Arg-Val-Asp)-Trp- Leu-Arg-Lys-Leu-Leu-Gln-Asp-Val amide
IS–MS=3577 (M+).

EXAMPLE 26

Cyclo($K^{18}$—$D^{22}$)[$A^1$,$G^8K^{18}$,$D^{22}$,$L^{27}$]hPTH(1–31) $NH_2$ (SEQ ID NO: 27)

Ala-Val-Ser-Glu-Ile-Gln-Leu-Gly-His-Asn-Leu-Gly-Lys-His-Leu-Asn-Ser-(Lys-Glu-Arg-Val-Asp)-Trp-Leu-Arg-Lys-Leu-Leu-Gln-Asp-Val amide
IS–MS=3577 (M+).

EXAMPLE 27

Cyclo($K^{18}$—$D^{22}$)[$A^1$,$G^9$,$Nle^8$,$K^{18}$,$D^{22}$,$L^{27}$]hPTH (1–31)$NH_2$ (SEQ ID NO: 28)

Ala-Val-Ser-Glu-Ile-Gln-Leu-Nle-Gly-Asn-Leu-Gly-Lys-His-Leu-Asn-Ser-(Lys-Glu-Arg-Val-Asp)-Trp-Leu-Arg-Lys-Leu-Leu-Gln-Asp-Val amide
IS–MS=3553 (M+).

EXAMPLE 28

Cyclo($K^{18}$—$D^{22}$)[$A^1$,$G^{10}$,$Nle^8$,$K^{18}$,$D^{22}$,$L^{27}$]hPTH (1–31)$NH_2$ (SEQ ID NO: 29)

Ala-Val-Ser-Glu-Ile-Gln-Leu-Nle-His-Gly-Leu-Gly-Lys-His-Leu-Asn-Ser-(Lys-Glu-Arg-Val-Asp)-Trp- Leu-Arg-Lys-Leu-Leu-Gln-Asp-Val amide
IS–MS=3576 (M+).

EXAMPLE 29

Cyclo($K^{18}$—$D^{22}$)[$A^1$,$G^{11}$,$Nle^8$,$K^{18,D22}$,$L^{27}$]hPTH (1–31)$NH_2$ (SEQ ID NO: 30)

Ala-Val-Ser-Glu-Ile-Gln-Leu-Nle-His-Asn-Gly-Gly-Lys-His-Leu-Asn-Ser-(Lys-Glu-Arg-Val-Asp)-Trp- Leu-Arg-Lys-Leu-Leu-Gln-Asp-Val amide
IS–MS=3577 (M+).

EXAMPLE 30

Cyclo($K^{18}$—$D^{22}$)[$A^1$,$G^{13}$,$Nle^8$,$K^{18}$,$D^{22}$,$L^{27}$]hPTH (1–31)$NH_2$ (SEQ ID NO: 31)

Ala-Val-Ser-Glu-Ile-Gln-Leu-Nle-His-Asn-Leu-Gly-Gly-His-Leu-Asn-Ser-(Lys-Glu-Arg-Val-Asp)-Trp-Leu-Arg-Lys-Leu-Leu-Gln-Asp-Val amide
IS–MS=3562 (M+).

EXAMPLE 31

Cyclo($K^{18}$—$D^{22}$)[$A^1$,$G^{14}$, $Nle^8$,$K^{18}$,$D^{22}$,$L^{27}$]hPTH (1–31)$NH_2$ (SEQ ID NO: 32)

Ala-Val-Ser-Glu-Ile-Gln-Leu-Nle-His-Asn-Leu-Gly-Lys-Gly-Leu-Asn-Ser-(Lys-Glu-Arg-Val-Asp)-Trp- Leu-Arg-Lys-Leu-Leu-Gln-Asp-Val amide
IS–MS=3553 (M+).

EXAMPLE 32

Cyclo($K^{18}$—$D^{22}$)[$A^1$,$G^{15}$,$Nle^8$,$K^{18}$,$D^{22}$,$L^{27}$]hPTH (1–31)$NH_2$ (SEQ ID NO: 33)

Ala-Val-Ser-Glu-Ile-Gln-Leu-Nle-His-Asn-Leu-Gly-Lys-His-Gly-Asn-Ser-(Lys-Glu-Arg-Val-Asp)-Trp- Leu-Arg-Lys-Leu-Leu-Gln-Asp-Val amide
IS–MS=3577 (M+).

EXAMPLE 33

Cyclo(K$^{18}$—D$^{22}$)[A$^1$,G$^{16}$,Nle$^8$,K$^{18}$,D$^{22}$,L$^{27}$]hPTH
(1–31)NH$_2$ (SEQ ID NO: 34)

Ala-Val-Ser-Glu-Ile-Gln-Leu-Nle-His-Asn-Leu-Gly-Lys-His-Leu-Gly-Ser-(Lys-Glu-Arg-Val-Asp)-Trp- Leu-Arg-Lys-Leu-Leu-Gln-Asp-Val amide
IS–MS=3576 (M+).

EXAMPLE 34

Cyclo(K$^{18}$—D$^{22}$)[A$^1$,G$^{17}$,Nle$^8$,K$^{18}$,D$^{22}$,L$^{27}$]hPTH
(1–31)NH$_2$ (SEQ ID NO: 35)

Ala-Val-Ser-Glu-Ile-Gln-Leu-Nle-His-Asn-Leu-Gly-Lys-His-Leu-Asn-Gly-(Lys-Glu-Arg-Val-Asp)-Trp- Leu-Arg-Lys-Leu-Leu-Gln-Asp-Val amide
IS–MS=3603 (M+).

EXAMPLES 35–51

A portion of the resin-bound peptide previously prepared using Method A and terminating with the K$^{18}$—D$^{22}$ amide bridge (0.46 g, 0.1 mmol) is evenly distributed amongst 17 three mL-wells of a 96-well block of an Advanced ChemTech 496 MBS instrument. In each well, the N-terminal Fmoc protective group is removed using a 20% piperidine/DMF solution (0.5 mL). A synthesis program which allows for the independent preparation of all seventeen PTH analogs where D-proline is systematically substituted in each of the seventeen N-terminal positions using standard Fmoc-coupling conditions (0.5 mmol Fmoc-amino acid per coupling step; triple couplings per residue) is employed. Following completion of the programmed synthesis, the PTH analogs are deprotected and removed from the resin using Reagent K (1.0 mL/well) over a two-hour period. The cleavage solutions are then individually added to diethyl ether (8 mL) at ambient temperature. The resulting heterogeneous mixtures of precipitated peptide in diethyl ether are then centrifuged and the supernatant is decanted away from the crude peptides. The solid peptides are washed successively with five portions of diethyl ether (8 mL) followed by drying in vacuo. The white solids are dissolved in water (2 mL) containing 0.1% TFA. frozen, and lyophilized.

The peptides are weighed, analyzed by ion-spray mass spectrometry, and assayed for their ability to stimulate the formation of cAMP in ROS 17.2/8 cells using the method described (vide infra).

EXAMPLE 35

Cyclo(K$^{18}$—D$^{22}$)[D-P$^1$,Nle$^8$,K$^{18}$,D$^{22}$,L$^{27}$]hPTH
(1–31)NH$_2$ (SEQ ID NO: 36)

D-Pro-Val-Ser-Glu-Ile-Gln-Leu-Nle-His-Asn-Leu-Gly-Lys-His-Leu-Asn-Ser-(Lys-Glu-Arg-Val-Asp)-Trp-Leu-Arg-Lys-Leu-Leu-Gln-Asp-Val amide
IS–MS=3659 (M+).

EXAMPLE 36

Cyclo(K$^{18}$—D$^{22}$)[A$^1$, D-P$^2$,Nle$^8$,K$^{18}$,D$^{22}$,L$^{27}$]hPTH
(1–31)NH$_2$ (SEQ ID NO: 82)

Ala-D-Pro-Ser-Glu-Ile-Gln-Leu-Nle-His-Asn-Leu-Gly-Lys-His-Leu-Asn-Ser-(Lys-Glu-Arg-Val-Asp)-Trp- Leu-Arg-Lys-Leu-Leu-Gln-Asp-Val amide
IS–MS=3631 (M+).

EXAMPLE 37

Cyclo(K$^{18}$—D$^{22}$)[A$^{1,\ D\text{-}P3}$,Nle$^8$,K$^{18}$,D$^{22}$,L$^{27}$]hPTH
(1–31)NH$_2$ (SEQ ID NO: 37)

Ala-Val-D-Pro-Glu-Ile-Gln-Leu-Nle-His-Asn-Leu-Gly-Lys-His-Leu-Asn-Ser-(Lys-Glu-Arg-Val-Asp)-Trp-Leu-Arg-Lys-Leu-Leu-Gln-Asp-Val amide
IS–MS=3643 (M+).

EXAMPLE 38

Cyclo(K$^{18}$—D$^{22}$)[A$^1$, D-P$^4$,Nle$^8$,K$^{18}$,D$^{22}$,L$^{27}$]hPTH
(1–31)NH$_2$ (SEQ ID NO: 83)

Ala-Val-Ser-D-Pro-Ile-Gln-Leu-Nle-His-Asn-Leu-Gly-Lys-His-Leu-Asn-Ser-(Lys-Glu-Arg-Val-Asp)-Trp-Leu-Arg-Lys-Leu-Leu-Gln-Asp-Val amide
IS–MS=3601 (M+).

EXAMPLE 39

Cyclo(K$^{18}$—D$^{22}$)[A$^1$, D-P$^5$,Nle, K$^{18}$,D$^{22}$,L$^{27}$]hPTH
(1–31)NH$_2$ (SEQ ID NO: 84)

Ala-Val-Ser-Glu-D-Pro-Gln-Leu-Nle-His-Asn-Leu-Gly-Lys-His-Leu-Asn-Ser-(Lys-Glu-Arg-Val-Asp)-Trp-Leu-Arg-Lys-Leu-Leu-Gln-Asp-Val amide
IS–MS=3617 (M+).

EXAMPLE 40

Cyclo(K$^{18}$—D$^{22}$)[A$^1$, D-P$^6$,Nle$^8$,K$^{18}$,D$^{22}$,L$^{27}$]hPTH
(1–31)NH$_2$ (SEQ ID NO: 38)

Ala-Val-Ser-Glu-Ile-D-Pro-Leu-Nle-His-Asn-Leu-Gly-Lys-His-Leu-Asn-Ser-(Lys-Glu-Arg-Val-Asp)-Trp-Leu-Arg-Lys-Leu-Leu-Gln-Asp-Val amide
IS–MS=3602 (M+).

EXAMPLE 41

Cyclo(K$^{18}$—D$^{22}$)[A$^1$,D-P$^7$,Nle$^8$,K$^{18}$,D$^{22}$ L$^{27}$]hPTH
(1–31)NH$_2$ (SEQ ID NO: 39)

Ala-Val-Ser-Glu-Ile-Gln-D-Pro-Nle-His-Asn-Leu-Gly-Lys-His-Leu-Asn-Ser-(Lys-Glu-Arg-Val-Asp)-Trp-Leu-Arg-Lys-Leu-Leu-Gln-Asp-Val amide
IS–MS=3617 (M+).

EXAMPLE 42

Cyclo(K$^{18}$—D$^{22}$)[A$^1$, D-P$^8$,K$^{18}$,D$^{22}$,L$^{27}$]hPTH
(1–31)NH$_2$ (SEQ ID NO: 85)

Ala-Val-Ser-Glu-Ile-Gln-Leu-D-Pro-His-Asn-Leu-Gly-Lys-His-Leu-Asn-Ser-(Lys-Glu-Arg-Val-Asp)-Trp-Leu-Arg-Lys-Leu-Leu-Gln-Asn-Val amide
IS–MS=3617 (M+).

EXAMPLE 43

Cyclo(K$^{18}$—D$^{22}$)[A$^1$,D-P$^9$,Nle$^8$,K$^{18}$,D$^{22}$,L$^{27}$]hPTH
(1–31)NH$_2$ (SEQ ID NO: 40)

Ala-Val-Ser-Glu-Ile-Gln-Leu-Nle-D-Pro-Asn-Leu-Gly-Lys-His-Leu-Asn-Ser-(Lys-Glu-Arg-Val-Asp)-Trp-Leu-Arg-Lys-Leu-Leu-Gln-Asp-Val amide
IS–MS=3593 (M+).

EXAMPLE 44

Cyclo($K^{18}$—$D^{22}$)[$A^1$,D-$P^{10}$,$Nle^8$,$K^{18}$,$D^{22}$, $L^{27}$] hPTH(1–3 l)$NH_2$ (SEQ ID NO: 41)

Ala-Val-Ser-Glu-Ile-Gln-Leu-Nle-His-D-Pro-Leu-Gly-Lys-His-Leu-Asn-Ser-(Lys-Glu-Arg-Val-Asp)-Trp-Leu-Arg-Lys-Leu-Leu-Gln-Asp-Val amide
IS–MS=3616 (M+).

EXAMPLE 45

Cyclo($K^{18}$—$D^{22}$)[$A^1$,D-$P^{11}$,$Nle^8$,$K^{18}$,$D^{22}$,$L^{27}$]hPTH (1–31)$NH_2$ (SEQ ID NO: 86)

Ala-Val-Ser-Glu-Ile-Gln-Leu-Nle-His-Asn-D-Pro-Gly-Lys-His-Leu-Asn-Ser-(Lys-Glu-Arg-Val-Asp)-Trp-Leu-Arg-Lys-Leu-Leu-Gln-Asp-Val amide
IS–MS=3617 (M+).

EXAMPLE 46

Cyclo($K^{18}$—$D^{22}$)[$A^1$,D-$P^{12}$,$Nle^8$,$K^{18}$,$D^{22}$,$L^{27}$]hPTH (1–31)$NH_2$ (SEQ ID NO: 87)

Ala-Val-Ser-Glu-Ile-Gln-Leu-Nle-His-Asn-Leu-D-Pro-Lys-His-Leu-Asn-Ser-(Lys-Glu-Arg-Val-Asp)-Trp-Leu-Arg-Lys-Leu-Leu-Gln-Asp-Val amide
IS–MS=3673 (M+).

EXAMPLE 47

Cyclo($K^{18}$—$D^{22}$)[$A^1$,D-$P^{13}$,$Nle^8$,$K^{18}$,$D^{22}$,$L^{27}$]hPTH (1–31)$NH_2$ (SEQ ID NO: 88)

Ala-Val-Ser-Glu-Ile-Gln-Leu-Nle-His-Asn-Leu-Gly-D-Pro-His-Leu-Asn-Ser-(Lys-Glu-Arg-Val-Asp)-Trp-Leu-Arg-Lys-Leu-Leu-Gln-Asp-Val amide
IS–MS=3602 (M+).

EXAMPLE 48

Cyclo($K^{18}$—$D^{22}$)[$A^1$,D-$P^{14}$,$Nle^8$,$K^{18}$,$D^{22}$,$L^{27}$]hPTH (1–31)$NH_2$ (SEQ ID NO: 42)

Ala-Val-Ser-Glu-Ile-Gln-Leu-Nle-His-Asn-Leu-Gly-Lys-D-Pro-Leu-Asn-Ser-(Lys-Glu-Arg-Val-Asp)-Trp- Leu-Arg-Lys-Leu-Leu-Gln-Asp-Val amide
IS–MS=3593 (M+).

EXAMPLE 49

Cyclo($K^{18}$—$D^{22}$)[$A^1$,D-$P^{15}$,$Nle^8$,$K^{18}$,$D^{22}$,$L^{27}$]hPTH (1–31)$NH_2$ (SEQ ID NO: 43)

Ala-Val-Ser-Glu-Ile-Gln-Leu-Nle-His-Asn-Leu-Gly-Lys-His-D-Pro-Asn-Ser-(Lys-Glu-Arg-Val-Asp)-Trp- Leu-Arg-Lys-Leu-Leu-Gln-Asp-Val amide
IS–MS=3617 (M+).

EXAMPLE 50

Cyclo($K^{18}$—$D^{22}$)[$A^1$,D-$P^{16}$,$Nle^8$,$K^{18}$,$D^{22}$ $L^{27}$]hPTH (1–3 l)$NH_2$ (SEQ ID NO: 44)

Ala-Val-Ser-Glu-Ile-Gln-Leu-Nle-His-Asn-Leu-Gly-Lys-His-Leu-D-Pro-Ser-(Lys-Glu-Arg-Val-Asp)-Trp- Leu-Arg-Lys-Leu-Leu-Gln-Asp-Val amide
IS–MS=3616 (M+).

EXAMPLE 51

Cyclo($K^{18}$—$D^{22}$)[$A^1$,D-$P^{17}Nle^8$,$K^{18}$,$D^{22}$,$L^{27}$]hPTH (1–31)$NH_2$ (SEQ ID NO: 45)

Ala-Val-Ser-Glu-Ile-Gln-Leu-Nle-His-Asn-Leu-Gly-Lys-His-Leu-Asn-D-Pro-(Lys-Glu-Arg-Val-Asp)-Trp- Leu-Arg-Lys-Leu-Leu-Gln-Asp-Val amide
IS–MS=3643 (M+).

EXAMPLE 52

Cyclo($K^{18}$—$D^{22}$)[$A^1$,$Nle^8$,$K^{18}$,$D^{22}$,$L^2$]hPTH(1–34) $NH_2$ (SEQ ID NO: 46)

Ala-Val-Ser-Glu-Ile-Gln-Leu-Nle-His-Asn-Leu-Gly-Lys-His-Leu-Asn-Ser-(Lys-Glu-Arg-Val-Asp)-Trp- Leu-Arg-Lys-Leu-Leu-Gln-Asp-Val-His-Asn-Phe amide The peptide is prepared in a fashion analogous to that described previously (Method B). Rink Amide MBHA resin (0.5 mmol) is placed in a reaction vessel which is then attached to a Protein Technologies PS3 Automated Peptide synthesizer. The following amino acids are added sequentially in a manner consistent with Fmoc-base SPPS: Fmoc-Phe-OH, Fmoc-Asn(Trt)-OH, Fmoc-His(Trt)-OH, Fmoc-Val-OH, Fmoc-Asp(OtBu)-OH, Fmoc-Gln(Trt)-OH, Fmoc-Leu-OH, Fmoc-Leu-OH, Fmoc-Lys(Boc)-OH, Fmoc-Arg(Pmc)-OH, Fmoc-Leu-OH, Fmoc-Trp(Boc)-OH, Fmoc-Asp(OAllyl)-OH, Fmoc-Val-OH, Fmoc-Arg(Pmc)-OH, Fmoc-Glu(tBu)-OH, Fmoc-Lys(Alloc)-OH, Fmoc-Ser(tBu)-OH, Fmoc-Asn(Trt)-OH, and Fmoc-Leu-OH. As described previously, the resin-bound peptide is then removed from the instrument for Pd-mediated side chain deprotection of the Lys(Alloc) and Asp(OAllyl) residues and subsequent intramolecular side chain-to-side chain cyclization. Following the described work-up procedures, the amide-containing resin-bound peptide is returned to the instrument for completion of the synthesis; the following amino acids are added sequentially: Fmoc-His(Trt)-OH, Fmoc-Lys(Boc)-O, Fmoc-Gly-OH, Fmoc-Leu-OH, Fmoc-Asn(Trt)-OH, Fmoc-His(Trt)-OH, Fmoc-Nle-OH, Fmoc-Leu-OH, Fmoc-Gln(Trt)-OH, Fmoc-Ile-OH, Fmoc-Glu(OtBu)-OH, Fmoc-Ser(tBu)-OH, Fmoc-Val-OH, and Fmoc-Ala-OH. The resin-bound Deptide is removed from the instrument and the N-terminal Fmoc protective group is removed over 5 minutes using a 20% piperidine/DMF solution (17 mL). The resin-bound peptide is washed successively with DMF (100 mL), THF (100 mL), and diethyl ether (100 mL). The air-dried resin is suspended in 40 mL of TFA containing water (2.0 mL), thioanisole (2.0 mL), phenol (3.0 g), and ethanedithiol (1.0 mL). After 2 hours, the TFA solution is filtered into tert-butylmethyl ether (160 mL) at 0° C. which effects precipitation of the crude peptide. The peptide mixture is centrifuged at 2500 rpm for 5 minutes and decanted. The crude, white solid is resuspended in diethyl ether (120 mL), centrifuged, and decanted. This washing procedure is repeated four times and the resulting peptide is dried in vacuo, dissolved in water containing 0.1% TFA (100 mL), and lyophilized to dryness.

The crude peptide is then purified by reverse-phase liquid chromatography to provide 320 mg of the final, purified peptide as a white solid. IS–MS: 4032 (M+). Amino Acid Analysis: Asp/Asn: 5.00 (5); Ser: 1.63 (2); Glu/Gln: 3.81 (4); Gly: 0.90 (l); Ala: 0.85 (1); Val: 2.71 (3); Ile: 0.84 (1); Leu: 6.35 (6); Nle: 0.77 (1); Phe: 1.07 (1); Lys: 2.90 (3); His: 2.80 (3); Arg: 1.96 (2); Trp: not determined (1).

EXAMPLE 53

Cyclo($D^{18}$-$K^{22}$)[$A^1$,Nle$^8$,$D^{18}$,$K^{22}$,$L^{27}$]hPTH(1–31)
NH$_2$ (SEQ ID NO: 47)

Ala-Val-Ser-Glu-Ile-Gln-Leu-Nle-His-Asn-Leu-Gly-Lys-His-Leu-Asn-Ser-(Asp-Glu-Arg-Val-Lys)-Trp- Leu-Arg-Lys-Leu-Leu-Gln-Asp-Val amide The peptide is prepared in a fashion analogous to that described previously (Method C). Rink Amide MBHA resin (0.5 mmol) is placed in a reaction vessel which is then attached to a Protein Technologies PS3 Automated Peptide synthesizer. The following amino acids are added sequentially in a manner consistent with Fmoc-base SPPS: Fmoc-Val-OH, Fmoc-Asp(OtBu)-OH, Fmoc-Gln(Trt)-OH, Fmoc-Leu-OH, Fmoc-Leu-OH, Fmoc-Lys(Boc)-OH, Fmoc-Arg(Pmc)-OH, Fmoc-Leu-OH, Fmoc-Trp(Boc)-OH, Fmoc-Lys(Alloc)-OH, Fmoc-Val-OH, Fmoc-Arg(Pmc)-OH, Fmoc-Glu(OtBu)-OH, Fmoc-Asp(OAllyl)-OH, Fmoc-Ser(tBu)-OH, Fmoc-Asn(Trt)-OH, Fmoc-Leu-OH, Fmoc-His(Trt)-OH, Fmoc-Lys(Boc)-OH, Fmoc-Gly-OH, Fmoc-Leu-OH, Fmoc-Asn(Trt)-OH, Fmoc-His(Trt)-OH, Fmoc-Nle-OH, Fmoc-Leu-OH, Fmoc-Gln(Trt)-OH, Fmoc-Ile-OH, Fmoc-Glu(OtBu)-OH, Fmoc-Ser(tBu)-OH, Fmoc-Val-OH, and Fmoc-Ala-OH. As described previously, the resin-bound peptide is then removed from the instrument for Pd-mediated side chain deprotection of the Lys(Alloc) and Asp(OAllyl) residues and subsequent intramolecular side chain-to-side chain cyclization. The N-terminal Fmoc protective group is removed over 5 minutes using a 20% piperidine/DMF solution (17 mL). The resin-bound peptide is washed successively with DMF (100 mL), THF (100 mL), and diethyl ether (100 mL). The air-dried resin is suspended in 40 mL of TFA containing water (2.0 mL), thioanisole (2.0 mL), phenol (3.0 g), and ethanedithiol (1.0 mL). After 2 hours, the TFA solution is filtered into tert-butylmethyl ether (160 mL) at 0° C. which effects precipitation of the crude peptide. The peptide mixture is centrifuged at 2500 rpm for 5 minutes and decanted. The crude, white solid is resuspended in diethyl ether (120 mL), centrifuged, and decanted. This washing procedure is repeated four times and the resulting peptide is dried in vacuo, dissolved in water containing 0.1% TFA (100 mL), and lyophilized to dryness.

The crude peptide is then purified by reverse-phase liquid chromatography as described previously to provide 252 mg of final, purified peptide as a white solid. IS–MS: 3634 (M+). Amino Acid Analysis: Asp/Asn: 3.97 (4); Ser: 1.88 (2); Glu/Gln: 3.95 (4); Gly: 1.00 (1); Ala: 0.99 (1); Val: 2.91 (3); Ile: 0.87 (1); Leu: 6.57 (6); Nle: 0.80 (1); Lys: 2.90 (3); His: 2.12 (2); Arg: 2.05 (2); Trp: not determined (1).

EXAMPLE 54

Cyclo($O^{18}$-$D^{22}$)[$A^1$,Nle$^8$,$O^{18}$,$D^{22}$,$L^{27}$]hPTH(1–31)NH$_2$ (SEQ ID NO: 48)

Ala-Val-Ser-Glu-Ile-Gln-Leu-Nle-His-Asn-Leu-Gly-Lys-His-Leu-Asn-Ser-(Orn-Glu-Arg-Val-Asp)-Trp- Leu-Arg-Lys-Leu-Leu-Gln-Asp-Val amide The peptide is prepared in a fashion analogous to that described previously (Method C). Rink Amide MBHA resin (0.5 mmol) is placed in a reaction vessel which is then attached to a Protein Technologies PS3 Automated Peptide synthesizer. The following amino acids are added sequentially in a manner consistent with Fmoc-base SPPS: Fmoc-Val-OH, Fmoc-Asp(OtBu)-OH, Fmoc-Gln(Trt)-OH, Fmoc-Leu-OH, Fmoc-Leu-OH, Fmoc-Lys(Boc)-OH, Fmoc-Arg(Pmc)-OH, Fmoc-Leu-OH, Fmoc-Trp(Boc)-OH, Fmoc-Asp(OAllyl)-OH, Fmoc-Val-OH, Fmoc-Arg(Pmc)-OH, Fmoc-Glu(OtBu)-OH, Fmoc-Orn(Alloc)-OH, Fmoc-Ser(tBu)-OH, Fmoc-Asn(Trt)-OH, Fmoc-Leu-OH, Fmoc-His(Trt)-OH, Fmoc-Lys(Boc)-OH, Fmoc-Gly-OH, Fmoc-Leu-OH, Fmoc-Asn(Trt)-OH, Fmoc-His(Trt)-OH, Fmoc-Nle-OH, Fmoc-Leu-OH, Fmoc-Gln(Trt)-OH, Fmoc-Ile-OH, Fmoc-Glu(OtBu)-OH, Fmoc-Ser(tBu)-OH, Fmoc-Val-OH, and Fmoc-Ala-OH. As described previously, the resin-bound peptide is then removed from the instrument for Pd-mediated side chain deprotection of Orn(Alloc) and Asp(OAllyl) residues and subsequent intramolecular side chain-to-side chain cyclization. The N-terminal Fmoc protective group is removed over 5 minutes using a 20% piperidine/DMF solution (17 mL). The resin-bound peptide is washed successively with DMF (100 mL), THF (100 mL), and diethyl ether (100 mL). The air-dried resin is suspended in 40 mL of TFA containing water (2.0 mL), thioanisole (2.0 mL), phenol (3.0 g), and ethanedithiol (1.0 mL). After 2 hours, the TFA solution is filtered into tert-butylmethyl ether (160 mL) at 0° C. which effects precipitation of the crude peptide. The peptide mixture is centrifuged at 2500 rpm for 5 minutes and decanted. The crude, white solid is resuspended in diethyl ether (120 mL), centrifuged, and decanted. This washing procedure is repeated four times and the resulting peptide is dried in vacuo, dissolved in water containing 0.1% TFA (100 mL), and lyophilized to dryness.

The crude peptide is then purified by reverse-phase liquid chromatography as described previously to provide 251 mg of final, purified peptide as a white solid. IS–MS: 3620 (M+). Amino Acid Analysis: Asp/Asn: 4.00 (4); Ser: 1.76 (2); Glu/Gln: 3.98 (4); Gly: 0.98 (1); Ala: 0.95 (1); Val: 2.94 (3); Ile: 0.88 (1); Leu: 6.52 (6); Nle: 0.84 (1); Lys: 2.03 (2); His: 1.94 (2); Arg: 2.01 (2); Trp: not determined (1).

EXAMPLE 55

Cyclo($D^{18}$-$O^{22}$)[$A^1$,Nle$^8$,$D^{18}$,$O^{22}$,$L^{27}$]hPTH(1–31)
NH$_2$ (SEQ ID NO: 49)

Ala-Val-Ser-Glu-Ile-Gln-Leu-Nle-His-Asn-Leu-Gly-Lys-His-Leu-Asn-Ser-(Asp-Glu-Arg-Val-Orn)-Trp- Leu-Arg-Lys-Leu-Leu-Gln-Asp-Val amide The peptide is prepared in a fashion analogous to that described previously (Method C). Rink Amide MBHA resin (0.5 mmol) is placed in a reaction vessel which is then attached to a Protein Technologies PS3 Automated Peptide synthesizer. The following amino acids are added sequentially in a manner consistent with Fmoc-base SPPS: Fmoc-Val-OH, Fmoc-Asp(OtBu)-OH, Fmoc-Gln(Trt)-OH, Fmoc-Leu-OH, Fmoc-Leu-OH, Fmoc-Lys(Boc)-OH, Fmoc-Arg(Pmc)-OH, Fmoc-Leu-OH, Fmoc-Trp(Boc)-OH, Fmoc-Orn(Alloc)-OH, Fmoc-Val-OH, Fmoc-Arg(Pmc)-OH, Fmoc-Glu(OtBu)-OH, Fmoc-Asp(OAllyl)-OH, Fmoc-Ser(tBu)-OH, Fmoc-Asn(Trt)-OH, Fmoc-Leu-OH, Fmoc-His(Trt)-OH, Fmoc-Lys(Boc)-OH, Fmoc-Gly-OH, Fmoc-Leu-OH, Fmoc-Asn(Trt)-OH, Fmoc-His(Trt)-OH, Fmoc-Nle-OH, Fmoc-Leu-OH, Fmoc-Gln(Trt)-OH, Fmoc-Ile-OH, Fmoc-Glu(OtBu)-OH, Fmoc-Ser(tBu)-OH, Fmoc-Val-OH, and Fmoc-Ala-OH. As described previously, the resin-bound peptide is then removed from the instrument for Pd-mediated side chain deprotection of Orn(Alloc) and Asp(OAllyl) residues and subsequent intramolecular side chain-to-side chain cyclization. The N-terminal Fmoc protective group is removed over 5 minutes using a 20% piperidine/DMF solution (17 mL). The resin-bound peptide is washed successively with DMF (100 mL), THF (100 mL), and diethyl ether (100 mL). The air-dried resin is suspended in 40 mL of TFA containing water (2.0 mL), thioanisole (2.0 mL), phenol (3.0 g), and ethanedithiol (1.0 mL). After 2 hours, the TFA solution is filtered into tert-butylmethyl ether (160 mL) at 0° C. which effects precipitation of the crude peptide. The peptide mixture is centrifuged at 2500 rpm for 5 minutes and decanted. The crude, white solid is resuspended in diethyl ether (120 mL), centrifuged, and decanted. This washing procedure is repeated four times and the resulting peptide is dried in vacuo, dissolved in water containing 0.1% TFA (100 mL), and lyophilized to dryness.

The crude peptide is then purified by reverse-phase liquid chromatography as described previously to provide 414 mg of final, purified peptide as a white solid. IS–MS: 3620 (M+). Amino Acid Analysis: Asp/Asn: 4.00 (4); Ser: 1.81 (2); Glu/Gln: 3.93 (4); Gly: 0.99 (1); Ala: 0.97 (1); Val: 2.67 (3); Ile: 0.87 (1); Leu: 6.39 (6); Nle: 0.79 (1); Lys: 1.98 (2); His: 1.97 (2); Arg: 1.97 (2); Trp: not determined (1).

EXAMPLE 56

Cyclo($K^{18}$—$E^{22}$)[$A^1$,$Nle^8$,$K^{18}$,$E^{22}$,$L^{27}$]hPTH(1–31) $NH_2$ (SEQ ID NO: 50)

Ala-Val-Ser-Glu-Ile-Gln-Leu-Nle-His-Asn-Leu-Gly-Lys-His-Leu-Asn-Ser-(Lys-Glu-Arg-Val-Glu)-Trp- Leu-Arg-Lys-Leu-Leu-Gln-Asp-Val amide The peptide is prepared in a fashion analogous to that described previously (Method C). Rink Amide MBHA resin (0.5 mmol) is placed in a reaction vessel which is then attached to a Protein Technologies PS3 Automated Peptide synthesizer. The following amino acids are added sequentially in a manner consistent with Fmoc-base SPPS: Fmoc-Val-OH, Fmoc-Asp(OtBu)-OH, Fmoc-Gln(Trt)-OH, Fmoc-Leu-OH, Fmoc-Leu-OH, Fmoc-Lys(Boc)-OH, Fmoc-Arg (Pmc)-OH, Fmoc-Leu-OH, Fmoc-Trp(Boc)-OH, Fmoc-Glu (OAllyl)-OH, Fmoc-Val-OH, Fmoc-Arg(Pmc)-OH, Fmoc-Glu(OtBu)-OH, Fmoc-Lys(Alloc)-OH, Fmoc-Ser(tBu)-OH, Fmoc-Asn(Trt)-OH, Fmoc-Leu-OH, Fmoc-His(Trt)-OH, Fmoc-Lys(Boc)-OH, Fmoc-Gly-OH, Fmoc-Leu-OH, Fmoc-Asn(Trt)-OH, Fmoc-His(Trt)-OH, Fmoc-Nle-OH, Fmoc-Leu-OH, Fmoc-Gln(Trt)-OH, Fmoc-Ile-OH, Fmoc-Glu (OtBu)-OH, Fmoc-Ser(tBu)-OH, Fmoc-Val-OH, and Fmoc-Ala-OH. As described previously, the resin-bound peptide is then removed from the instrument for Pd-mediated side chain deprotection of Lys(Alloc) and Glu(OAllyl) residues and subsequent intramolecular side chain-to-side chain cyclization. The N-terminal Fmoc protective group is removed over 5 minutes using a 20% piperidine/DMF solution (17 mL). The resin-bound peptide is washed successively with DMF (100 mL), THF (100 mL), and diethyl ether (100 mL). The air-dried resin is suspended in 40 mL of TFA containing water (2.0 mL), thioanisole (2.0 mL), phenol (3.0 g), and ethanedithiol (1.0 mL). After 2 hours, the TFA solution is filtered into tert-butylmethyl ether (160 mL) at 0° C. which effects precipitation of the crude peptide. The peptide mixture is centrifuged at 2500 rpm for 5 minutes and decanted. The crude, white solid is resuspended in diethyl ether (120 mL), centrifuged, and decanted. This washing procedure is repeated four times and the resulting peptide is dried in vacuo, dissolved in water containing 0.1% TFA (100 mL), and lyophilized to dryness.

The crude peptide is then purified by reverse-phase liquid chromatography as described previously to provide 95 mg of final, purified peptide as a white solid. IS–MS: 3648 (M+). Amino Acid Analysis: Asp/Asn: 3.00 (3); Ser: 1.70 (2); Glu/Gln: 4.75 (5); Gly: 0.93 (1); Ala: 0.89 (1); Val: 2.80 (3); Ile: 0.89 (1); Leu: 6.16 (6); Nle: 0.87 (1); Lys: 2.99 (3); His: 1.86 (2); Arg: 1.90 (2); Trp: not determined (1).

EXAMPLE 57

Cyclo($O^{18}$-$E^{22}$)[$A^1$,$Nle^8$,$O^{18}$,$E^{22}$,$L^{27}$]hPTH(1–31) $NH_2$ (SEQ ID NO: 51)

Ala-Val-Ser-Glu-Ile-Gln-Leu-Nle-His-Asn-Leu-Gly-Lys-His-Leu-Asn-Ser-(Orn-Glu-Arg-Val-Glu)-Trp- Leu-Arg-Lys-Leu-Leu-Gln-Asp-Val amide The peptide is prepared in a fashion analogous to that described previously (Method C). Rink Amide MBRA resin (0.5 mmol) is placed in a reaction vessel which is then attached to a Protein Technologies PS3 Automated Peptide synthesizer. The following amino acids are added sequentially in a manner consistent with Fmoc-base SPPS: Fmoc-Val-OH, Fmoc-Asp(OtBu)-OH, Fmoc-Gln(Trt)-OH, Fmoc-Leu-OH, Fmoc-Leu-OH, Fmoc-Lys(Boc)-OH, Fmoc-Arg (Pmc)-OH, Fmoc-Leu-OH, Fmoc-Trp(Boc)-OH, Fmoc-Glu (OAllyl)-OH, Fmoc-Val-OH, Fmoc-Arg(Pmc)-OH, Fmoc-Glu(OtBu)-OH, Fmoc-Orn(Alloc)-OH, Fmoc-Ser(tBu)-OH, Fmoc-Asn(Trt)-OH, Fmoc-Leu-OH, Fmoc-His(Trt)-OH, Fmoc-Lys(Boc)-OH, Fmoc-Gly-OH, Fmoc-Leu-OH, Fmoc-Asn(Trt)-OH, Fmoc-His(Trt)-OH, Fmoc-Nle-OH, Fmoc-Leu-OH, Fmoc-Gln(Trt)-OH, Fmoc-Ile-OH, Fmoc-Glu (OtBu)-OH, Fmoc-Ser(tBu)-OH, Fmoc-Val-OH, and Fmoc-Ala-OH. As described previously, the resin-bound peptide is then removed from the instrument for Pd-mediated side chain deprotection of Orn(Alloc) and Glu(OAllyl) residues and subsequent intramolecular side chain-to-side chain cyclization. The N-terminal Fmoc protective group is removed over 5 minutes using 20% piperidine/DMF solution (17 mL). The resin-bound peptide is washed successively with DMF (100 mL), THF (100 mL), and diethyl ether (100 mL). The air-dried resin is suspended in 40 mL of TFA containing water (2.0 mL), thioanisole (2.0 mL), phenol (3.0 g), and ethanedithiol (1.0 mL). After 2 hours, the TFA solution is filtered into tert-butylmethyl ether (160 mL) at 0° C. which effects precipitation of the crude peptide. The peptide mixture is centrifuged at 2500 rpm for 5 minutes and decanted. The crude, white solid is resuspended in diethyl ether (120 mL), centrifuged, and decanted. This washing procedure is repeated four times and the resulting peptide is dried in vacuo, dissolved in water containing 0.1% TFA (100 mL), and lyophilized to dryness.

The crude peptide is then purified by reverse-phase liquid chromatography as described previously to provide 237 mg of final, purified peptide as a white solid. IS–MS: 3634 (M+). Amino Acid Analysis: Asp/Asn: 3.09 (3); Ser: 1.74 (2); Glu/Gln: 5.02 (5); Gly: 0.97 (1); Ala: 0.93 (1); Val: 2.95 (3); Ile: 0.88 (1); Leu: 6.44 (6); Nle: 0.85 (1); Lys: 2.06 (2); His: 1.89 (2); Arg: 1.98 (2); Trp: not determined (1).

EXAMPLE 58

Cyclo($K^{18}$—$D^{22}$)[$A^1$,$Nle^8$,$K^{18}$,$D^{22}$,$L^{27}$]hPTH(1–30) $NH_2$ (SEQ ID NO: 52)

Ala-Val-Ser-Glu-Ile-Gln-Leu-Nle-His-Asn-Leu-Gly-Lys-His-Leu-Asn-Ser-(Lys-Glu-Arg-Val-Asp)-Trp- Leu-Arg-Lys-Leu-Leu-Gln-Asp amide The peptide is prepared in a fashion analogous to that described previously (Method C). Rink Amide MBHA resin (0.5 mmol) is placed in a reaction vessel which is then attached to a Protein Technologies PS3 Automated Peptide synthesizer. The following amino acids are added sequentially in a manner consistent with Fmoc-base SPPS: Fmoc-Asp(OtBu)-OH, Fmoc-Gln(Trt)-OH, Fmoc-Leu-OH, Fmoc-Leu-OH, Fmoc-Lys(Boc)-OH, Fmoc-Arg(Pmc)-OH, Fmoc-Leu-OH, Fmoc-Trp(Boc)-OH, Fmoc-Asp(OAllyl)-OH, Fmoc-Val-OH, Fmoc-Arg(Pmc)-OH, Fmoc-Glu(OtBu)-OH, Fmoc-Lys(Alloc)-OH, Fmoc-Ser(tBu)-OH, Fmoc-Asn(Trt)-OH, Fmoc-Leu-OH, Fmoc-His(Trt)-OH, Fmoc-Lys(Boc)-OH, Fmoc-Gly-OH, Fmoc-Leu-OH, Fmoc-Asn(Trt)-OH, Fmoc-His(Trt)-OH, Fmoc-Nle-OH, Fmoc-Leu-OH, Fmoc-Gln(Trt)-OH, Fmoc-Ile-OH, Fmoc-Glu(OtBu)-OH, Fmoc-Ser(tBu)-OH, Fmoc-Val-OH, and Fmoc-Ala-OH. As described previously, the resin-bound peptide is then removed from the instrument for Pd-mediated side chain deprotection of Lys(Alloc) and Asp(OAllyl) residues and subsequent intramolecular side,chain-to-side chain cyclization, The N-terminal Fmoc protective group is removed over 5 minutes using a 20% piperidine/DMF solution (17 mL). The resin-bound peptide is wasted successively with DMF (100 mL), THF (100 mL), and diethyl ether (100 mL). The air-dried resin is suspended in 40 mL of TFA containing water (2.0 mL), thioanisole (2.0 mL), phenol (3.0 g), and ethanedithiol (1.0 mL). After 2 hours, the TFA solution is filtered into tert-butylmethyl ether (160 mL) at 0° C. which effects precipitation of the crude peptide. The peptide mixture is centrifuged at 2500 rpm for 5 minutes and decanted. The crude, white solid is resuspended in diethyl ether (120 mL), centrifuged, and decanted. This washing procedure is repeated four times and the resulting peptide is dried in vacuo, dissolved in water containing 0.1% TFA (100 mL), and lyophilized to dryness.

A portion of the crude peptide is then purified by reverse-phase liquid chromatography as described previously to provide 53 mg of final, purified peptide as a white solid. IS–MS: 3534 (M+). Amino Acid Analysis: Asp/Asn: 4.00 (4); Ser: 1.71 (2); Glu/Gln: 3.89 (4); Gly: 0.93 (1); Ala: 0.92 (1); Val: 1.87 (2); Ile: 0.90 (1); Leu: 6.46 (6); Nle: 0.82 (1); Lys: 2.89 (3); His: 2.01 (2); Arg: 2.03 (2); Arg: 2.03 (2); Trp: not determined (1).

EXAMPLE 59

Cyclo($K^{18}$—$D^{22}$)[$A^1$,$Nle^8$,$K^{18}$,$D^{22}$,$L^{27}$]hPTH(1–29) $NH_2$ (SEQ ID NO: 53)

Ala-Val-Ser-Glu-Ile-Gln-Leu-Nle-His-Asn-Leu-Gly-Lys-His-Leu-Asn-Ser-(Lys-Glu-Arg-Val-Asp)-Trp- Leu-Arg-Lys-Leu-Leu-Gln amide The peptide is prepared in a fashion analogous to that described previously (Method C). Rink Amide MBHA resin (0.5 mmol) is placed in a reaction vessel which is then attached to a Protein Technologies PS3 Automated Peptide synthesizer. The following amino acids are added sequentially in a manner consistent with Fmoc-base SPPS: Fmoc-Gln(Trt)-OH, Fmoc-Leu-OH, Fmoc-Leu-OH, Fmoc-Lys (Boc)-OH, Fmoc-Arg(Pmc)-OH, Fmoc-Leu-OH, Fmoc-Trp (Boc)-OH, Fmoc-Asp(OAllyl)-OH, Fmoc-Val-OH, Fmoc-Arg(Pmc)-OH, Fmoc-Glu(OtBu)-OH, Fmoc-Lys(Alloc)-OH, Fmoc-Ser(tBu)-OH, Fmoc-Asn(Trt)-OH, Fmoc-Leu-OH, Fmoc-His(Trt)-OH, Fmoc-Lys(Boc)-OH, Fmoc-Gly-OH, Fmoc-Leu-OH, Fmoc-Asn(Trt)-OH, Fmoc-His(Trt)-OH, Fmoc-Nle-OH, Fmoc-Leu-OH, Fmoc-Gln(Trt)-OH, Fmoc-Ile-OH, Fmoc-Glu(OtBu)-OH, Fmoc-Ser(tBu)-OH, Fmoc-Val-OH, and Fmoc-Ala-OH. As described previously, the resin-bound peptide is then removed from the instrument for Pd-mediated side chain deprotection of Lys(Alloc) and Asp(OAllyl) residues and subsequent intramolecular side chain-to-side chain cyclization. The N-terminal Fmoc protective group is removed over 5 minutes using a 20% piperidine/DMF solution (17 mL). The resin-bound peptide is washed successively with DMF (100 mL), THF(100 mL), and diethyl ether (100 mL). The air-dried resin is suspended in 40 mL of TFA containing water (2.0 mL), thioanisole (2.0 mL), phenol (3.0 g), and ethanedithiol (1.0 mL). After 2 hours, the TFA solution is filtered into tert-butylmethyl ether (160 mL) at 0° C. which effects precipitation of the crude peptide. The peptide mixture is centrifuged at 2500 rpm for 5 minutes and decanted. The crude, white solid is resuspended in diethyl ether (120 mL), centrifuged, and decanted. This washing procedure is repeated four times and the resulting peptide is dried in vacuo, dissolved in water containing 0.1% TFA (100 mL), and lyophilized to dryness.

A portion of the crude peptide is then purified by reverse-phase liquid chromatography as described previously to provide 100 mg of final, purified peptide as a white solid. IS–MS: 3419 (M+). Amino Acid Analysis: Asp/Asn: 2.85 (3); Ser: 1.73 (2); Glu/Gln: 3.98 (4); Gly: 1.00 (1); Ala: 0.98 (1); Val: 2.00 (2); Ile: 0.93 (1); Leu: 6.47 (6); Nle: 0.97 (1); Lys: 2.99 (3); His: 2.09 (2); Arg: 1.99 (2); Trp: not determined (1).

EXAMPLE 60

Cyclo($K^{18}$—$D^{22}$)[$A^1$,$Nle^8$,$K^{18}$,$D^{22}$,$L^{27}$]hPTH(1–28) $NH_2$ (SEQ ID NO: 54)

Ala-Val-Ser-Glu-Ile-Gln-Leu-Nle-His-Asn-Leu-Gly-Lys-His-Leu-Asn-Ser-(Lys-Glu-Arg-Val-Asp)-Trp- Leu-Arg-Lys-Leu-Leu amide The peptide is prepared in a fashion analogous to that described previously (Method C). Rink Amide MBHA resin (0.5 mmol) is placed in a reaction vessel which is then attached to a Protein Technologies PS3 Automated Peptide synthesizer. The following amino acids are added sequentially in a manner consistent with Fmoc-base SPPS: Fmoc-Leu-OH, Fmoc-Leu-OH, Fmoc-Lys(Boc)-OH, Fmoc-Arg (Pmc)-OH, Fmoc-Leu-OH, Fmoc-Trp(Boc)-OH, Fmoc-Asp (OAllyl)-OH, Fmoc-Val-OH, Fmoc-Arg(Pmc)-OH, Fmoc-Glu(OtBu)-OH, Fmoc-Lys(Alloc)-OH, Fmoc-Ser(tBu)-OH, Fmoc-Asn(Trt)-OH, Fmoc-Leu-OH, Fmoc-His(Trt)-OH, Fmoc-Lys(Boc)-OH, Fmoc-Gly-OH, Fmoc-Leu-OH, Fmoc-Asn(Trt)-OH, Fmoc-His(Trt)-OH, Fmoc-Nle-OH, Fmoc-Leu-OH, Fmoc-Gln(Trt)-OH, Fmoc-Ile-OH, Fmoc-Glu (OtBu)-OH, Fmoc-Ser(tBu)-OH, Fmoc-Val-OH, and Fmoc-Ala-OH. As described previously, the resin-bound peptide is then removed from the instrument for Pd-mediated side chain deprotection of Lys(Alloc) and Asp(OAllyl) residues and subsequent intramolecular side chain-to-side chain cyclization. The N-terminal Fmoc protective group is removed over 5 minutes using a 20% piperidine/DMF solution (17 mL). The resin-bound peptide is washed successively with DMF(100 mL), THF (100 mL), and diethyl ether (100 mL). The air-dried resin is suspended in 40 mL of TFA containing water (2.0 mL), thioanisole (2.0 mL), phenol (3.0 g), and ethanedithiol (1.0 mL). After 2 hours, the TFA solution is filtered into tert-butylmethyl ether (160 mL) at 0° C. which effects precipitation of the crude peptide. The peptide mixture is centrifuged at 2500 rpm for 5 minutes and decanted. The crude, white solid is resuspended in diethyl ether (120 mL), centrifuged, and decanted. This washing procedure is repeated four times and the resulting peptide is dried in vacuo, dissolved in water containing 0.1% TFA (100 mL), and lyophilized to dryness.

A portion of the crude peptide is then purified by reverse-phase liquid chromatography as described previously to provide 51 mg of final, purified peptide as a white solid. IS–MS: 3291 (M+). Amino Acid Analysis: Asp/Asn: 2.81 (3); Ser: 1.71 (2); Glu/Gln: 2.86 (3); Gly: 0.97 (1); Ala: 1.00 (1); Val: 1.93 (2); Ile: 0.91 (1); Leu: 6.30 (6); Nle: 0.92 (1); Lys: 2.88 (3); His: 2.03 (2); Arg: 1.93 (2); Trp: not determined (1).

EXAMPLE 61

Cyclo($K^{18}$—$D^{22}$)[$A^1$,$Nle^8$,$K^{18}$,$D^{22}$,$L^{27}$]hPTH(1–27) $NH_2$ (SEQ ID NO: 55)

Ala-Val-Ser-Glu-Ile-Gln-Leu-Nle-His-Asn-Leu-Gly-Lys-His-Leu-Asn-Ser-(Lys-Glu-Arg-Val-Asp)-Trp- Leu-Arg-Lys-Leu amide The peptide is prepared in a fashion analogous to that described previously (Method C). Rink Amide MBHA resin (0.5 mmol) is placed in a reaction vessel which is then attached to a Protein Technologies PS3 Automated Peptide synthesizer. The following amino acids are added sequentially in a manner consistent with Fmoc-base SPPS: Fmoc-Leu-OH, Fmoc-Lys(Boc)-OH, Fmoc-Arg(Pmc)-OH, Fmoc-Leu-OH, Fmoc-Trp(Boc)-OH, Fmoc-Asp(OAllyl)-OH, Fmoc-Val-OH, Fmoc-Arg(Pmc)-OH, Fmoc-Glu(OtBu)-OH, Fmoc-Lys(Alloc)-OH, Fmoc-Ser(tBu)-OH, Fmoc-Asn(Trt)-OH, Fmoc-Leu-OH, Fmoc-His(Trt)-OH, Fmoc-Lys(Boc)-OH, Fmoc-Gly-OH, Fmoc-Leu-OH, Fmoc-Asn(Trt)-OH, Fmoc-His(Trt)-OH, Fmoc-Nle-OH, Fmoc-Leu-OH, Fmoc-Gln(Trt)-OH, Fmoc-Ile-OH, Fmoc-Glu(OtBu)-OH, Fmoc-Ser(tBu)-OH, Fmoc-Val-OH, and Fmoc-Ala-OH. As described previously, the resin-bound peptide is then removed from the instrument for Pd-mediated side chain deprotection of Lys(Alloc) and Asp(OAllyl) residues and subsequent intramolecular side chain-to-side chain cyclization. The N-terminal Fmoc protective group is removed over 5 minutes using a 20% piperidine/DMF solution (17 mL). The resin-bound peptide is washed successively with DMF (100 mL), THF (100 mL), and diethyl ether (100 mL). The air-dried resin is suspended in 40 mL of TFA containing water (2.0 mL), thioanisole (2.0 mL), phenol (3.0 g), and ethanedithiol (1.0 mL). After 2 hours, the TFA solution is filtered into tert-butylmethyl ether (160 mL) at 0° C. which effects precipitation of the crude peptide. The peptide mixture is centrifuged at 2500 rpm for 5 minutes and decanted. The crude, white solid is resuspended in diethyl ether (120 mL), centrifuged, and decanted. This washing procedure is repeated four times and the resulting peptide is dried in vacuo, dissolved in water containing 0.1% TFA (100 mL), and lyophilized to dryness.

A portion of the crude peptide is then purified by reverse-phase liquid chromatography as described previously to provide 65 mg of final, purified peptide as a white solid. IS–MS: 3178 (M+). Amino Acid Analysis: Asp/Asn: 2.74 (3); Ser: 1.75 (2); Glu/Gln: 2.88 (3); Gly: 0.95 (1); Ala: 1.00 (1); Val: 1.94 (2); Ile: 0.93 (1); Leu: 5.16 (5); Nle: 0.88 (1); Lys: 2.84 (3); His: 2.01 (2); Arg: 1.93 (2); Trp: not determined (1).

EXAMPLE 62

Cyclo($K^{18}$—$D^{22}$)[$K^{18}$,$D^{22}$,$L^{27}$]hPTH(10–31)$NH_2$ (SEQ ID NO: 56)

Asn-Leu-Gly-Lys-His-Leu-Asn-Ser-(Lys-Glu-Arg-Val-Asp)-Trp-Leu-Arg-Lys-Leu-Leu-Gln-Asp-Val amide The peptide is prepared in a fashion analogous to that described previously (Method B). Rink Amide MBHA resin (0.5 mmol) is placed in a reaction vessel which is then attached to a Protein Technologies PS3 Automated Peptide synthesizer. The following amino acids are added sequentially in a manner consistent with Fmoc-base SPPS: Fmoc-Val-OH, Fmoc-Asp(OtBu)-OH, Fmoc-Gln(Trt)-OH, Fmoc-Leu-OH, Fmoc-Leu-OH, Fmoc-Lys(Boc)-OH, Fmoc-Arg(Pmc)-OH, Fmoc-Leu-OH, Fmoc-Trp(Boc)-OH, Fmoc-Asp(OAllyl)-OH; Fmoc-Val-OH, Fmoc-Arg(Pmc)-OH, Fmoc-Glu(OtBu)-OH, Fmoc-Lys(Alloc)-OH, Fmoc-Ser(tBu)-OH, Fmoc-Asn(Trt)-OH, and Fmoc-Leu-OH. As described previously, the resin-bound peptide is then removed from the instrument for Pd-mediated side chain deprotection of the Lys(Alloc) and Asp(OAllyl) residues and subsequent intramolecular side chain-to-side chain cyclization. Following the described work-up procedures, the amide-containing resin-bound peptide is returned to the instrument for completion of the synthesis; the following amino acids are added sequentially: Fmoc-His(Trt)-OH, Fmoc-Lys(Boc)-OH, Fmoc-Gly-OH, Fmoc-Leu-OH, and Fmoc-Asn(Trt)-OH. A portion of the resin-bound peptide (~50 mg) is then removed from the instrument and the N-terminal Fmoc protective group is removed over 5 minutes using a 20% piperidine/DMF solution (1 mL). The resin-bound peptide is washed successively with DMF (10 mL). THF (10 mL), and diethyl ether (10 mL). The air-dried resin is suspended in 2 mL of TFA containing water, thioanisole, phenol, and ethanedithiol in proportions described earlier. After 2 hours, the TFA solution is filtered into tert-butylmethyl ether (8 mL) at 0° C. which effects precipitation of the crude peptide. The peptide mixture is centrifuged at 2500 rpm for 5 minutes and decanted. The crude, white solid is resuspended in diethyl ether (10 mL), centrifuged, and decanted. This washing procedure is repeated four times and the resulting peptide is dried in vacuo, dissolved in water containing 0.1% TFA (10 mL), and lyophilized to dryness. IS–MS: 2642 (M+).

EXAMPLE 63

Cyclo($K^{18}$—$D^{22}$)[$K^{18}$,$D^{22}$,$L^{27}$]hPTH(9–31)$NH_2$ (SEQ ID NO: 57)

His-Asn-Leu-Gly-Lys-His-Leu-Asn-Ser-(Lys-Glu-Arg-Val-Asp)-Trp-Leu-Arg-Lys-Leu-Leu-Gln-Asp-Val amide The peptide is prepared in a fashion analogous to that described previously (Method B). Rink Amide MBHA resin (0.5 mmol) is placed in a reaction vessel which is then attached to a Protein Technologies PS3 Automated Peptide synthesizer. The following amino acids are added sequentially in a manner consistent with Fmoc-base SPPS: Fmoc-Val-OH, Fmoc-Asp(OtBu)-OH, Fmoc-Gln(Trt)-OH, Fmoc-Leu-OH, Fmoc-Leu-OH, Fmoc-Lys(Boc)-OH, Fmoc-Arg(Pmc)-OH, Fmoc-Leu-OH, Fmoc-Trp(Boc)-OH, Fmoc-Asp(OAllyl)-OH, Fmoc-Val-OH, Fmoc-Arg(Pmc)-OH, Fmoc-Glu(OtBu)OH, Fmoc-Lys(Alloc)-OH, Fmoc-Ser(tBu)-OH, Fmoc-Asn(Trt)-OH, and Fmoc-Leu-OH. As described previously, the resin-bound peptide is then removed from the instrument for Pd-mediated side chain deprotection of the Lys(Alloc) and Asp(OAllyl) residues and subsequent intramolecular side chain-to-side chain cyclization. Following the described work-up procedures, the amide-containing resin-bound peptide is returned to the instrument for completion of the synthesis; the following amino acids are added sequentially: Fmoc-His(Trt)-OH, Fmoc-Lys(Boc)-OH, Fmoc-Gly-OH, Fmoc-Leu-OH, Fmoc-Asn(Trt)-OH, and Fmoc-His(Trt)-OH. A portion of the resin-bound peptide (~50 mg) is then removed from the instrument and the N-terminal Fmoc protective group is removed over 5 minutes using a 20% piperidine/DMF solution (1 mL). The resin-bound peptide is washed successively with DMF(10 mL). THF (10 mL), and diethyl ether (10 mL). The air-dried resin is suspended in 2 mL of TFA containing water, thioanisole, phenol, and ethanedithiol in proportions described earlier. After 2 hours, the TFA solution is filtered into tert-butylmethyl ether (8 mL) at 0° C. which effects precipitation of the crude peptide. The peptide mixture is centrifuged at 2500 rpm for 5 minutes and decanted. The crude, white solid is resuspended in diethyl ether (10 mL), centrifuged, and decanted. This washing procedure is repeated four times and the resulting peptide is dried in vacuo, dissolved in water containing 0.1% TFA (10 mL), and lyophilized to dryness. IS–MS: 2780 (M+).

EXAMPLE 64

Cyclo($K^{18}$—$D^{22}$)[$Nle^8,K^{18},D^{22},L^{27}$]hPTH(8–31) $NH_2$ (SEQ ID NO: 58)

Nle-His-Asn-Leu-Gly-Lys-His-Leu-Asn-Ser-(Lys-Glu-Arg-Val-Asp)-Trp-Leu-Arg-Lys-Leu-Leu-Gln-Asp-Val amide The peptide is prepared in a fashion analogous to that described previously (Method B). Rink Amide MBHA resin (0.5 mmol) is placed in a reaction vessel which is then attached to a Protein Technologies PS3 Automated Peptide synthesizer. The following amino acids are added sequentially in a manner consistent with Fmoc-base SPPS: Fmoc-Val-OH, Fmoc-Asp(OtBu)-OH, Fmoc-Gln(Trt)-OH, Fmoc-Leu-OH, Fmoc-Leu-OH, Fmoc-Lys(Boc)-OH, Fmoc-Arg(Pmc)-OH, Fmoc-Leu-OH, Fmoc-Trp(Boc)-OH, Fmoc-Asp(OAllyl)-OH, Fmoc-Val-OH, Fmoc-Arg(Pmc)-OH, Fmoc-Glu(OtBu)-OH, Fmoc-Lys(Alloc)-OH, Fmoc-Ser(tBu)-OH, Fmoc-Asn(Trt)-OH, and Fmoc-Leu-OH. As described previously, the resin-bound peptide is then removed from the instrument for Pd-mediated side chain deprotection of the Lys(Alloc) and Asp(OAllyl) residues and subsequent intramolecular side chain-to-side chain cyclization. Following the described work-up procedures, the amide-containing resin-bound peptide is returned to the instrument for completion of the synthesis; the following amino acids are added sequentially: Fmoc-His(Trt)-OH, Fmoc-Lys(Boc)-OH, Fmoc-Gly-OH, Fmoc-Leu-OH, Fmoc-Asn(Trt)-OH, Fmoc-His(Trt)-OH, and Fmoc-Nle-OH. A portion of the resin-bound peptide (50 mg) is then removed from the instrument and the N-terminal Fmoc protective group is removed over 5 minutes using a 20% piperidine/DMF solution (1 mL). The resin-bound peptide is washed successively with. DMF (10 mL), THF (10 mL), and diethyl ether (10 mL). The air-dried resin is suspended in 2 mL of TFA containing water, thioanisole, phenol, and ethanedithiol in proportions described earlier. After 2 hours, the TFA solution is filtered into tert-butylmethyl ether (8 mL) at 0° C. which effects precipitation of the crude peptide. The peptide mixture is centrifuged at 2500 rpm for 5 minutes and decanted. The crude, white solid is resuspended in diethyl ether (10 mL), centrifuged, and decanted. This washing procedure is repeated four times and the resulting peptide is dried in vacuo, dissolved in water containing 0.1% TFA (10 mL), and lyophilized to dryness. IS–MS: 2892 (M+).

EXAMPLE 65

Cyclo($K^{18}$—$D^{22}$)[$Nle^8,K^{18},D^{22},L^{27}$]hPTH(7–31) $NH_2$ (SEQ ID NO: 59)

Leu-Nle-His-Asn-Leu-Gly-Lys-His-Leu-Asn-Ser-(Lys-Glu-Arg-Val-Asp)-Trp-Leu-Arg-Lys-Leu-Leu-Gln-Asp-Val amide The peptide is prepared in a fashion analogous to that described previously (Method B). Rink Amide MBHA resin (0.5 mmol) is placed in a reaction vessel which is then attached to a Protein Technologies PS3 Automated Peptide synthesizer. The following amino acids are added sequentially in a manner consistent with Fmoc-base SPPS: Fmoc-Val-OH, Fmoc-Asp(OtBu)-OH, Fmoc-Gln(Trt)-OH, Fmoc-Leu-OH, Fmoc-Leu-OH, Fmoc-Lys(Boc)-OH, Fmoc-Arg(Pmc)-OH, Fmoc-Leu-OH, Fmoc-Trp(Boc)-OH, Fmoc-Asp(OAllyl)-OH, Fmoc-Val-OH, Fmoc-Arg(Pmc)-OH, Fmoc-Glu(OtBu)-OH, Fmoc-Lys(Alloc)-OH, Fmoc-Ser(tBu)-OH, Fmoc-Asn(Trt)-OH, and Fmoc-Leu-OH. As described previously, the resin-bound peptide is then removed from the instrument for Pd-mediated side chain deprotection of the Lys(Alloc) and Asp(OAllyl) residues and subsequent intramolecular side chain-to-side chain cyclization. Following the described work-up procedures, the amide-containing resin-bound peptide is returned to the instrument for completion of the synthesis; the following amino acids are added sequentially: Fmoc-His(Trt)-OH, Fmoc-Lys(Boc)-OH, Fmoc-Gly-OH, Fmoc-Leu-OH, Fmoc-Asn(Trt)-OH, Fmoc-His(Trt)-OH, Fmoc-Nle-OH, and Fmoc-Leu-OH. A portion of the resin-bound peptide (50 mg) is then removed from the instrument and the N-terminal Fmoc protective group is removed over 5 minutes using a 20% piperidine/DMF solution (1 mL). The resin-bound peptide is washed successively with DMF (10 mL), THF (10 mL), and diethyl ether (10 mL). The air-dried resin is suspended in 2 mL of TFA containing water, thioanisole, phenol, and ethanedithiol in proportions described earlier. After 2 hours, the TFA solution is filtered into tert-butylmethyl ether (8 mL) at 0° C. which effects precipitation of the crude peptide. The peptide mixture is centrifuged at 2500 rpm for 5 minutes and decanted. The crude, white solid is resuspended in diethyl ether (10 mL), centrifuged, and decanted. This washing procedure is repeated four times and the resulting peptide is dried in vacuo, dissolved in water containing 0.1% TFA (10 mL), and lyophilized to dryness. IS–MS: 3006 (M+).

EXAMPLE 66

Cyclo($K^{78}$—$D^{22}$)[$Nle^8,K^{18},D^{22},L^{27}$]hPTH(6–31) $NH_2$ (SEQ ID NO: 60)

Gln-Leu-Nle-His-Asn-Leu-Gly-Lys-His-Leu-Asn-Ser-(Lys-Glu-Arg-Val-Asp)-Trp-Leu-Arg-Lys-Leu-Leu-Gln-Asp-Val amide The peptide is prepared in a fashion analogous to that described previously (Method B). Rink Amide MBHA resin (0.5 mmol) is placed in a reaction vessel which is then attached to a Protein Technologies PS3 Automated Peptide synthesizer. The following amino acids are added sequentially in a manner consistent with Fmoc-base SPPS: Fmoc-Val-OH, Fmoc-Asp(OtBu)-OH, Fmoc-Gln(Trt)-OH, Fmoc-Leu-OH, Fmoc-Leu-OH, Fmoc-Lys(Boc)-OH, Fmoc-Arg(Pmc)-OH, Fmoc-Leu-OH, Fmoc-Trp(Boc)-OH, Fmoc-Asp(OAllyl)-OH, Fmoc-Val-OH, Fmoc-Arg(Pmc)-OH, Fmoc-Glu(OtBu)-OH, Fmoc-Lys(Alloc)-OH, Fmoc-Ser(tBu)-OH, Fmoc-Asn(Trt)-OH, and Fmoc-Leu-OH. As described previously, the resin-bound peptide is then removed from the instrument for Pd-mediated side chain deprotection of the Lys(Alloc) and Asp(OAllyl) residues and subsequent intramolecular side chain-to-side chain cyclization. Following the described work-up procedures, the amide-containing resin-bound peptide is returned to the instrument for completion of the synthesis; the following amino acids are added sequentially: Fmoc-His(Trt)-OH, Fmoc-Lys(Boc)-

OH, Fmoc-Gly-OH, Fmoc-Leu-OH, Fmoc-Asn(Trt)-OH, Fmoc-His(Trt)-OH, Fmoc-Nle-OH, Fmoc-Leu-OH, and Fmoc-Gln(Trt)-OH. A portion of the resin-bound peptide (50 mg) is then removed from the instrument and the N-terminal Fmoc protective group is removed over 5 minutes using a 20% piperidine/DMF solution (1 mL). The resin-bound peptide is washed successively with DMF (10 mL), THF (10 mL), an diethyl ether (10 mL). The air-dried resin is suspended in 2 mL of TFA containing water, thioanisole, phenol, and ethanedithiol in proportions described earlier. After 2 hours, the TFA solution is filtered into tert-butylmethyl ether (8 mL) at 0° C. which effects precipitation of the crude peptide. The peptide mixture is centrifuged at 2500 rpm for 5 minutes and decanted. The crude, white solid is resuspended in diethyl ether (10 mL), centrifuged, and decanted. This washing procedure is repeated four times and the resulting peptide is dried in vacuo, dissolved in water containing 0.1% TFA (10 mL), and lyophilized to dryness. IS–MS: 3135 (M+).

EXAMPLE 67

Cyclo($K^{18}$—$D^{22}$)[$Nle^8$,$K^{18}$,$D^{22}$,$L^{27}$]hPTH(5–31) $NH_2$ (SEQ ID NO: 61)

Ile-Gln-Leu-Nle-His-Asn-Leu-Gly-Lys-His-Leu-Asn-Ser-(Lys-Glu-Arg-Val-Asp)-Trp-Leu-Arg-Lys-Leu-Leu-Gln-Asp-Val amide The peptide is prepared in a fashion analogous to that described previously (Method B). Rink Amide MBHA resin (0.5 mmol) is placed in a reaction vessel which is then attached to a Protein Technologies PS3 Automated Peptide synthesizer. The following amino acids are added sequentially in a manner consistent with Fmoc-base SPPS: Fmoc-Val-OH, Fmoc-Asp(OtBu)-OH, Fmoc-Gln(Trt)-OH, Fmoc-Leu-OH, Fmoc-Leu-OH, Fmoc-Lys(Boc)-OH, Fmoc-Arg(Pmc)-OH, Fmoc-Leu-OH, Fmoc-Trp(Boc)-OH, Fmoc-Asp(OAllyl)-OH, Fmoc-Val-OH, Fmoc-Arg(Pmc)-OH, Fmoc-Glu(OtBu)-OH, Fmoc-Lys(Alloc)-OH, Fmoc-Ser(tBu)-OH, Fmoc-Asn(Trt)-OH, and Fmoc-Leu-OH. As described previously, the resin-bound peptide is then removed from the instrument for Pd-mediated side chain deprotection of the Lys(Alloc) and Asp(OAllyl) residues and subsequent intramolecular side chain-to-side chain cyclization. Following the described work-up procedures, the amide-containing resin-bound peptide is returned to the instrument for completion of the synthesis; the following amino acids are added sequentially: Fmoc-His(Trt)-OH, Fmoc-Lys(Boc)-OH, Fmoc-Gly-OH, Fmoc-Leu-OH, Fmoc-Asn(Trt)-OH, Fmoc-His(Trt)-OH, Fmoc-Nle-OH, Fmoc-Leu-OH, Fmoc-Gln(Trt)-OH, and Fmoc-Ile-OH. A portion of the resin-bound peptide (~50 mg) is then removed from the instrument and the N-terminal Fmoc protective group is removed over 5 minutes using a 20% piperidine/DMF solution (1 mL) The resin-bound peptide is washed successively with DMF (10 mL), THF (10 mL), and diethyl ether (10 mL). The air-dried resin is suspended in 2 mL of TFA containing water, thioanisole, phenol, and ethanedithiol in proportions described earlier. After 2 hours, the TFA solution is filtered into tert-butylmethyl ether (8 mL) at 0° C. which effects precipitation of the crude peptide. The peptide mixture is centrifuged at 2500 rpm for 5 minutes and decanted. The crude, white solid is resuspended in diethyl ether (10 mL), centrifuged, and decanted. This washing procedure is repeated four times and the resulting peptide is dried in vacuo, dissolved in water containing 0.1% TFA (10 mL), and lyophilized to dryness. IS–MS: 3247 (M+).

EXAMPLE 68

Cyclo($K^{18}$—$D^{22}$)[$Nle^8$,$K^{18}$,$D^{22}$,$L^{27}$]hPTH(4–31) $NH_2$ (SEQ ID NO: 62)

Glu-Ile-Gln-Leu-Nle-His-Asn-Leu-Gly-Lys-His-Leu-Asn-Ser-(Lys-Glu-Arg-Val-Asp)-Trp-Leu-Arg-Lys-Leu-Leu-Gln-Asp-Val amide The peptide is prepared in a fashion analogous to that described previously (Method B). Rink Amide MBHA resin (0.5 mmol) is placed in a reaction vessel which is then attached to a Protein Technologies PS3 Automated Peptide synthesizer. The following amino acids are added sequentially in a manner consistent with Fmoc-base SPPS: Fmoc-Val-OH, Fmoc-Asp(OtBu)-OH, Fmoc-Gln(Trt)-OH, Fmoc-Leu-OH, Fmoc-Leu-OH, Fmoc-Lys(Boc)-OH, Fmoc-Arg(Pmc)-OH, Fmoc-Leu-OH, Fmoc-Trp(Boc)-OH, Fmoc-Asp(OAllyl)-OH, Fmoc-Val-OH, Fmoc-Arg(Pmc)-OH, Fmoc-Glu(OtBu)-OH, Fmoc-Lys(Alloc)-OH, Fmoc-Ser(tBu)-OH, Fmoc-Asn(Trt)-OH, and Fmoc-Leu-OH. As described previously, the resin-bound peptide is then removed from the instrument for Pd-mediated side chain deprotection of the Lys(Alloc) and Asp(OAllyl) residues and subsequent intramolecular side chain-to-side chain cyclization. Following the described work-up procedures, the amide-containing resin-bound peptide is returned to the instrument for completion of the synthesis; the following amino acids are added sequentially: Fmoc-His(Trt)-OH, Fmoc-Lys(Boc)-OH, Fmoc-Gly-OH, Fmoc-Leu-OH, Fmoc-Asn(Trt)-OH, Fmoc-His(Trt)-OH, Fmoc-Nle-OH, Fmoc-Leu-OH, Fmoc-Gln(Trt)-OH, Fmoc-Ile-OH, and Fmoc-Glu(OtBu)-OH. A portion of the resin-bound peptide (~50 mg) is then removed from the instrument and the N-terminal Fmoc protective group is removed over 5 minutes using a 20% piperidine/DMF solution (1 mL). The resin-bound peptide is washed successively with DMF (10 mL), THF (10 mL), and diethyl ether (10 mL). The air-dried resin is suspended in 2 mL of TFA containing water, thioanisole, phenol, and ethanedithiol in proportions described earlier. After 2 hours, the TFA solution is filtered into tert-butylmethyl ether (8 mL) at 0° C. which effects precipitation of the crude peptide. The peptide mixture is centrifuged at 2500 rpm for 5 minutes and decanted. The crude, white solid is resuspended in diethyl ether (10 mL), centrifuged, and decanted. This washing procedure is repeated four times and the resultant peptide is dried in vacuo, dissolved in water containing 0.1% TFA (10 mL), and lyophilized to dryness. IS–MS: 3377 (M+).

EXAMPLE 69

Cyclo($K^{18}$—$D^{22}$)[$Nle^8$,$K^{18}$,$D^{22}$,$L^{27}$]hPTH(3–31) $NH_2$ (SEQ ID NO: 63)

Ser-Glu-Ile-Gln-Leu-Nle-His-Asn-Leu-Gly-Lys-His-Leu-Asn-Ser-(Lys-Glu-Arg-Val-Asp)-Trp-Leu-Arg-Lys-Leu-Leu-Gln-Asp-Val amide The peptide is prepared in a fashion analogous to that described previously (Method B). Rink Amide MBHA resin (0.5 mmol) is placed in a reaction vessel which is then attached to a Protein Technologies PS3 Automated Peptide synthesizer. The following amino acids are added sequentially in a manner consistent with Fmoc-base SPPS: Fmoc-Val-OH, Fmoc-Asp(OtBu)-OH, Fmoc-Gln(Trt)-OH, Fmoc-Leu-OH, Fmoc-Leu-OH, Fmoc-Lys(Boc)-OH, Fmoc-Arg(Pmc)-OH, Fmoc-Leu-OH, Fmoc-Trp(Boc)-OH, Fmoc-Asp(OAllyl)-OH, Fmoc-Val-OH, Fmoc-Arg(Pmc)-OH, Fmoc-Glu(OtBu)-OH, Fmoc-Lys(Alloc)-OH, Fmoc-Ser(tBu)-OH, Fmoc-Asn(Trt)-OH, and Fmoc-Leu-OH. As described previously, the resin-bound peptide is then removed from the instrument for Pd-mediated side chain deprotection of the Lys(Alloc) and Asp(OAllyl) residues and subsequent intramolecular side chain-to-side chain cyclization. Following the described work-up procedures, the amide-containing resin-bound peptide is returned to the instrument for completion of the synthesis; the following amino acids are added sequentially: Fmoc-His(Trt)-OH, Fmoc-Lys(Boc)-OH, Fmoc-Gly-OH, Fmoc-Leu-OH, Fmoc-Asn(Trt)-OH, Fmoc-His(Trt)-OH, Fmoc-Nle-OH, Fmoc-Leu-OH, Fmoc-Gln(Trt)-OH, Fmoc-Ile-OH, Fmoc-Glu(OtBu)-OH, and Fmoc-Ser(tBu)-OH. A portion of the resin-bound peptide (~50 mg) is then removed from the instrument and the N-terminal Fmoc protective group is removed over 5 minutes using a 20% piperidine/DMF solution (1 mL). The resin-bound peptide is washed successively with DMF (10 mL), THF (10 mL), and diethyl ether (10 mL). The air-dried resin is suspended in 2 mL of TFA containing water, thioanisole, phenol, and ethanedithiol in proportions described earlier. After 2 hours, the TFA solution is filtered into tert-butylmethyl ether (8 mL) at 0° C. which effects precipitation of the crude peptide. The peptide mixture is centrifuged at 2500 rpm for 5 minutes and decanted. The crude, white solid is resuspended in diethyl ether (10 mL), centrifuged, and decanted. This washing procedure is repeated four times and the resulting peptide is dried in vacuo, dissolved in water containing 0.1% TFA (10 mL), and lyophilized to dryness. IS–MS: 3463 (M+).

EXAMPLE 70

Cyclo($K^{18}$—$D^{22}$)[$Nle^8$,$K^{18}$,$D^{22}$,$L^{27}$]hPTH(2–31)$NH_2$ (SEQ ID NO: 64)

Val-Ser-Glu-Ile-Gln-Leu-Nle-His-Asn-Leu-Gly-Lys-His-Leu-Asn-Ser-(Lys-Glu-Arg-Val-Asp)-Trp-Leu- Arg-Lys-Leu-Leu-Gln-Asp-Val amide The peptide is prepared in a fashion analogous to that described previously (Method B). Rink Amide MBHA resin (0.5 mmol) is placed in a reaction vessel which is then attached to a Protein Technologies PS3 Automated Peptide synthesizer. The following amino acids are added sequentially in a manner consistent with Fmoc-base SPPS: Fmoc-Val-OH, Fmoc-Asp(OtBu)-OH, Fmoc-Gln(Trt)-OH, Fmoc-Leu-OH, Fmoc-Leu-OH, Fmoc-Lys(Boc)-OH, Fmoc-Arg(Pmc)-OH, Fmoc-Leu-OH, Fmoc-Trp(Boc)-OH, Fmoc-Asp(OAllyl)-OH, Fmoc-Val-OH, Fmoc-Arg(Pmc)-OH, Fmoc-Glu(OtBu)-OH, Fmoc-Lys(Alloc)-OH, Fmoc-Ser(tBu)-OH, Fmoc-Asn(Trt)-OH, and Fmoc-Leu-OH. As described previously, the resin-bound peptide is then removed from the instrument for Pd-mediated side chain deprotection of the Lys(Alloc) and Asp(OAllyl) residues and subsequent intramolecular side chain-to-side chain cyclization. Following the described work-up procedures, the amide-containing resin-bound peptide is returned to the instrument for completion of the synthesis and the following amino acids are added sequentially: Fmoc-His(Trt)-OH, Fmoc-Lys(Boc)-OH, Fmoc-Gly-OH, Fmoc-Leu-OH, Fmoc-Asn(Trt)-OH, Fmoc-His(Trt)-OH, Fmoc-Nle-OH, Fmoc-Leu-OH, Fmoc-Gln(Trt)-OH, Fmoc-Ile-OH, Fmoc-Glu(OtBu)-OH, Fmoc-Ser(tBu)-OH, and Fmoc-Val-OH. A portion of the resin-bound peptide (~50 mg) is then removed from the instrument and the N-terminal Fmoc protective group is removed over 5 minutes using a 20% piperidine/DMF solution (1 mL): The resin-bound peptide is washed successively with DMF (10 mL), THF (10 mL), and diethyl ether (10 mL). The air-dried resin is suspended in 2 mL of TFA containing water, thioanisole, phenol, and ethanedithiol in proportions described earlier. After 2 hours, the TFA solution is filtered into tert-butylmethyl ether (8 mL) at 0° C. which effects precipitation of the crude peptide. The peptide mixture is centrifuged at 2500 rpm for 5 minutes and decanted. The crude, white solid is resuspended in diethyl ether (10 mL), centrifuged, and decanted. This washing procedure is repeated four times and the resulting peptide is dried in vacuo, dissolved in water containing 0.1% TFA (10 mL), and lyophilized to dryness. IS–MS: 3564 (M+).

EXAMPLE 71

Cyclo($K^{18-}D^{22}$)[$Nle^8$,$K^{18}$,$D^{22}$,$L^{27}$]hPTH(7–34)$NH_2$ (SEQ ID NO: 65)

Leu-Nle-His-Asn-Leu-Gly-Lys-His-Leu-Asn-Ser-(Lys-Glu-Arg-Val-Asp)-Trp-Leu-Arg-Lys-Leu-Leu-Gln-Asp-Val-His-Asn-Phe amide The peptide is prepared in a fashion analogous to that described previously (Method B). Rink Amide MBHA resin (0.5 mmol) is placed in a reaction vessel which is then attached to a Protein Technologies PS3 Automated Peptide synthesizer. The following amino acids are added sequentially in a manner consistent with Fmoc-base SPPS: Fmoc-Phe-OH, Fmoc-Asn(Trt)-OH, Fmoc-His(Trt)-OH, Fmoc-Val-OH, Fmoc-Asp(OtBu)-OH, Fmoc-Gln(Trt)-OH, Fmoc-Leu-OH, Fmoc-Leu-OH, Fmoc-Lys(Boc)-OH, Fmoc-Arg(Pmc)-OH, Fmoc-Leu-OH, Fmoc-Trp(Boc)-OH, Fmoc-Asp(OAllyl)-OH, Fmoc-Val-OH, Fmoc-Arg(Pmc)-OH, Fmoc-Glu(OtBu)-OH, Fmoc-Lys(Alloc)-OH, Fmoc-Ser(tBu)-OH, Fmoc-Asn(Trt)-OH, and Fmoc-Leu-OH. As described previously, the resin-bound peptide is then removed from the instrument for Pd-mediated side chain deprotection of the Lys(Alloc) and Asp(OAllyl) residues and subsequent intramolecular side chain-to-side chain cyclization. Following the described work-up procedures, the amide-containing resin-bound peptide is returned to the instrument for completion of the synthesis; the following amino acids are added sequentially: Fmoc-His(Trt)-OH, Fmoc-Lys(Boc)-OH, Fmoc-Gly-OH, Fmoc-Leu-OH, Fmoc-Asn(Trt)-OH, Fmoc-His(Trt)-OH, Fmoc-Nle-OH, Fmoc-Leu-OH. The crude peptide is cleaved from the resin and deprotected using 40 mL of TFA containing water (2.0 mL), thioanisole (2.0 mL). phenol (3.0 g). and ethanedithiol (1.0 mL) and precipitated by the addition of the cleavage mixture to cold tert-butylmethyl ether. The crude peptide is then purified by reverse-phase liquid chromatography.

EXAMPLE 72

Cyclo($K^{18}$—$D^{14}$)[$A^1$,$Nle^{8,18}$,$K^{10}$,$D^{14}$,$L^{27}$]hPTH(1–31)$NH_2$ (SEQ ID NO: 66)

Ala-Val-Ser-Glu-Ile-Gln-Leu-Nle-His-(Lys-Leu-Gly-Lys-Asp)-Leu-Asn-Ser-Nle-Glu-Arg-Val-Glu-Trp-Leu-Arg-Lys-Leu-Leu-Gln-Asp-Val amide The peptide is prepared in a fashion analogous to that described previously (Method C). Rink Amide MBHA resin (0.5 mmol) is placed in a reaction vessel which is then attached to a Protein Technologies PS3 Automated Peptide synthesizer. The following amino acids are added sequentially in a manner consistent with Fmoc-base SPPS: Fmoc-Val-OH, Fmoc-Asp(OtBu)-OH, Fmoc-Gln(Trt)-OH, Fmoc-Leu-OH, Fmoc-Leu-OH, Fmoc-Lys(Boc)-OH, Fmoc-Arg(Pmc)-OH, Fmoc-Leu-OH, Fmoc-Trp(Boc)-OH, Fmoc-Glu (OtBu)-OH, Fmoc-Val-OH, Fmoc-Arg(Pmc)-OH, Fmoc-Glu(OtBu)-OH, Fmoc-Nle-OH, Fmoc-Ser(tBu)-OH, Fmoc-Asn(Trt)-OH, Fmoc-Leu-OH, Fmoc-Asp(OAllyl)-OH, Fmoc-Lys(Boc)-OH, Fmoc-Gly-OH, Fmoc-Leu-OH, Fmoc-Lys(Alloc)-OH, Fmoc-His(Trt)-OH, Fmoc-Nle-OH, Fmoc-Leu-OH, Fmoc-Gln(Trt)-OH, Fmoc-Ile-OH, Fmoc-Glu(OtBu)-OH, Fmoc-Ser(tBu)-OH, Fmoc-Val-OH, and Fmoc-Ala-OH. As described previously, the resin-bound peptide is then removed from the instrument for Pd-mediated side chain deprotection of Lys(Alloc) and Asp(OAllyl) residues and subsequent intramolecular side chain-to-side chain cyclization. The N-terminal Fmoc protective group is removed over 5 minutes using a 20% piperidine/DMF solution (17 mL). The resin-bound peptide is washed successively with DMF (100 mL), THF (100 mL), and diethyl ether (100 mL). The air-dried resin is suspended in 40 mL of TFA containing water (2.0 mL), thioanisole (2.0 mL), phenol (3.0 g), and ethanedithiol (1.0 mL). After 2 hours, the TFA solution is filtered into tert-butylmethyl ether (160 mL) at 0° C. which effects precipitation of the crude peptide. The peptide mixture is centrifuged at 2500 rpm for 5 minutes and decanted. The crude, white solid is resuspended in diethyl ether (120 mL), centrifuged, and decanted. This washing procedure is repeated four times and the resulting peptide is dried in vacuo, dissolved in water containing 0.1% TFA (100 mL), and lyophilized to dryness.

A portion of the crude peptide is then purified by reverse-phase liquid chromatography as described previously to provide 85 mg of final, purified peptide as a white solid. IS–MS: 3626 (M+). Amino Acid Analysis: Aso/Asn: 3.00 (3); Ser: 1.69 (2): Glu/Gln: 4.91 (5); Gly: 0.94 (1); Ala: 0.91 (1); Val 2.86 (3); Ile: 0.94 (1); Leu: 6.33 (6); Nle: 1.94 (2); Lys: 2.90 (3); His: 0.99 (1); Arg: 1.96 (2); Trp: not determined (1).

EXAMPLE 73

Cyclo($K^{14}$—$D^{18}$)[$A^1$,Nle$^8$,$K^{14}$,$D^{18}$,$L^{27}$]hPTH(1–31)NH$_2$ (SEQ ID NO: 67)

Ala-Val-Ser-Glu-Ile-Gln-Leu-Nle-His-Asn-Leu-Gly-Lys-(Lys-Leu-Asn-Ser-Asp)-Glu-Arg-Val-Glu-Trp- Leu-Arg-Lys-Leu-Leu-Gln-Asp-Val amide The peptide is prepared in a fashion analogous to that described previously (Method C). Rink Amide MBHA resin (0.5 mmol) is placed in a reaction vessel which is then attached to a Protein Technologies PS3 Automated Peptide synthesizer. The following amino acids are added sequentially in a manner consistent with Fmoc-base SPPS: Fmoc-Val-OH, Fmoc-Asp(OtBu)-OH, Fmoc-Gln(Trt)-OH, Fmoc-Leu-OH, Fmoc-Leu-OH, Fmoc-Lys(Boc)-OH, Fmoc-Arg(Pmc)-OH, Fmoc-Leu-OH, Fmoc-Trp(Boc)-OH, Fmoc-Glu(OtBu)-OH, Fmoc-Val-OH, Fmoc-Arg(Pmc)-OH, Fmoc-Glu(OtBu)-OH, Fmoc-Asp(OAllyl)-OH, Fmoc-Ser(tBu)-OH, Fmoc-Asn(Trt)-OH, Fmoc-Leu-OH, Fmoc-Lys(Alloc)-OH, Fmoc-Lys(Boc)-OH, Fmoc-Gly-OH, Fmoc-Leu-OH, Fmoc-Asn(Trt)-OH, Fmoc-His(Trt)-OH, Fmoc-Nle-OH, Fmoc-Leu-OH, Fmoc-Gln(Trt)-OH, Fmoc-Ile-OH, Fmoc-Glu(OtBu)-OH, Fmoc-Ser(tBu)-OH, Fmoc-Val-OH, and Fmoc-Ala-OH. As described previously, the resin-bound peptide is then removed from the instrument for Pd-mediated side chain deprotection of Lys(Alloc) and Asp(OAllyl) residues and subsequent intramolecular side chain-to-side chain cyclization. The N-terminal Fmoc protective group is removed over 5 minutes using a 20% piperidine/DMF solution (17 mL). The resin-bound peptide is washed successively with DMF (100 mL), THF (100 mL), and diethyl ether (100 mL). The air-dried resin is suspended in 40 mL of TFA containing water (2.0 mL), thioanisole (2.0 mL), phenol (3.0 g), and ethanedithiol (1.0 mL). After 2 hours, the TFA solution is filtered into tert-butylmethyl ether (160 mL) at 0° C. which effects precipitation of the crude peptide. The peptide mixture is centrifuged at 2500 rpm for 5 minutes and decanted. The crude, white solid is resuspended in diethyl ether (120 mL), centrifuged, and decanted. This washing procedure is repeated four times and the resulting peptide is dried in vacuo, dissolved in water containing 0.1% TFA (100 mL), and lyophilized to dryness.

A portion of the crude peptide is then purified by reverse-phase liquid chromatography as described previously to provide 57 mg of final, purified peptide as a white solid. IS–MS: 3627 (M+). Amino Acid Analysis: Asp/Asn: 4.00 (4): Ser: 1.69 (2): Glu/Gln: 4.86 (5); Gly: 0.94 (1); Ala: 0.98 (1); Val: 2.82 (3); Ile: 6.90 (1); Leu: 6.35 (6); Nle: 0.87 (1); Lys 2.89 (3); His: 1.00 (1); Arg. 1.9 (2); Trp: not determined (1).

EXAMPLE 74

Cyclo($K^{17}$-$D^{21}$)[$A^1$,Nle$^{8,18}$,$K^{17}$,$D^{21}$,$L^{27}$]hPTH(1–31)NH$_2$ (SEQ ID NO: 68)

Ala-Val-Ser-Glu-Ile-Gln-Leu-Nle-His-Asn-Leu-Gly-Lys-His-Leu-Asn-(Lys-Nle-Glu-Arg-Asp)-Glu-Trp- Leu-Arg-Lys-Leu-Leu-Gln-Asp-Val amide The peptide is prepared in a fashion analogous to that described previously (Method C). Rink Amide MBHA resin (0.5 mmol) is placed in a reaction vessel which is then attached to a Protein Technologies PS3 Automated Peptide synthesizer. The following amino acids are added sequentially in a manner consistent with Fmoc-base SPPS: Fmoc-Val-OH, Fmoc-Asp(OtBu)-OH, Fmoc-Gln(Trt)-OH, Fmoc-Leu-OH, Fmoc-Leu-OH, Fmoc-Lys(Boc)-OH, Fmoc-Arg(Pmc)-OH, Fmoc-Leu-OH, Fmoc-Trp(Boc)-OH, Fmoc-Glu(OtBu)-OH, Fmoc-Asp(OAllyl)-OH, Fmoc-Arg(Pmc)-OH, Fmoc-Glu(OtBu)-OH, Fmoc-Nle-OH, Fmoc-Lys(Alloc)-OH, Fmoc-Asn(Trt)-OH, Fmoc-Leu-OH, Fmoc-His(Trt)-OH, Fmoc-Lys(Boc)-OH, Fmoc-Gly-OH, Fmoc-Leu-OH, Fmoc-Asn(Trt)-OH, Fmoc-His(Trt)-OH, Fmoc-Nle-OH, Fmoc-Leu-OH, Fmoc-Gln(Trt)-OH, Fmoc-Ile-OH, Fmoc-Glu(OtBu)-OH, Fmoc-Ser(tBu)-OH, Fmoc-Val-OH, and Fmoc-Ala-OH. As described previously, the resin-bound peptide is then removed from the instrument for Pd-mediated side chain deprotection of Lys(Alloc) and Asp(OAllyl) residues and subsequent intramolecular side chain-to-side chain cyclization. The N-terminal Fmoc protective group is removed over 5 minutes using a 20% piperidine/DMF solution (17 mL). The resin-bound peptide is washed successively with DMF (100 mL), THF (100 mL), and diethyl ether (100 mL). The air-dried resin is suspended in 40 mL of TFA containing water (2.0 mL), thioanisole (2.0 mL), phenol (3.0 g), and ethanedithiol (1.0 mL). After 2 hours, the TFA solution is filtered into tert-butylmethyl ether (160 mL) at 0° C. which effects precipitation of the crude peptide. The peptide mixture is centrifuged at 2500 rpm for 5 minutes and decanted. The crude, white solid is resuspended in diethyl ether (120 mL), centrifuged, and decanted. This washing procedure is repeated four times and the resulting peptide is dried in vacuo, dissolved in water containing 0.1% TFA (100 mL), and lyophilized to dryness.

A portion of the crude peptide is then purified by reverse-phase liquid chromatography as described previously to provide 136 mg of final, purified peptide as a white solid. IS–MS: 3689 (M+). Amino Acid Analysis. Asp/Asn: 4.00

(4); Ser: 0.83 (1); Glu/Gln: 4.84 (5); Gly: 0.93 (1); Ala: 0.96 (1); Val: 1.93 (2); Ile: 0.84 (1); Leu: 6.32 (6); Nle: 1.80 (2); Lys: 2.87(3); His: 1.95(2); Arg: 2.04(2); Trp: not determined (1).

EXAMPLE 75

Cyclo($K^{21}$-$D^{25}$)[$A^{1,Nle8,18}$,$K^{21}$,$D^{25}$,$L^{27}$]hPTH(1–31)NH$_2$ (SEQ ID NO: 69)

Ala-Val-Ser-Glu-Ile-Gln-Leu-Nle-His-Asn-Leu-Gly-Lys-His-Leu-Asn-Ser-Nle-Glu-Arg-(Lys-Glu-Trp-Leu-Asp)-Lys-Leu-Leu-Gln-Asp-Val amide The peptide is prepared in a fashion analogous to that described previously (Method C). Rink Amide MBHA resin (0.5 mmol) is placed in a reaction vessel which is then attached to a Protein Technologies PS3 Automated Peptide synthesizer. The following amino acids are added sequentially in a manner consistent with Fmoc-base SPPS: Fmoc-Val-OH, Fmoc-Asp(OtBu)-OH, Fmoc-Gln(Trt)-OH, Fmoc-Leu-OH, Fmoc-Leu-OH, Fmoc-Lys(Boc)-OH, Fmoc-Asp(OAllyl)-OH, Fmoc-Leu-OH, Fmoc-Trp(Boc)-OH, Fmoc-Glu(OtBu)-OH, Fmoc-Lys(Alloc)-OH, Fmoc-Arg(Pmc)-OH, Fmoc-Glu(OtBu)-OH, Fmoc-Nle-OH, Fmoc-Ser(tBu)-OH, Fmoc-Asn(Trt)-OH, Fmoc-Leu-OH, Fmoc-His(Trt)-OH, Fmoc-Lys(Boc)-OH, Fmoc-Gly-OH, Fmoc-Leu-OH, Fmoc-Asn(Trt)-OH, Fmoc-His(Trt)-OH, Fmoc-Nle-OH, Fmoc-Leu-OH, Fmoc-Gln(Trt)-OH, Fmoc-Ile-OH, Fmoc-Glu(OtBu)-OH, Fmoc-Ser(tBu)-OH, Fmoc-Val-OH, and Fmoc-Ala-OH. As described previously, the resin-bound peptide is then removed from the instrument for Pd-mediated side chain deprotection of Lys(Alloc) and Asp(OAllyl) residues and subsequent intramolecular side chain-to-side chain cyclization. The N-terminal Fmoc protective group is removed over 5 minutes using a 20% piperidine/DMF solution (17 mL). The resin-bound peptide is washed successively with DMF (100 mL), THF (100 mL), and diethyl ether (100 mL). The air-dried resin is suspended in 40 mL of TFA containing water (2.0 mL), thioanisole (2.0 mL), phenol (3.0 g), and ethanedithiol (1.0 mL). After 2 hours, the TFA solution is filtered into tert-butylmethyl ether (160 mL) at 0° C. which effects precipitation of the crude peptide. The peptide mixture is centrifuged at 2500 rpm for 5 minutes and decanted. The crude, white solid is resuspended in diethyl ether (120 mL), centrifuged, and decanted. This washing procedure is repeated four times and the resulting peptide is dried in vacuo, dissolved in water containing 0.1% TFA (100 mL), and lyophilized to dryness.

A portion of the crude peptide is then purified by reverse-phase liquid chromatography as described previously to provide 131 mg of final, purified peptide as a white solid. IS–MS: 3620 (M+). Amino Acid Analysis: Asp/Asn: 4.00 (4): Ser:. 1.71 (2): Glu/Gln: 4.84 (5); Gly: 9.96 (1): Ala: 0.97 (1); Val: 2.07 (2); Ile: 0.92 (1); Leu: 6.22(6); Nle: 1.90 (2); Lys: 2.90 (3); His: 1.97 (2); Arg: 0.97 (1); Trp: not determined (1).

EXAMPLE 76

Cyclo($K^{25}$-$D^{29}$)[$A^1$,$Nle^{8,18}$,$K^{25}$,$D^{29}$,$L^{27}$]hPTH(1–31)NH$^2$ (SEQ ID NO: 70)

Ala-Val-Ser-Glu-Ile-Gln-Leu-Nle-His-Asn-Leu-Gly-Lys-His-Leu-Asn-Ser-Nle-Glu-Arg-Val-Glu-Trp-Leu-(Lys-Lys-Leu-Leu-Asp)-Asp-Val amide The peptide is prepared in a fashion analogous to that described previously (Method C). Rink Amide MBHA resin (0.5 mmol) is placed in a reaction vessel which is then attached to a Protein Technologies PS3 Automated Peptide synthesizer. The following amino acids are added sequentially in a manner consistent with Fmoc-base SPPS: Fmoc-Val-OH, Fmoc-Asp(OtBu)-OH, Fmoc-Asp(OAllyl)-OH, Fmoc-Leu-OH, Fmoc-Leu-OH, Fmoc-Lys(Boc)-OH, Fmoc-Lys(Alloc)-OH, Fmoc-Leu-OH, Fmoc-Trp(Boc)-OH, Fmoc-Glu(OtBu)-OH, Fmoc-Val-OH, Fmoc-Arg(Pmc)-OH, Fmoc-Glu(OtBu)-OH, Fmoc-Nle-OH, Fmoc-Ser(tBu)-OH, Fmoc-Asn(Trt)-OH, Fmoc-Leu-OH, Fmoc-His(Trt)-OH, Fmoc-Lys(Boc)-OH, Fmoc-Gly-OH, Fmoc-Leu-OH, Fmoc-Asn(Trt)-OH, Fmoc-His(Trt)-OH, Fmoc-Nle-OH, Fmoc-Leu-OH, Fmoc-Gln(Trt)-OH, Fmoc-Ile-OH, Fmoc-Glu(OtBu)-OH, Fmoc-Ser(tBu)-OH, Fmoc-Val-OH, and Fmoc-Ala-OH. As described previously, the resin-bound peptide is then removed from the instrument for Pd-mediated side chain deprotection of Lys(Alloc) and Asp(OAllyl) residues and subsequent intramolecular side chain-to-side chain cyclization. The N-terminal Fmoc protective group is removed over 5 minutes using a 20% piperidine/DMF solution (17 mL). The resin-bound peptide is washed successively with DMF (100 mL), THF (100 mL), and diethyl ether (100 mL). The air-dried resin is suspended in 40 mL of TFA containing water (2.0 mL), thioanisole (2.0 mL), phenol (3.0 g), and ethanedithiol (1.0 mL). After 2 hours, the TFA solution is filtered into tert-butylmethyl ether (160 mL) at 0° C. which effects precipitation of the crude peptide. The peptide mixture is centrifuged at 2500 rpm for 5 minutes and decanted. The crude, white solid is resuspended in diethyl ether (120 mL), centrifuged, and decanted. This washing procedure is repeated four times and the resulting peptide is dried in vacuo, dissolved in water containing 1% TFA (100 mL) and lyophilized to dryness.

A portion of the crude peptide is then purified by reverse-phase liquid chromatography as described previously to provide 134 mg of final, purified peptide as a white solid. IS–MS: 3591 (M+). Amino Acid Analysis: Asp/Asn: 4.11 (4); Ser: 1.69 (2); Glu/Gln: 3.89 (4); Gly: 0.97 (1); Ala: 1.00 (1); Val: 3.12 (3); Ile: 0.92(1); Leu: 6.45 (6): Nle; 1.85 (2); Lys: 3.02 (3): His: 1.99 (2); Arg 0.98 (1); Trp: not determined (1).

EXAMPLE 77

Cyclo($K^{18}$—$D^{22}$)[$K^{18}$,$D^{22}$]hPTHrP(1–34)NH$_2$ (SEQ ID NO: 71)

Ala-Val-Ser-Glu-His-Gln-Leu-Leu-His-Asp-Lys-Gly-Lys-Ser-Ile-Gln-Asp-(Lys-Arg-Arg-Arg-Asp)-Phe-Leu-His-His-Leu-Ile-Ala-Glu-Ile-His-Thr-Ala amide The peptide is prepared in a fashion analogous to that described previously (Method B). Rink Amide MBHA resin (0.5 mmol) is placed in a reaction vessel which is then attached to a Protein Technologies PS3 Automated Peptide synthesizer. The following amino acids are added sequentially in a manner consistent with Fmoc-base SPPS: Fmoc-Ala-OH, Fmoc-Thr(tBu)-OH, Fmoc-His(Trt)-OH, Fmoc-Ile-OH, Fmoc-Glu(OtBu)-OH, Fmoc-Ala-OH, Fmoc-Ile-OH, Fmoc-Leu-OH, Fmoc-His(Trt)-OH, Fmoc-His(Trt)-OH, Fmoc-Leu-OH, Fmoc-Phe-OH, Fmoc-Asp(OAllyl)-OH, Fmoc-Arg(Pmc)-OH, Fmoc-Arg(Pmc)-OH, Fmoc-Arg(Pmc)-OH, Fmoc-Lys(Alloc)-OH, Fmoc-Asp(OtBu)-OH, Fmoc-Gln(Trt)-OH, Fmoc-Ile-OH. As described previously, the resin-bound peptide is then removed from the instrument for Pd-mediated side chain deprotection of the Lys(Alloc) and Asp(OAllyl) residues and subsequent intramolecular side chain-to-side chain cyclization. Following the described work-up procedures, the amide-containing resin-bound peptide is returned to the instrument for completion of the synthesis and the following amino acids are added sequentially: Fmoc-Ser(tBu)-OH, Fmoc-Lys(Boc)-OH, Fmoc-Gly-OH, Fmoc-Lys(Boc)-OH, Fmoc-Asp(OtBu)-OH, Fmoc-His(Trt)-OH, Fmoc-Leu-OH, Fmoc-Leu-OH, Fmoc-Gln(Trt)-OH, Fmoc-His(Trt)-OH, Fmoc-Glu(OtBu)-OH, Fmoc-Ser(tBu)-OH, Fmoc-Val-OH, and Fmoc-Ala-OH. The resin-bound peptide is then removed from the instrument and the N-terminal Fmoc protective group is removed over 5 minutes using a 20% piperidine/DMF solution (17 mL). The resin-bound peptide is washed successively with DMF (100 mL), THF (100 mL), and diethyl ether (100 mL). The air-dried resin is suspended in 40 mL of TFA containing water (2.0 mL), thioanisole (2.0 mL), phenol (3.0 g), and ethanedithiol (1.0 mL). After 2 hours, the TFA solution is filtered into tert-butylmethyl ether (160 mL) at 0° C. which effects precipitation of the crude peptide. The peptide mixture is centrifuged at 2500 rpm for 5 minutes and decanted. The crude, white solid is resuspended in diethyl ether (120 mL), centrifuged, and decanted. This washing procedure is repeated four times and the resulting peptide is dried in vacuo, dissolved in water containing 0.1% TFA (100 mL), and lyophilized to dryness.

The crude peptide is then purified by reverse-phase liquid chromatography to provide 110 mg of final peptide as a white solid. IS–MS: 3980 (M+). Amino Acid Analysis: Asp/Asn: 3.11 (3); Thr: 1.05 (1); Ser: 1.78 (2); Glu/Gln: 3.93 (4); Gly: 0.98 (1); Ala: 3.12 (3); Val: 1.00 (1); Ile: 2.73 (3); Leu: 4.00 (4); Lys: 2.86 (3); Phe: 1.13 (1); His: 4.93 (5); Arg: 3.12 (3).

EXAMPLE 78

Cyclo($K^{18}$—$D^{22}$)[$K^{18,26,30}$,$D^{22}$,$L^{23,28,31}$,$E^{25,29}$] hPTHrP(1–34)$NH_2$ (SEQ ID NO: 72)

Ala-Val-Ser-Glu-His-Gln-Leu-Leu-His-Asp-Lys-Gly-Lys-Ser-Ile-Gln-Asp-(Lys-Arg-Arg-Arg-Asp)- Leu-Leu-Glu-Lys-Leu-Leu-Glu-Lys-Leu-His-Thr-Ala amide The peptide is prepared in a fashion analogous to that described previously (Method B). Rink Amide MBHA resin (0.5 mmol) is placed in a reaction vessel which is then attached to a Protein Technologies PS3 Automated Peptide synthesizer. The following amino acids are added sequentially in a manner consistent with Fmoc-base SPPS: Fmoc-Ala-OH, Fmoc-Thr(tBu)-OH, Fmoc-His(Trt)-OH, Fmoc-Leu-OH, Fmoc-Lys(Boc)-OH, Fmoc-Glu(OtBu)-OH, Fmoc-Leu-OH, Fmoc-Leu-OH, Fmoc-Lys(Boc)-OH, Fmoc-Glu(OtBu)-OH, Fmoc-Leu-OH, Fmoc-Leu-OH, Fmoc-Asp(OAllyl)-OH, Fmoc-Arg(Pmc)-OH, Fmoc-Arg(Pmc)-OH, Fmoc-Arg(Pmc)-OH, Fmoc-Lys(Alloc)-OH, Fmoc-Asp(OtBu)-OH, Fmoc-Gln(Trt)-OH, and Fmoc-Ile-OH. As described previously, the resin-bound peptide is then removed from the instrument for Pd-mediated side chain deprotection of the Lys(Alloc) and Asp(OAllyl) residues and subsequent intramolecular side chain-to-side chain cyclization. Following the described work-up procedures, the amide-containing resin-bound peptide is returned to the instrument for completion of the synthesis and the following amino acids are added sequentially: Fmoc-Ser(tBu)-OH, Fmoc-Lys(Boc)-OH, Fmoc-Gly-OH, Fmoc-Lys(Boc)-OH, Fmoc-Asp(OtBu)-OH, Fmoc-His(Trt)-OH, Fmoc-Leu-OH, Fmoc-Leu-OH, Fmoc-Gln(Trt)-OH, Fmoc-His(Trt)-OH, Fmoc-Glu(OtBu)-OH, Fmoc-Ser(tBu)-OH. Fmoc-Val-OH, and Fmoc-Ala-OH. The resin-bound peptide is then removed from the instrument and the terminal Fmoc protective group is removed using 20% piperidine in DMF (20 mL). The crude peptide is cleaved from the resin and deprotected using 40 mL of TFA containing water (2.0 mL), thioanisole (2.0 mL), phenol (3.0 g), and ethanedithiol (1.0 mL) and precipitated by the addition of the cleavage mixture to cold tert-butylmethyl ether.

The crude peptide is then purified by reverse-phase liquid chromatography to provide 31 mg of final peptide as a white solid. IS–MS: 3986 (M+). Amino Acid Analysis: Asp/Asn: 2.60 (3); Thr: 1.26 (1); Ser: 1.61 (2); Glu/Gln: 5.02 (5); Gly: 0.96 (1); Ala: 2.37 (2); Val: 0.96 (1); Ile: 0.81 (1); Leu: 7.71 (7); Lys: 5.17 (5); His: 3.17 (3); Arg: 2.37 (3).

EXAMPLE 79

Bicyclo($K^{13}$—$D^{17}$,$K^{18}$—$D^{22}$)[$A^1$,$Nle^8$,$D^{17,22}$,$K^{18}$, $L^{27}$]hPTH(1–31)$NH_2$ (SEQ ID NO: 73)

Ala-Val-Ser-Glu-Ile-Gln-Leu-Nle-His-Asn-Leu-Gly-(Lys-His-Leu-Asn-Asp)-(Lys-Glu-Arg-Val-Asp)-Trp-Leu-Arg-Lys-Leu-Leu-Gln-Asp-Val amide A portion of the previously prepared resin-bound peptide terminating with the $D^{22}$—$K^{18}$ amide bridge (approx. 0.5 mmol) is returned to the automated peptide synthesizer and the N-terminal Fmoc protective group is removed as described earlier. The following amino acid residues are added successively using standard HBTU coupling procedures: Fmoc-Asp(OAllyl)-OH, Fmoc-Asn(Trt)-OH, Fmoc-Leu-OH, Fmoc-His(Trt)-OH, and Fmoc-Lys(Alloc)-OH. The resin is removed from the instrument and washed successively with DMF (100 mL), THF (100 mL), diethyl ether(100 mL), then air-dried. The Allyl and Alloc protective groups are removed under Pd-catalysis as previously described and the cyclization between residues $Asp^{17}$ and $K^{13}$ is accomplished in two cycles using HBTU (284 mg), HOBt (101 mg), and NMM (165 mL) in DMF (20 mL). The resin is then washed successively with DMF (100 mL), THF (100 mL), and diethyl ether (100 mL). The resin is returned to the instrument and the synthesis is completed following the addition of the following amino acids: Fmoc-Gly-OH, Fmoc-Leu-OH, Fmoc-Asn(Trt)-OH, Fmoc-His(Trt)-OH, Fmoc-Nle-OH, Fmoc-Leu-OH, Fmoc-Gln(Trt)-OH, Fmoc-Ile-OH, Fmoc-Glu(OtBu)-OH, Fmoc-Ser(tBu)-OH, Fmoc-Val-OH, and Fmoc-Ala-OH. The N-terminal Fmoc protective group is removed over 5 minutes using a 20% piperidine/DMF solution (17 mL). The resin-bound peptide is removed from the instrument and washed successively with DMF (100 mL), THF (100 mL), and diethyl ether (100 mL). The air-dried resin is suspended in 40 mL of TFA containing water (2.0 mL), thioanisole (2.0 mL), phenol (3.0 g), and ethanedithiol (1.0 mL). After 2 hours, the TFA solution is filtered into tert-butylmethyl ether (160 mL) at 0° C. which effects precipitation of the crude peptide. The peptide mixture is centrifuged at 2500 rpm for 5 minutes and decanted. The crude, white solid is resuspended in diethyl ether (120 mL), centrifuged, and decanted. This washing procedure is repeated four times and the resulting peptide is dried in vacuo, dissolved in water containing 0.1% TFA (100 mL), and lyophilized to dryness.

The crude peptide is purified by reverse-phase high performance liquid chromatography as previously described to afford 13 mg of final peptide as a white solid. IS–MS: 3643 (M+). Amino Acid Analysis: Asp/Asn: 4.83 (5); Ser: 0.97 (1); Glu/Gln: 3.98 (4); Gly: 0.97 (1); Ala: 0.96 (1); Val: 3.14 (3); Ile: 0.88 (1); Leu: 6.47 (6); Nle: 0.80 (1); Lys: 2.91 (3); His: 2.03 (2); Arg: 2.07 (2); Trp: not determined (1). The positions of the amide bridges are confirmed by Edman degradation.

EXAMPLE 80

Bicyclo($K^{18}$—$D^{22}$,$K^{26}$-$D^{30}$)[$A^1$,$Nle^8$,$K^{18}$,$D^{22}$,$L^{27}$] hPTH(1–31)$NH_2$ (SEQ ID NO: 74)

Ala-Val-Ser-Glu-Ile-Gln-Leu-Nle-His-Asn-Leu-Gly-Lys-His-Leu-Asn-Ser-(Lys-Glu-Arg-Val-Asp)-Trp-Leu-Arg-(Lys-Leu-Leu-Gln-Asp)-Val amide The title compound is prepared in a fashion analogous to those previously described. Rink Amide MBHA Resin (Nova Biochem, La Jolla, Calif., USA) (0.80 g, 0.45 mmol) is loaded into a reaction vessel and swelled for 10 minutes using DMF (10 mL). The following amino acid residues are added successively using standard HBTU coupling procedures: Fmoc-Val-OH, Fmoc-Asp(OAllyl)-OH, Fmoc-Gln (Trt)-OH, Fmoc-Leu-OH, Fmoc-Leu-OH, Fmoc-Lys (Alloc)-OH, Fmoc-Arg(Pmc)-OH, Fmoc-Leu-OH, and Fmoc-Trp(Boc)-OH. The resin is removed from the instrument and washed successively with DMF (100 mL), THF (100 mL), diethyl ether(100 mL), then air-dried. The Allyl and Alloc protective groups are removed under Pd-catalysis as previously described and the cyclization between residues $Asp^{30}$ and $K^{26}$ is accomplished in two cycles using HBTU (284 mg), HOBt (101 mg), and NMM (165 mL) in DMF (20 mL). The resin is then washed successively with DMF (100 mL), THF (100 mL), and diethyl ether (100 mL). The resin is returned to the instrument and the synthesis is completed following the addition of the following amino acids: Fmoc-Asp(OAllyl)-OH, Fmoc-Val-OH, Fmoc-Arg(Pmc)-OH, Fmoc-Glu(OtBu)-OH, Fmoc-Lys(Alloc)-OH, Fmoc-Ser (tBu)-OH, Fmoc-Asn(Trt)-OH, Fmoc-Leu-OH, Fmoc-His (Trt)-OH, Fmoc-Lys(Boc)-OH. Fmoc-Gly-OH, Fmoc-Leu-OH, Fmoc-Asn(Trt)-OH, Fmoc-His(Trt)-OH, Fmoc-Nle-OH, Fmoc-Leu-OH, Fmoc-Gln(Trt)-OH, Fmoc-Ile-OH, Fmoc-Glu(OtBu)-OH, Fmoc-Ser(tBu)-OH, Fmoc-Val-OH, and Fmoc-Ala-OH. The resin is then removed from the instrument, washed successively with DMF (100 mL), THF (100 mL), diethyl ether (100 mL), and air-dried. The Allyl and Alloc protective groups are removed under Pd-catalysis as previously described and the cyclization between residues $Asp^{22}$ and $K^{18}$ is accomplished in two cycles using HBTU (284 mg), HOBt (101 mg), and NMM (165 mL) in DMF (20 mL). The resin is then washed successively with DMF (100 mL), THF (100 mL), and diethyl ether (100 mL). The N-terminal Fmoc protective group is removed over 5 minutes using a 20% piperidine/DMF solution (25 mL). The resin-bound peptide is washed successively with DMF (100 mL), THF (100 mL), and diethyl ether (100 mL). The air-dried resin is suspended in 40 mL of TFA containing water (2.0 mL), thioanisole (2.0 mL), phenol (3.0 g), and ethanedithiol (1.0 mL). After 2 hours, the TFA solution is filtered into tert-butylmethyl ether (120 mL) at 0° C. which effects precipitation of the crude peptide. The peptide mixture is centrifuged at 2500 rpm for 5 minutes and decanted. The crude, white solid is resuspended in diethyl ether (120 mL), centrifuged, and decanted. This washing procedure is repeated four times and the resulting peptide is dried in vacuo, dissolved in water containing 0.1% TFA (100 mL), and lyophilized to dryness.

The crude peptide is purified by reverse-phase high performance liquid chromatography as described previously to provide 90 mg of final peptide as a white solid. IS–MS: 3615 (M+). Amino Acid Analysis: Asp/Asn: 3.79 (4); Ser: 1.84 (2); Glu/Gln: 3.84 (4); Gly: 1.19 (1); Ala: 1.00 (1); Val: 2.82 (3); Ile: 0.89 (1); Leu: 6.16 (6); Nle: 0.74 (1); Lys: 2.73 (3); His: 1.94 (2); Arg: 1.93 (2); Trp: not determined (1). The positions of the amide bridges are confirmed by Edman degradation.

EXAMPLE 81

Bicyclo($K^{13}$—$D^{17}$,$K^{18}$—$D^{22}$)[$A^1$,$Nle^8$,$D^{17,22}$,$K^{18}$, $L^{27}$]hPTH(1–34)$NH_2$ (SEQ ID NO: 75)

Ala-Val-Ser-Glu-Ile-Gln-Leu-Nle-His-Asn-Leu-Gly-(Lys-His-Leu-Asn-Asp)-(Lys-Glu-Arg- Val-Asp)-Trp-Leu-Arg-Lys-Leu-Leu-Gln-Asp-Val-His-Asn-Phe amide A portion of the previously prepared resin-bound peptide beginning with $Phe^{34}$ and terminating with the $Asp^{22}$-$Lys^{18}$ amide bridge (0.46 g, approx. 1.0 mmol) is returned to the automated peptide synthesizer and the N-terminal Fmoc protective group is removed as described earlier. The following amino acid residues are added successively using standard HBTU coupling procedures: Fmoc-Asp(OAllyl)-OH, Fmoc-Asn(Trt)-OH, Fmoc-Leu-OH, Fmoc-His(Trt)-OH, and Fmoc-Lys(Alloc)-OH. The resign is then removed from the instrument, washed successively with DMF 100 mL), THF (100 mL), diethyl ether (100 mL), and air-dried. The allyl and alloc protective groups are removed as previously described and the cyclization between residues $Lys^{13}$ and $Asp^{17}$ is accomplished in two cycles using HBTU, HOBt and NMM. After washing and drying, the resin is returned to the instrument and the synthesis is completed by adding the following amino acids in the order indicated: Fmoc-Gly-OH, Fmoc-Leu-OH, Fmoc-Asn(Trt)-OH, Fmoc-His(Trt)-OH, Fmoc-Nle-OH, Fmoc-Leu-OH, Fmoc-Gln (Trt)-OH, Fmoc-Ile-OH, Fmoc-Glu(OtBu)-OH, Fmoc-Ser (tBu)-OH, Fmoc-Val-OH and Fmoc-Ala-OH. The crude peptide is cleaved from the resin and deprotected using 40 mL of TFA containing water (2.0 mL), thioanisole (2.0 mL), phenol (3.0 g), and ethanedithiol (1.0 mL) and precipitated by the addition of the cleavage mixture to cold tert-butylmethyl ether. The crude peptide is then purified by reverse-phase liquid chromatography.

EXAMPLE 82

Bicyclo($K^{13}$—$D^{17}$,$K^{26}$-$D^{30}$)[$A^1$,$Nle^{8,18}$,$D^{17}$,$L^{27}$] hPTH(1–31)$NH_2$ (SEQ ID NO: 76)

Ala-Val-Ser-Glu-Ile-Gln-Leu-Nle-His-Asn-Leu-Gly-(Lys-His-Leu-Asn-Asp)-Nle-Glu-Arg-Val-Glu-Trp-Leu-Arg-(Lys-Leu-Leu-Gln-Asp)-Val amide The title compound is prepared in a fashion analogous to those previously described. Rink Amide MBHA Resin (Nova Biochem, La Jolla, Calif., USA) (0.80 g, 0.45 mmol) is loaded into a reaction vessel and swelled for 10 minutes using DMF (10 mL). The following amino acid residues are added successively using standard HBTU coupling procedures: Fmoc-Val-OH, Fmoc-Asp(OAllyl)-OH, Fmoc-Gln (Trt)-OH, Fmoc-Leu-OH, Fmoc-Leu-OH, Fmoc-Lys (Alloc)-OH, Fmoc-Arg(Pmc)-OH, Fmoc-Leu-OH, and Fmoc-Trp(Boc)-OH. The resin is removed from the instrument and washed successively with DMF (100 mL), THF (100 mL), diethyl ether(100 mL), then air-dried. The Allyl and Alloc protective groups are removed under Pd-catalysis as previously described and the cyclization between residues $Asp^{30}$ and $K^{26}$ is accomplished in two cycles using HBTU (284 mg), HOBt (101 mg), and NMM (165 mL) in DMF (20 mL). The resin is then washed successively with DMF (100 mL), THF (100 mL), and diethyl ether (100 mL). The resin is returned to the instrument and the synthesis is completed following the addition of the following amino acids: Fmoc-Glu(OtBu)-OH, Fmoc-Val-OH, Fmoc-Arg(Pmc)-OH, Fmoc-Glu(OtBu)-OH, Fmoc-Nle-OH, Fmoc-Asp(OAllyl)-

OH, Fmoc-Asn(Trt)-OH, Fmoc-Leu-OH, Fmoc-His(Trt)-OH, Fmoc-Lys(Alloc)OH, Fmoc-Gly-OH, Fmoc-Leu-OH, Fmoc-Asn(Trt)-OH, Fmoc-His(Trt)-OH, Fmoc-Nle-OH, Fmoc-Leu-OH, Fmoc-Gln(Trt)-OH, Fmoc-Ile-OH, Fmoc-Glu(OtBu)-OH, Fmoc-Ser(tBu)-OH, Fmoc-Val-OH, and Fmoc-Ala-OH. The resin is then removed from the instrument, washed successively with DMF (100 mL), THF (100 mL), diethyl ether (100 mL), and air-dried. Again, the Allyl and Alloc protective groups are removed under Pd-catalysis as previously described and the cyclization between residues $Asp^{22}$ and $K^{18}$ is again accomplished in two cycles using HBTU (284 mg), HOBt (101 mg), and NMM (165 mL) in DMF (20 mL). The resin is then washed successively with DMF (100 mL), THF (100 mL), and diethyl ether (100 mL). The N-terminal Fmoc protective group is removed over 5 minutes using a 20% piperidine/DMF solution (25 mL). The resin-bound peptide is washed successively with DMF (100 mL), THF (100 mL), and diethyl ether (100 mL). The air-dried resin is suspended in 40 mL of TFA containing water (2.0 mL), thioanisole (2.0 mL), phenol (3.0 g), and ethanedithiol (1.0 mL). After 2 hours, the TFA solution is filtered into tert-butylmethyl ether (120 mL) at 0° C. which effects precipitation of the crude peptide. The peptide mixture is centrifuged at 2500 rpm for 5 minutes and decanted. The crude, white solid is resuspended in diethyl ether (120 mL), centrifuged, and decanted. This washing procedure is repeated four times and the resultant peptide is dried in vacuo, dissolved in water containing 0.1% TFA (100 mL), and lyophilized to dryness.

The crude peptide is purified by reverse-phase high performance liquid chromatography as described previously to provide 22 mg of final peptide as a white solid. IS–MS: 3642 (M+). Amino Acid Analysis: Asp/Asn: 4.00 (4); Ser: 0.99 (1); Glu/Gln: 4.95 (5); Gly: 0.96 (1); Ala: 0.95 (1); Val: 3.05 (3); Ile: 0.92 (1); Leu: 6.40 (6); Nle: 1.78 (2); Lys: 1.81 (2); His: 2.17 (2); Arg: 2.03 (2); Trp: not determined (1). The positions of the amide bridges are confirmed by Edman degradation.

EXAMPLE 83

Cyclo($K^{18}$—$D^{22}$)[$K^{18}$,$D^{22}$]hPTHrP(7–34)NH$_2$ (SEQ ID NO: 77)

Leu-Leu-His-Asp-Lys-Gly-Lys-Ser-Ile-Gln-Asp-(Lys-Arg-Arg-Arg-Asp)-Phe-Leu-His-His-Leu-Ile-Ala-Glu-Ile-His-Thr-Ala amide The peptide is prepared in a fashion analogous to that described previously (Method B). Rink Amide MBHA resin (0.5 mmol) is placed in a reaction vessel which is then attached to a Protein Technologies PS3 Automated Peptide synthesizer. The following amino acids are added sequentially in a manner consistent with Fmoc-base SPPS: Fmoc-Ala-OH, Fmoc-Thr(tBu)-OH, Fmoc-His(Trt)-OH, Fmoc-Ile-OH, Fmoc-Glu(OtBu)-OH, Fmoc-Ala-OH, Fmoc-Ile-OH, Fmoc-Leu-OH, Fmoc-His(Trt)-OH, Fmoc-His(Trt)-OH. Fmoc-Leu-OH, Fmoc-Phe-OH, Fmoc-Asn(OAllyl)-OH, Fmoc-Arg(Pmc)-OH, Fmoc-Arg(Pmc)-OH, Pmoc-Arg (Pmc)-OH, Fmoc-Lys(Alloc)-OH, Fmoc-Asp(OtBu)-OH, Fmoc-Gln(Trt)-OH, and Fmoc-Ile-OH. As described previously, the resin-bound peptide is then removed from the instrument for Pd-mediated side chain deprotection of the Lys(Alloc) and Asp(OAllyl) residues and subsequent intramolecular side chain-to-side chain cyclization. Following the described work-up procedures, the amide-containing resin-bound peptide is returned to the instrument for completion of the synthesis; the following amino acids are added sequentially: Fmoc-Ser(tBu)-OH, Fmoc-Lys(Boc)-OH, Fmoc-Gly-OH, Fmoc-Lys(Boc)-OH, Fmoc-Asp (OtBu)-OH, Fmoc-His(Trt)-OH, Fmoc-Leu-OH and Fmoc-Leu-OH. The crude peptide is cleaved from the resin and deprotected using 40 mL of TFA containing water (2.0 mL), thioanisole (2.0 mL), phenol (3.0 g), and ethanedithiol (1.0 mL) and precipitated by the addition of the cleavage mixture to cold tert-butylmethyl ether. The crude peptide is then purified by reverse-phase liquid chromatography.

EXAMPLE 84

Bicyclo($K^{13}$—$D^{17}$,$K^{18}$—$D^{22}$)[$Nle^8$,$K^{13}$,$D^{17,22}$,$L^{27}$] hPTH(7–34)NH$_2$ (SEQ ID NO: 78)

Leu-Nle-His-Asn-Leu-Gly-(Lys-His-Leu-Asn-Asp)-(Lys-Glu-Arg-Val-Asp)-Trp-Leu-Arg-Lys-Leu-Leu-Gln-Asp-Val-His-Asn-Phe amide A portion of the resin-bound peptide terminating with the $Lys^{18}$-$Asp^{22}$ amide bridge prepared in Example 23 is returned to the automated peptide synthesizer and the N-terminal Fmoc protective group is removed as described earlier. The following amino acid residues are added successively using standard HBTU coupling procedures: Fmoc-Asp(OAllyl)-OH, Fmoc-Asn(Trt)-OH, Fmoc-Leu-OH, Fmoc-His(Trt)-OH, and Fmoc-Lys(Alloc)-OH. The resin is then removed from the instrument, washed successively with DMF (100 mL), THF (100 mL), diethyl ether (100 mL), and air-dried. The allyl and alloc protective groups are removed as previously described and the cyclization between residues $Lys^{13}$ and $Asp^{17}$ is accomplished in two cycles using HBTU, HOBt and NMM. After washing and drying, the resin is returned to the instrument and the synthesis is completed by adding the following amino acids in the order indicated: Fmoc-Gly-OH, Fmoc-Leu-OH, Fmoc-Asn(Trt)-OH, Fmoc-His(Trt)-OH, Fmoc-Nle-OH, Fmoc-Leu-OH. The crude peptide is cleaved from the resin and deprotected using 40 mL of TFA containing water (2.0 mL), thioanisole (2.0 mL), phenol (3.0 g), and ethanedithiol (1.0 mL) and precipitated by the addition of the cleavage mixture to cold tert-butylmethyl ether. The crude peptide is then purified by reverse-phase liguid chromatography.

EXAMPLE 85

Bicyclo($K^{18}$—$D^{22}$,$K^{26}$-$D^{30}$)[$Nle^8$,$K^{18}$,$D^{22}$,$L^{27}$] hPTH(7–34)NH$_2$ (SEQ ID NO: 79)

Leu-Nle-His-Asn-Leu-Gly-Lys-His-Leu-Asn-Ser-(Lys-Glu-Arg-Val-Asp)-Trp-Leu-Arg-(Lys-Leu-Leu-Gln-Asp)-Val-His-Asn-Phe amide The title peptide is prepared in a fashion analogous to those previously described. Rink Amide MBHA Resin (Nova Biochem, La Jolla, Calif., USA) (0.75 g, 0.41 mmol) is loaded into a reaction vessel and swelled for 10 minutes using DMF (10 mL). The following amino acid residues are added successively using standard HBTU coupling procedures: Fmoc-Phe-OH, Fmoc-Asn(Trt)-OH, Fmoc-His(Trt)-OH, Fmoc-Val-OH, Fmoc-Asp(OAllyl)-OH, Fmoc-Gln (Trt)-OH, Fmoc-Leu-OH, Fmoc-Leu-OH, and Fmoc-Lys (Alloc)-OH. The resin is then removed from the instrument, washed successively with DMF (100 mL), THF (100 mL), diethyl ether (100 mL), and air-dried. The allyl and alloc protective groups are removed as previously described and the cyclization between residues $Lys^{26}$ and $Asp^{30}$ is accomplished in two cycles using HBTU, HOBt and NMM. After washing and drying, the resin is returned to the instrument and the following amino acid residues are added using the described coupling conditions: Fmoc-Arg(Pmc)-OH, Fmoc-Leu-OH, Fmoc-Trp(Boc)-OH, Fmoc-Asp(OAllyl)-OH, Fmoc-Val-OH, Fmoc-Arg(Pmc)-OH, Fmoc-Glu(OtBu)-OH, and Fmoc-Lys(Alloc)-OH. The resin is then removed from the instrument, washed successively with DMF (100 mL), THF (100 mL), diethyl ether (100 mL), and air-dried. The allyl and alloc protective groups are removed as previously described and the cyclization between residues Lys$^{18}$ and Asp$^{22}$ is accomplished in two cycles using HBTU, HOBt and NMM. After washing and drying, the resin is returned to the instrument and the synthesis is completed by adding the following amino acid residues in the order indicated: Fmoc-Ser(tBu)-OH, Fmoc-Asn(Trt)-OH, Fmoc-Leu-OH, Fmoc-His(Trt)-OH, Fmoc-Lys(Boc)-OH, Fmoc-Gly-OH, Fmoc-Leu-OH, Fmoc-Asn(Trt)-OH, Fmoc-His(Trt)-OH, Fmoc-Nle-OH, Fmoc-Leu-OH. The crude peptide is cleaved from the resin and deprotected using 40 mL of TFA containing water (2.0 mL), thioanisole (2.0 mL), phenol (3.0 g), and ethanedithiol (1.0 mL) and precipitated by the addition of the cleavage mixture to cold tert-butylmethyl ether. The crude peptide is then purified by reverse-phase liquid chromatography.

EXAMPLE 86

Tricyclo(K$^{13}$—D$^{17}$,K$^{18}$—D$^{22}$,K$^{26}$-D$^{30}$)[A$^1$,Nle$^8$, K$^{18}$,D$^{17,22}$,L$^{27}$]hPTH(1–31)NH$_2$ (SEQ ID NO: 80)

Ala-Val-Ser-Glu-Ile-Gln-Leu-Nle-His-Asn-Leu-Cly-(Lys-His-Leu-Asn-Asp)-(Lys-Glu-Arg-Val-Asp)-Trp-Leu-Arg-(Lys-Leu-Leu-Gln-Asp)-Val amide The title compound is prepared in a fashion analogous to those previously described. Rink Amide MBHA Resin (Nova Biochem, La Jolla, Calif., USA) (0.80 g, 0.45 mmol) is loaded into a reaction vessel and swelled for 10 minutes using DMF (10 mL). The following amino acid residues are added successively using standard HBTU coupling procedures: Fmoc-Val-OH, Fmoc-Asp(OAllyl)-OH, Fmoc-Gln(Trt)-OH, Fmoc-Leu-OH, Fmoc-Leu-OH, Fmoc-Lys(Alloc)-OH, Fmoc-Arg(Pmc)-OH, Fmoc-Leu-OH, and Fmoc-Trp(Boc)-OH. The resin is removed from the instrument and washed successively with DMF (100 mL), THF (100 mL), diethyl ether (100 mL), then air-dried. The Allyl and Alloc protective groups are removed under Pd-catalysis as previously described and the cyclization between residues Asp$^{30}$ and K$^{26}$ is accomplished in two cycles using HBTU (284 mg), HOBt (101 mg), and NMM (165 mL) in DMF (20 mL). The resin is then washed successively with DMF (100 mL), THF (100 mL), and diethyl ether (100 mL). The resin is returned to the instrument and the synthesis is continued with the addition of the following amino acids: Fmoc-Asp(OAllyl)-OH, Fmoc-Val-OH, Fmoc-Arg(Pmc)-OH, Fmoc-Glu(OtBu)-OH, Fmoc-Lys(Alloc)-OH. The resin is removed from the instrument and washed successively with DMF (100 mL), THF (100 mL), diethyl ether (100 mL), then air-dried. The Allyl and Alloc protective groups are removed under Pd-catalysis and the cyclization between residues Asp$^{18}$ and K$^{22}$ is accomplished in two cycles using HBTU (284 mg), HOBt (101 mg), and NMM (165 mL) in DMF (20 mL). The resin is then washed successively with DMF (100 mL), THF (100 mL), and diethyl ether (100 mL). The resin is returned to the instrument and the synthesis is completed by the addition of the following amino acids: Fmoc-Asp(OAllyl)-OH, Fmoc-Asn(Trt)-OH, Fmoc-Leu-OH, Fmoc-His(Trt)-OH, Fmoc-Lys(Alloc)-OH, Fmoc-Gly-OH, Fmoc-Leu-OH, Fmoc-Asn(Trt)-OH, Fmoc-His(Trt)-OH, Fmoc-Nle-OH, Fmoc-Leu-OH, Fmoc-Gln(Trt)-OH, Fmoc-Ile-OH, Fmoc-Glu(OtBu)-OH, Fmoc-Ser(tBu)-OH, Fmoc-Val-OH, and Fmoc-Ala-OH. The resin is again removed from the instrument, washed successively with DMF (100 mL), THF (100 mL), diethyl ether (100 mL), and air-dried. The Allyl and Alloc protective groups are removed under Pd-catalysis as previously described and the cyclization between residues Asp$^{17}$ and K$^{13}$ is accomplished in two cycles using HBTU (284 mg), HOBt (101 mg), and NMM (165 mL) in DMF (20 mL). The resin is then washed successively with DMF (100 mL), THF (100 mL), and diethyl ether (100 mL). The N-terminal Fmoc protective group is removed over 5 minutes using a 20% piperidine/DMF solution (25 mL). The resin-bound peptide is washed successively with DMF (100 mL), THF (100 mL), and diethyl ether (100 mL). The air-dried resin is suspended in 40 mL of TFA containing water (2.0 mL), thioanisole (2.0 mL), phenol (3.0 g), and ethanedithiol (1.0 mL). After 2 hours, the TFA solution is filtered into tert-butylmethyl ether (120 mL) at 0° C. which effects precipitation of the crude peptide. The peptide mixture is centrifuged at 2500 rpm for 5 minutes and decanted. The crude, white solid is resuspended in diethyl ether (120 mL), centrifuged, and decanted. This washing procedure is repeated four times and the resulting peptide is dried in vacuo, dissolved in water containing 0.1% TFA (100 mL), and lyophilized to dryness.

The crude peptide is purified by reverse-phase high performance liquid chromatography as described previously to provide 16 mg of final peptide as a white solid. IS–MS: 3625 (M+). Amino Acid Analysis: Asp/Asn: 4.88 (5); Ser: 0.95 (1); Glu/Gln: 4.00 (4); Gly: 1.01 (1); Ala: 0.97 (1); Val: 2.93 (3); Ile: 0.93 (1); Leu: 6.41 (6); Nle: 0.84 (1); Lys: 2.73 (3); His: 2.28 (2); Arg: 2.07 (2); Trp: not determined (1).

Pharmaceutical Compositions

The peptide compounds of formula I exhibit useful pharmacological activity and accordingly are incorporated into pharmaceutical compositions and used in the treatment of patients suffering from certain medical disorders.

More especially, certain peptide compounds within the scope of the invention bind to PTH receptors and stimulate adenylyl cyclase activity. Increased adenylyl cyclase activity is associated with positive bone growth and therefore, for example, the peptide compounds of the invention are useful for the treatment of physiological conditions including hypocalcemia; osteoporosis, osteopenia and disorders associated with osteoporosis and osteopenia such as hyperparathyroidism and Cushings syndrome; glucocorticoid- and immunosuppresant-induced osteopaenia; and bone fracture and refracture repair.

Additionally, certain peptide compounds of formula I bind to PTH receptors but do not stimulate adenylyl cyclase activity. These peptide compounds are useful in the treatment of disease states characterized by an excess of PTH including hyperparathyrodism and hyperparathyrodism-related hypercalcemia crisis, hypercalcemia of malignancy, renal failure and hypertension.

A special embodiment of the therapeutic methods of the present invention is the treatment of osteoporisis.

Reference herein to treatment should be understood to include prophylactic therapy as well as treatment of established conditions.

The present invention also provides pharmaceutical compositions which comprise peptide compounds of the present invention formulated together with one or more non-toxic pharmaceutically acceptable carriers. The pharmaceutical compositions of this invention can be administered to humans and other animals orally, intrapulmonarily, transmucousally, intraocularly, rectally, parenterally, intracisternally, intravaginally, intraperitoneally, topically (as by powders, ointments, or drops), transdermally, ionophoretically, bucally, or as an oral or nasal spray. Intrapulmonary and subcutaneous delivery are especially preferred methods of administration of the peptide compounds of the invention.

The term "parenteral" administration as used herein refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. This suspension may contain additional excipients such as trehalose. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active peptide compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active peptide compounds can also be in microencapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Compositions for rectal or vaginal administration are preferably suppositories which can be prepared by mixing the peptide compounds of this invention with suitable non-irritating excipients or carriers such as cocoa butter, polyethylene glycol or a suppository wax which are solid at room temperature but liquid at body temperature and therefore melt in the rectum or vaginal cavity and release the active peptide compound.

For delivery to the buccal or sublingual membranes, oral dosage forms such as lozenges, tablets or capsules as described above are typically used. Alternatively, the formulation may be applied to the oral mucosa with an adhesive such as hydroxypropyl cellulose as described in U.S. Pat. No. 4,940,587, incorporated herein by reference. This formulation allows for controlled release of the drug into the mouth and through the buccal mucosa.

Compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a peptide compound of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et seq.

Dosage forms for topical administration of a peptide compound of this invention include powders, sprays, ointments and inhalants. The active peptide compound is mixed under sterile conditions with a pharmaceutically acceptable carrier and any needed preservatives, buffers, or propellants which may be required. Opthalmic formulations, eye ointments, powders and solutions are also contemplated as being within the scope of this invention.

The peptide compounds of this invention may be delivered transdermally via iontophoresis. In general, iontophoresis refers to the transport of ionic solutes through biological membranes under the influence of an electric field. Iontophoretic drug delivery has the ability to bypass the gastrointestinal and hepatic "first pass" effects which render enteral routes of peptide administration relatively ineffective.

In general, iontophoretic devices comprise at least two electrodes, an electrical energy source and at least one reservoir which contains the peptide compound to be delivered. The reservoir can be in the form of any material suitable for making contact between the iontophoresis unit and the skin. Suitable materials include foams, gels and matrices.

Iontophoresis gels can be karaya gum, other polysaccharide gels, or similar hydrophilic aqueous gels capable of carrying ions. Representative gels include polyvinyl alcohol, polymethyl pyrollidine, methyl cellulose, polyacrylamide, polyhemas, polyhema derivatives, and the like. The matrix selected should have nonirritating properties to avoid irritating the patient's skin or tissue, suitable conductivity properties to obtain good electrical contact with the skin or tissue, and the ability to act as a carrier medium for the peptide compound.

Other means for the iontophoretic delivery of peptide compounds include a patch comprising the peptide compound as well as reusable or refillable inotophoretic devices. The iontophoretic delivery of peptides is described in U.S. Pat. No. 5,494,679. The ionthophoretic delivery of hPTH analogs is discussed in WO 95/11988-A1.

Another method of transdermal delivery is the needleless system developed by PowderJect Pharmaceuticals (Magdalen Centre, Oxford Science Park, Oxford OX4 4GA, UK) in which a jet of helium gas is used to deliver drugs through the skin or mucosa of the mouth. In particular, drug powders are accelerated to about 750 m/sec for about 3 milliseconds, thereby enabling the powder to pass into or around the cells of the skin and into the systemic circulation of the patient.

Intrapulmonary or intranasal delivery of the peptide compound is preferably accomplished by administration of an aerosol to the bronchioles or nasal passages of the patient using a metered dose inhalation device (MDI). For use in MDI's, the peptide compound is dissolved or suspended in a physiologically inert aerosol propellant. Propellants useful in MDI devices include chlorofluorocarbons (CFC's) such as CFC-11 (trifluorochloromethane), CFC-12 (dichlorodifluoromethane) and CFC-114 (dichlorotetrafluoroethane) and non-chlorofluorocarbons (NCFC's) including, halogenated alkanes such as HCFC-123 (1,1,1-trifluoro-2,2-dichloroethane), HCFC-124 (1,1,1,2-tetrafluorochloroethane), HCFC-141b, HCFC-225, HFC-125, FC-C51-12 (perfluorodimethylcyclobutane), DYMEL A (dimethyl ether) and DYMEL 152a (1,1-difluoroethane).

The peptide compound may be dissolved in the propellant, or may take the form of a suspension of droplets or a fine dispersion of solid particles. The aerosol composition may also contain additional co-solvents, surfactants, excipients and flavoring or taste masking agents.

Surfactants are necessary to prevent aggregation (in the form of "caking" or crystallization, for example) of the medicinally active peptide compound in the reservoir of the inhaler, to facilitate uniform dosing upon aerosol administration, and to provide an aerosol spray discharge having a favorable respirable fraction (that is, a particle size distribution such that a large portion of the discharge reaches the alveoli where absorption takes place, and thus produces high lung deposition efficiencies). Surfactants useful for formulating aerosols in CFC propellants are well known in the art. Representative surfactants include oleic acid, sorbitan trioleate, and various long-chain diglycerides and phospholipids.

Halogenated alkane propellants such as HFC-134a and HFC-227ea are substantially less polar than traditional CFC propellants and many surfactants which are generally used in known MDI formulations have been found to be immiscible with or insoluble in, and therefore incompatible with, these new, non-CFC propellants.

U.S. Pat. No. 5,225,183 discloses a formulation comprising HFC-134a, a surface active agent, and an adjuvant or co-solvent having a higher polarity than HFC-134a. Representative adjuvants or co-solvents having a higher polarity than HFC-134a include alcohols such as ethanol, isopropanol and propylene glycol; hydrocarbons such as propane, butane, isobutane, pentane, isopentane and neopentane; and other propellants such as Propellants 11, 12, 114, 113 and 142b. The adjuvant is claimed to provide a propellant system having comparable properties to those based on CFC propellants and therefore allow the use of traditional surfactants. Blends of HFC-134a with other solvents or propellants including dimethyl ether; fluorocarbons such as perfluoropropane, perfluorobutane and perfluoropentane; and hydrochlorofluorocarbons such as HCFC-123 are disclosed in U.S. Pat. No. 5,190,029.

Another approach to solving the incompatibility of HFC-134a with many surfactants is to substitute other surface active agents for those traditionally used in CFC aerosols. The use of polar surfactants such as polyethylene glycol, diethylene glycol monoethyl ether, polyoxyethylene (20) sorbitan monooleate, propoxylated polyethylene glycol, and polyoxyethylene (4) lauryl ether is disclosed in U.S. Pat. No. 5,492,688, incorporated herein by reference. U.S. Pat. No. 5,182,097, incorporated herein by reference, discloses that HFC-134a can be used as the sole propellant if oleic acid is used as the surfactant. U.S. Pat. No. 5,182,697, incorporated herein by reference discloses that using fluorinated surtactants allows the HFC-134a as the sole propellant. PCT Application No. WO 91/11173 discloses that mixtures of fluorinated surfactants with conventional surfactants or other adjuvants such as poloxamers or polyethylene glycols allow the use of hydrofluorocarbon propellants. Non conventional excipients which have been used to prepare aerosol formulations with halogenated alkane propellants include protective colloids, see PCT Application No. WO 95/15151, and tocopherol, see PCT Application No. WO 95/24892.

Suspension aerosol formulations are prepared by combining any surfactants, excipients and flavoring or taste masking agents with a peptide compound which has been milled or otherwise reduced to a desired particle size, and placing the mixture in a suitable aerosol container or vial. After sealing the container, an aerosol propellant is introduced and the system is agitated to fully blend the ingredients. In some instances, it may be necessary to wet-mill the peptide compound in a closed system, as for example under temperature and pressure conditions which permit the peptide compound to be milled while mixed with a liquid-phase aerosol propellant. It is expected that, for any particular combination of peptide compound, propellant and excipients, the ideal order of addition of ingredients and the conditions under which they are to be combined may readily be determined.

In addition to delivery via metered dose inhalers, other pulmonary delivery systems include dry powders and liquid solutions or suspensions suitable for nebulization. Aqueous and non-aqueous based solutions or dispersions may also be administered via tracheal instillation.

Dry powder formulations will typically comprise the peptide compound in a dry, usually lyophilized form, with a particle size within the preferred range for deposition within the alveolar region of the lung. Particle size preferably is from about 0.5 μm to 5 μm. Particles in the preferred size range can be produced by a variety of techniques well known in the art including jet-milling, spray drying, solvent precipitation and the like. Dry powders are administered to the patient in conventional dry powder inhalers (DPI's) that use the patients inspiratory breath or an air-assisted device that uses an external power source to disperse the powder into an aerosol cloud. The peptide compound may be combined with a pharmaceutically acceptable dry bulking powder. Preferred dry bulking powders include sucrose, lactose, trehalose, human serum albumin (HSA), and glycine. Other suitable dry bulking powders include cellubiose, dextrans, maltotriose, pectin, sodium citrate, sodium ascorbate, mannitol, and the like.

Liquid peptide compound formulations for nebulization may employ slightly acidic (pH 4–6 buffers) including acetate, ascorbate, and citrate. These buffers can act as antioxidants, or other pharmaceutically acceptable antioxidants can be added to protect any free methionines from oxidation. Other agents may be added to enhance or maintain chemical stability, including chelating agents, protease inhibitors, isotonic modifiers, inert gases, and the like.

Aqueous solutions or suspensions of the peptide compound may be administered by intratracheal instillation. The aqueous vehicle is selected from pure water, substantially pure water or water combined with other excipients such as salts, ions or other excipients as described above which are generally used in aqueous based systems. The liquid formulations are in the form of solution based dispersions or solutions in solvents or cosolvents such as alcohols or glycols with water. Non-aqueous solutions include those alchohol or glycol based systems which may have some water but which are not comprised of a majority percentage of water and which are known to those of skill in the art as effective and safe delivery vehicles.

Actual dosage levels of active ingredients in the pharmaceutical compositions of this invention may be varied so as to obtain an amount of the active peptide compound(s) that is effective to achieve the desired therapeutic response for a particular patient, compositions, and mode of administration. The selected dosage level will depend upon the activity of the particular peptide compound, the route of administration, the severity of the condition being treated, and the condition and prior medical history of the patient being treated. However, it is within the skill of the art to start doses of the peptide compound at levels lower than required for to achieve the desired therapeutic effect and to gradually increase the dosage until the desired effect is achieved.

Generally, for subcutaneous administration dosage levels of about 0.5 μg to about 1500 μg are preferred, of about 0.5 μg to about 1000 μg are more preferred and of about 1 μg to about 200 μg are most preferred. For intrapulmonary delivery, dosage levels of about 0.5 μg to about 10,000 μg are preferred, and of about 1 μg to about 5000 μg are most preferred. In an especially preferred aspect, from about 1 μg to about 5000 μg of the peptide compound of this invention is administered once a day to a mammalian patient, preferably subcutaneously or intrapulmonarily.

In Vitro and In Vivo Test Procedures

Compounds within the scope of this invention exhibit marked pharmacological activities in tests described in the literature which are accepted in the art and recognized to correlate with pharmacological activity in humans and other mammals. The following pharmacological in vivo and in vitro tests are typical for characterizing compounds of this invention.

1. Stimulation of Adenylate Cyclase in ROS 17/2.8 Cells

The ability of the compounds of the invention to stimulate adenylate cyclase (AC) via occupation or the PTH receptor is measured using a cAMP Assay in ROS 17/2.8 cells as follows: Ros 17/2.8 cells are plated at $1\times10^5$ cells/well in 24 well plates. After 3–5 days, the culture media is aspirated and replaced with 0.5 mL of the cAMP assay buffer which contained Ham's F12 medium, 2 mM IBMX, 1 mg/mL BSA, 35 mM HEPES and 20 μg/mL ascorbic acid. The cells are equilibrated in the assay buffer by incubating the cells for 30 minutes at 37° C. The cAMP buffer is then aspirated. The PTH analogs are diluted in the assay buffer at several concentrations and added to the wells. The cells are then incubated at 37° C. for 20 minutes. Following incubation, the cells are solubilized by the addition of 1% Triton. Total cAMP is measured using a cAMP Scintillation Proximity Assay screening system (Amersham, Arlington Heights, Ill.) and the samples are counted using a Wallac microtitre plate scintillation counter. Data represent mean cAMP values of duplicate samples +/− SD. $EC_{50}$ values are defined as the concentration required to elicit half-maximal stimulation and are calculated using a 4-parameter fit equation.

2. Binding to the PTH Receptor in ROS 17/2.8 Cells

Competition of the compounds of the invention with PTH for binding to the PTH receptor is measured using the PTH Receptor Binding Assay described below:

ROS 17/2.8 cells are plated and prepared as described for the cAMP assay. After 3–5 days, the culture media is aspirated and the cells are washed twice with 1 mL of binding buffer [50 mM Tris-HCl (pH 7.7), 100 mM NaCl, 2 mM $CaCl_2$, 5 mM KCl, 0.5% HIFCS, 5% HI horse serum]. The cells are incubated with 100 pM $^{125}$I-[Nle$^{8,18}$, Tyr$^{34}$] hPTH(1–34)NH$_2$ (Amersham, Arlington Heights, Ill.) in both the presence and absence of the unlabeled PTH analog. After incubation at 22° C. for 2 hours, binding is terminated by aspirating the buffer and washing the cells three times in chilled assay buffer solution. Cell-bound radioactivity is recovered by the addition of 0.1 N NaOH and counted using a Packard gamma counter. Total specific binding is determined from the wells which contained no unlabeled peptide compound. Data represent mean % of total binding of duplicate samples +/- SD. $IC_{50}$ values for competition binding are calculated using a 4-parameter fit equation.

3. Stimulation of Adenylate Cyclase in Mouse and Rat Calvarial Cell Cultures

The cAMP response of mouse and rat calvarial cell cultures to the compounds of the invention is determined as follows:

Osteoblast cells are isolated from fetal rat calvariae (day 19–20 of gestation), or neonatal mice calvariae (days 1–2 of age). Frontal and parietal bone is isolated, cleaned of periosteal and loose connective tissue and minced with scissors. Minced calvariae are then sequentially digested for 20 minutes in type 1 collagenase (0.1 %) with trypsin (0.5%) and EDTA (0.53 mM). Released cells from digestions 4–7 are pooled and washed free of collagenase. The cells are plated at a concentration of 1×10$^5$/mL in a-MEM with 10% FBS in 24-well plates. The cells are equilibrated in assay buffer by incubating the cells for 30 minutes at 37° C. The cAMP buffer is then aspirated. Various concentrations of the PTH peptide compounds are diluted in assay buffer and then added. The cells are incubated at 37° C. for 20 minutes. After incubation, the cells are solubilized by the addition of 1% Triton. Total cAMP is measured using a cAMP Scintillation Proximity Assay screening system (Amersham, Arlington Heights, Ill.) and the samples are counted using a Wallac microtitre plate scintillation counter. Data represent mean cAMP values of duplicate samples +/- SD. $EC_{50}$ values are defined as the concentration required to elicit half-maximal stimulation and are calculated using a 4-parameter fit equation.

4. Stimulation of cAMP Production in the Rat

Female Harlan Sprague-Dawley rats (Lewis strain, 200 g) are anesthetized using a ketamine (70 mg/kg)/xylazine (6 mg/kg) mixture. The peptide compound to be tested is then administered by the desired route (e.g. intravenous, subcutaneous or intratracheal) in a phosphate-buffered saline vehicle (1 mL/kg). After 1 hour, urine is collected either via a urethral catheter or manually by applying gentle pressure over the area of the bladder. A blood sample is also collected by cardiac puncture. The urine sample is assayed for cAMP levels using a radioimmunoassay (Incstar, Stillwater, Minn.) as described by Jaffé (Jaffé, M., *Hoppe Seylers Z. Physiol. Chem.*, 1886, 10, 391). Serum and urine creatinine are also measured and the creatinine levels are used to express cAMP levels as a function of glomular filtration.

5. Measurement of Bone Effects in the Rat

Retired breeder female rats (Sprague-Dawley, 8–10 months of age) are subjected to bilateral ovariectomy. Two months following ovariectomy, treatment with a representative peptide compound is initiated. The peptide compound is prepared in isotonic, phosphate-buffered saline containing 2% heat-inactiviated rat serum. Animals received daily subcutaneous injection (5 days/week) for four weeks. On the day after the last treatment, whole body bone mineral density is measured by dual energy X-ray absorptiometry (DEXA) to determine the extent of the anabolic response.

6. In Vitro Measurement of PTH Antagonist Activity

Antagonist activity of the compounds of this invention is determined by measuring output of cAMP using cultured mouse osteoblast MC3T3-E1 as described in U.S. Pat. No. 5,446,130, incorporated herein by reference.

7. In Vivo Measurement of PTH Antagonist Activity

The in vivo effectiveness of the peptide compounds of this invention as PTH antagonists is determined by measuring the urinary phosphate and cAMP using standard procedures well known in the art as valid measures of PTH activity as described in U.S. Pat. No. 4,423,037, incorporated herein by reference.

What is claimed is:

1. A cyclic peptide compound of formula $$X\text{-}A_{10}\text{-}A_{11}\text{-}A_{12}\text{-}A_{13}\text{-}A_{14}\text{-}A_{15}\text{-}A_{16}\text{-}A_{17}\text{-}A_{18}\text{-}A_{19}\text{-}A_{20}\text{-}A_{21}\text{-}A_{22}\text{-}A_{23}\text{-}A_{24}\text{-}A_{25}\text{-}A_{26}\text{-}A_{27}\text{-}Y$$

or a pharmaceutically acceptable salt or prodrug thereof wherein

X is selected from the group consisting of
    (a) $R_{1a}\text{-}A_0\text{-}A_1\text{-}A_2\text{-}A_3\text{-}A_4\text{-}A_5\text{-}A_6\text{-}A_7\text{-}A_8\text{-}A_9\text{-}$,
    (b) $R_{1a}\text{-}A_2\text{-}A_3\text{-}A_4\text{-}A_5\text{-}A_6\text{-}A_7\text{-}A_8\text{-}A_9\text{-}$,
    (c) $R_{1b}\text{-}A_3\text{-}A_4\text{-}A_5\text{-}A_6\text{-}A_7\text{-}A_8\text{-}A_9\text{-}$,
    (d) $R_{1a}\text{-}A_4\text{-}A_5\text{-}A_6\text{-}A_7\text{-}A_8\text{-}A_9\text{-}$,
    (e) $R_{1a}\text{-}A_5\text{-}A_6\text{-}A_7\text{-}A_8\text{-}A_9\text{-}$,
    (f) $R_{1a}\text{-}A_6\text{-}A_7\text{-}A_8\text{-}A_9\text{-}$,
    (g) $R_{1a}\text{-}A_7\text{-}A_8\text{-}A_9\text{-}$,
    (h) $R_{1a}\text{-}A_8\text{-}A_9\text{-}$,
    (i) $R_{1a}\text{-}A_9\text{-}$, and
    (j) $R_{1a}\text{-}$;

Y is selected from the group consisting of
    (a) $\text{-}R_3$,
    (b) $\text{-}A_{28}\text{-}R_3$,
    (c) $\text{-}A_{28}\text{-}A_{29}\text{-}R_3$,
    (d) $\text{-}A_{28}\text{-}A_{29}\text{-}A_{30}\text{-}R_3$,
    (e) $\text{-}A_{28}\text{-}A_{29}\text{-}A_{30}\text{-}A_{31}\text{-}R_3$,
    (f) $\text{-}A_{28}\text{-}A_{29}\text{-}A_{30}\text{-}A_{31}\text{-}A_{32}\text{-}R_3$,
    (g) $\text{-}A_{28}\text{-}A_{29}\text{-}A_{30}\text{-}A_{31}\text{-}A_{32}\text{-}A_{33}\text{-}R_3$, and
    (h) $\text{-}A_{28}\text{-}A_{29}\text{-}A_{30}\text{-}A_{31}\text{-}A_{32}\text{-}A_{33}\text{-}A_{34}\text{-}R_3$;

$R_{1a}$ is H, alkyl, aralkyl or $\text{—}COR_2$;

$R_{1b}$ is $R_{1a}$ or a group of formula

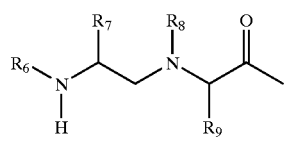 or

-continued

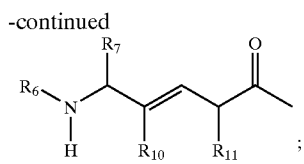

$R_2$ is alkyl, alkenyl, alkynyl, aryl or aralkyl;
$R_3$ is a group of formula $A_{35}$—$OR_4$ or $A_{35}$—$NR_4R_5$;
$R_4$ and $R_5$ are independently H or lower alkyl;
$R_6$ and $R_9$ are independently H or alkyl:
$R_7$ is alkyl;
$R_8$ is H, alkyl or $COR_2$;
$R_{10}$ is H or halogen;
$R_{11}$ is alkyl or aralkyl;
m is 1, 2 or 3;
n is 3 or 4;
$A_0$ is absent or a peptide of from one to six amino acid residues;
$A_1$ is Ser, Ala, Gly or D-Pro, or an equivalent amino acid thereof;
$A_2$ is Ala, Val or Gly, or an equivalent amino acid thereof;
$A_3$ is Ala, Ser, Gly or D-Pro, or an equivalent amino acid thereof;
$A_4$ is Glu, Ala or Gly, or an equivalent amino acid thereof;
$A_5$ is Ile, His, Ala or Gly, or an equivalent amino acid thereof;
$A_6$ is Ala, Gln, Gly or D-Pro, or an equivalent amino acid thereof;
$A_7$ is Ala, Leu, Gly, or an equivalent amino acid thereof;
$A_8$ is Leu, Nle, Gly or D-Pro, or an equivalent amino acid thereof;
$A_9$ is His, Ala, D-Pro or Gly, or an equivalent amino acid thereof;
$A_{10}$ is Ala, Asn, Asp, Cys, homo-Cys, Glu, Gly, Lys, Orn, Ser, Thr, D-Pro, —NHCH$(CH_2)_m$NH$_2$)CO— or —NHCH[$(CH_2)_n$CO$_2$H]CO—;
$A_{11}$ is Ala, Gly, Leu or Lys, or an equivalent amino acid thereof;
$A_{12}$ is Ala or Gly, or an equivalent amino acid thereof;
$A_{13}$ is Ala, Asn, Asp, Cys, homo-Cys, Glu, Gly, Lys, Orn, Ser, Thr, —NHCH$(CH_2)_m$NH$_2$)CO— or —NHCH[$(CH_2)_n$CO$_2$H]CO—;
$A_{14}$ is Ala, Asn, Asp, Cys, homo-Cys, Glu, Gly, His, Lys, Orn, Ser, Thr, D-Pro, —NHCH$(CH_2)_m$NH$_2$)CO— or —NHCH[$(CH_2)_n$CO$_2$H]CO—;
$A_{15}$ is Ala, Gly, Ile, D-Pro or Leu, or an equivalent amino acid thereof;
$A_{16}$ is Asn, Ala, Gly, D-Pro or Gln, or an equivalent amino acid thereof;
$A_{17}$ is Ala, Asn, Asp, Cys, homo-Cys, Glu, Gly, Lys, Orn, Ser, Thr, D-Pro, —NHCH$(CH_2)_m$NH$_2$)CO— or —NHCH[$(CH_2)_n$CO$_2$H]CO—;
$A_{18}$ is Asp, Cys, homo-Cys, Glu, His, Leu, Lys, Orn, Nle, Ser, Thr, —NHCH$(CH_2)_m$NH$_2$)CO— or —NHCH[$(CH_2)_n$CO$_2$H]CO—;
$A_{19}$ is Arg or Glu, or an equivalent amino acid thereof;
$A_{20}$ is Arg or an equivalent amino acid thereof;
$A_{21}$ is Arg, Asp, Cys, homo-Cys, Glu, Lys, Orn, Ser, Thr, Val, —NHCH$(CH_2)_m$NH$_2$)CO— or —NHCH[$(CH_2)_n$CO$_2$H]CO—;
$A_{22}$ is Asp, Cys, homo-Cys, Glu, His, Lys, Orn, Phe, Ser, Thr, —NHCH$(CH_2)_m$NH$_2$)CO— or —NHCH[$(CH_2)_n$CO$_2$H]CO—;
$A_{23}$ is Leu, Phe or Trp, or an equivalent amino acid thereof;
$A_{24}$ is Leu or an equivalent amino acid thereof;
$A_{25}$ is Arg, Asp, Cys, homo-Cys, Glu, His, Lys, Orn, D-Pro, Ser, Thr, —NHCH$(CH_2)_m$NH$_2$)CO— or —NHCH[$(CH_2)_n$CO$_2$H]CO—;
$A_{26}$ is Asp, Cys, homo-Cys, Glu, His, Lys, Orn, Ser, Thr, —NHCH$(CH_2)_m$NH$_2$)CO— or —NHCH[$(CH_2)_n$CO$_2$H]CO—;
$A_{27}$ is Leu or Lys, or an equivalent amino acid thereof;
$A_{28}$ is Ile or Leu, or an equivalent amino acid thereof;
$A_{29}$ is Ala, Asp, Cys, homo-Cys, Glu, Gln, Lys, Orn, Ser, Thr, —NHCH$(CH_2)_m$NH$_2$)CO— or —NHCH[$(CH_2)_n$CO$_2$H]CO—;
$A_{30}$ is Asp, Cys, homo-Cys, Glu, Gly, Lys, Orn, Ser, Thr, —NHCH$(CH_2)_m$NH$_2$)CO— or —NHCH[$(CH_2)_n$CO$_2$H]CO—;
$A_{31}$ is Ile, Leu or Val, or an equivalent amino acid thereof;
$A_{32}$ is His, or an equivalent amino acid thereof;
$A_{33}$ is Asn or Thr, or an equivalent amino acid thereof;
$A_{34}$ is Ala or Phe, or an equivalent amino acid thereof;
$A_{35}$ is absent or a peptide of from 1 to 4 amino acids; and
the side chains of at least one of the following pairs of amino acid residues, $A_{10}$ and $A_{14}$, $A_{13}$ and $A_{17}$, $A_{14}$ and $A_{18}$, $A_{17}$ and $A_{21}$, $A_{18}$ and $A_{22}$, $A_{21}$ and $A_{25}$, $A_{25}$ and $A_{29}$ and $A_{26}$ and $A_{30}$ are linked through an amide, ester, disulfide or lanthionine bond to form a bridge, and the side chain of each of $A_{10}$, $A_{13}$, $A_{14}$, $A_{17}$, $A_{18}$, $A_{21}$, $A_{22}$, $A_{25}$, $A_{26}$, $A_{29}$, and $A_{30}$, contributes, at most, to the formation of a single bridge; provided that when the side chains of $A_{13}$ and $A_{17}$ or $A_{26}$ and $A_{30}$ are linked through an amide, disulfide or lanthionine bond to form a bridge, then the side chains of at least one of the following pairs of amino acid residues, $A_{10}$ and $A_{14}$, $A_{14}$ and $A_{18}$, $A_{17}$ and $A_{21}$, $A_{18}$ and $A_{22}$, $A_{21}$ and $A_{25}$ and $A_{25}$ and $A_{29}$ are also linked through an amide, ester, disulfide or lanthionine bond.

2. A peptide compound according to claim 1, or a pharmaceutically acceptable salt or prodrug thereof wherein the bridge formed from the side chains of one pair of amino acid residues is non-overlapping with a bridge formed between the side chains of another pair of amino acid residues.

3. A peptide compound according to claim 1 selected from
Cyclo($K^{18}$—$D^{22}$)[$A^1$,Nle$^8$,$K^{18}$,$D^{22}$,$L^{27}$]hPTH(1–31)NH$_2$ (SEQ ID NO: 3);
Cyclo($K^{18}$—$D^{22}$)[$A^{1,2}$,Nle$^8$,$K^{18}$,$D^{22}$,$L^{27}$]hPTH(1–31)NH$_2$ (SEQ ID NO: 5);
Cyclo($K^{18}$—$D^{22}$)[$A^{1,3}$,Nle$^8$,$K^{18}$,$D^{22}$,$L^{27}$]hPTH(1–31)NH$_2$ (SEQ ID NO: 6);
Cyclo($K^{18}$—$D^{22}$)[$A^{1,4}$,Nle$^8$,$K^{18}$,$D^{22}$,$L^{27}$]hPTH(1–31)NH$_2$ (SEQ ID NO: 7);
Cyclo($K^{18}$—$D^{22}$)[$A^{1,5}$,Nle$^8$,$K^{18}$,$D^{22}$,$L^{27}$]hPTH(1–31)NH$_2$ (SEQ ID NO: 8);
Cyclo($K^{18}$—$D^{22}$)[$A^{1,6}$,Nle$^8$,$K^{18}$,$D^{22}$,$L^{27}$]hPTH(1–31)NH$_2$ (SEQ ID NO: 9);
Cyclo($K^{18}$—$D^{22}$)[$A^{1,7}$,Nle$^8$,$K^{18}$,$D^{22}$,$L^{27}$]hPTH(1–31)NH$_2$ (SEQ ID NO: 10);
Cyclo($K^{18}$—$D^{22}$)[$A^{1,9}$,Nle$^8$,$K^{18}$,$D^{22}$,$L^{27}$]hPTH(1–31)NH$_2$ (SEQ ID NO: 11);
Cyclo($K^{18}$—$D^{22}$)[$A^{1,10}$,Nle$^8$,$K^{18}$,$D^{22}$,$L^{27}$]hPTH(1–31)NH$_2$ (SEQ ID NO: 12);

Cyclo($K^{18}$—$D^{22}$)[$A^{1,11}$,$Nle^8$,$K^{18}$,$D^{22}$,$L^{27}$]hPTH(1–31)$NH_2$ (SEQ ID NO: 13);
Cyclo($K^{18}$—$D^{22}$)[$A^{1,12}$,$Nle^8$,$K^{18}$,$D^{22}$,$L^{27}$]hPTH(1–31)$NH_2$ (SEQ ID NO: 14);
Cyclo($K^{18}$—$D^{22}$)[$A^{1,13}$,$Nle^8$,$K^{18}$,$D^{22}$,$L^{27}$]hPTH(1–31)$NH_2$ (SEQ ID NO: 15);
Cyclo($K^{18}$—$D^{22}$)[$A^{1,14}$,$Nle^8$,$K^{18}$,$D^{22}$,$L^{27}$]hPTH(1–31)$NH_2$ (SEQ ID NO: 16);
Cyclo($K^{18}$—$D^{22}$)[$A^{1,15}$,$Nle^8$,$K^{18}$,$D^{22}$,$L^{27}$]hPTH(1–31)$NH_2$ (SEQ ID NO: 17);
Cyclo($K^{18}$—$D^{22}$)[$A^{1,16}$,$Nle^8$,$K^{18}$,$D^{22}$,$L^{27}$]hPTH(1–31)$NH_2$ (SEQ ID NO: 18);
Cyclo($K^{18}$—$D^{22}$)[$A^{1,17}$,$Nle^8$,$K^{18}$,$D^{22}$,$L^{27}$]hPTH(1–31)$NH_2$ (SEQ ID NO: 19);
Cyclo($K^{18}$—$D^{22}$)[$G^1$,$Nle^8$,$K^{18}$,$D^{22}$,$L^{27}$]hPTH(1–31)$NH_2$ (SEQ ID NO: 20);
Cyclo($K^{18}$—$D^{22}$)[$A^1$,$G^2$,$Nle^8$,$K^{18}$,$D^{22}$,$L^{27}$]hPTH(1–31)$NH_2$ (SEQ ID NO: 21);
Cyclo($K^{18}$—$D^{22}$)[$A^1$,$G^3$,$Nle^8$,$K^{18}$,$D^{22}$,$L^{27}$]hPTH(1–31)$NH_2$ (SEQ ID NO: 22);
Cyclo($K^{18}$—$D^{22}$)[$A^1$,$G^4$,$Nle^8$,$K^{18}$,$D^{22}$,$L^{27}$]hPTH(1–31)$NH_2$ (SEQ ID NO: 23);
CyClo($K^{18}$—$D^{22}$)[$A^1$,$G^5$,$Nle^8$,$K^{18}$,$D^{22}$,$L^{27}$]hPTH(1–31)$NH_2$ (SEQ ID NO: 24);
Cyclo($K^{18}$—$D^{22}$)[$A^1$,$G^6$,$Nle^8$,$K^{18}$,$D^{22}$,$L^{27}$]hPTH(1–31)$NH_2$ (SEQ ID NO: 25);
Cyclo($K^{18}$—$D^{22}$)[$A^1$,$G^7$,$Nle^8$,$K^{18}$,$D^{22}$,$L^{27}$]hPTH(1–31)$NH_2$ (SEQ ID NO: 26);
Cyclo($K^{18}$—$D^{22}$)[$A^1$,$G^8$,$K^{18}$,$D^{22}$,$L^{27}$]hPTH(1–31)$NH_2$ (SEQ ID NO: 27);
Cyclo($K^{18}$—$D^{22}$)[$A^1$,$G^9$,$Nle^8$,$K^{18}$,$D^{22}$,$L^{27}$]hPTH(1–31)$NH_2$ (SEQ ID NO: 28);
Cyclo($K^{18}$—$D^{22}$)[$A^1$,$G^{10}$,$Nle^8$,$K^{18}$,$D^{22}$,$L^{27}$]hPTH(1–31)$NH_2$ (SEQ ID NO: 29);
Cyclo($K^{18}$—$D^{22}$)[$A^1$,$G^{11}$,$Nle^8$,$K^{18}$,$D^{22}$,$L^{27}$]hPTH(1–31)$NH_2$ (SEQ ID NO: 30);
Cyclo($K^{18}$—$D^{22}$)[$A^1$,$G^{13}$,$Nle^8$,$K^{18}$,$D^{22}$,$L^{27}$]hPTH(1–31)$NH_2$ (SEQ ID NO: 31);
Cyclo($K^{18}$—$D^{22}$)[$A^1$,$G^{14}$,$Nle^8$,$K^{18}$,$D^{22}$,$L^{27}$]hPTH(1–31)$NH_2$ (SEQ ID NO: 32);
Cyclo($K^{18}$—$D^{22}$)[$A^1$,$G^{15}$,$Nle^8$,$K^{18}$,$D^{22}$,$L^{27}$]hPTH(1–31)$NH_2$ (SEQ ID NO: 33);
Cyclo($K^{18}$—$D^{22}$)[$A^1$,$G^{16}$,$Nle^8$,$K^{18}$,$D^{22}$,$L^{27}$]hPTH(1–31)$NH_2$ (SEQ ID NO: 34);
Cyclo($K^{18}$—$D^{22}$)[$A^1$,$G^{17}$,$Nle^8$,$K^{18}$,$D^{22}$,$L^{27}$]hPTH(1–31)$NH_2$ (SEQ ID NO: 35);
Cyclo($K^{18}$—$D^{22}$)[D-$P^1$,$Nle^8$,$K^{18}$,$D^{22}$,$L^{27}$]hPTH(1–31)$NH_2$ (SEQ ID NO: 36);
Cyclo($K^{18}$—$D^{22}$)[$A^1$,D-$P^3$,$Nle^8$,$K^{18}$,$D^{22}$,$L^{27}$]hPTH(1–31)$NH_2$ (SEQ ID NO: 37);
Cyclo($K^{18}$—$D^{22}$)[$A^1$,D-$P^6$,$Nle^8$,$K^{18}$,$D^{22}$,$L^{27}$]hPTH(1–31)$NH_2$ (SEQ ID NO: 38);
Cyclo($K^{18}$—$D^{22}$)[$A^1$,D-$P^7$,$Nle^8$,$K^{18}$,$D^{22}$,$L^{27}$]hPTH(1–31)$NH_2$ (SEQ ID NO: 39);
Cyclo($K^{18}$—$D^{22}$)[$A^1$,D-$P^9$,$Nle^8$,$K^{18}$,$D^{22}$,$L^{27}$]hPTH(1–31)$NH_2$ (SEQ ID NO: 40);
Cyclo($K^{18}$—$D^{22}$)[$A^1$,D-$P^{10}$,$Nle^8$,$K^{18}$,$D^{22}$,$L^{27}$]hPTH(1–31)$NH_2$ (SEQ ID NO: 41);
Cyclo($K^{18}$—$D^{22}$)[$A^1$,D-$P^{14}$,$Nle^8$,$K^{18}$,$D^{22}$,$L^{27}$]hPTH(1–31)$NH_2$ (SEQ ID NO: 42);
Cyclo($K^{18}$—$D^{22}$)[$A^1$,D-$P^{15}$,$Nle^8$,$K^{18}$,$D^{22}$,$L^{27}$]hPTH(1–31)$NH_2$ (SEQ ID NO: 43);
Cyclo($K^{18}$—$D^{22}$)[$A^1$,D-$P^{16}$,$Nle^8$,$K^{18}$,$D^{22}$,$L^{27}$]hPTH(1–31)$NH_2$ (SEQ ID NO: 44);
Cyclo($K^{18}$—$D^{22}$)[$A^1$,D-$P^{17}$,$Nle^8$,$K^{18}$,$D^{22}$,$L^{27}$]hPTH(1–31)$NH_2$ (SEQ ID NO: 45);
Cyclo($K^{18}$—$D^{22}$)[$A^1$,$Nle^8$,$K^{18}$,$D^{22}$,$L^{27}$]hPTH(1–34)$NH_2$ (SEQ ID NO: 46);
Cyclo($D^{18}$-$K^{22}$)[$A^1$,$Nle^8$,$D^{18}$,$K^{22}$,$L^{27}$]hPTH(1–31)$NH_2$ (SEQ ID NO: 47);
Cyclo($O^{18}$-$D^{22}$)[$A^1$,$Nle^8$,$O^{18}$,$D^{22}$,$L^{27}$]hPTH(1–31)$NH_2$ (SEQ ID NO: 48);
Cyclo($D^{18}$-$O^{22}$)[$A^1$,$Nle^8$,$D^{18}$,$O^{22}$,$L^{27}$]hPTH(1–31)$NH_2$ (SEQ ID NO: 49);
Cyclo($K^{18}$—$E^{22}$)[$A^1$,$Nle^8$,$K^{18}$,$E^{22}$,$L^{27}$]hPTH(1–31)$NH_2$ (SEQ ID NO: 50);
Cyclo($O^{18}$-$E^{22}$)[$A^1$,$Nle^8$,$O^{18}$,$E^{22}$,$L^{27}$]hPTH(1–31)$NH_2$ (SEQ ID NO: 51);
Cyclo($K^{18}$—$D^{22}$)[$A^1$,$Nle^8$,$K^{18}$,$D^{22}$,$L^{27}$]hPTH(1–30)$NH_2$ (SEQ ID NO: 52);
Cyclo($K^{18}$—$D^{22}$)[$A^1$,$Nle^8$,$K^{18}$,$D^{22}$,$L^{27}$]hPTH(1–29)$NH_2$ (SEQ ID NO: 53);
Cyclo($K^{18}$—$D^{22}$)[$A^1$,$Nle^8$,$K^{18}$,$D^{22}$,$L^{27}$]hPTH(1–28)$NH_2$ (SEQ ID NO: 54);
Cyclo($K^{18}$—$D^{22}$)[$A^1$,$Nle^8$,$K^{18}$,$D^{22}$,$L^{27}$]hPTH(1–27)$NH_2$ (SEQ ID NO: 55);
Cyclo($K^{18}$—$D^{22}$)[$Nle^8$,$K^{18}$,$D^{22}$,$L^{27}$]hPTH(3–31)$NH_2$ (SEQ ID NO: 63);
Cyclo($K^{18}$—$D^{22}$)[$Nle^8$,$K^{18}$,$D^{22}$,$L^{27}$]hPTH(2–31)$NH_2$ (SEQ ID NO: 64);
Cyclo($K^{10}$-$D^{14}$)[$A^1$,$Nle^{8,18}$,$K^{10}$,$D^{14}$,$L^{27}$]hPTH(1–31)$NH_2$ (SEQ ID NO: 66);
Cyclo($K^{14}$-$D^{18}$)[$A^1$,$Nle^8$,$K^{14}$,$D^{18}$,$L^{27}$]hPTH(1–31)$NH_2$ (SEQ ID NO: 67);
Cyclo($K^{17}$-$D^{21}$)[$A^1$,$Nle^{8,18}$,$K^{17}$,$D^{21}$,$L^{27}$]hPTH(1–31)$NH_2$ (SEQ ID NO: 68);
Cyclo($K^{21}$-$D^{25}$)[$A^1$,$Nle^{8,18}$,$K^{21}$,$D^{25}$,$L^{27}$]hPTH(1–31)$NH_2$ (SEQ ID NO: 69);
Cyclo($K^{25}$-$D^{29}$)[$A^1$,$Nle^{8,18}$,$K^{25}$,$D^{29}$,$L^{27}$]hPTH(1–31)$NH_2$ (SEQ ID NO: 70);
Cyclo($K^{18}$—$D^{22}$)[$K^{18}$,$D^{22}$]hPTHrP(1–34)$NH^2$ (SEQ ID NO: 71);
Cyclo($K^{18}$—$D^{22}$)[$K^{18,26,30}$,$D^{22}$,$L^{23,28,31}$,$F^{25,29}$]hPTHrP(1–34)$NH_2$ (SEQ ID NO: 72);
BiCyclo($K^{13}$-$D^{17}$,$K^{18}$—$D^{22}$)[$A^1$,$Nle^8$,$D^{17,22}$,$K^{18}$,$L^{27}$]hPTH(1–31)$NH_2$ (SEQ ID NO: 73);
BiCyclo($K^{18}$—$D^{22}$,$K^{26}$-$D^{30}$)[$A^1$,$Nle^8$,$K^{18}$,$D^{22}$,$L^{27}$]hPTH(1–31)$NH_2$ (SEQ ID NO: 74); and
TriCyclo($K^{13}$-$D^{17}$,$K^{18}$—$D^{22}$,$K^{26}$-$D^{30}$)[$A^1$,$Nle^8$,$K^{18}$,$D^{17,22}$,$L^{27}$]hPTH(1–31)$NH_2$ (SEQ ID NO: 80);
or a pharmaceutically acceptable salt or prodrug thereof.

4. A peptide compound according to claim 1 selected from
Cyclo($K^{18}$—$D^{22}$)[$A^1$,$Nle^8$,$K^{18}$,$D^{22}$,$L^{27}$]hPTH(1–31)$NH_2$ (SEQ ID NO: 3);
Cyclo($K^{18}$—$D^{22}$)[$A^1$,$Nle^8$,$K^{18}$,$D^{22}$,$L^{27}$]hPTH(1–34)$NH_2$ (SEQ ID NO: 46);
Cyclo($K^{18}$—$D^{22}$)[$A^{1,3}$,$Nle^8$,$K^{18}$,$D^{22}$,$L^{27}$]hPTH(1–31)$NH_2$ (SEQ ID NO: 6);
Cyclo($K^{18}$—$D^{22}$)[$A^{1,6}$,$Nle^8$,$K^{18}$,$D^{22}$,$L^{27}$]hPTH(1–31)$NH_2$ (SEQ ID NO: 9);
Cyclo($K^{18}$—$D^{22}$)[$A^{1,10}$,$Nle^8$,$K^{18}$,$D^{22}$,$L^{27}$]hPTH(1–31)$NH_2$ (SEQ ID NO: 12);
Cyclo(($K^{18}$—$D^{22}$)[$A^{1,11}$,$Nle^8$,$K^{18}$,$D^{22}$,$L^{27}$]hPTH(1–31)$NH_2$ (SEQ ID NO: 13);

Cyclo(K$^{18}$—D$^{22}$)[A$^{1,12}$,Nle$^8$,K$^{18}$,D$^{22}$,L$^{27}$]hPTH(1–31)NH$_2$ (SEQ ID NO: 14);
Cyclo(K$^{18}$—D$^{22}$)[A$^{1,13}$,Nle$^8$,K$^{18}$,D$^{22}$,L$^{27}$]hPTH(1–31)NH$_2$ (SEQ ID NO: 15);
Cyclo(K$^{18}$—D$^{22}$)[A$^{1,14}$,Nle$^8$,K$^{18}$,D$^{22}$,L$^{27}$]hPTH(1–31)NH$_2$ (SEQ ID NO: 16);
Cyclo(K$^{18}$—D$^{22}$)[A$^{1,15}$,Nle$^8$,K$^{18}$,D$^{22}$,L$^{27}$]hPTH(1–31)NH$_2$ (SEQ ID NO: 17);
Cyclo(K$^{18}$—D$^{22}$)[A$^{1,16}$,Nle$^8$,K$^{18}$,D$^{22}$,L$^{27}$]hPTH(1–31)NH$_2$ (SEQ ID NO: 18);
Cyclo(K$^{18}$—D$^{22}$)[A$^{1,17}$,Nle$^8$,K$^{18}$,D$^{22}$,L$^{27}$]hPTH(1–31)NH$_2$ (SEQ ID NO: 19);
Cyclo(K$^{18}$—D$^{22}$)[G$^1$,Nle$^8$,K$^{18}$,D$^{22}$,L$^{27}$]hPTH(1–31)NH$_2$ (SEQ ID NO: 20);
Cyclo(K$^{18}$—D$^{22}$)[A$^1$,G$^2$,Nle$^8$,K$^{18}$,D$^{22}$,L$^{27}$]hPTH(1–31)NH$_2$ (SEQ ID NO: 21);
Cyclo(K$^{18}$—D$^{22}$)[A$^1$,G$^3$,Nle$^8$,K$^{18}$,D$^{22}$,L$^{27}$]hPTH(1–31)NH$_2$ (SEQ ID NO: 22);
Cyclo(K$^{18}$—D$^{22}$)[A$^1$,G$^{10}$,Nle$^8$,K$^{18}$,D$^{22}$,L$^{27}$]hPTH(1–31)NH$_2$ (SEQ ID NO: 29);
Cyclo(K$^{18}$—D$^{22}$)[A$^1$,G$^{13}$,Nle$^8$,K$^{18}$,D$^{22}$,L$^{27}$]hPTH(1–31)NH$_2$ (SEQ ID NO: 31);
Cyclo(K$^{18}$—D$^{22}$)[A$^1$,G$^{16}$,Nle$^8$,K$^{18}$,D$^{22}$,L$^{27}$]hPTH(1–31)NH$_2$ (SEQ ID NO: 34);
Cyclo(K$^{18}$—D$^{22}$)[A$^1$,G$^{17}$,Nle$^8$,K$^{18}$,D$^{22}$,L$^{27}$]hPTH(1–31)NH$_2$ (SEQ ID NO: 35);
Cyclo(K$^{18}$—D$^{22}$)[D-P$^1$,Nle$^8$,K$^{18}$,D$^{22}$,L$^{27}$]hPTH(1–31)NH$_2$ (SEQ ID NO: 36);
Cyclo(D$^{18}$-K$^{22}$)[A$^1$,Nle$^8$,D$^{18}$,K$^{22}$,L$^{27}$]hPTH(1–31)NH$_2$ (SEQ ID NO: 47);
Cyclo(O$^{18}$-D$^{22}$)[A$^1$,Nle$^8$,O$^{18}$,D$^{22}$,L$^{27}$]hPTH(1–31)NH$_2$ (SEQ ID NO: 48);
Cyclo(D$^{18}$,O$^{22}$)[A$^1$,Nle$^8$,D$^{18}$,O$^{22}$,L$^{27}$]hPTH(1–31)NH$_2$ (SEQ ID NO: 49);
Cyclo(K$^{18}$—E$^{22}$)[A$^1$,Nle$^8$,K$^{18}$,E$^{22}$,L$^{27}$]hPTH(1–31)NH$_2$ (SEQ ID NO: 50);
Cyclo(O$^{18}$-E$^{22}$)[A$^1$,Nle$^8$,O$^{18}$,E$^{22}$,L$^{27}$]hPTH(1–31)NH$_2$ (SEQ ID NO: 51);
Cyclo(K$^{18}$—D$^{22}$)[A$^1$,Nle$^8$,K$^{18}$,D$^{22}$,L$^{27}$]hPTH(1–30)NH$_2$ (SEQ ID NO: 52);
Cyclo(K$^{18}$—D$^{22}$)[A$^1$,Nle$^8$,K$^{18}$,D$^{22}$,L$^{27}$]hPTH(1–29)NH$_2$ (SEQ ID NO: 53);
Cyclo(K$^{18}$—D$^{22}$)[A$^1$,Nle$^8$,K$^{18}$,D$^{22}$,L$^{27}$]hPTH(1–28)NH$_2$ (SEQ ID NO: 54);
Cyclo(K$^{10}$-D$^{14}$)[A$^1$,Nle$^{8,18}$,K$^{10}$,D$^{14}$,L$^{27}$]hPTH(1–31)NH$_2$ (SEQ ID NO: 66);
Cyclo(K$^{14}$-D$^{18}$)[A$^1$,Nle$^8$,K$^{14}$,D$^{18}$,L$^{27}$]hPTH(1–31)NH$^2$ (SEQ ID NO: 67);
Cyclo(K$^{17}$-D$^{21}$)[A$^1$,Nle$^{8,18}$,K$^{17}$,D$^{21}$,L$^{27}$]hPTH(1–31)NH$_2$ (SEQ ID NO: 68);
Cyclo(K$^{21}$-D$^{25}$)[A$^1$,Nle$^{8,18}$,K$^{21}$,D$^{25}$,L$^{27}$]hPTH(1–31)NH$_2$ (SEQ ID NO: 69);
Cyclo(K$^{25}$-D$^{29}$)[A$^1$,Nle$^{8,18}$,K$^{25}$,D$^{29}$,L$^{27}$]hPTH(1–31)NH$_2$ (SEQ ID NO: 70);
Cyclo(K$^{18}$—D$^{22}$)[K$^{18}$,D$^{22}$]hPTHrP(1–34)NH$_2$ (SEQ ID NO: 71);
Cyclo(K$^{18}$—D$^{22}$)[K$^{18,26,30}$,D$^{22}$,L$^{23,28,31}$,E$^{25,29}$]hPTHrP(1–34)NH$_2$ (SEQ ID NO: 72);
Bicyclo(K$^{13}$-D$^{17}$,K$^{18}$—D$^{22}$)[A$^1$,Nle$^8$,D$^{17,22}$,K$^{18}$,L$^{27}$]hPTH(1–31)NH$_2$ (SEQ ID NO: 73);
Bicyclo(K$^{18}$—D$^{22}$,K$^{26}$-D$^{30}$)[A$^1$,Nle$^8$,K$^{18}$,D$^{22}$,L$^{27}$]hPTH(1–31)NH$_2$ (SEQ ID NO: 74); and
Tricyclo(K$^{13}$-D$^{17,}$K$^{18}$—D$^{22}$,K$^{26}$-D$^{30}$)[A$^1$,Nle$^8$,K$^{18}$,D$^{17,22}$,L$^{27}$]hPTH(1–31)NH$_2$ (SEQ ID NO: 80);

or a pharmaceutically acceptable salt or prodrug thereof.

5. A peptide compound according to claim 1 selected from
Cyclo(K$^{18}$—D$^{22}$)[A$^1$,Nle$^8$,K$^{18}$,D$^{22}$,L$^{27}$]hPTH(1–31)NH$_2$ (SEQ ID NO: 3);
Cyclo(K$^{18}$—D$^{22}$)[A$^1$,Nle$^8$,K$^{18}$,D$^{22}$,L$^{27}$]hPTH(1–34)NH$_2$ (SEQ ID NO: 46);
Cyclo(K$^{18}$—D$^{22}$)[A$^{1,10}$,Nle$^8$,K$^{18}$,D$^{22}$,L$^{27}$]hPTH(1–31)NH$_2$ (SEQ ID NO: 12);
Cyclo(K$^{18}$—D$^{22}$)[A$^{1,12}$,Nle$^8$,K$^{18}$,D$^{22}$,L$^{27}$]hPTH(1–31)NH$_2$ (SEQ ID NO: 14);
Cyclo(K$^{18}$—D$^{22}$)[A$^{1,13}$,Nle$^8$,K$^{18}$,D$^{22}$,L$^{27}$]hPTH(1–31)NH$_2$ (SEQ ID NO: 15);
Cyclo(K$^{18}$—D$^{22}$)[A$^{1,14}$,Nle$^8$,K$^{18}$,D$^{22}$,L$^{27}$]hPTH(1–31)NH$_2$ (SEQ ID NO: 16);
Cyclo(K$^{18}$—D$^{22}$)[A$^{1,16}$,Nle$^8$,K$^{18}$,D$^{22}$,L$^{27}$]hPTH(1–31)NH$_2$ (SEQ ID NO: 18);
Cyclo(K$^{18}$—D$^{22}$)[A$^{1,17}$,Nle$^8$,K$^{18}$,D$^{22}$,L$^{27}$]hPTH(1–31)NH$_2$ (SEQ ID NO: 19);
Cyclo(K$^{18}$—D$^{22}$)[A$^1$,G$^3$,Nle$^8$,K$^{18}$,D$^{22}$,L$^{27}$]hPTH(1–31)NH$_2$ (SEQ ID NO: 22);
Cyclo(K$^{18}$—D$^{22}$)[A$^1$,G$^{13}$,Nle$^8$,K$^{18}$,D$^{22}$,L$^{27}$]hPTH(1–31)NH$_2$ (SEQ ID NO: 31);
Cyclo(K$^{18}$—D$^{22}$)[A$^1$,G$^{16}$,Nle$^8$,K$^{18}$,D$^{22}$,L$^{27}$]hPTH(1–31)NH$_2$ (SEQ ID NO: 34);
Cyclo(K$^{18}$—D$^{22}$)[A$^1$,G$^{17}$,Nle$^8$,K$^{18}$,D$^{22}$,L$^{27}$]hPTH(1–31)NH$_2$ (SEQ ID NO: 35);
Cyclo(K$^{18}$—D$^{22}$)[D-P$^1$,Nle$^8$,K$^{18}$,D$^{22}$,L$^{27}$]hPTH(1–31)NH$_2$ (SEQ ID NO: 36);
Cyclo(D$^{18}$-K$^{22}$)[A$^1$,Nle$^8$,D$^{18}$,K$^{22}$,L$^{27}$]hPTH(1–31)NH$_2$ (SEQ ID NO: 47);
Cyclo(K$^{18}$—E$^{22}$)[A$^1$,Nle$^8$,K$^{18}$,E$^{22}$,L$^{27}$]hPTH(1–31)NH$_2$ (SEQ ID NO: 50);
Cyclo(O$^{18}$-E$^{22}$)[A$^1$,Nle$^8$,O$^{18}$,E$^{22}$,L$^{27}$]hPTH(1–31)NH$_2$ (SEQ ID NO: 51);
Cyclo(K$^{18}$—D$^{22}$)[A$^1$,Nle$^8$,K$^{18}$,D$^{22}$,L$^{27}$]hPTH(1–30)NH$_2$ (SEQ ID NO: 52);
Cyclo(K$^{18}$—D$^{22}$)[A$^1$,Nle$^8$,K$^{18}$,D$^{22}$,L$^{27}$]hPTH(1–31)NH$_2$ (SEQ ID NO: 67);
Cyclo(K$^{18}$—D$^{22}$)[K$^{18}$,D$^{22}$]hPTHrP(1–34)NH$_2$ (SEQ ID NO: 71);
BiCyclo(K$^{13}$-D$^{17}$,K$^{18}$—D$^{22}$)[A$^1$,Nle$^8$,D$^{17,22}$,K$^{18}$,L$^{27}$]hPTH(1–31)NH$_2$ (SEQ ID NO: 73);
BiCyclo(K$^{18}$—D$^{22}$,K$^{26}$-D$^{30}$)[A$^1$,Nle$^8$,K$^{18}$,D$^{22}$,L$^{27}$]hPTH(1–31)NH$_2$ (SEQ ID NO: 74); and
Triyclo(K$^{13}$-D$^{17}$,K$^{18}$—D$^{22}$,K$^{26}$-D$^{30}$)[A$^1$,Nle$^8$,K$^{18}$,D$^{17,22}$,L$^{27}$]hPTH(1–31)NH$_2$ (SEQ ID NO: 80);

or a pharmaceutically acceptable salt or prodrug thereof.

6. A pharmaceutical composition comprising a peptide compound of claim 1, or a pharmaceutically acceptable salt or prodrug thereof and a pharmaceutically acceptable carrier.

7. A method of treating diseases associated with calcium regulation in a patient in need of such treatment comprising administering to the patient a therapeutically effective amount of a peptide compound of claim 1, or a pharmaceutically acceptable salt or prodrug thereof.

8. A peptide compound according to claim 1 which is
Cyclo(K$^{18}$—D$^{22}$)[A$^1$,Nle$^8$,K$^{18}$,D$^{22}$,L$^{27}$]hPTH(1–31)NH$_2$ (SEQ ID NO: 3)

or a pharmaceutically acceptable salt or prodrug thereof.

* * * * *